US008067447B2

(12) United States Patent
Sheppeck et al.

(10) Patent No.: US 8,067,447 B2
(45) Date of Patent: Nov. 29, 2011

(54) MODULATORS OF GLUCOCORTICOID RECEPTOR, AP-1, AND/OR NF-κB ACTIVITY AND USE THEREOF

(75) Inventors: James E. Sheppeck, Newtown, PA (US); John L. Gilmore, Yardley, PA (US); T. G. Murali Dhar, Newtown, PA (US); Hai-Yun Xiao, Belle Mead, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 120 days.

(21) Appl. No.: 12/513,192

(22) PCT Filed: Oct. 31, 2007

(86) PCT No.: PCT/US2007/083084
§ 371 (c)(1),
(2), (4) Date: Aug. 6, 2009

(87) PCT Pub. No.: WO2008/057856
PCT Pub. Date: May 15, 2008

(65) Prior Publication Data
US 2010/0076014 A1  Mar. 25, 2010

Related U.S. Application Data

(60) Provisional application No. 60/855,951, filed on Nov. 1, 2006.

(51) Int. Cl.
| | |
|---|---|
| *A61K 31/433* | (2006.01) |
| *A61K 31/416* | (2006.01) |
| *C07D 285/135* | (2006.01) |
| *C07D 231/56* | (2006.01) |
| *C07D 231/40* | (2006.01) |

(52) U.S. Cl. ...... 514/363; 514/406; 548/139; 548/362.5
(58) Field of Classification Search .................. None
See application file for complete search history.

(56) References Cited

U.S. PATENT DOCUMENTS

| | | | |
|---|---|---|---|
| 4,882,342 A | 11/1989 | von der Saal et al. | |
| 4,894,386 A | 1/1990 | Brown et al. | |
| 5,599,951 A | 2/1997 | Plaquevent et al. | |
| 2006/0122250 A1 | 6/2006 | Chaturvedula et al. | |

FOREIGN PATENT DOCUMENTS

| | | | |
|---|---|---|---|
| WO | WO 96/26918 | | 9/1996 |
| WO | WO 03/104236 | * | 12/2003 |
| WO | WO 2004/099143 | | 11/2004 |
| WO | WO 2005/056550 | | 6/2005 |
| WO | WO 2006/076633 | | 7/2006 |
| WO | WO 2006/138373 | | 12/2006 |
| WO | WO 2007/062996 | * | 6/2007 |
| WO | WO2008/021926 | | 2/2008 |
| WO | WO2008/057857 | | 5/2008 |
| WO | WO2008/057859 | | 5/2008 |
| WO | WO2008/057862 | | 5/2008 |
| WO | WO 2008/070507 | | 6/2008 |
| WO | WO 2008/079073 | | 7/2008 |

OTHER PUBLICATIONS

Morissette et al. "High-throughput crystallization: polymorphs, salts, co-crystals and solvates of pharmaceutical solids." Advanced Drug Delivery Reviews 2004, 56, 275-300.*
Souillac, et al., Characterization of Delivery Systems, Differential Scanning Calorimetry, pp. 217-218 (in Encyclopedia of Controlled Drug Delivery, 1999, John Wiley & Sons, pp. 212-227).*
Vippagunta, Sudha R. "Crystalline Solids." Advanced Drug Delivery Reviews 48(2001): 3-26.*
Ahluwalia, G.S. et al., "The Condensation of Aromatic Aldehydes with Malonanilic Acid and its Derivatives", Journal of the Chemical Society, pp. 2059-2062 (1931).
Baldwin, Jr., A.S., "The transcription factor Nf-κB and human disease", The Journal of Clinical Investigation, vol. 107, No. 1, pp. 3-6 (2001).
Burke, J.R., "Targeting IκB kinase for the treatment of inflammatory and other disorders", Current Opinion in Drug Discovery & Development, vol. 6, No. 5, pp. 720-728 (2003).
Caldenhoven, E. et al., "Negative Cross-Talk between RelA and the Glucocorticoid Receptor: A Possible Mechanism for the Antiinflammatory Action of Glucocorticoids", Molecular Endocrinology, vol. 9, No. 4, pp. 401-412 (1995).
Chakravarti, D. et al., "Role of CBP/P300 in nuclear receptor signalling", Nature, vol. 383, pp. 99-103 (1996).
Diamond, M.I. et al., "Transcription Factor Interactions: Selectors of Positive or Negative Regulation from a Single DNA Element", Science, vol. 249, pp. 1266-1272 (1990).
Firestein, G.S. et al., "Signal Transduction and Transcription Factors in Rheumatic Disease", Arthritis & Rheumatism, vol. 42, No. 4, pp. 609-621 (1999).
Jonat, C. et al., "Antitumor Promotion and Antiinflammation: Down-Modulation of AP-1 (Fos/Jun) Activity by Glucocorticoid Hormone", Cell, vol. 62, pp. 1189-1204 (1990).
Kamei, Y. et al., "A CBP Integrator Complex Mediates Transcriptional Activation and AP-1 Inhibition by Nuclear Receptors", Cell, vol. 85, pp. 403-414 (1996).
Manning, A.M., et al., "Targeting JNK for Therapeutic Benefit: from Junk to Gold?", Nature, vol. 2, pp. 554-565 (2003).
Miesfeld, R. et al., "Characterization of a steroid hormone receptor gene and mRNA in wild-type and mutant cells", Nature, vol. 312, pp. 779-781 (1984).
Peltz, G., "Transcription factors in immune-mediated disease", Current Opinion in Biotechnology, vol. 8, pp. 467-473 (1997).

(Continued)

*Primary Examiner* — Rebecca Anderson
*Assistant Examiner* — Alicia L Otton
(74) *Attorney, Agent, or Firm* — Burton Rodney

(57) ABSTRACT

Novel non-steroidal compounds are provided which are useful in treating diseases associated with modulation of the glucocorticoid receptor, and/or AP-1, and/or NF-κB activity including inflammatory and immune diseases, obesity and diabetes having the structure of formula (I), its enantiomers, diastereomers, or a pharmaceutically-acceptable salt, or hydrate, thereof, wherein (Ia) is heterocycle or heteroaryl; J, Ja, E, F, G, Ma, M, Q, Za and Z are as defined herein. Also provided are pharmaceutical compositions and methods of treating inflammatory- or immune-associated diseases and obesity and diabetes employing said compounds.

12 Claims, No Drawings

OTHER PUBLICATIONS

Reichardt, H.M. et al., "DNA Binding of the Glucocorticoid Receptor is Not Essential for Survival", Cell, vol. 93, pp. 531-541 (1998).

Reichardt, H.M. et al., "Repression of inflammatory responses in the absence of DNA binding by the glucocorticoid receptor", The EMBO Journal, vol. 20, No. 24, pp. 7168-7173 (2001).

Schäcke, H. et al., "Dissociated non-steroidal glucocorticoid receptor modulators: an update on new compounds", Expert Opin. Ther. Patents, vol. 18, No. 3, pp. 339-352 (2008).

Thoms, H. et al., "Fagaramide, a New Substance, Containing Nitrogen from the Root of Fagara xanthoxyloides Lam", Berichte der Deutschen Chemischen Gesellschaft, vol. 44, pp. 3717-3730 (1912).

Weinberger, C. et al., "Domain structure of human glucocorticoid receptor and its relationship to the v-erb-A oncogene product", Nature, vol. 318, pp. 670-672 (1985).

Weinberger, C. et al., "Identification of Human Glucocorticoid Receptor Complementary DNA Clones by Epitope Selection", Science, vol. 228, pp. 740-742 (1985).

Yang-Yen, H.-F. et al., "Transcriptional Interference between c-Jun and the Glucocorticoid Receptor: Mutual Inhibition of DNA Binding Due to Direct Protein-Protein Interaction", Cell, vol. 62, pp. 1205-1215 (1990).

* cited by examiner

US 8,067,447 B2

MODULATORS OF GLUCOCORTICOID RECEPTOR, AP-1, AND/OR NF-κB ACTIVITY AND USE THEREOF

FIELD OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and to a method for using such compounds to treat these and related diseases.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation*, 107:3 (2001); Firestein, G. S., and Manning, A. M., *Arthritis and Rheumatism*, 42:609 (1999); and Peltz, G., *Curr. Opin. in Biotech.*, 8:467 (1997).

There are many signaling molecules (kinases and phosphatases) upstream of AP-1 and NF-κB which are potential therapeutic drug targets. The kinase JNK plays an essential role in regulating the phosphorylation and subsequent activation of c-jun, one of the subunits which constitute the AP-1 complex (fos/c-jun). Compounds which inhibit JNK have been shown to be efficacious in animal models of inflammatory disease. See Manning, A. M. and Davis, R. J., *Nature Rev. Drug Disc.*, 2:554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.*, 6(5):720-728, (September 2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228:740-742 (1985); Weinberger et al., *Nature*, 318:670-672 (1986) and for results in rats see Miesfeld, R., *Nature*, 312:779-781 (1985).

Glucocorticoids which interact with GR have been used for over 50 years to treat inflammatory diseases. It has been clearly shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62:1189 (1990); Yang-Yen, H. F. et al., *Cell*, 62:1205 (1990); Diamond, M. I. et al., *Science*, 249:1266 (1990); and Caldenhoven, E. et al., *Mol. Endocrinol.*, 9:401 (1995). Other mechanisms such as sequestration of co-activators by GR have also been proposed. See Kamei, Y. et al., *Cell*, 85:403 (1996); and Chakravarti, D. et al., *Nature*, 383:99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas, transrepression, which does not require DNA binding leads to suppression of inflammation. See Reichardt, H. M. et al., *Cell*, 93:531 (1998) and Reichardt, H. M., *EMBO J.*, 20:7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents. However their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

DESCRIPTION OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and to a method for using such compounds to treat these and related diseases.

In accordance with one aspect of the invention, compounds are provided having the structure of formula I

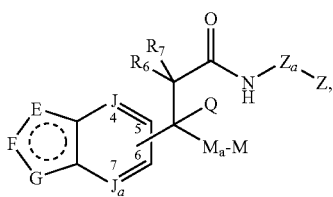

its enantiomers, diastereomers, tautomers, a prodrug ester thereof, or a pharmaceutically-acceptable salt, or hydrate, thereof, wherein:
the side chain group

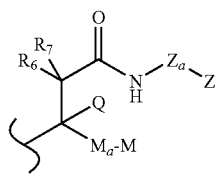

is attached to the bicyclic ring

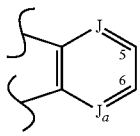

at the 5- or 6-position;

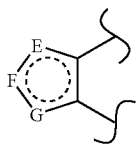

is heterocyclo or heteroaryl;
E is selected from —N—, —$NR_1$—, —O—, C(=O)—, —S—, —$SO_2$—, and —$CR_2$—;
F is selected from —N—, —$NR_{1a}$—, —O—, —C(=O)—, —S—, $SO_2$—, and —$CR_{2a}$—;
G is selected from N, —$NR_{1b}$—, —O—, —C(=O)—, —S—, —$SO_2$—, and —$CR_{2b}$—, provided that the E-F-G containing heterocyclic ring formed does not contain a S—S or S—O bond, and at least one of E, F and G is a heteroatom;
J is C or N;
$J_a$ is C or N, provided that only one of J and $J_a$ can be N, but each of J and $J_a$ can be C; and when E is $CR_2$, F is N and G is $NR_{1b}$, that is the bicyclic ring is an indazole, then $J_a$ is C;
M is selected from hydrogen, alkyl, alkenyl, cycloalkyl, cycloalkenyl, aryl, heteroaryl, and heterocyclo other than piperidinyl;
$M_a$ is a linker between C and M and is selected from a bond; $C_1$-$C_5$ alkylene; $C_1$-$C_5$ alkylene which includes at any position in the chain a) a nitrogen which is substituted with alkyl, b) an oxygen, c) a sulfur, or d) an $SO_2$ group; —C($R_{m^1}$)($R_{m^2}$)C(=O)N($R_{m^3}$)—; —C($R_{m^1}$)($R_{m^2}$)S(=O)$_2$N($R_{m^3}$)—; —Oalkyl; —N($R_{m^3}$)C(=O)C($R_{m^1}$)($R_{m^2}$)—; —S(=O)$_2$N($R_{m^1}$)C($R_{m^2}$)($R_{m^3}$)—; and —N($R_{m^1}$)C(=O)N($R_{m^2}$)—; where $R_{m^1}$, $R_{m^2}$ and $R_{m^3}$ at each occurrence are independently selected from H and $C_1$-$C_4$ alkyl; or $R_{m^1}$ and $R_{m^2}$ combine to form a $C_{3-6}$ carbocyclic or heterocyclic ring;
Q is selected from
 (i) hydrogen, halogen, nitro, cyano, hydroxy, and $C_1$-$C_4$ alkyl; or
 (ii) Q and $R_6$ are combined with the carbons to which they are attached to form a 3- to 6-membered cycloalkyl; or
 (iii) Q and -$M_a$-M are combined with the carbons to which they are attached to form a 3- to 7-membered ring containing 0, 1 or 2 heteroatoms which are the same or different and are independently selected from the group consisting of O, S, $SO_2$, and

which ring may be optionally substituted with 0-2 $R_3$ groups or carbonyl;
Z is selected from alkyl, cycloalkyl, heterocyclo, aryl, alkylsulfonyl, haloalkylsulfonyl, and heteroaryl other than substituted or unsubstituted 4-pyridyl;
$Z_a$ is a linker between N and Z and is selected from a bond; $C_1$-$C_5$ alkylene; $C_1$-$C_5$ alkylene which includes at any position in the chain a nitrogen which is substituted with alkyl or an $SO_2$ group; —C($R_{z^1}$)($R_{z^2}$)C(=O)N($R_{z^3}$)—; —C(=O)N($R_{z^1}$)C($R_{z^2}$)($R_{z^3}$)—; —C($R_{z^1}$)($R_{z^2}$)S(=O)$_2$N($R_{z^3}$)—; or —S(=O)$_2$N($R_{z^1}$)C($R_{z^2}$)($R_{z^3}$)—; where $R_{z^1}$, $R_{z^2}$ and $R_{z^3}$ are independently selected from H and $C_1$-$C_4$ alkyl;
$R_1$, $R_{1a}$ and $R_{1b}$ are the same or different and at each occurrence are independently selected from hydrogen, alkyl, alkenyl, alkynyl, cycloalkyl, cycloalkenyl, aryl, heteroaryl, and heterocyclo;
$R_2$, $R_{2a}$ and $R_{2b}$ are the same or different and at each occurrence are independently selected from hydrogen, halogen, alkyl, alkenyl, alkynyl, nitro, cyano, —$OR_{10}$, —$NR_{10}R_{11}$, —C(=O)$R_{10}$, —$CO_2R_{10}$, —C(=O)$NR_{10}R_{11}$, —O—C(=O)$R_{10}$, —$NR_{10}$C(=O)$R_{11}$, —$NR_{10}$C(=O)$OR_{11}$, —$NR_{10}$C(S)$OR_{11}$, —S(=O)$_p R_{12}$, —$NR_{10}SO_2R_{12}$, —$SO_2NR_{10}R_{11}$, cycloalkyl, cycloalkenyl, cycloalkynyl, heterocyclo, aryl, and heteroaryl;
$R_3$ at each occurrence is independently selected from hydrogen, halogen, alkyl, alkenyl, alkynyl, nitro, cyano, —$OR_{13}$, —$NR_{13}R_{14}$, —C(=O)$R_{13}$, —$CO_2R_{13}$, —C(=O)$NR_{13}R_{14}$, —O—C(=O)$R_{13}$, —$NR_{13}$C(=O)$R_{14}$, —$NR_{13}$C(=O)$OR_{14}$, —$NR_{13}$C(S)$OR_{14}$, —S(=O)$_p R_{15}$, —$NR_{13}SO_2R_{15}$, —$SO_2NR_{13}R_{14}$, cycloalkyl, cycloalkenyl, cycloalkynyl, heterocyclo, aryl, and heteroaryl;
$R_4$ is selected from hydrogen, alkyl, halogen, and $C_1$-$C_4$ alkoxy;
$R_6$ is selected from hydrogen, halogen, alkyl, alkenyl, alkynyl, nitro, cyano, —$OR_{16}$, —$NR_{16}R_{17}$, —C(=O)$R_{17}$, —$CO_2R_{17}$, —C(=O)$NR_{16}R_{17}$, —O—C(=O)$R_{16}$, —$NR_{16}$C(=O)$R_{17}$, —$NR_{16}$C(=O)$OR_{17}$, —$NR_{16}$C(=S)$OR_{17}$, —S(=O)$_p R_{18}$, —$NR_{16}SO_2R_{18}$, —$SO_2NR_{16}R_{17}$, cycloalkyl, cycloalkenyl, heterocyclo, aryl, and heteroaryl;
$R_7$ is selected from hydrogen, halogen, alkyl, alkenyl, alkynyl, nitro, cyano, —$OR_{19}$, —$NR_{19}R_{20}$, —C(=O)$R_{19}$, —$CO_2R_{19}$, —C(=O)$NR_{19}R_{20}$, —O—C(=O)$R_{19}$, —$NR_{19}$C(=O)$R_{20}$, —$NR_{19}$C(=O)$OR_{20}$, —$NR_{19}$C(=S)$OR_{20}$, —S(=O)$_p R_{21}$, —$NR_{19}SO_2R_{21}$, —$SO_2NR_{19}R_{20}$, cycloalkyl, cycloalkenyl, cycloalkynyl, heterocyclo, aryl, and heteroaryl;

or R$_6$ and R$_7$ are taken together with the carbon to which they are attached to form a cycloalkyl, cycloalkenyl, or heterocyclo group;

R$_5$, R$_{10}$, R$_{11}$, R$_{13}$, R$_{14}$, R$_{16}$, R$_{17}$, R$_{19}$ and R$_{20}$ are the same or different and at each occurrence are independently selected from (i) hydrogen, alkyl, alkenyl, alkynyl, cycloalkyl, cycloalkenyl, aryl, heteroaryl, and heterocyclo; or (ii) with respect to R$_3$, R$_{13}$ is taken together with R$_{14}$; and/or with respect to R$_6$, R$_{16}$ is taken together with R$_{17}$; and/or with respect to R$_7$, R$_{19}$ is taken together with R$_{20}$ to form a 4- to 6-membered heteroaryl or heterocyclo ring;

R$_{12}$, R$_{15}$, R$_{18}$, and R$_{21}$ are the same or different and are independently selected from alkyl, alkenyl, alkynyl, cycloalkyl, cycloalkenyl, aryl, heteroaryl, or heterocyclo; and p is 0, 1 or 2, provided that 1) at least one of Q, M$_a$-M, R$_6$ and R$_7$ must be other than hydrogen; or 2) when Q and R$_6$ (and the carbons to which they are attached) combine to form a 3- to 7-membered carbocyclic ring, then —Z$_a$-Z cannot be C$_1$-C$_5$ alkyl; or 3) when Q and M$_a$-M combine to form a 3- to 7-membered carbocyclic ring, then —Z$_a$-Z cannot be C$_1$-C$_5$ alkyl; or 4) when Z$_a$ is a bond, then Z is other than

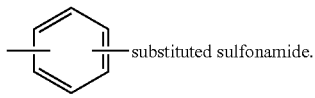

-substituted sulfonamide.

It is preferred that the group

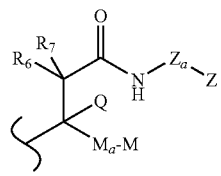

is attached to the benzo ring portion of the bicyclic ring at the 5- or 6-position; and

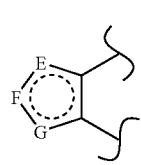

is a heteroaryl ring.

It is preferred that when the bicyclic ring is an indazole or indole of the structure

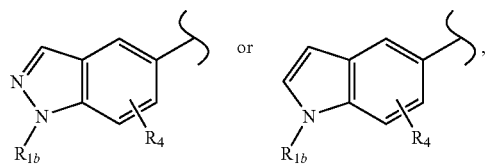

where the side chain group is linked to the 5-position and not the 6-position.

The bicyclic ring system

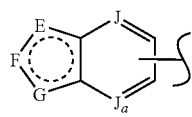

employed in the compounds of formula I includes the following ring systems:

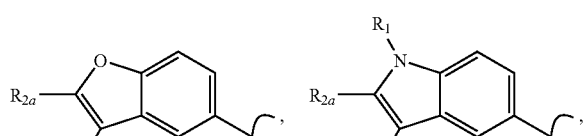

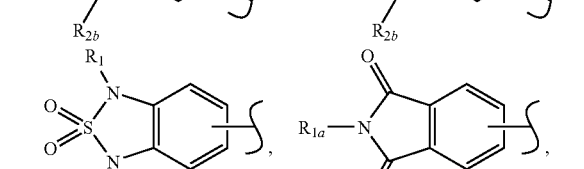

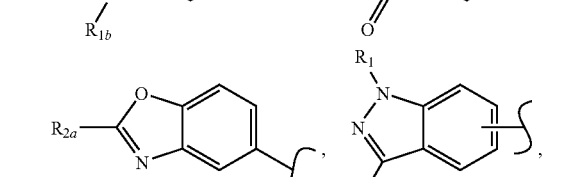

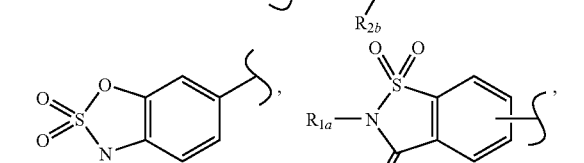

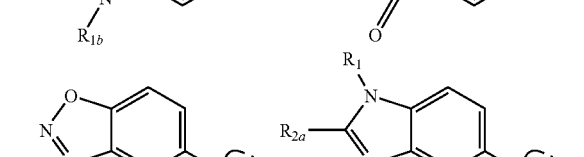

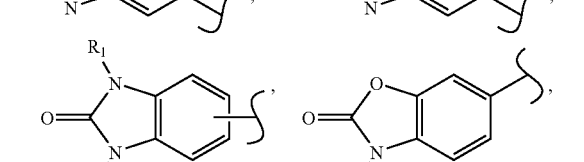

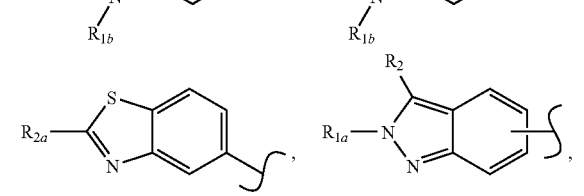

-continued

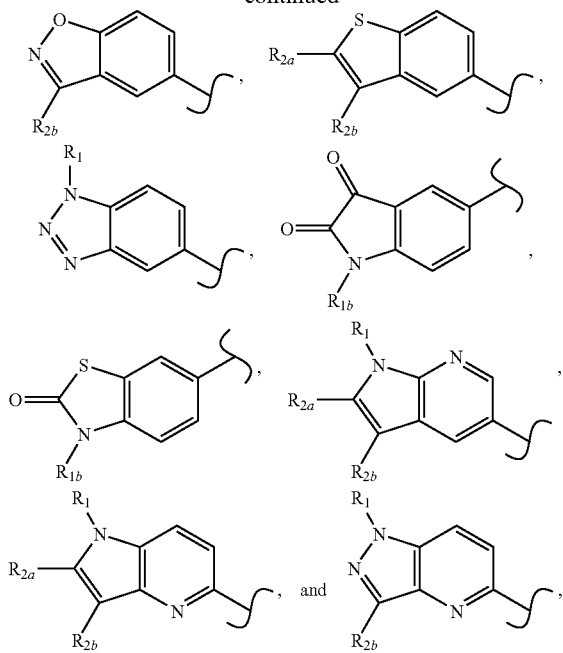

wherein each of the above ring systems may optionally include an $R_4$ group.

It is more preferred that in compounds of formula I

E is $CR_2$ or $NR_1$;

F is N, $NR_{1a}$ or $CR_{2a}$; and

G is $NR_{1b}$ or $CR_{2b}$; and one of $J_a$ or J is optionally N.

provided that a) where E is $NR_1$, F is $CR_{2a}$ and G is $CR_{2b}$, or G is $NR_{1b}$, F is $CR_{2a}$ and E is $CR_2$ so that the resulting bicyclic ring is an indole, then $R_{1a}$, $R_{2a}$ and/or $R_{2b}$ cannot be $-NH_2$; or b) where E is $NR_1$, F is N, and G is $CR_{2b}$ or G is $NR_{1b}$, F is N and E is $CR_2$, so that the resulting bicyclic ring is an indazole, then $R_1$, $R_{1b}$, $R_2$ and $R_{2a}$ cannot be $NH_2$; or c) when the bicyclic ring is an indazole and Q and $M-M_a$ (and the carbon to which they are attached) combine to form a 5- or 6-membered ring, then $-Z_a-Z$ cannot be $C_1-C_5$ alkyl; or d) when the bicyclic ring is an indazole, Q and $M-M_a$ (and the carbon to which they are attached) cannot combine to form a cyclohexane ring, or a cyclohexene ring or a cyclohexadiene ring; or e) when the bicyclic ring is an indazole and $R_6$ or $R_7$ is independently H or $C_1-C_7$ alkyl, then $Z_a$ cannot be $(CH_2)_{0-4}$.

It is preferred that when $-M_a-M$ is alkyl, arylalkyl, cycloalkyl, aryl, heteroaryl, or heteroarylalkyl, the $-Z_a-Z$ is other than $C_1-C_7$ alkyl or aryl.

It is more preferred that in the compounds of formula I

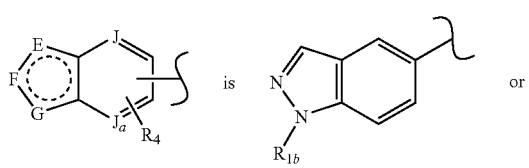

In more preferred embodiments of compounds of formula I, $R_{1b}$ is H, aryl, alkyl, heterocyclo, alkylsulfonylalkyl, heteroaryl, or hydroxyalkyloxyalkyl;

$Z_a$ is a bond;

Z is heteroaryl, cycloalkyl, alkylsulfonyl, haloalkylsulfonyl, or haloalkyl;

M is aryl, alkyl, cycloalkyl, heteroaryl, arylalkyl, or hydroxyheteroaryl;

$M_a$ is a bond or alkyl;

Q is hydrogen or alkyl, or Q and $M-M_a$ and the carbons to which they are attached can combine to form a heterocyclo ring, or a cycloalkyl ring, or Q and $R_6$ and the carbons to which they are attached can combine to form a heterocyclo ring, or a cycloalkyl ring.

In still more preferred embodiments of compounds of formula I, $Z_a$ is a bond;

Z is heteroaryl substituted with one, two or three groups which are the same or different and are independently selected from hydrogen, halogen, alkyl, substituted alkyl, alkenyl, substituted alkenyl, alkynyl, substituted alkynyl, nitro, cyano, $OR_1^c$, $NR_1^aR_1^b$, $C(=O)R_1^c$, $CO_2R_1^c$, $C(=O)NR_1^aR_1^b$, $-O-C(=O)R_1^c$, $NR_1^aC(=O)R_1^b$, $NR_1^aC(=O)OR_1^b$, $NR_1^aC(=S)OR_1^b$, $S(=O)_{p_1}R_1^c$, $NR_1^aSO_2 R_1^b$, $SO_2NR_1^aR_1^b$, cycloalkyl, cycloalkenyl, heterocyclo, aryl, and heteroaryl; and $R_1a$, $R_1^b$, and $R_1^c$, are the same or different and are independently selected from (i) hydrogen, alkyl, substituted alkyl, alkenyl, substituted alkenyl, alkynyl, substituted alkynyl, cycloalkyl, cycloalkenyl, aryl, heteroaryl, and heterocyclo; or (ii) where possible $R^a$ is taken together with $R^b$ to form a heteroaryl or heterocyclo ring; and $p_1$ is 0, 1 or 2.

Where Z is heteroaryl, preferred heteroaryls are selected from:

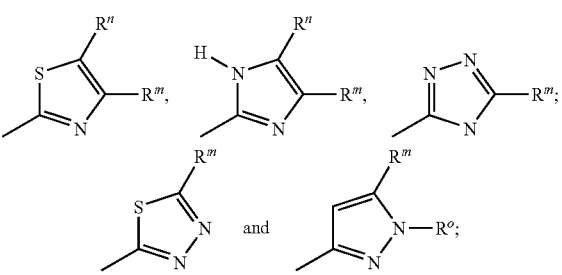

$R^m$ and $R^n$ are the same or different and at each occurrence are independently selected from hydrogen, halogen, cycloalkyl, cyano, haloalkyl, thioalkyl, $-CO_2R^c$, $-NR^aR^b$, $-C(=O)R^c$, $-C(O)N(R^a)(R^b)$, $OR^c$, alkyl, substituted alkyl, aryl, heteroaryl and heterocyclo;

or $R^m$ and $R^n$ combine to form a 5-, 6- or 7-membered carbocyclic, aryl, heteroaryl or heterocyclo ring which contains 0, 1, 2 or 3 hetero atoms which can be N, O, or S;

$R^a$ and $R^b$ are the same or different and at each occurrence are independently selected from hydrogen, alkyl, substituted alkyl, C(=O)alkyl, CO$_2$(alkyl), SO$_2$alkyl, alkenyl, substituted alkenyl, alkynyl, substituted alkynyl, amino, substituted amino (NR$^{a^1}$R$^{b^1}$ where R$^{a^1}$ and R$^{b^1}$ are independently selected from H, alkyl or any of the R$^c$ groups defined below), aryl, heteroaryl, cycloalkenyl, heterocyclo, and cycloalkyl, provided R$^a$ and R$^b$ are not both alkoxy, amino, or substituted amino, or where possible R$^a$ is taken together with R$^b$ to form a heteroaryl or heterocyclo ring;

$R^c$ is selected from hydrogen, alkyl, substituted alkyl, alkenyl, substituted alkenyl, alkynyl, substituted alkynyl, alkoxy, amino, substituted amino, heteroaryl, heterocyclo, cycloalkyl, and aryl; and $R^o$ is selected from alkyl, substituted alkyl, aryl, heteroaryl and heterocyclo;

or $R^m$ and $R^o$ combine to form a 5-, 6- or 7-membered carbocyclic, aryl, heteroaryl or heterocyclo ring which contains 0, 1, 2 or 3 hetero atoms which can be N, O or S.

In preferred embodiments of compounds of formula I of the invention,

E is CH;
F is N;
G is NR$_{1b}$;
R$_{1b}$ is haloalkylaryl, haloaryl, haloalkylalkyl(halo)aryl, alkoxyaryl, alkoxycarbonylaryl, H, hydroxyalkyl, heterocyclo, alkylheterocyclo, alkylsulfonylalkyl, alkyl, heteroaryl, hydroxyaryl, alkoxyalkyl, arylalkyl, cycloalkyl, alkoxycarbonylaryl, or carboxyaryl;
Z is heteroaryl, alkoxycarbonylheteroaryl, alkylheteroaryl, cycloalkyl, aminoheteroaryl, cycloheteroaryl, cycloalkylheteroaryl, hydroxyheteroaryl, alkylthioheteroaryl, dialkylheteroaryl, haloalkylheteroaryl, haloheteroaryl, hydroxycycloalkyl, aminocycloalkyl, alkylcarbonylaminocycloalkyl, alkylsulfonyl, haloalkylsulfonyl, alkyl, or haloalkyl;
Z$_a$ is a bond;
M is alkyl, aryl, cycloalkyl, heteroayl, arylalkyl, heterocyclo, alkylarylalkyl, alkylaryl, or haloaryl;
M$_a$ is a bond;
Q is H or alkyl, or
Q and R$_6$ and the carbons to which they are attached can be combined to form

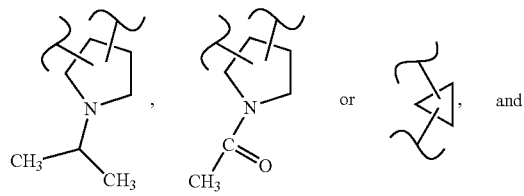

Q and M-M$_a$ and the carbons to which they are attached can be combined to form

In more preferred embodiments of the compounds of formula I of the invention,
E is CH or NR$_1$;

F is N, NR$_{1a}$ or CR$_{2a}$; and
G is NR$_{1b}$ or CR$_{2b}$;
R$_1$ is CH, H or —C=O;
R$_{1a}$ is H,

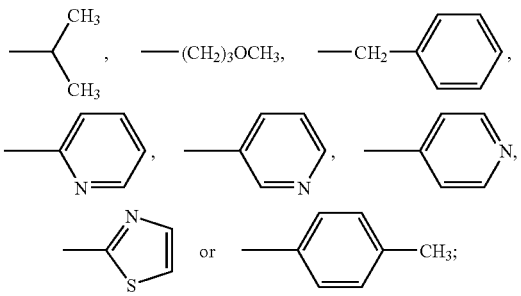

R$_{2a}$ is

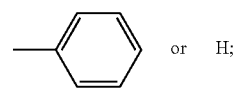

R$_{1b}$ is

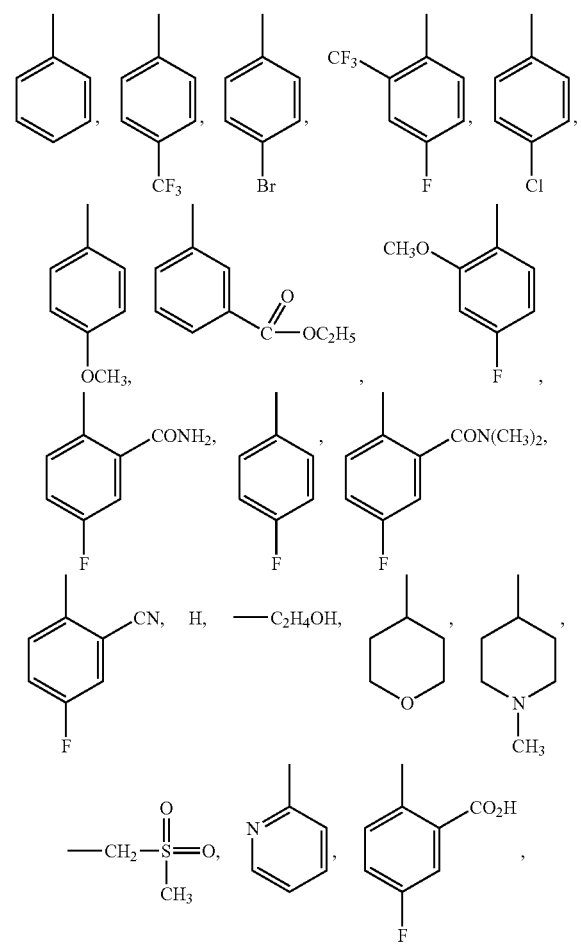

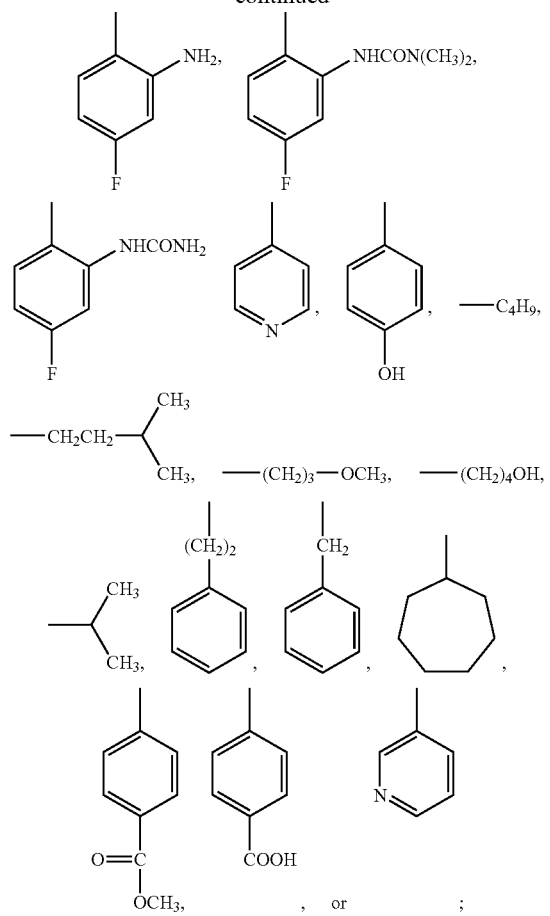
—$Z_a$-Z is
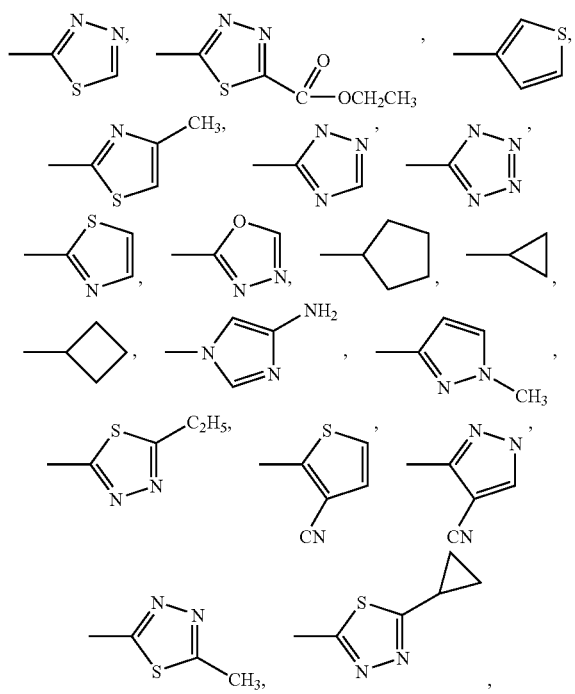
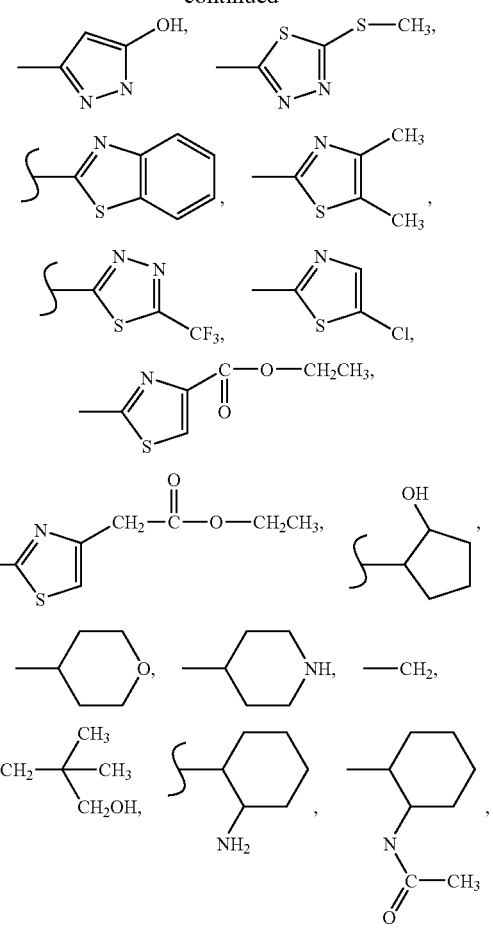
-$M_a$M is $CH_3$,
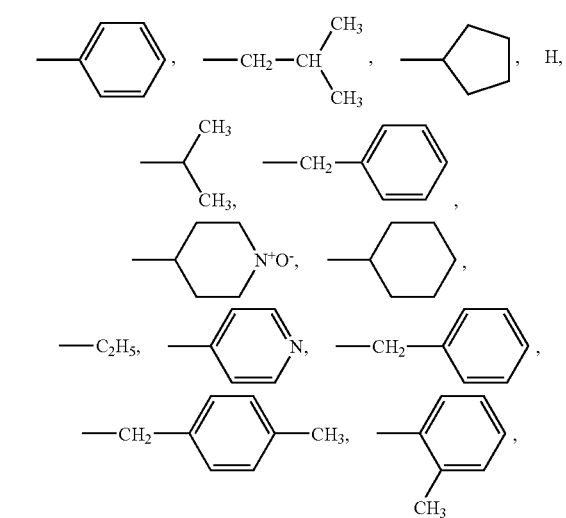

-continued

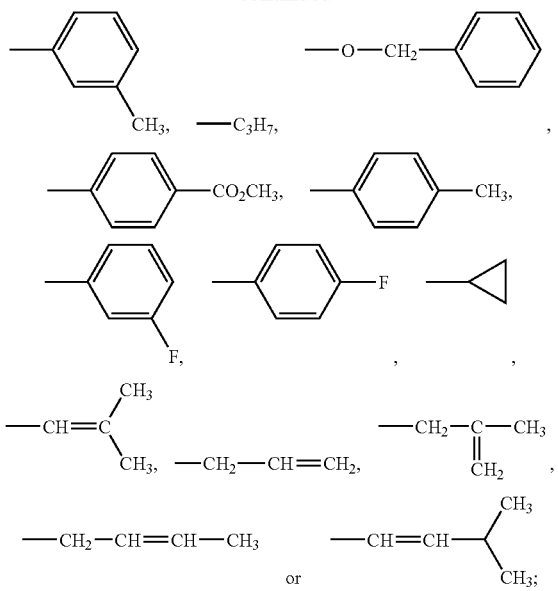

Q is H or CH₃; or

Q and R₆ together with the carbons to which they are attached can be combined to form

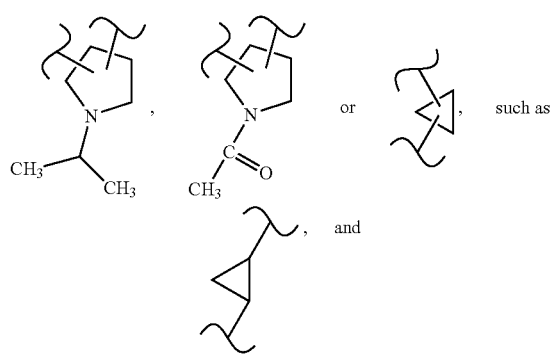

Q and M-M$_a$ together with the carbons to which they are attached can be combined to form

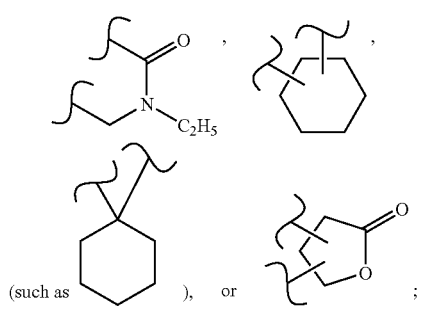

R₄ is H or CH₃;
R₆ is CH₃, C₂H₅, C₃H₇, i-C₃H₇, or H or is combined with Q as described above;
R₇ is CH₃, C₂H₅, C₃H₇, i-C₃H₇, C₆H₅, —CH₂C₆H₅,

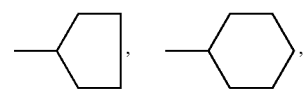

—CH₂OC(=O)CH₃, —CH₂OH, or H.

Most preferred are compounds of the structure

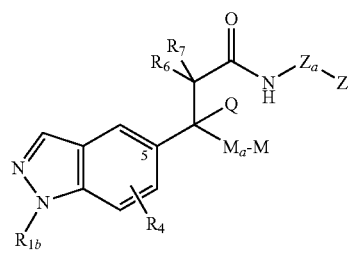

where $R_{1b}$ is p-F—C₆H₄—;
R₄ is H or CH₃;
R₆ is H or CH₃;
R₇ is H or CH₃;
Q is H;
M is C₆H₅;
M$_a$ is a bond;
Z is

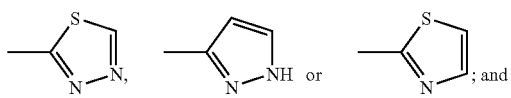

Z$_a$ is a bond, or a pharmaceutically acceptable salt thereof.

The following compounds represent preferred embodiments of the invention

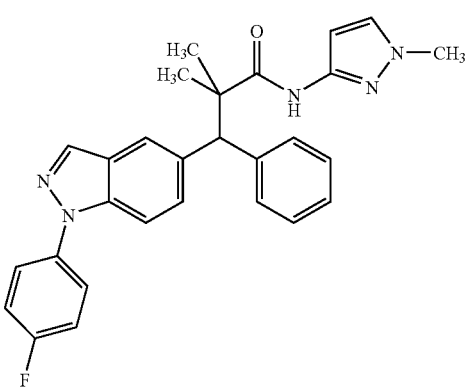

and

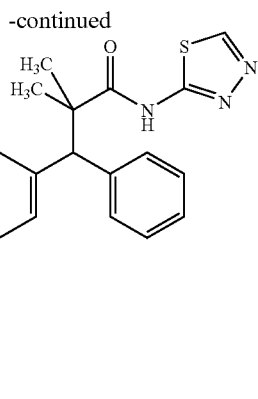

or a pharmaceutically acceptable salt thereof.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, metabolic disease, inflammatory disease, autoimmune disease, and neoplastic disease, as well as other uses as described herein, which including a therapeutically effective amount (depending upon use) of a compound of formula (I) of the invention and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, immune disease, metabolic disease (diabetes and/or obesity), and neoplastic disease. A disease associated with the expression product of a gene whose transcription is stimulated or repressed by glucocorticoid receptors, or a disease associated with AP-1- and/or NF-κB-induced transcription, or a disease associated with AP-1 and/or NF-κB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κβ (particularly AP-1), such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes (including Type II diabetes), obesity, glaucoma, muscle loss, facial swelling, personality changes, hypertension, obesity, depression, and AIDS, the condition of wound healing, primary or secondary andrenocortical insufficiency, and Addison's disease.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger et al., *Science*, 228:740-742 (1985), and in Weinberger, et al., *Nature*, 318:670-672 (1986); rat glucocorticoid receptor as disclosed in Miesfeld, R., *Nature*, 312:779-781 (1985); mouse glucocorticoid receptor as disclosed in Danielson, M. et al., *EMBO J.*, 5:2513 (1986); sheep glucocorticoid receptor as disclosed in Yang, K. et al., *J. Mol. Endocrinol.*, 8:173-180 (1992); marmoset glucocorticoid receptor as disclosed in Brandon, D. D. et al., *J. Mol. Endocrinol.*, 7:89-96 (1991); and human GR-beta as disclosed in Hollenberg, S. M. et al., *Nature*, 318:635 (1985); Bamberger, C. M. et al., *J. Clin. Invest.*, 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I diabetes, juvenile diabetes, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis; eczema, seborrhea, pulmonary inflammation, eye uveitis, hepatitis, Graves' disease, Hashimoto's thyroiditis, autoimmune thyroiditis, Behcet's or Sjorgren's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (depigmentation of the skin), alopecia areata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hayfever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, chronic obstructive pulmonary disease, solid organ transplant rejection and sepsis.

Accordingly, one embodiment of the present invention is a method of treating a disease or disorder selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, which includes the step of administering to a patient in need of treatment, a therapeutically effective amount of a compound as defined in Claim 1.

Metabolic diseases to be treated in accordance with the method of the invention can include Type II diabetes and obesity. Type I diabetes and juvenile diabetes may also be considered as metabolic diseases to be treated in accordance with the method of the invention.

In a preferred embodiment of the invention, the disease to be treated is an inflammatory or immune associated disease or disorder as defined hereinbefore.

In a preferable embodiment the disease or disorder is an inflammatory or autoimmune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis; eczema, seborrhoea, pulmonary inflammation, eye uveitis, hepatitis, Graves' disease, Hashimoto's thyroiditis, autoimmune thyroiditis, Behcet's or Sjorgren's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia areata, autoimmune alopecia, autoimmune hypopituitarism, Guillain-Barre syndrome, and alveolitis; contact hypersensitivity, delayed-type hypersensitivity, contact dermatitis, uticaria, skin allergies, respiratory allergies, hayfever, allergic rhinitis and gluten-sensitive enteropathy, osteoarthritis, acute pancreatitis, chronic pancreatitis, acute respiratory distress syndrome, Sezary's syndrome, restenosis, stenosis and atherosclerosis, congenital adrenal hyperplasia, nonsuppurative thyroiditis, hypercalcemia associated with cancer, juvenile rheumatoid arthritis, Ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetitformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

In an even more preferable embodiment, the disease or disorder is selected from transplant rejection, rheumatoid arthritis, psoriatic arthritis, multiple sclerosis, asthma, inflammatory bowel disease, systemic lupus, erythematosis, and psoriasis.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

In still another embodiment, pharmaceutical combinations are contemplated comprising a compound as defined in Claim 1, an enantiomer, diastereomer, or tautomer thereof, or a prodrug ester thereof, or a pharmaceutically-acceptable salt thereof, and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid-lowering agent is an MTP inhibitor, an HMG CoA reductase inhibitor, a squalene synthetase inhibitor, a fabric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

More preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, NN-2344, L895645, YM-440, R-119702, AJ9677, repaglinide, nateglinide, KAD1129, AR-H039242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid-lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2, 2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment are meant to be combined with any and all other elements from any of the embodiments to describe additional embodiments.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Additionally, the various steps in the synthesis may be performed in an alternate sequence in order to give the desired compound or compounds. Examples of compounds of the present invention prepared by methods described in the general schemes are given in the preparations and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

As shown in Scheme 1, intermediates on the path to compounds of Formula I may be synthesized from benzannulated heterocyclic aldehydes II which are reported in the literature or synthesized by one skilled in the art. Grignard or aryl (alkyl)lithium reagents add to give alcohol III. This compound may be reacted with silyl ketene acetals in the presence of TiCl$_4$ to yield the alkylated product IV, and finally hydrolyzed (e.g., NaOH, DMSO, MeOH) to acid V. Alternatively, compound III can be oxidized to the ketone/aldehyde VII using a suitable oxidant (e.g., Dess-Martin periodinane) and then reacted with various enolates (the aldol reaction) or with silyl ketene acetals in the presence of a Lewis acid such as BF$_3$OEt$_2$ (the Mukaiyama aldol reaction) to give compound VIII. Compound VIII may be readily deoxygenated using trifluoroacetic acid in the presence of triethylsilane (or via a Barton deoxygenation: *Org. Lett.*, 4:39-42 (2002)) to give compound IV or hydrolyzed to form compound IX. By starting with benzannulated heterocyclic ester VI, one can use the Weinreb amidation procedure (Me$_3$Al, MeONHMe) followed by organometallic addition to also synthesize intermediate VII. In the cases where M-M$_a$- and Q are the same (or form a symmetrical ring), a parallel route can be employed by using two equivalents of the M-M$_a$-organometallic reagent to form alcohol X (also accessible from VII) that undergoes TiCl$_4$-mediated alkylation with silyl ketene acetals followed by hydrolysis as before to yield acid XII where Q and M-M$_a$ may be the same or different.

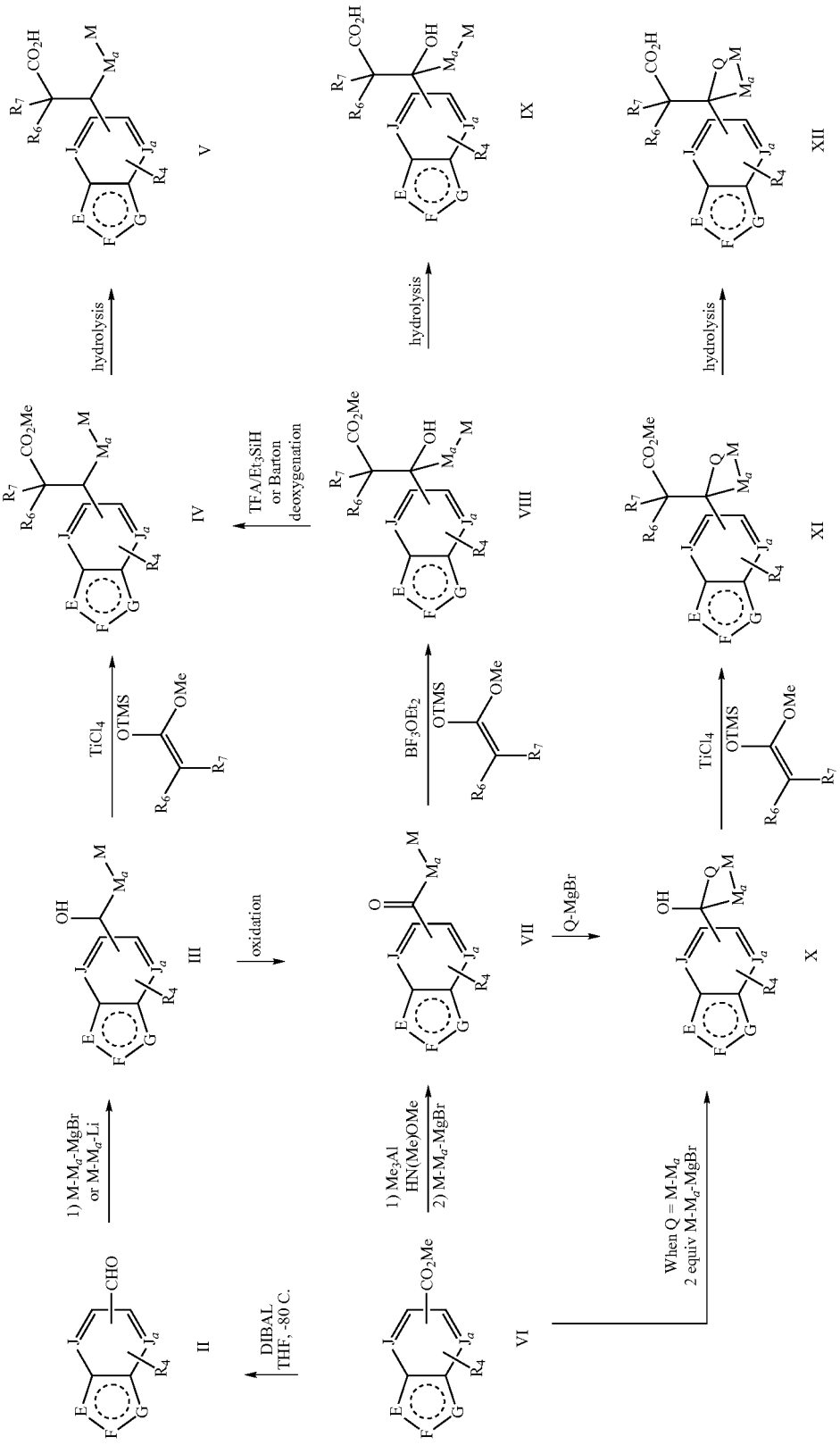

Many of the heterocyclic substituents of intermediates in Scheme 1 can be synthesized by one skilled in the art of organic synthesis. Other functional group manipulations that complement those in Scheme 1 are shown in Schemes 2 and 3.

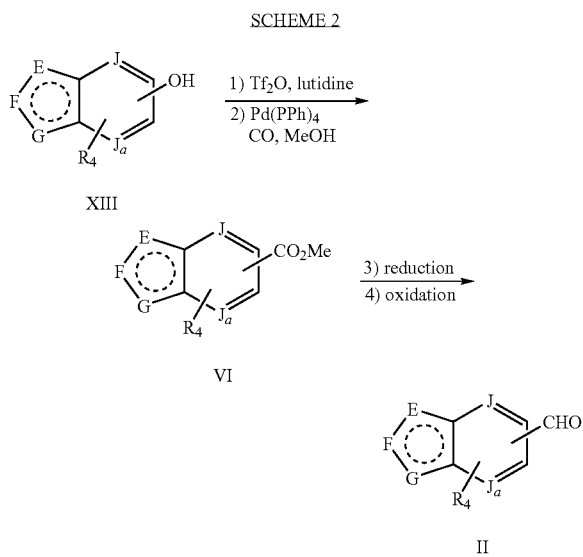

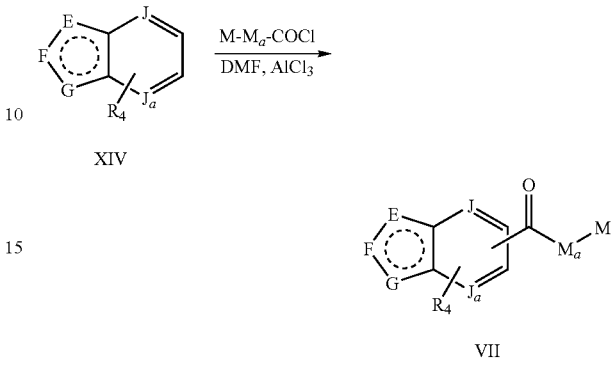

Scheme 2 shows how phenolic intermediates such as XIII can be converted to a triflate followed by palladium-mediated carbonylation to form ester VI. The ester functionality can be transposed into an aldehyde (compound II) or other groups shown in Scheme 1.

Scheme 3 shows how an unsubstituted heterocycle XIV can be functionalized to intermediate VII using a modification of the classical Friedel-Crafts acylation (see *J. Med. Chem.*, 26:806 (1983)).

A more specific implementation of the synthetic scheme outlined in Scheme 1 is shown in Scheme 4 using indazoles as a representative heterocycle. Starting aniline XV is converted to (1H-indazol-5-yl)methanol XVI-A using standard literature procedures (Sun et al., *J. Org. Chem.*, 62:5627-5629 (1997)). Functionalization of the indazole N-1 nitrogen (or N-2 nitrogen, not shown) via a Buchwald arylation procedure (*J. Org. Chem.*, 69:5578-5587 (2004); *J. Am. Chem. Soc.*, 123:7727-7729 (2001)) can be effected at multiple points during the synthetic scheme to ultimately provide compounds of Formula I. Alternatively, alkylation of the indazole N-1 nitrogen (or N-2 nitrogen) using a base and an $R_1$ alkylator (herein defined as a diverse electrophilic reagent that may undergo an SN2 reaction, e.g., a non-tertiary alkyl iodide or bromide, epoxide, etc.) in a suitable solvent may also provide intermediates in route to compounds of Formula I.

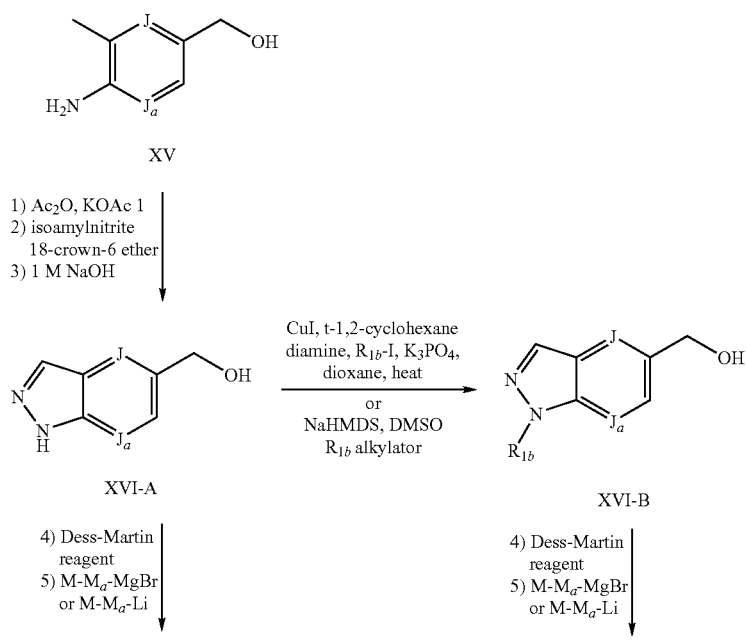

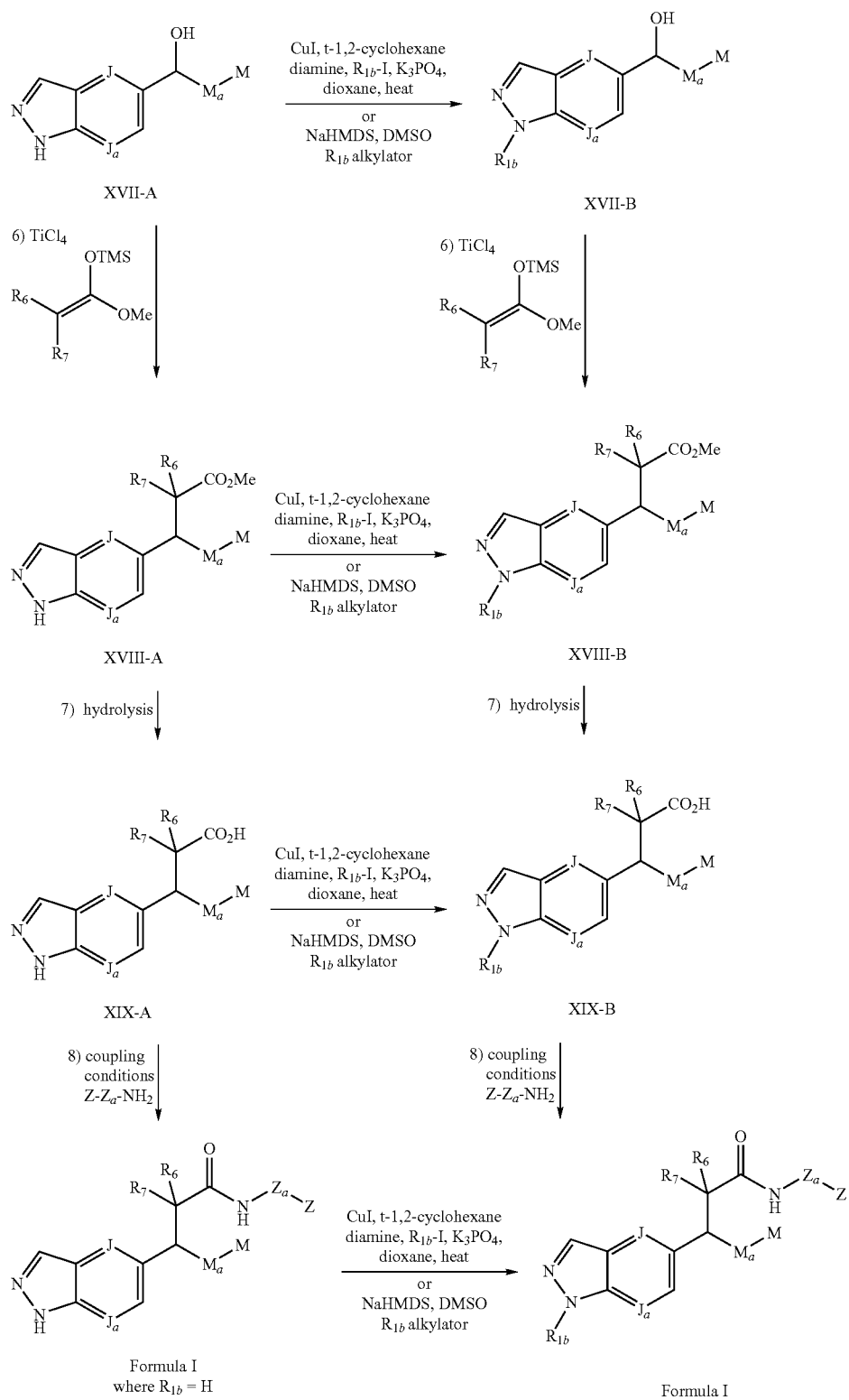

Thus, compound XVI-A may be functionalized using a Buchwald arylation procedure or alkylated to give compound XVI-B. Oxidation of XVI-A/B using a suitable oxidant (e.g., Dess-Martin reagent) followed by addition of a Grignard reagent or aryl/alkyllithium reagent provides XVII-A/B, respectively. XVII-A can be converted at this stage to XVII-B using the Buchwald arylation procedure or alkylated and XVII-A/B can be reacted with silyl ketene acetals in the presence of $TiCl_4$ to yield products XVIII-A/B. Again, XVIII-A may be optionally converted to XVIII-B at this point using the Buchwald procedure or alkylation. XVIII-A/B can then be hydrolyzed to XIX-A/B which in turn are converted to amides of Formula I using coupling conditions described below in Scheme 8. Compound XIX-A can be converted to compounds of Formula I (where $R_1$=H) which in turn can be further functionalized using the Buchwald arylation procedure or alkylation.

A complementary route to Scheme 1 for making precursors to Formula I is shown in Scheme 5. Ketone/aldehyde VII can be homologated using the Homer-Wadsworth-Emmons procedure to make $\alpha,\beta$-unsaturated ester XX which can be hydrogenated under palladium catalysis (to form XXI) and then hydrolyzed to form compound XXII (same as compound V, where $R_6$, $R_7$=H.). Alternatively, intermediate XX can be treated with a cuprate reagent containing the Q diversity to give XXIII and then hydrolyzed to XXIV. Alkylation of compound XXIII using LDA followed by an $R_6$ electrophile (such as an alkyl iodide) provides XXVI after hydrolysis. Intermediate XXV can be alkylated again using an $R_7$ electrophile to provide acid XII after hydrolysis.

Another means of making intermediates on route to Formula I compounds is shown in Scheme 6. Metal-halogen exchange of compound XXVII using an alkyllithium reagent followed by treatment with a ketone or aldehyde provides compound X which can be transposed to compound XII as previously described in Scheme 1.

SCHEME 6

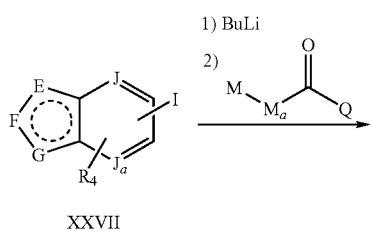

XXVII

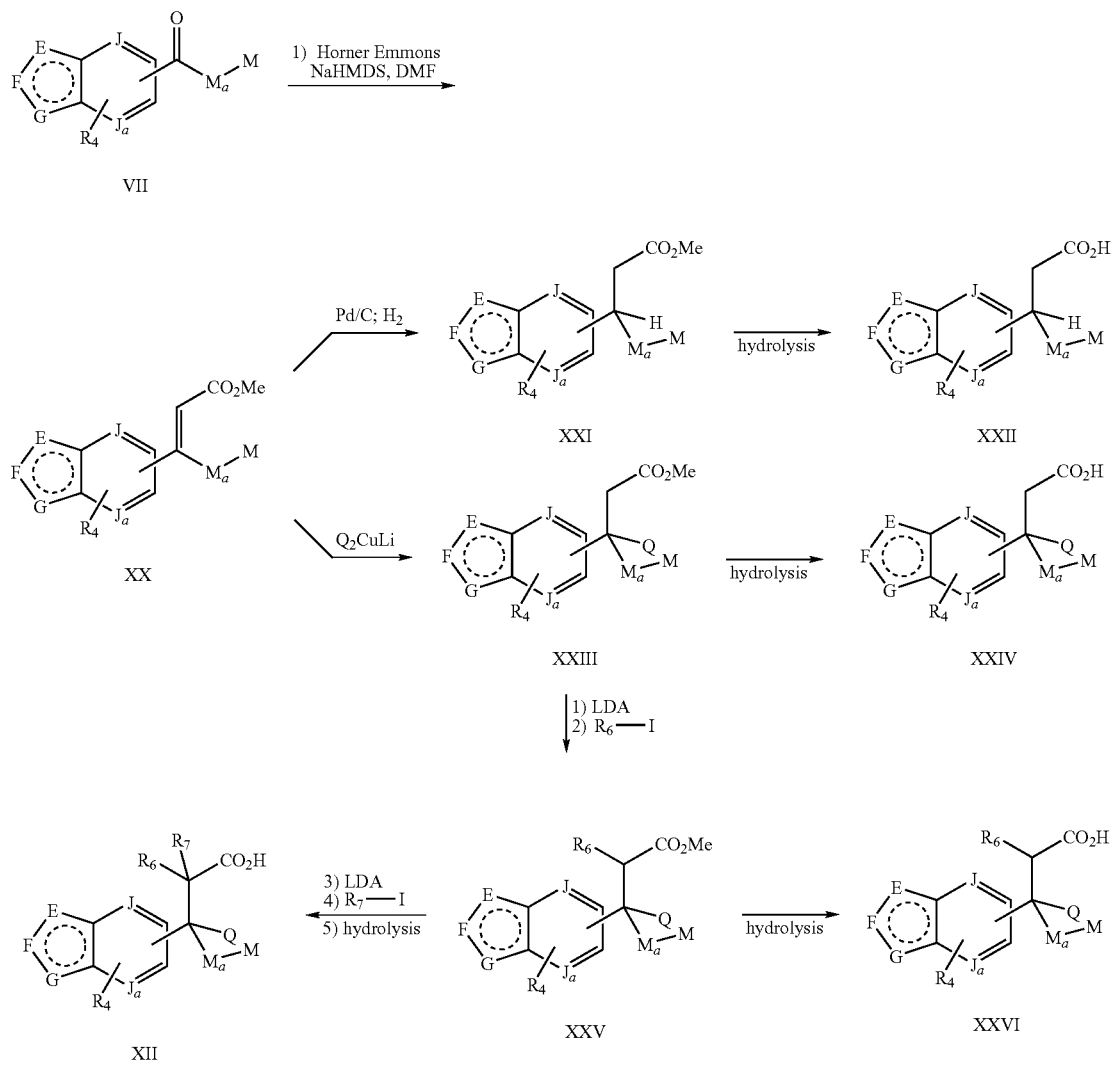

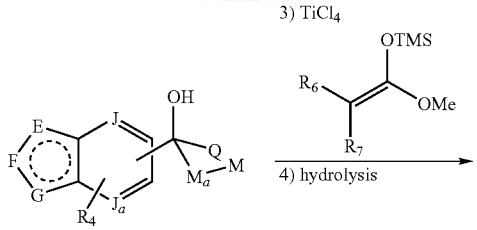

X

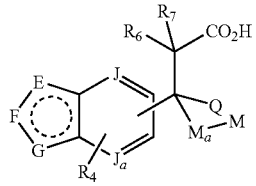

XII

Scheme 7 illustrates a synthetic method to make a precursor of Formula I wherein Q and $R_6$ form a ring (cyclopropyl shown here). Treatment of compound VII with MeMgBr yields a tertiary alcohol which can be eliminated in hot glacial acetic acid to olefin XXVIII. Rhodium-carbenoid addition to this olefin provides a cyclopropyl ester which can be hydrolyzed to give acid XXIX.

SCHEME 7

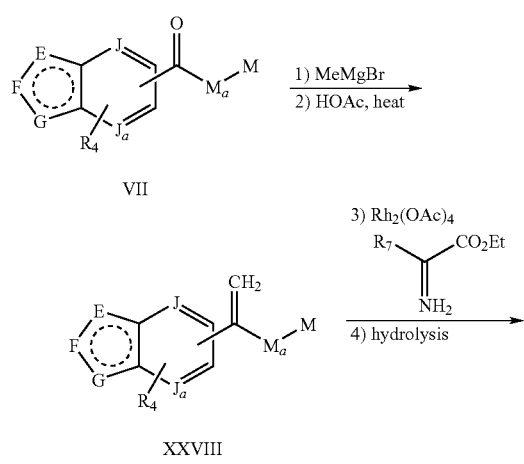

VII

XXVIII

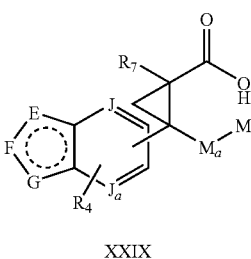

XXIX

The synthetic Schemes 1 to 7 above detail synthetic sequences that make carboxylic acids-the penultimate precursor to compounds of Formula I. The final step involves converting the carboxylic acid to an amide as shown in Scheme 8 for which there are many methods in the literature (Humphrey, *Chem. Rev.*, 97:2243-2266 (1997)). Preferred methods in this invention involve activation of the acid to an intermediate acid fluoride using cyanuric fluoride followed by heating with an appropriate amine nucleophile. Another preferred method is conversion of the acid to an intermediate "active" ester (such as an HOBt or an HOAt ester) using the carbodiimide EDC, HOBt (or HOAt), and Et$_3$N in a suitable solvent such as DMF or NMP followed by heating with the amine nucleophile.

SCHEME 8

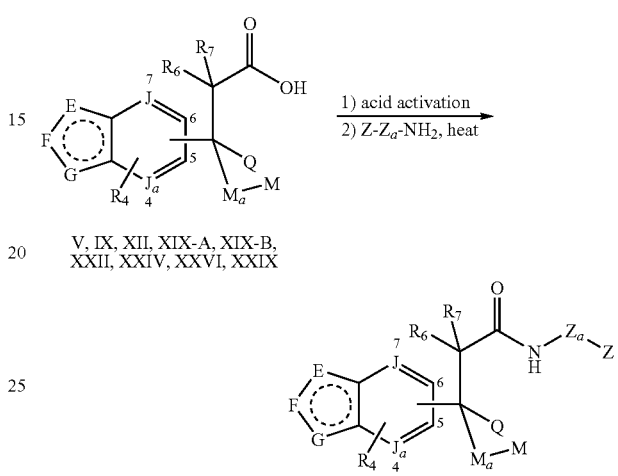

V, IX, XII, XIX-A, XIX-B, XXII, XXIV, XXVI, XXIX

Formula I

Protecting Groups for the Heterocyclic Core

It should be understood that protecting groups may be utilized as appropriate throughout synthetic Schemes 1 to 8 above. Common protecting groups for amine-containing heterocycles (where E, F, or G in Formula I are nitrogen, e.g., indole, indazole, benzimidazole, etc.) are ureas, sulfonamides, carbamates, and alkyl groups (such as benzyl). The judicious use of protecting groups is known to one skilled in the art and is described in Greene and Wuts, *Protecting Groups in Organic Synthesis*, 3rd Ed. (1999).

DEFINITIONS

The following are definitions of terms used in this specification and appended claims. The initial definition provided for a group or term herein applies to that group or term throughout the specification and claims, individually or as part of another group, unless otherwise indicated.

The term "alkyl" alone or as part of another group refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl.

"Alkyl" includes "unsubstituted" and "substituted alkyl" where the alkyl may be substituted with any of the substituents for substituted alkyl set out below.

The term "substituted alkyl" refers to an alkyl group as defined above having one, two, or three substituents independently selected from the group consisting of halo (e.g., trifluoromethyl), alkenyl, substituted alkenyl, alkynyl, nitro, cyano, oxo (=O), $OR_a$, $SR_a$, (=S), $-NR_aR_b$, $-N(alkyl)_3^1$, $-NR_aSO_2$, $-NR_aSO_2R_c$, $-SO_2R_c$, $-SO_2NR_aR_b$, $-SO_2NR_aC(=O)R_b$, $SO_3H$, $-PO(OH)_2$, $-C(=O)R_a$, $-CO_2R_a$, $-C(=O)NR_aR_b$, $-C(=O)(C_{1-4}alkylene)NR_aR_b$, $-C(=O)NR_a(SO_2)R_b$, $-CO_2(C_{1-4}alkylene)NR_aR_b$, $-CH_2OC(=O)alkyl$, $-NR_aC(=O)R_b$, $-NR_aCO_2R_b$, $-NR_a(C_{1-4}alkylene)CO_2 R_b$, =N-OH, =N-O-alkyl, aryl, cycloalkyl, heterocyclo, and/or heteroaryl, wherein $R_a$ and $R_b$ are the same or different and are independently selected from hydrogen, alkyl, alkenyl, $CO_2H$, $CO_2(alkyl)$, $C_{3-7}cycloalkyl$, phenyl, benzyl, phenylethyl, naphthyl, a four to seven membered heterocyclo, or a five to six membered heteroaryl, or when attached to the same nitrogen atom may join to form a heterocyclo or heteroaryl, and $R_c$ is selected from same groups as $R_a$ and $R_b$ but is not hydrogen. Each group $R_a$ and $R_b$ when other than hydrogen, and each $R_c$ group optionally has up to three further substituents attached at any available carbon or nitrogen atom of $R_a$, $R_b$, and/or $R_c$, said substituent(s) being the same or different and are independently selected from the group consisting of $(C_{1-6})alkyl$, $(C_{2-6})alkenyl$, hydroxy, halogen, cyano, nitro, $CF_3$, $O(C_{1-6}alkyl)$, $OCF_3$, $C(=O)H$, $C(=O)(C_{1-6}alkyl)$, $CO_2H$, $CO_2(C_{1-6}alkyl)$, $NHCO_2(C_{1-6}alkyl)$, $-S(C_{1-6}alkyl)$, $-NH_2$, $NH(C_{1-6}alkyl)$, $N(C_{1-6}alkyl)_2$, $N(CH_3)_3^+$, $SO_2(C_{1-6}alkyl)$, $-NHC(=O)alkyl$, $C(=O)(C_{1-4}alkylene)NH_2$, $C(=O)(C_{1-4}alkylene)NH(alkyl)$, $C(=O)(C_{1-4}alkylene)N(C_{1-4}alkyl)_2$, $C_{3-7}cycloalkyl$, phenyl, benzyl, phenylethyl, phenyloxy, benzyloxy, naphthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below and/or as defined for substituted alkyl.

One skilled in the field will understand that, when the designation "$CO_2$" is used herein, this is intended to refer to the group

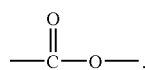

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$) alkyl includes a substituted lower alkyl having at least one aryl substituent and also includes an aryl directly bonded to another group, i.e., aryl($C_0$)alkyl.

The term "alkenyl" (which includes unsubstituted or substituted alkenyl) alone or as part of another group refers to straight or branched chain hydrocarbon groups having 2 to 12 carbon atoms and at least one double bond. Alkenyl groups of 2 to 6 carbon atoms and having one double bond are most preferred.

The term "alkynyl" (which includes unsubstituted or substituted alkynyl) alone or as part of another group refers to straight or branched chain hydrocarbon groups having 2 to 12 carbon atoms and at least one triple bond. Alkynyl groups of 2 to 6 carbon atoms and having one triple bond are most preferred.

The term "alkylene" (which includes unsubstituted or substituted alkylene) alone or as part of another group refers to bivalent straight or branched chain hydrocarbon groups having 1 to 12 carbon atoms, preferably 1 to 8 carbon atoms, e.g., $\{-CH_2-\}_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" (which includes unsubstituted and "substituted heteroalkylene") alone or as part of another group is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —$SO_2$—, —NH—, and —$NHSO_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—$(CH_2)_{1-5}$NH—$CH_2$—, —O—$(CH_2)_{1-5}$S(=O)—$CH_2$—, —$NHSO_2$—$CH_2$—, —$CH_2$—NH—, and so forth. Preferably, a heteroalkylene does not have two adjacent atoms simultaneously selected from —O— and —S—. When a subscript is used with the term heteroalkylene, e.g., as in $C_{2-3}$heteroalkylene, the subscript refers to the number of carbon atoms in the group in addition to heteroatoms. Thus, for example, a $C_{1-2}$heteroalkylene may include groups such as —NH—$CH_2$—, —$CH_2$—NH—$CH_2$—, —$CH_2$—$CH_2$—NH—, —S—$CH_2$—, —$CH_2$—S—$CH_2$—, —O—$CH_2$—NH—$CH_2$—, $CH_2$—O—$CH_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or $A_1$-Q-$A_2$-$R_h$, wherein $A_1$ is a bond, $C_{1-2}$alkylene, or $C_{2-3}$alkenylene; Q is a bond, —C(=O)—, —C(=O)$NR_d$—, —C(=S)$NR_d$—, —$SO_2$—, —$SO_2NR_d$—, —$CO_2$—, or —$NR_d CO_2$—; $A_2$ is a bond, $C_{1-3}$alkylene, $C_{2-3}$alkenylene, —$C_{1-4}$alkylene-$NR_d$—, —$C_{1-4}$alkylene-$NR_dC(=O)$—, —$C_{1-4}$alkylene-S—, —$C_{1-4}$alkylene-$SO_2$—, or —$C_{1-4}$alkylene-O—, wherein said $A_2$ alkylene groups are branched or straight chain and optionally substituted as defined herein for substituted alkylene; $R_h$ is hydrogen, alkyl, substituted alkyl, alkenyl, substituted alkenyl, aryl, heteroaryl, heterocyclo, or cycloalkyl; and $R_d$ is selected from hydrogen, alkyl, and substituted alkyl, as defined herein, provided, however, that for a substituted heteroalkylene $R_h$ is not hydrogen when $A_1$, Q and $A_2$ are each bonds. When $R_h$ is aryl, heteroaryl, cycloalkyl, or heterocyclo, these rings are, in turn, optionally substituted with one to three groups as defined below in the definitions for these terms.

The term "alkoxy" refers to an unsubstituted alkyl or substituted alkyl group as defined above having one or two oxygen atoms (—O—) in the alkyl chain. For example, the term "alkoxy" includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an unsubstituted alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an unsubstituted alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —$CH_2$—$NH_2$, —NH—$CH_3$, —$(CH_2)_2$—$NH_2$, —NH—$CH_2$—$CH_3$, —$CH_2$—$NH_2$—$CH_3$, and —N—$(CH_3)_2$. A lower aminoalkyl comprises an aminoalkyl having one to four carbon atoms.

"Amino" refers to the group $NH_2$.

The term "substituted amino" alone or as part of another group refers to the group —$NR_aR_b$ (or other substituent groups other than $R_a$ or $R_b$ linked to an N atom) wherein the groups $R_a$ and $R_b$ or other substituent groups are defined above in the definition of substituted alkyl groups.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

The term "carbonyl" is intended to designate the group —C(O)—.

It should be understood that the selections for alkoxy, thioalkyl, and aminoalkyl will be made by one skilled in the field to provide stable compounds. Thus, for example, in compounds of formula I, when $R_5$, $R_6$, $R_7$ or $R_8$ is attached to a nitrogen atom (N*) of ring B and is selected from an alkoxy or alkylthio group, the alkoxy and alkylthio groups will have at least one carbon atom bonded directly to ring B (at N*), with the oxygen or sulfur atoms being at least one atom away from said nitrogen atom.

The term "acyl" alone or as part of another group refers to a carbonyl group linked to an organic radical, more particularly, the group C(=O)$R_e$, as well as the bivalent groups —C(=O)— or —C(=O)$R_e$—, which are linked to organic radicals or a ring in compounds of formula I. The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of formula I, when it is recited that $R_1$ to $R_8$ can be "acyl," this is intended to encompass a selection for $R_1$ to $R_8$ of —C(=O)— and also the groups —C(=O)$R_e$— or —$R_e$C(=O)—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" alone or as part of another group refers to a carboxy group

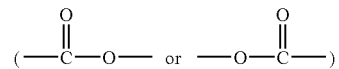

linked to an organic radical ($CO_2R_e$), as well as the bivalent groups —$CO_2$—, —$CO_2R_e$— which are linked to organic radicals in compounds of formula I, wherein $R_e$ is as defined above for acyl. The organic radical to which the carboxy group is attached may be monovalent (e.g., —$CO_2$-alkyl or —OC(=O)alkyl), or bivalent (e.g., —$CO_2$-alkylene, —OC(=O)alkylene, etc.). Accordingly, "alkoxycarbonyl," is intended to encompass the groups —$CO_2R_e$— or —$R_eCO_2$—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" alone or as part of another group refers to the group C(=O)$NR_aR_b$ (or other R groups other than $R_a$ or $R_b$ linked to an N atom), wherein the groups $R_a$ and $R_b$ are defined as recited above in the definition for substituted alkyl groups.

The term "sulfonyl" alone or as part of another group refers to a sulphoxide group linked to an organic radical in compounds of formula I, more particularly, the monovalent group $S(O)_{1-2}$—$R_e$, or the bivalent group —$S(O)_{1-2}$— linked to organic radicals in compounds of formula I. Accordingly, in compounds of formula I, "sulfonyl," is intended to encompass —S(=O)— or —$SO_2$— as well as the groups —S(=O)$R_e$—, —$R_eS(=O)$—, —$SO_2R_e$—, or —$R_eSO_2$—, wherein in this instance, the group $R_e$ will be selected from those recited above for acyl and alkoxycarbonyl groups.

The term "sulfonamidyl" alone or as part of another group refers to the group —$S(O)_2NR_aR_b$ (or other R groups other than $R_a$ or $R_b$ linked to an N atom), wherein $R_a$ and $R_b$ are as defined above for substituted alkyl groups. Additionally, the sulfonamidyl group may be bivalent, in which case one of the groups $R_a$ and $R_b$ will be a bond. Thus, in compounds of formula I, sulfonamidyl is intended to mean the group —$S(O)_2NR_a$—.

The term "cycloalkyl" alone or as part of another group (which includes unsubstituted cycloalkyl and substituted cycloalkyl) refers to fully saturated and partially unsaturated hydrocarbon rings of 3 to 15, preferably 3 to 10 carbon atoms. Accordingly, the term "cycloalkyl" is intended to include a cycloalkenyl (e.g., cyclohexenyl) ring. The term "cycloalkyl" includes monocyclic, bicyclic and tricyclic rings, such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$—$SO_2NR_aR_b$, —$SO_2NR_aC(=O)R_b$, $SO_3H$, —$PO(OH)_2$, —C(=O)$R_a$, —$CO_2R_a$, —C(=O)$NR_aR_b$, —C(=O)($C_{1-4}$alkylene)$NR_aR_b$, —C(=O)$NR_a(SO_2)R_b$, —$CO_2(C_{1-4}$alkylene)$NR_aR_b$, —$NR_aC(=O)R_b$, —$NR_aCO_2R_b$, —$NR_a(C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, cycloalkyl, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of (C$_{1-4}$alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)$_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems,

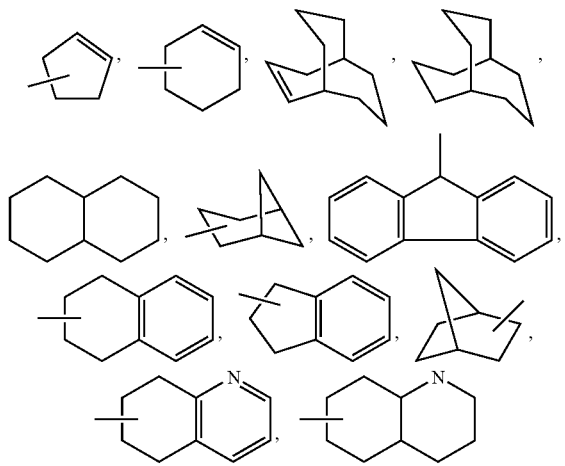

and the like, which optionally may be substituted at any available atoms of the ring(s). Preferred cycloalkyl groups include cyclopropyl, cyclobutyl, cyclopentyl, cyclohexyl,

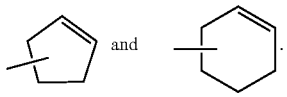

The term "halo" or "halogen" alone or as part of another group refers to chloro, bromo, fluoro and iodo.

The term "haloalkyl" alone or as part of another group means a substituted alkyl having one or more halo substituents. For example, "haloalkyl" includes mono, bi, and trifluoromethyl.

The term "haloalkoxy" alone or as part of another group means an alkoxy group having one or more halo substituents. For example, "haloalkoxy" includes OCF$_3$.

The term "aryl" alone or as part of another group (includes unsubstituted aryl and substituted aryl) refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$ —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$ alkylene)NR$_a$R$_b$, —C(=O)NR$_a$(SO$_2$)R$_b$, —NHC(=O)NR$_a$R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, aryl, cycloalkyl, heterocyclo, and/or heteroaryl, wherein R$_a$, R$_b$ and R$_c$ are as defined above for substituted alkyl groups, and are also in turn optionally substituted as recited above, or any of the substituents for alkyl set out hereinbefore. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to four, preferably one or two of (C$_{1-4}$)alkyl, (C$_{2-4}$)alkenyl, halogen, hydroxy, cyano, nitro, CF$_3$, O(C$_{1-4}$alkyl), OCF$_3$, C(=O)H, C(=O)(C$_{1-4}$alkyl), CO$_2$H, CO$_2$(C$_{1-4}$alkyl), NHCO$_2$(C$_{1-4}$alkyl), —S(C$_{1-4}$alkyl), —NH$_2$, NH(C$_{1-4}$alkyl), N(C$_{1-4}$alkyl)$_2$, N(C$_{1-4}$alkyl)$_3$$^+$, C(=O)NH$_2$, SO$_2$(C$_{1-4}$alkyl), C(=O)(C$_{1-4}$alkylene)NH$_2$, C(=O)(C$_{1-4}$alkylene)NH(alkyl), and/or C(=O)(C$_{1-4}$alkylene)N(C$_{1-4}$alkyl)$_2$.

Thus, examples of aryl groups include:

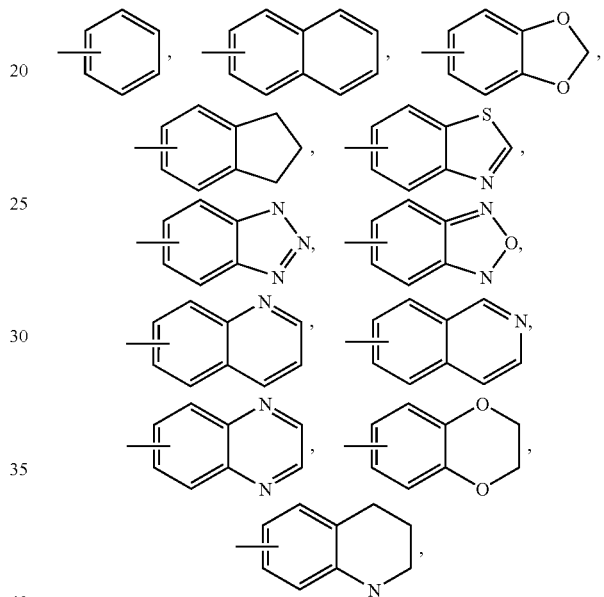

and the like, which optionally may be substituted at any available carbon or nitrogen atom. A preferred aryl group is optionally-substituted phenyl.

The terms "heterocyclo" or "heterocyclic" or "cycloheteroalkyl" alone or as part of another group refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), OR$_a$, SR$_a$, (=S), —NR$_a$R$_b$, —N(alkyl)$_3$$^+$, —NR$_a$SO$_2$, —NR$_a$SO$_2$R$_c$, —SO$_2$R$_c$ —SO$_2$NR$_a$R$_b$, —SO$_2$NR$_a$C(=O)

$R_b$, $SO_3H$, —$PO(OH)_2$, —$C(=O)R_a$, —$CO_2R_a$, —$C(=O)NR_aR_b$, —$C(=O)(C_{1-4}\text{alkylene})NR_aR_b$, —$C(=O)NR_a(SO_2)R_b$, —$CO_2(C_{1-4}\text{alkylene})NR_aR_b$, —$NR_aC(=O)R_b$, —$NR_aCO_2R_b$, —$NR_a(C_{1-4}\text{alkylene})CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of ($C_{1-4}$alkyl, ($C_{2-4}$)alkenyl, halogen, hydroxy, cyano, nitro, $CF_3$, $O(C_{1-4}\text{alkyl})$, $OCF_3$, $C(=O)H$, $C(=O)(C_{1-4}\text{alkyl})$, $CO_2H$, $CO_2(C_{1-4}\text{alkyl})$, $NHCO_2(C_{1-4}\text{alkyl})$, —$S(C_{1-4}\text{alkyl})$, —$NH_2$, $NH(C_{1-4}\text{alkyl})$, $N(C_{1-4}\text{alkyl})_2$, $N(C_{1-4}\text{alkyl})_3^+$, $SO_2(C_{1-4}\text{alkyl})$, $C(=O)(C_{1-4}\text{alkylene})NH_2$, $C(=O)(C_{1-4}\text{alkylene})NH(\text{alkyl})$, and/or $C(=O)(C_{1-4}\text{alkylene})N(C_{1-4}\text{alkyl})_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

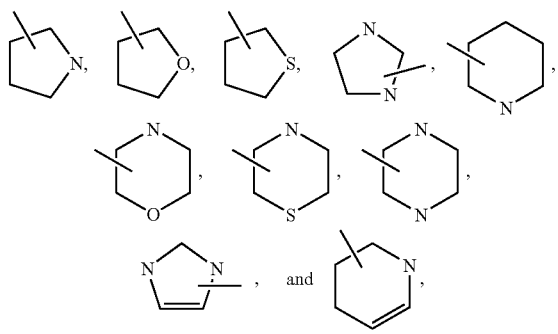

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(\text{alkyl})_3^+$, —$NR_aSO_2$, —$NR_aSO_2R_c$, —$SO_2R_c$ —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}\text{alkylene})NR_aR_b$, —$C(=O)NR_a(SO_2)R_b$, —$CO_2(C_{1-4}\text{alkylene})NR_aR_b$, oxo(=O), —$NR_aC(=O)R_b$, —$NR_aCO_2R_b$, —$NR_a(C_{1-4}\text{alkylene})CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of ($C_{1-4}$alkyl, ($C_{2-4}$)alkenyl, halogen, hydroxy, cyano, nitro, $CF_3$, $O(C_{1-4}\text{alkyl})$, $OCF_3$, $C(=O)H$, $C(=O)(C_{1-4}\text{alkyl})$, $CO_2H$, $CO_2(C_{1-4}\text{alkyl})$, $NHCO_2(C_{1-4}\text{alkyl})$, —$S(C_{1-4}\text{alkyl})$, —$NH_2$, $NH(C_{1-4}\text{alkyl})$, $N(C_{1-4}\text{alkyl})_2$, $N(C_{1-4}\text{alkyl})_3^+$, $SO_2(C_{1-4}\text{alkyl})$, $C(=O)(C_{1-4}\text{alkylene})NH_2$, $C(=O)(C_{1-4}\text{alkylene})NH(\text{alkyl})$, and/or $C(=O)(C_{1-4}\text{alkylene})N(C_{1-4}\text{alkyl})_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

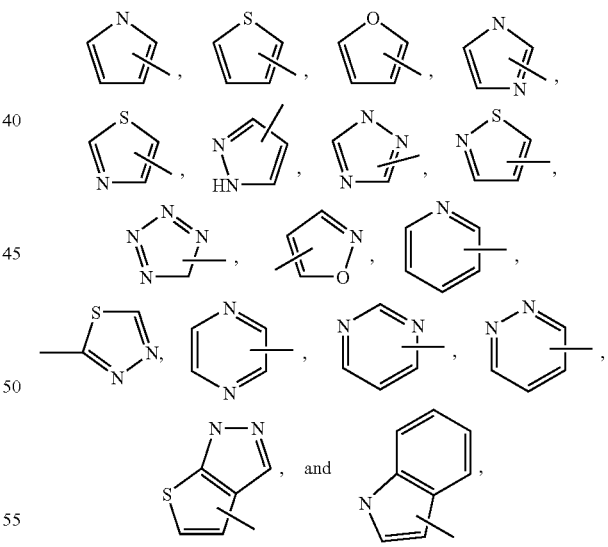

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups:

(1-alkanoyloxy)alkyl such as,

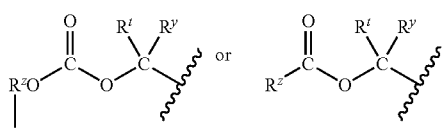

wherein $R^z$, $R^t$ and $R^y$ are H, alkyl, aryl or arylalkyl; however, $R^zO$ cannot be HO.

Examples of such prodrug esters include

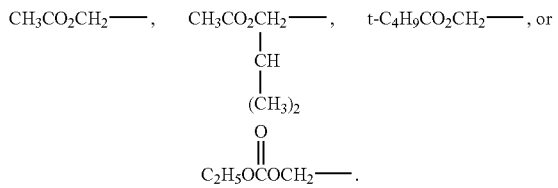

Other examples of suitable prodrug esters include

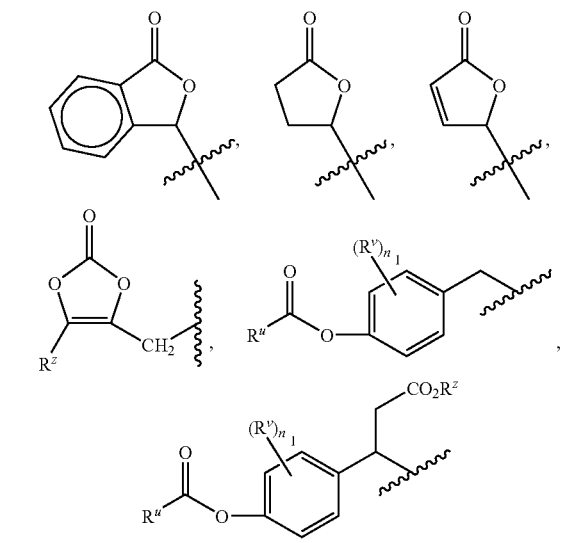

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, 112:309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8:1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g., hydrate) form.

Combinations

Where desired, the compounds of structure I may be used in combination with one or more other types of therapeutic agents such as immunosuppressants, anticancer agents, antiviral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, antiobesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of formula I of the invention include cyclosporins, for example cyclosporin A, mycophenolate, interferon-beta, deoxyspergolin, FK-506 or Ant.-IL-2.

The anti-cancer agents which may be optionally employed in combination with compounds of formula I of the invention include azathiprine, 5-fluorouracil, cyclophosphamide, cisplatin, methotrexate, thiotepa, carboplatin, and the like.

The anti-viral agents which may be optionally employed in combination with compounds of formula I of the invention include abacavir, aciclovir, ganciclovir, zidanocin, vidarabine, and the like.

The anti-inflammatory agents which may be optionally employed in combination with compounds of formula I of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g., CD40Ig and CD8gp39), inhibitors, such as nuclear translocation inhibitors, of NF-kappa B function, such as deoxyspergualin (DSG).

The anti-fungal agents which may be optionally employed in combination with compounds of formula I of the invention include fluconazole, miconazole, amphotericin B, and the like.

The antibiotics which may be optionally employed in combination with compounds of formula I of the invention include penicillin, tetracycline, amoxicillin, ampicillin, erythromycin, doxycycline, vancomycin, minocycline, clindamycin or cefalexin.

The anti-vascular hyperproliferation agents which may be optionally employed with compounds of formula I of the invention include methotrexate, leflunomide, FK506 (tacrolimus, Prograf).

The hypolipidemic agent or lipid-lowering agent or lipid modulating agents which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

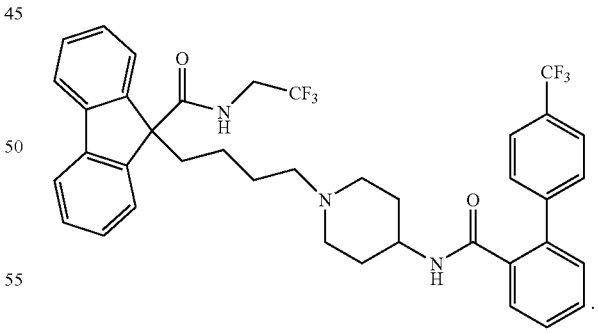

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31(10):1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey and Volante, *J. Am. Chem. Soc.*, 98:1291-1293 (1976), phosphinylphosphonates reported by McClard, R. W. et al., *J. Am. Chem. Soc.*, 109:5544 (1987), and cyclopropanes reported by Capson, T. L., Ph.D., dissertation, Dept. Med. Chem. U. of Utah, Abstract, Table of Contents, pp. 16, 17, 40-43, 48-51, Summary (June, 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, *Drugs of the Future*, 24:9-15 (1999) (Avasimibe); Nicolosi et al., "The ACAT inhibitor, C1-1011 is effective in the prevention and regression of aortic fatty streak area in hamsters", *Atherosclerosis* (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C. et al., "RP 73163: a bioavailable alkylsulfinyl-diphenylimidazole ACAT inhibitor", *Bioorg. Med. Chem. Lett.*, 6(1):47-50 (1996); Krause et al., "ACAT inhibitors: physiologic mechanisms for hypolipidemic and anti-atherosclerotic activities in experimental animals", *Inflammation: Mediators Pathways*, Publisher: CRC, Boca Raton, Fla., Editor(s): Ruffolo, Robert R., Jr., Hollinger, Mannfred A., pp. 173-198 (1995); Sliskovic et al., "ACAT inhibitors: potential anti-atherosclerotic agents", *Curr. Med. Chem.*, 1(3):204-225 (1994); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", *Chemtracts: Org. Chem.*, 8(6):359-e62 (1995), or TS-962 (acetamide, N-[2,6-bis(1-methylethyl)phenyl]-2-(tetradecylthio)-) (Taisho Pharmaceutical Co. Ltd.).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis*, 115:45-63 (1995) and *J. Med. Chem.*, 41:973 (1998).

The hypolipidemic agent may be an ileal $Na^+$/bile acid cotransporter inhibitor such as disclosed in *Drugs of the Future*, 24:425-430 (1999).

The lipid-modulating agent may be a cholesteryl ester transfer protein (CETP) inhibitor such as Pfizer's CP 529,414 (torcetrapib) (WO/0038722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physicians' Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the

MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physicians' Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999).

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of formula I may be 1, 2, 3 or more antidiabetic agents or antihyperglycemic agents including insulin secretagogues or insulin sensitizers, or other antidiabetic agents preferably having a mechanism of action different from the compounds of formula I of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of structure I will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.05:1 to about 10:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), NN-2344 (balaglitazone) (Dr. Reddy/NN), or YM-440 ((Z)-1,4-bis-4-[(3,5-dioxo-1,2,4-oxadiazolidin-2-yl-methyl)]phenoxybut-2-ene) (Yamanouchi), preferably rosiglitazone and pioglitazone.

The compounds of structure I will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. No. 5,346,701 (TheraTech), U.S. Pat. No. 5,614,492 and U.S. Pat. No. 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2,4-dioxo-5-thiazolidinyl)methyl]-2-methoxy-N-[[4-(trifluoromethyl)phenyl]methyl]-(Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma Effect on PPAR alpha Activation on Abnormal Lipid Metabolism in Liver of Zucker Fatty Rats", *Diabetes*, 47:1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., *Biochemistry*, 38(36):11597-11603 (1999), TSL-225 (tryptophyl-1,2,3,4-tetrahydro-isoquinoline-3-carboxylic acid (disclosed by Yamada et al, *Bioorg. & Med. Chem. Lett.*, 8:1537-1540 (1998), 2-cyanopyrrolidides and 4-cyanopyrrolidides as disclosed by Ashworth et al., *Bioorg. & Med. Chem. Lett.*, 6(22):1163-1166 and 2745-2748 (1996) employing dosages as set out in the above references.

The meglitinide which may optionally be employed in combination with the compound of formula I of the invention may be repaglinide, nateglinide (Novartis) or KAD1229 (mitiglinide) (PF/Kissei), with repaglinide being preferred.

The compound of formula I will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of formula I may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of formula I may be AJ9677 (rafabegron) (Takeda/Dainippon), L750355 (benzenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor agonist which may be optionally employed in combination with a compound of formula I may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The antihypertensive agents which may be employed in combination with the compound of formula I of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in *Clin. Exp. Pharmacol. Physiol.*, 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxy-carbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in *Eur. Therap. Res.,* 39:671 (1986); 40:543 (1986); ramipril (Hoechst) disclosed in Euro. Patent No. 79-022 and *Curr. Ther. Res.,* 40:74 (1986); Ru 44570 (Hoechst) disclosed in *Arzneimittelforschung,* 34:1254 (1985), cilazapril (Hoffman-LaRoche) disclosed in *J. Cardiovasc. Pharmacol.,* 9:39 (1987); R 31-2201 (Hoffman-LaRoche) disclosed in *FEBS Lett.,* 165:201 (1984); lisinopril (Merck), indalapril (delapril) disclosed in U.S. Pat. No. 4,385,051; indolapril (Schering) disclosed in *J. Cardiovasc. Pharmacol.,* 5:643, 655 (1983), spirapril (Schering) disclosed in *Acta. Pharmacol. Toxicol.,* 59(Supp. 5):173 (1986); perindopril (Servier) disclosed in *Eur. J. Clin. Pharmacol.,* 31:519 (1987); quinapril (Warner-Lambert) disclosed in U.S. Pat. No. 4,344,949 and CI925 (Warner-Lambert) ([3S-[2[R(*)R(*)]]3R(*)]-2-[2-[[1-(ethoxy-carbonyl)-3-phenylpropyl]amino]-1-oxopropyl]-1,2,3,4-tetrahydro-6,7-dimethoxy-3-isoquinolinecarboxylic acid HCl) disclosed in *Pharmacologist,* 26:243, 266 (1984), WY-44221 (Wyeth) disclosed in *J. Med. Chem.,* 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat ([S-(R*,R*)]-hexahydro-6-[(2-mercapto-1-oxo-3-phenylpropyl)amino]-2,2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of formula I include hydrochlorothiazide, torasemide, furosemide, spironolactono, and indapamide.

Antiplatelet agents which may be employed in combination with compounds of formula I of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of formula I of the invention include parathyroid hormone or bisphosphonates, such as MK-217 (alendronate) (Fosamax®).

Dosages employed for the above drugs will be as set out in the Physicians' Desk Reference.

Pharmaceutical Formulations

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$- and $\gamma$-cyclodextrin, or chemically modified derivatives such as hydroxyalkylcyclodextrins, including 2- and 3-hydroxypropyl-$\beta$-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

The compounds of the examples are inhibitors of AP-1 activity and/or compete with known ligands of the glucocorticoid receptor.

Compounds of the invention, including the compounds described in the examples, have been tested in at least one of the assays described below and have glucocorticoid receptor (GR)/Dexamethasone (Dex) inhibitory activity and/or AP-1 inhibitory activity.

Assays

GR Binding Assays
Glucocorticoid Receptor Binding Assay (I)

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hour incubation at room temperature in the dark, the fluorescence polarization (FP) of the samples was measured. The FP of a mixture of receptor, fluorescent probe (i.e. Fluormone GS Red) and 5 $\mu$M dexamethasone represented background fluorescence or 100% inhibition, whereas, the FP of the mixture without dexamethasone (but in the presence of vehicle) was taken to be 100% binding. The percentage inhibition of test compounds were then compared to the sample with 5 $\mu$M dexamethasone and expressed as % relative binding activity with dexamethasone being 100% and no inhibition being 0%. Test compounds were analyzed in the concentration range from 8.5E-05 μM to 5 μM.

Glucocorticoid Receptor Binding Assay (II)

In order to measure the binding of compounds on the glucocorticoid receptor a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of test compound. After one hour at room temperature, the fluorescence polarization (FP) of the samples were measured. The FP of a mixture of receptor, fluorescent probe (i.e. Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition being 0%. Test molecules were analyzed in the concentration range from 2.4 nM to 40 microMolar.

Cellular Transrepressional Assay

To measure the ability of test molecules to inhibit AP-1 induced transcriptional activity an A549 cell was utilized which was stably transfected with a plasmid containing 7× AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 μM. EC50s were determined by using standard curve fitting methods such as Excel fit (Microsoft Co.). An EC50 is the test molecule concentration at which there is a 50% repression of the maximal inhibition of transcription, i.e. a 50% reduction of AP-1 activity. In the absence of an EC50 the maximum % inhibition recorded is the inhibition of AP-1 at a compound concentration of 10 micromolar.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K. et al., *J. Biol. Chem.*, 270(52):31315-31320 (Dec. 29, 1995) may be used.

The cellular transrepressional assays described above may be used to measure transrepression by any NHR. One of skill in the art will understand that assays may require the addition of components, such as a stimulus (e.g., PMA, lipopolysaccharide, TNF-α, etc.) which will induce transcription mediated by AP-1 or NF-κB.

Additionally, AR mediated transrepression may be measured by the assay described in Palvimo. J. J. et al., *J. Biol. Chem.*, 271(39):24151-24156 (Sep. 27, 1996), and PR mediated transrepression may be measured by the assay described in Kalkhoven E. et al., *J. Biol. Chem.*, 271(11):6217-6224 (Mar. 15, 1996).

ABBREVIATIONS

The following abbreviations are employed in the following Preparations and Examples:

| | |
|---|---|
| Ph = | phenyl |
| Bn = | benzyl |
| t-Bu = | tertiary butyl |
| Me = | methyl |
| Et = | ethyl |
| ACN = | acetonitrile |
| TMS = | trimethylsilyl |
| TMSN$_3$ = | trimethylsilyl azide |
| TBS = | tert-butyldimethylsilyl |
| FMOC = | fluorenylmethoxycarbonyl |
| Boc = | tert-butoxycarbonyl |
| Cbz = | carbobenzyloxy or carbobenzoxy or benzyloxycarbonyl |
| THF = | tetrahydrofuran |
| Et$_2$O = | diethyl ether |
| hex = | hexanes |
| EtOAc = | ethyl acetate |
| DMF = | dimethyl formamide |
| MeOH = | methanol |
| EtOH = | ethanol |
| i-PrOH = | isopropanol |
| DMSO = | dimethyl sulfoxide |
| DME = | 1,2 dimethoxyethane |
| DCE = | 1,2 dichloroethane |
| HMPA = | hexamethyl phosphoric triamide |
| HOAc or AcOH = | acetic acid |
| TFA = | trifluoroacetic acid |
| TFAA = | trifluoroacetic anhydride |
| i-Pr$_2$NEt = | diisopropylethylamine |
| Et$_3$N = | triethylamine |
| NMM = | N-methyl morpholine |
| DMAP = | 4-dimethylaminopyridine |
| NaBH$_4$ = | sodium borohydride |
| NaBH(OAc)$_3$ = | sodium triacetoxyborohydride |
| DIBALH = | diisobutyl aluminum hydride |
| LAH or LiAlH$_4$ = | lithium aluminum hydride |
| n-BuLi = | n-butyllithium |
| LDA = | lithium diisopropylamide |
| Pd/C = | palladium on carbon |
| PtO$_2$ = | platinum oxide |
| KOH = | potassium hydroxide |
| NaOH = | sodium hydroxide |
| LiOH = | lithium hydroxide |
| K$_2$CO$_3$ = | potassium carbonate |
| NaHCO$_3$ = | sodium bicarbonate |
| DBU = | 1,8-diazabicyclo[5.4.0]undec-7-ene |
| EDC (or EDC•HCl) or EDCI (or EDCI•HCl) or EDAC = | 3-ethyl-3'-(dimethylamino)propyl-carbodiimide hydrochloride (or 1-(3-dimethylaminopropyl)-3-ethylcarbodiimide hydrochloride) |
| HOBT or HOBT•H$_2$O = | 1-hydroxybenzotriazole hydrate |
| HOAT = | 1-Hydroxy-7-azabenzotriazole |
| BOP reagent = | benzotriazol-1-yloxy-tris (dimethylamino) phosphonium hexafluorophosphate |
| NaN(TMS)$_2$ = | sodium hexamethyldisilazide or sodium bis(trimethylsilyl)amide |
| Ph$_3$P = | triphenylphosphine |
| Pd(OAc)$_2$ = | Palladium acetate |
| (Ph$_3$P)4Pd° = | tetrakis triphenylphosphine palladium |
| DEAD = | diethyl azodicarboxylate |
| DIAD = | diisopropyl azodicarboxylate |
| Cbz-Cl = | benzyl chloroformate |
| CAN = | ceric ammonium nitrate |
| SAX = | Strong Anion Exchanger |
| SCX = | Strong Cation Exchanger |
| Ar = | argon |
| N$_2$ = | nitrogen |
| min = | minute(s) |
| h or hr = | hour(s) |
| L = | liter |
| mL = | milliliter |
| μL = | microliter |
| g = | gram(s) |
| mg = | milligram(s) |
| mol = | moles |

| | |
|---|---|
| mmol = | millimole(s) |
| meq = | milliequivalent |
| rt or RT = | room temperature |
| sat or sat'd = | saturated |
| aq. = | aqueous |
| TLC = | thin layer chromatography |
| HPLC = | high performance liquid chromatography |
| Reverse phase HPLC = | reverse phase high performance liquid chromatography, using a YMC ODS S5 column and a binary solvent A/solvent B eluents |
| Solvent A = | 10% MeOH - 90% $H_2O$ - 0.1% TFA |
| Solvent B = | 90% MeOH - 10% $H_2O$ - 0.1% TFA; or |
| Solvent A = | $H_2O$ containing 0.1% TFA |
| Solvent B = | ACN containing 0.1% TFA |
| LC/MS = | high performance liquid chromatography/mass spectrometry |
| MS or Mass Spec = | mass spectrometry |
| NMR = | nuclear magnetic resonance |
| NMR spectral data: | s = singlet; d = doublet; m = multiplet; br = broad; t = triplet |
| mp = | melting point |

EXAMPLES

The following Examples illustrate embodiments of the inventive compounds and starting materials, and are not intended to limit the scope of the claims.

Preparations

The preparations set out below are for the synthesis of reagents that were not obtained from commercial sources and were employed for the preparation of compounds of formula I of the invention. All chiral compounds in the tables and schemes are racemic unless specified otherwise.

Reverse-phase preparative high performance liquid chromatography ("HPLC") was performed with Shimadzu 8A liquid chromatographs using YMC S5 ODS columns (20× 100, 20×250, or 30×250 millimeter ("mm")). Gradient elution was performed with methanol ("MeOH")/water mixtures in the presence of 0.1% trifluoroacetic acid ("TFA").

Analytical HPLC Method Employed in Characterization of Examples

Analytical HPLC was performed on Shimadzu LC10AS liquid chromatographs using the following methods:
Method A (Used in All Cases, Unless Otherwise Indicated):
Linear gradient of 0 to 100% solvent B over 4 minutes ("min"), with 1 minute ("min") hold at 100% B.
Ultraviolet ("UV") visualization at 220 nanometers ("nm")
Column: YMC S5 ODS Ballistic 4.6×50 mm
Flow rate: 4 milliliters ("mL")/min
Solvent A: 0.2% phosphoric acid, 90% water, 10% methanol
Solvent B: 0.2% phosphoric acid, 90% methanol, 10% water
Method B:

| | |
|---|---|
| Column: | Phenomenex Luna C18(2), 4.6 × 50 mm × 5 um |
| Mobile Phase: | (A) 10:90 methanol:water; (B) 90:10 methanol:water |
| Buffer: | 0.1% TFA |
| Gradient Range: | 0-100% B |
| Gradient Time: | 4 min |
| Flow Rate: | 4 mL/min |
| Analysis Time: | 5 min |
| Detection: | |
| Detector 1: | UV at 220 nm |
| Detector 2: | MS (ESI+) |
| Detector 3: | ELSD |

Purification of Final Compounds of Formula I

All of the examples that are described below that contain one or more chiral centers can be resolved using standard or chiral HPLC chromatography. Purification of diastereomers or regioisomers was performed using HPLC (Phenomenex Luna column: 3×25 cm 5 mM C18; solvent: water (containing 0.5% TFA) with increasing acetonitrile (containing 0.5% TFA) gradients over 25 min; flow rate: 40 mL/min; uv detection at 215 nM). Another HPLC method makes use of a YMC S5 CombiScreen column: 4.6×50 mm C18; solvent: 10-90% aqueous methanol over 4 minutes containing 0.2% phosphoric acid; flow rate: 4 mL/min; uv detection at 220 nM Chiral separation of enantiomers was performed using preparative Chiracel AD, OJ, or AS columns and isocratic mobile phases of EtOH or MeOH mixed with heptane. Alternatively, the same Chiracel columns could be run using SFC methods with mobile phases such as $CO_2$, MeOH, and diethylamine. Note that enantiomers may be separated after the final stage of synthesis or earlier at any intermediate chiral precursor in the synthetic route and then taken to the end of the synthetic sequence enantiomerically pure.

General Coupling Method A:

To a solution of carboxylic acid (0.15 mmol) in DMF (1-2 mL) was added hydroxybenzotriazole (31 mg, 0.23 mmol), triethylamine (0.3 mmol), and N-(3-dimethylaminopropyl)-N'-ethylcarbodiimide (43 mg, 0.23 mmol). After stirring for 10 min, the Z—$Z_a$—$NH_2$ amine (0.23 mmol) was added and the reaction is heated between 80-100 C for 3-24 h. The reaction was cooled and the reaction purified by HPLC. Products were identified by MS and consistent $^1$H-NMR spectra.

General Coupling Method B:

To a solution of carboxylic acid (e.g., 3-(1-(4-fluorophenyl)-1H-indazol-5-yl)-2,2-dimethyl-3-phenylpropanoic acid) (16 mmol) and pyridine (1.5 mL, 18.5 mmol) in 300 mL of $CH_2Cl_2$ was added cyanuric fluoride (1.6 mL, 18.8 mmol). The reaction was stirred for 1 hr, then quenched with 1N HCl and extracted with 2×$CH_2Cl_2$. The $CH_2Cl_2$ extracts were dried over $MgSO_4$, filtered, and concentrated by rotary evaporator to give the corresponding crude acid fluoride. This intermediate was characterized using MS and $^1$H-NMR. The crude acid fluoride was combined with the Z—$Z_a$—$NH_2$ amine in a suitable solvent (DCM, THF, DMF) without base and heated to 85° C. for 16 hr. For hindered acids, the acid fluoride (0.06 mmol), the Z—$Z_a$—$NH_2$ amine (0.12 mmol), and DMAP (0.03 mmol) are dissolved in dry NMP and reacted in a microwave at 150° C. for approximately 30 min. The final products were purified using HPLC and the final products were identified by MS and consistent $^1$H-NMR spectra.

SCHEME A

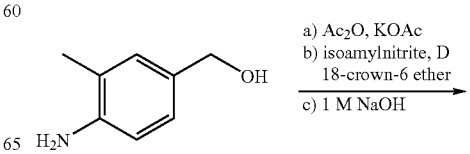

a) $Ac_2O$, KOAc
b) isoamylnitrite, D 18-crown-6 ether
c) 1 M NaOH

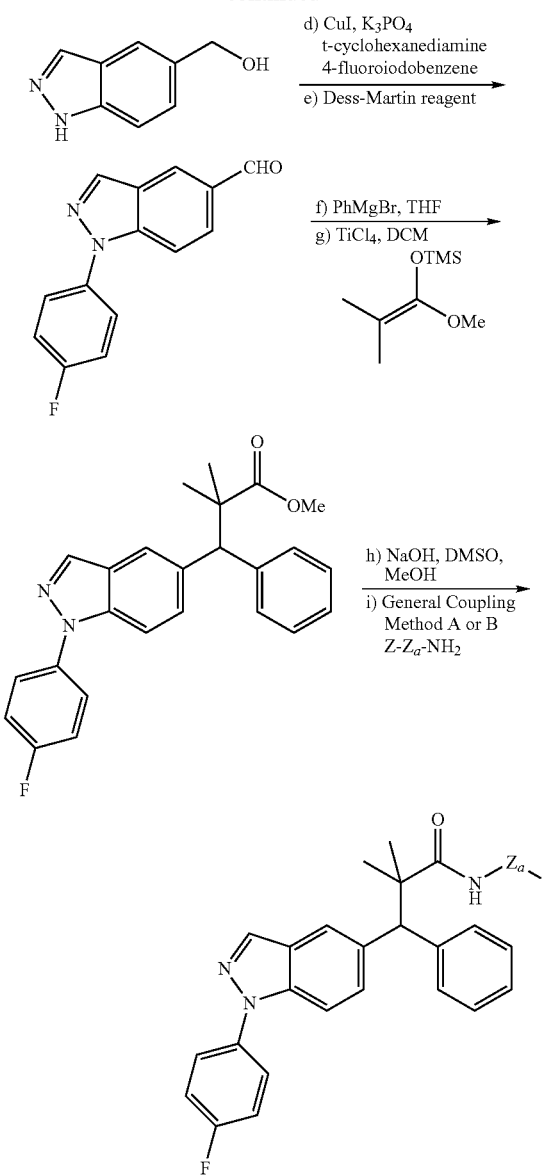

Example 1

3-(1-(4-Fluorophenyl)-1H-indazol-5-yl)-2,2-dimethyl-3-phenyl-N-(thiazol-2-yl)propanamide

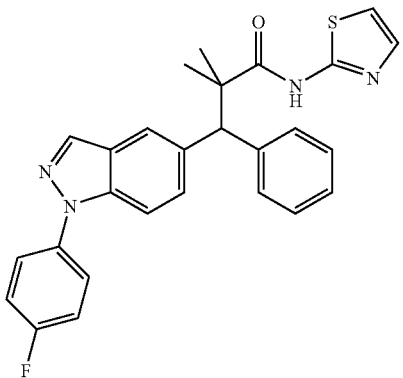

The procedure of Scheme A was used in preparing the Example 1 compound.

(a) Following the general procedure of Sun et al. (*J. Org. Chem.*, 62:5627-5629 (1997)), 4-amino-3-methyl-benzyl alcohol (36.8 g, 269 mmol) was dissolved in dry chloroform (1 L) followed by potassium acetate (53 g, 540 mmol), and acetic anhydride (83 g, 810 mmol). After 2 h, the reaction was refluxed for 3 h and then cooled to rt and stirred overnight.

(b) The next day, 18-crown-6 ether (3.6 g, 13.5 mmol) was added followed by isoamyl nitrite (71.3 g, 608 mmol). The reaction was refluxed for 20 h, cooled to rt, washed with sat NaHCO$_3$, and the organic layer was dried over MgSO$_4$, filtered, and concentrated in vacuo. The crude oil was passed through a SiO$_2$ plug first with 5% EtOAc in hexanes, then 20% EtOAc in hexanes and concentrated. The residue was triturated with Et$_2$O/hexane to obtain 23.3 g of solid, bis-acetylated product. The supernatant was concentrated and the titration procedure repeated twice to give an additional 12.2 g. Total yield: 35.5 g (57% yield). MS found: (M+H)$^+$=233.

(c) The solid was dissolved in MeOH (350 mL) and treated with 1 M NaOH (150 mL). After stirring overnight, the MeOH was removed in vacuo, the residue acidified with conc HCl to pH 4-5 and extracted with EtOAc×3. The organic layer was dried with MgSO$_4$, filtered, concentrated in vacuo to give 20.1 g (90%) of (1H-indazol-5-yl)methanol. MS found: (M+H)$^+$=149.

(d) (1H-Indazol-5yl)methanol (2.7 g, 18.2 mmol) was dissolved in 20 mL dry dioxane in a stainless steel pressure tube. Trans-1,2-cyclohexanediamine (1.1 mL, 9.12 mmol) was added followed by CuI (174 mg, 0.91 mmol) and then K$_3$PO$_4$ (6.97 g, 32.8 mmol). After the addition of 4-fluoro-1-iodobenzene (2.1 mL, 18.2 mmol), the reactor was sealed and heated at 100 C for 24 h. The reactor was cooled and the contents were taken up in EtOAc, filtered through a SiO$_2$ plug with EtOAc and concentrated in vacuo. The crude product was chromatographed using 31:1 EtOAc/hexanes to give 4.25 g (96% yield) of a pale yellow oil (1-(4-fluorophenyl)-1H-indazol-5-yl)methanol that solidified on standing. MS found: (M+H)$^+$=243.

(e) (1-(4-Fluorophenyl)-1H-indazol-5-yl)methanol (2.46 g, 10.2 mmol) was dissolved in 80 mL DCM and treated with commercially available Dess-Martin periodinane (4.3 g, 10.2 mmol). The reaction was complete in 2 h and was filtered through a plug of SiO$_2$ using DCM/hexane (3:1) and concentrated to give 2.47 g (100%) of 1-(4-fluorophenyl)-1H-indazol-5-carboxaldehyde. MS found: (M+H)$^+$=241.

(f) 1-(4-Fluorophenyl)-1H-indazol-5-carboxaldehyde (2.47 g, 10.2 mmol) was dissolved in 25 mL THF, cooled in a 0° C. ice bath, and treated with PhMgBr (4.6 mL of 1.0 M in THF, 4.58 mmol). After 1 h, the reaction was quenched with sat. NH$_4$Cl and extracted with EtOAc×3. The organic layers were dried over MgSO$_4$, filtered, and concentrated to give 3.2 g (100%) of product (1-(4-fluorophenyl)-1H-indazol-5-yl)(phenyl)methanol. MS found: (M+H)$^+$=319.

(g) (1-(4-Fluorophenyl)-1H-indazol-5-yl)(phenyl)methanol (16.0 g, 50 mmol) was dissolved in 400 mL of dry THF and TiCl$_4$ (60 mL of 1.0 M DCM solution, 60 mmol) was added portionwise and then stirred 30 min. The flask was put on a rotary evaporator until the THF began to distill to degas the HCl and then the reaction was treated with 1-methoxy-2-methyl-1-(trimethylsiloxy)propene (17.4 g, 100 mmol). The reaction was quenched with aqueous sodium bicarbonate and extracted 2×EtOAc, the organic layers dried over MgSO$_4$, filtered, concentrated, and then chromatographed using DCM to give 16.2 g (81% yield) of methyl 3-(1-(4-fluorophenyl)-1H-indazol-5-yl)-2,2-dimethyl-3-phenylpropanoate. MS found: (M+H)$^+$=403.

(h) Methyl 3-(1-(4-fluorophenyl)-1H-indazol-5-yl)-2,2-dimethyl-3-phenylpropanoate (16.2 g, 40.2 mmol) was heated to 100 C overnight in a mixture of 2 M NaOH/MeOH/DMSO (1:1:1). The next day, the reaction was cooled, acidified to pH 5 with HCl and extracted 2×EtOAc. The organic layers were washed with water×2, dried over MgSO$_4$, filtered, and concentrated in vacuo to give 15.4 g (99% yield) of acid 3-(1-(4-fluorophenyl)-1H-indazol-5-yl)-2,2-dimethyl-3-phenylpropanoic acid. MS found: (M+H)$^+$=389.

(i) Example 1 was prepared from 3-(1-(4-fluorophenyl)-1H-indazol-5-yl)-2,2-dimethyl-3-phenylpropanoic acid (100 mg, 0.26 mmol) and 2-aminothiazole using General Coupling Method A to give 52 mg (42% yield). MS found: (M+H)$^+$=471. 400 MHz $^1$H-NMR (DMSO-d6) δ 12.0 (s, 1H); 8.36 (s, 1H); 7.93 (s, 1H); 7.77 (dd, 2H); 7.70 (d, 1H); 7.46 (dd, 2H); 7.40 (m, 4H); 7.28 (app t, 2H); 7.20 (app t, 1H); 7.16 (d, 1H); 5.10 (s, 1H); 1.36 (s, 6H) Resolution of this compound into its enantiomers could be accomplished using chiral HPLC as described above.

Examples 2 to 28

Following a procedure similar to that set out in Scheme A and Example 1, the following compounds were obtained.

| Ex. | Name | Product Structure | Amine | (M + H)+/ selected NMR | Coupling Method |
|---|---|---|---|---|---|
| 2 | 3-(1-(4-fluoro-phenyl)-1H-indazol-5-yl)-2,2-dimethyl-3-phenyl-N-(1,3,4-thiadiazol-2-yl)propanamide | | | (M − H)$^-$ 470 | A |

400 MHz $^1$H-NMR (DMSO-d6) δ 12.5 (s, 1 H); 9.09 (s, 1 H); 8.36 (s, 1 H); 7.92 (s, 1 H); 7.77 (dd, 2 H); 7.68 (d, 1 H); 7.41 (m, 5 H); 7.27 (app t, 2 H); 7.19 (app t, 1 H); 5.07 (s, 1 H); 1.36 (s, 6 H).

| 3 | N-cyclopentyl-3-(1-(4-fluorophenyl)-1H-indazol-5-yl)-2,2-dimethyl-3-phenylpropanamide | | | 456 | A |

| Ex. | Name | Product Structure | Amine | (M + H)+/ selected NMR | Coupling Method |
|---|---|---|---|---|---|
| 4 | 3-(1-(4-fluorophenyl)-1H-indazol-5-yl)-2,2-dimethyl-N-(1-methyl-1H-pyrazol-3-yl)-3-phenylpropanamide | | | 468 | B |

NMR (CDCl$_3$) δ 8.05 (s, 1 H); 7.76 (s, 1 H) 7.5-7.6 (m, 2 H); 7.4-7.45 (d, 1 H); 7.28-7.4 (m, 4 H); 7.1-7.26 (m, 5 H); 6.70 (d, 1 H); 4.63 (s, 1 H); 3.73 (s, 3 H); 1.36 (s, 3 H); 1.33 (s, 3 H).

| Ex. | Name | Product Structure | Amine | (M+H)+ | Method |
|---|---|---|---|---|---|
| 5 | 3-(1-(4-fluorophenyl)-1H-indazol-5-yl)-2,2-dimethyl-N-(methylsulfonyl)-3-phenylpropanamide | | MeSO$_2$NH$_2$ | 467 | B |
| 6 | 3-(1-(4-fluorophenyl)-1H-indazol-5-yl)-2,2-dimethyl-3-phenyl-N-(trifluoromethylsulfonyl)propanamide | | CF$_3$SO$_2$NH$_2$ | 520 | B |

-continued

| Ex. | Name | Product Structure | Amine | (M + H)+/ selected NMR | Coupling Method |
|---|---|---|---|---|---|
| 7 | 3-(1-(4-fluorophenyl)-1H-indazol-5-yl)-2,2-dimethyl-N-neopentyl-3-phenylpropanamide | | | 458 | B |
| 8 | 3-(1-(4-fluorophenyl)-1H-indazol-5-yl)-2,2-dimethyl-3-phenyl-N-(2,2,2-trifluoroethyl)prop-anamide | | | 470 | B |
| 9 | 3-(1-(4-fluorophenyl)-1H-indazol-5-yl)-2,2-dimethyl-3-phenyl-N-(3,3,3-trifluoropropyl)-propanamide | | | 484 | B |
| 10 | ethyl 5-(3-(1-(4-fluorophenyl)-1H-indazol-5-yl)-2,2-dimethyl-3-phenylprop-anamido)-1,3,4-thiadiazole-2-carboxylate | | | 544 | B |

-continued

| Ex. | Name | Product Structure | Amine | (M + H)+/ selected NMR | Coupling Method |
|---|---|---|---|---|---|
| 11 | 3-(1-(4-fluorophenyl)-1H-indazol-5-yl)-2,2-dimethyl-3-phenyl-N-(thiophen-3-yl)propanamide | | | 470 | B |
| 12 | 3-(1-(4-fluorophenyl)-1H-indazol-5-yl)-2,2-dimethyl-N-(4-methylthiazol-2-yl)-3-phenylpropan-amide | | | 485 | B |
| 13 | 3-(1-(4-fluorophenyl)-1H-indazol-5-yl)-2,2-dimethyl-3-phenyl-N-(1H-1,2,4-triazol-3-yl)propanamide | | | 455 | B |
| 14 | 3-(1-(4-fluorophenyl)-1H-indazol-5-yl)-2,2-dimethyl-3-phenyl-N-(1H-tetrazol-5-yl)propanamide | | | 456 | B |

-continued

| Ex. | Name | Product Structure | Amine | (M + H)+/ selected NMR | Coupling Method |
|---|---|---|---|---|---|
| 15 | 3-(1-(4-fluorophenyl)-1H-indazol-5-yl)-N-(5-hydroxy-1H-pyrazol-3-yl)-2,2-dimethyl-3-phenylpropanamide | | | 470 | B |
| 16 | N-(4-cyano-1H-pyrazol-3-yl)-3-(1-(4-fluorophenyl)-1H-indazol-5-yl)-2,2-dimethyl-3-phenylpropanamide | | | 479 | B |
| 17 | 3-(1-(4-fluorophenyl)-1H-indazol-5-yl)-2,2-dimethyl-N-(5-methylthiazol-2-yl)-3-phenylpropanamide | | | 485 | B |
| 18 | 3-(1-(4-fluorophenyl)-1H-indazol-5-yl)-2,2-dimethyl-N-(5-methyl-1,3,4-thiadiazol-2-yl)-3-phenylpropanamide | | | 486 | B |

-continued

| Ex. | Name | Product Structure | Amine | (M + H)+/ selected NMR | Coupling Method |
|---|---|---|---|---|---|
| 19 | N-(3-cyanothiophen-2-yl)-3-(1-(4-fluorophenyl)-1H-indazol-5-yl)-2,2-dimethyl-3-phenylpropanamide | | | 495 | B |
| 20 | N-(5-ethyl-1,3,4-thiadiazol-2-yl)-3-(1-(4-fluorophenyl)-1H-indazol-5-yl)-2,2-dimethyl-3-phenylpropanamide | | | 500 | B |
| 21 | N-(5-cyclopropyl-1,3,4-thiadiazol-2-yl)-3-(1-(4-fluorophenyl)-1H-indazole-5-yl)-2,2-dimethyl-3-phenylpropanamide | | | 512 | B |
| 22 | 3-(1-(4-fluorophenyl)-1H-indazol-5-yl)-2,2-dimethyl-N-(5-(methylthio)-1,3,4-thiadiazol-2-yl)-3-phenylpropanamide | | | 518 | B |
| 23 | N-(benzyl[d]thiazol-2-yl)-3-(1-(4-fluorophenyl)-1H-indazol-5-yl)-2,2-dimethyl-3-phenylpropanamide | | | 521 | B |

-continued

| Ex. | Name | Product Structure | Amine | (M + H)+/selected NMR | Coupling Method |
|---|---|---|---|---|---|
| 24 | N-(4,5-dimethylthiazol-2-yl)-3-(1-(4-fluorophenyl)-1H-indazol-5-yl)-2,2-dimethyl-3-phenylpropanamide | 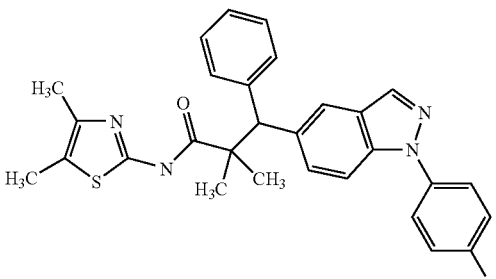 | 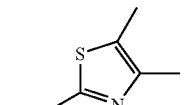 | 499 | B |
| 25 | 3-(1-(4-fluorophenyl)-1H-indazol-5-yl)-2,2-dimethyl-3-phenyl-N-(5-(trifluoromethyl)-1,3,4-thiadiazol-2-yl)propanamide | 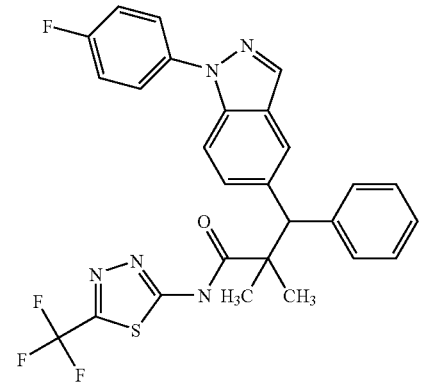 | 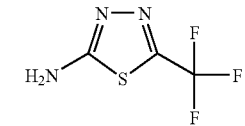 | 540 | B |
| 26 | N-(5-chlorothiazol-2-yl)-3-(1-(4-fluorophenyl)-1H-indazol-5-yl)-2,2-dimethyl-3-phenylpropanamide | 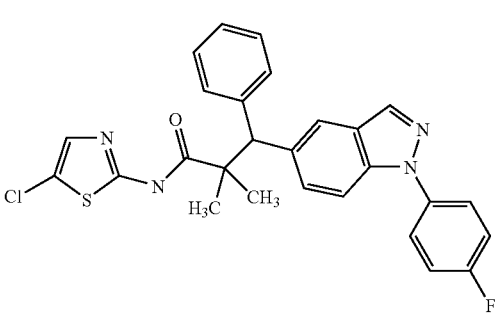 | 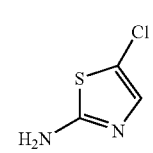 | 505 | B |
| 27 | ethyl 2-(3-(1-(4-fluorophenyl)-1H-indazol-5-yl)-2,2-dimethyl-3-phenylpropanamido)thiazol-4-carboxylate | 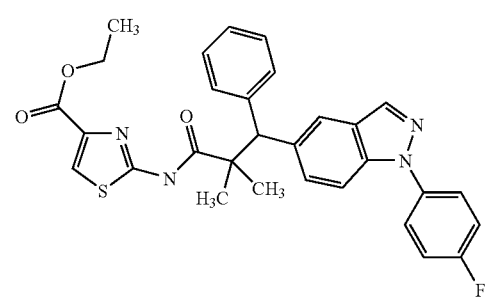 | 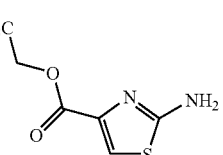 | 543 | B |

| Ex. | Name | Product Structure | Amine | (M + H)+/ selected NMR | Coupling Method |
|---|---|---|---|---|---|
| 28 | ethyl 2-(2-(3-(1-(4-fluorophenyl)-1H-indazol-5-yl)-2,2-dimethyl-3-phenylpropanamido)thiazol-4-yl)acetate | | | 557 | B |

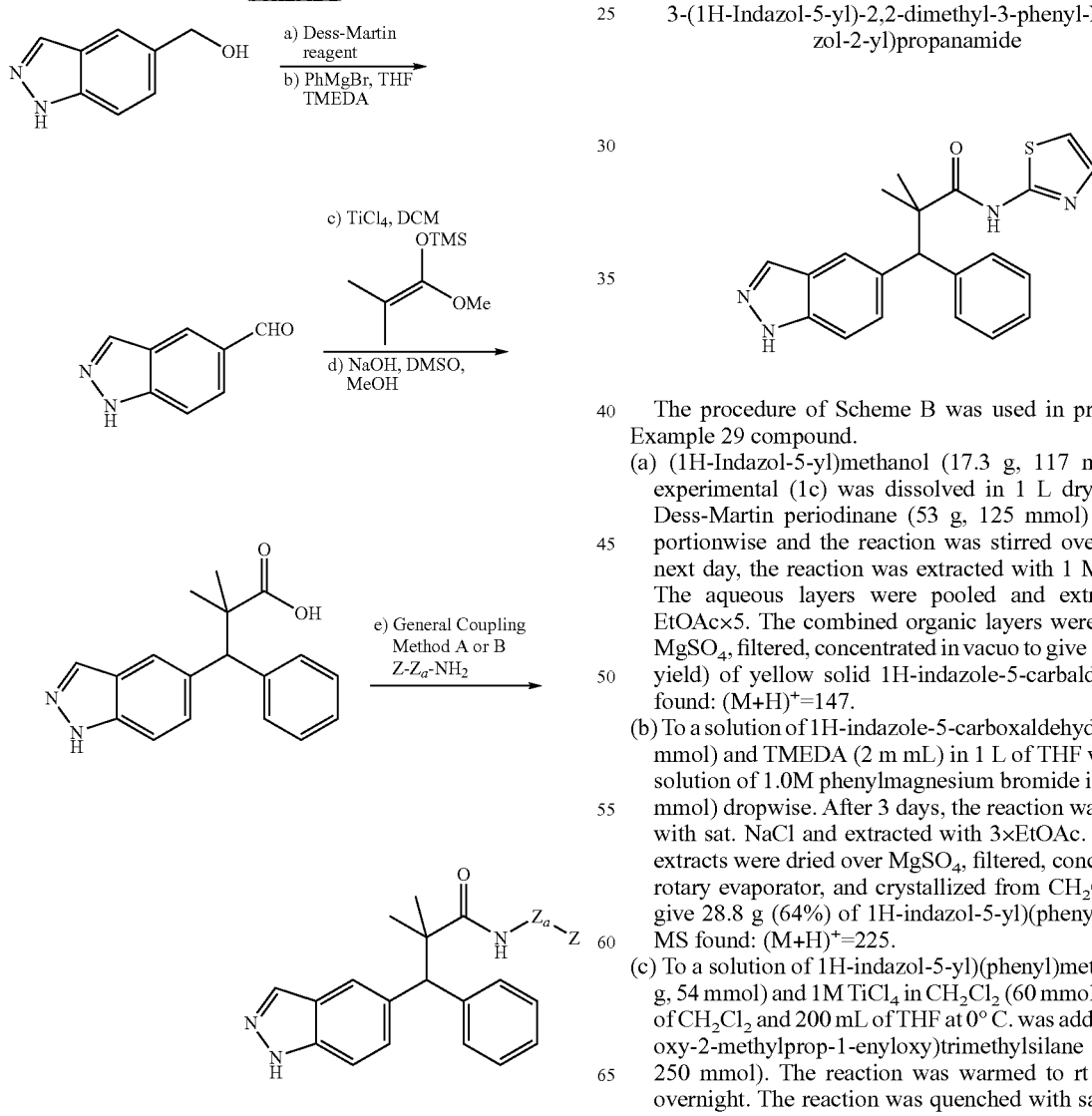

Example 29

3-(1H-Indazol-5-yl)-2,2-dimethyl-3-phenyl-N-(thiazol-2-yl)propanamide

The procedure of Scheme B was used in preparing the Example 29 compound.

(a) (1H-Indazol-5-yl)methanol (17.3 g, 117 mmol) from experimental (1c) was dissolved in 1 L dry DCM and Dess-Martin periodinane (53 g, 125 mmol) was added portionwise and the reaction was stirred overnight. The next day, the reaction was extracted with 1 M NaOH×3. The aqueous layers were pooled and extracted with EtOAc×5. The combined organic layers were dried over MgSO$_4$, filtered, concentrated in vacuo to give 14.1 g (82% yield) of yellow solid 1H-indazole-5-carbaldehyde. MS found: $(M+H)^+=147$.

(b) To a solution of 1H-indazole-5-carboxaldehyde (28 g, 200 mmol) and TMEDA (2 m mL) in 1 L of THF was added a solution of 1.0M phenylmagnesium bromide in THF (800 mmol) dropwise. After 3 days, the reaction was quenched with sat. NaCl and extracted with 3×EtOAc. The EtOAc extracts were dried over MgSO$_4$, filtered, concentrated by rotary evaporator, and crystallized from CH$_2$Cl$_2$/ether to give 28.8 g (64%) of 1H-indazol-5-yl)(phenyl)methanol. MS found: $(M+H)^+=225$.

(c) To a solution of 1H-indazol-5-yl)(phenyl)methanol (12.1 g, 54 mmol) and 1M TiCl$_4$ in CH$_2$Cl$_2$ (60 mmol) in 200 mL of CH$_2$Cl$_2$ and 200 mL of THF at 0° C. was added (1-methoxy-2-methylprop-1-enyloxy)trimethylsilane (50.8 mL, 250 mmol). The reaction was warmed to rt and stirred overnight. The reaction was quenched with sat NaCl and extracted with 3×CH$_2$Cl$_2$. The CH$_2$Cl$_2$ extracts were dried over MgSO₄, filtered, concentrated by rotary evaporator, and chromatographed on SiO₂ using EtOAc/hexanes (1:2) to give 11.1 g (66%) of Methyl 3-(1H-indazol-5-yl)-2,2-dimethyl-3-phenylpropanoate. MS found: (M+H)⁺=309.

(d) Methyl 3-(1H-indazol-5-yl)-2,2-dimethyl-3-phenylpropanoate (2.5 g, 8.1 mmol) was dissolved in 50 mL of DMSO, 50 mL of 1 NaOH and 50 mL of MeOH and heated at 100° C. overnight. The reaction was quenched with sat. NaCl and extracted with 2×EtOAc. The EtOAc extracts were dried over MgSO₄, filtered, and concentrated by rotary evaporator to give 2.4 g of 3-(1H-indazol-5-yl)-2,2-dimethyl-3-phenylpropanoic acid. MS found: (M+H)⁺=295.

(e) 3-(1H-Indazol-5-yl)-2,2-dimethyl-3-phenylpropanoic acid (44 mg, 0.15 mmol) and 2-aminothiazole using General Coupling Method A to give 22 mg (39% yield) of Example 29. MS found: (M+H)⁺=377. 400 MHz ¹H-NMR (DMSO-d6) δ 12.9 (br s, 1H); 11.9 (s, 1H); 7.94 (s, 1H); 7.70 (s, 1H); 7.35 d, 1H); 7.31 (t, 3H); 7.18 (t, 3H); 7.09 (t, 1H); 7.05 (d, 1H); 4.94 (s, 1H); 1.24 (s, 6H).

Example 30

3-(1H-Indazol-5-yl)-2,2-dimethyl-3-phenyl-N-(1,3,4-thiadiazol-2-yl)propanamide

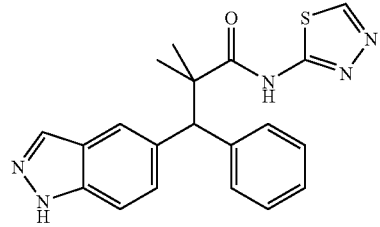

The title compound was prepared from 3-(1H-indazol-5-yl)-2,2-dimethyl-3-phenylpropanoic acid (Example 29(d)) (44 mg, 0.15 mmol) and 2-amino-1,3,4-thiadiazole using General Coupling Method A to give 29 mg (51% yield) of Example 30. MS found: (M+H)⁺=378.

SCHEME C

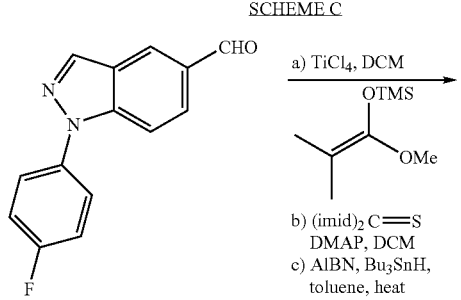

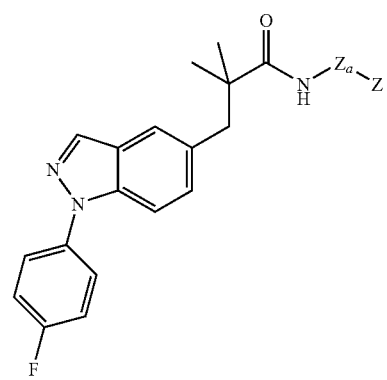

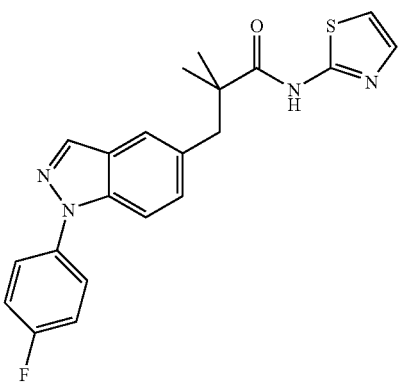

Example 31

3-(1-(4-Fluorophenyl)-1H-indazol-5-yl)-2,2-dimethyl-N-(thiazol-2-yl)propanamide

The title compound was prepared following the procedure in Scheme C.

(a) A solution of 1-(4-fluorophenyl)-1H-indazole-5-carbaldehyde (1.0 g, 4.17 mmol) from experimental (1e) in 30 mL DCM was cooled to −78 C and treated with TiCl₄ (4.2 mL of 1.0 M solution in DCM). The reaction was warmed to rt and treated with 1-methoxy-2-methyl-1-(trimethylsiloxy)propene (799 mg, 4.58 mmol), stirred for 1 h, and quenched with sat NaHCO₃. The mixture was extracted 2×EtOAc, sat NH₄Cl was added to the aqueous layer and then extracted 1×EtOAc. Dried organic layers with MgSO₄, filtered, conc, and chromatographed on SiO₂ using 25% EtOAc in hexanes. Obtained 820 mg (57%) of white solid methyl 3-(1-(4-fluorophenyl)-1H-indazol-5-yl)-3-hydroxy-2,2-dimethylpropanoate. MS found: $(M+H)^+=343$.

(b) Methyl 3-(1-(4-fluorophenyl)-1H-indazol-5-yl)-3-hydroxy-2,2-dimethylpropan-oate (250 mg, 0.73 mmol) was taken up in DCM and treated with 10 mg DMAP followed by thiocarbonyldiimidazole (650 mg, 3.65 mmol). Stirred at rt for 72 h, extracted from brine 1×DCM and 2×EtOAc. Then combined organic layers were dried over $MgSO_4$, filtered, conc. and then dissolved in 40 mL dry toluene.

(c) Tributyltin hydride (637 mg, 2.19 mmol) was added followed by AIBN (36 mg, 0.22 mmol) and the reaction was refluxed for 3 h. The reaction was concentrated in vacuo, extracted from brine with EtOAc×2, dried over $MgSO_4$, filtered, and conc. The residue was purified by HPLC to give 151 mg (63% yield) of deoxygenated compound methyl 3-(1-(4-fluorophenyl)-1H-indazol-5-yl)-2,2-dimethylpropanoate. MS found: $(M+H)^+=327$.

(d) Methyl 3-(1-(4-fluorophenyl)-1H-indazol-5-yl)-2,2-dimethylpropanoate was dissolved in 5:1 MeOH/DMSO (12 mL) and treated with 3 mL 1 M NaOH and heated at 85 C overnight. The next day, the reaction was acidified with TFA and purified by HPLC to give 52 mg of a colorless oil 3-(1-(4-fluorophenyl)-1H-indazol-5-yl)-2,2-dimethylpropanoic acid. MS found: $(M+H)^+=313$.

(e) 3-(1-(4-Fluorophenyl)-1H-indazol-5-yl)-2,2-dimethylpropanoic acid (26 mg, 0.08 mmol) was coupled to 2-aminothiazole using General Coupling Method A to give 20 mg (61% yield) of Example 31. MS found: $(M+H)^+=395$.

Example 32

3-(1-(4-Fluorophenyl)-1H-indazol-5-yl)-2,2-dimethyl-N-(1,3,4-thiadiazol-2-yl)propanamide

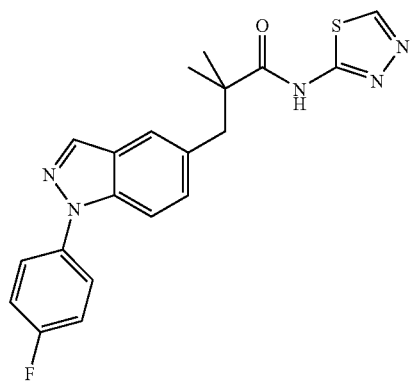

3-(1-(4-Fluorophenyl)-1H-indazol-5-yl)-2,2-dimethylpropanoic acid (26 mg, 0.08 mmol) from Example 31(d) was coupled to 2-amino-1,3,4-thiadiazole using General Coupling Method A to give 21 mg (61% yield) of Example 32. MS found: $(M+H)^+=396$.

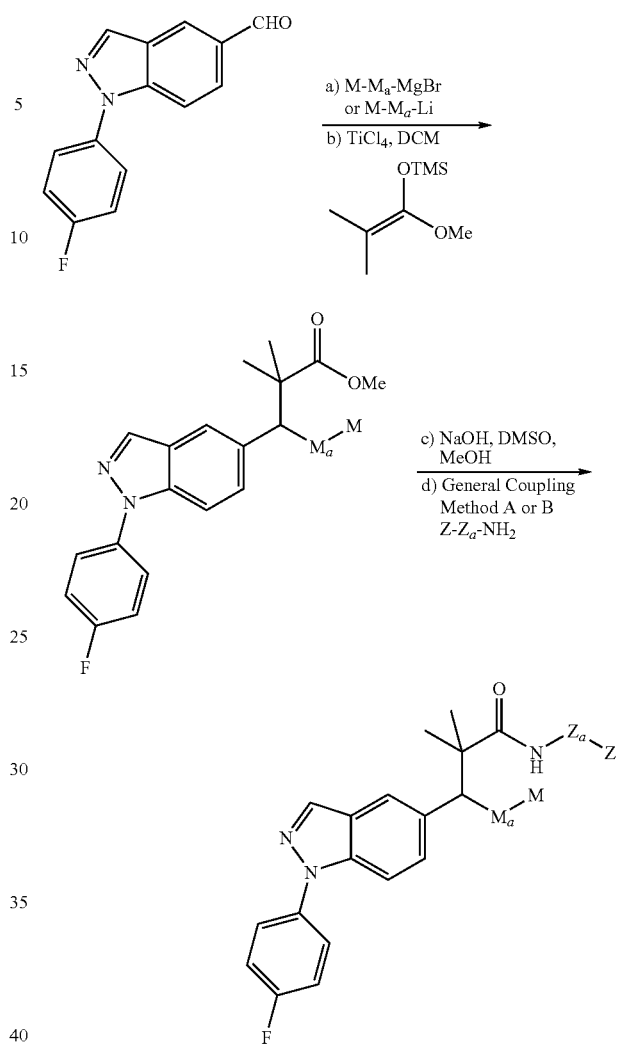

The Scheme D procedure was used in preparing the Examples 33 to 39 compounds.

Example 33

3-(1-(4-Fluorophenyl)-1H-indazol-5-yl)-2,2,5-trimethyl-N-(thiazol-2-yl)hexanamide

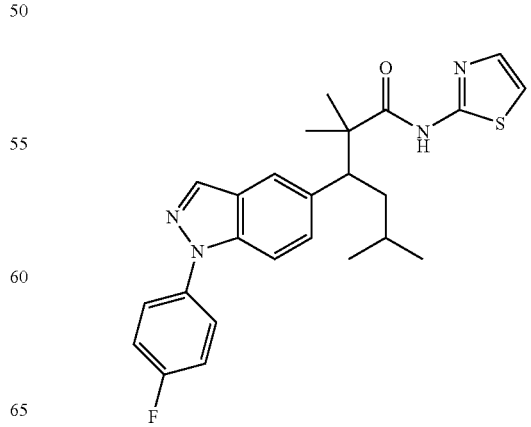

(a) To a solution of 1-(4-fluorophenyl)-1H-indazole-5-carboxaldehyde (100 mg, 0.416 mmol) from experimental (1e) in 5 mL of THF was added a solution of 2.0M isobutylmagnesium bromide in THF (0.5 mmol) dropwise. After 1 hr, the reaction was quenched with sat. $NH_4Cl$ and extracted with 2×EtOAc. The EtOAc extracts were dried over $MgSO_4$, filtered, and concentrated by rotary evaporator to give 1-(1-(4-fluorophenyl)-1H-indazol-5-yl)-3-methylbutan-1-ol. MS found: $(M+H)^+=299$.

(b) To a solution of 1-(1-(4-fluorophenyl)-1H-indazol-5-yl)-3-methylbutan-1-ol (0.41 mmol) in 20 mL of $CH_2Cl_2$ at 0° C. was added 1M $TiCl_4$ in $CH_2Cl_2$ (0.5 mmol) all at once. After 30 min, (1-methoxy-2-methylprop-1-enyloxy)trimethylsilane (0.24 mL, 1.2 mmol) was added and the reaction was warmed to rt and stirred overnight. The reaction was quenched with water and extracted with $CH_2Cl_2$. The $CH_2Cl_2$ extracts were dried over $MgSO_4$, filtered, and concentrated by rotary evaporator to give methyl 3-(1-(4-fluorophenyl)-1H-indazol-5-yl)-2,2,5-trimethylhexanoate. MS found: $(M+H)^+=383$.

(c) Methyl 3-(1-(4-fluorophenyl)-1H-indazol-5-yl)-2,2,5-trimethylhexanoate (0.4 mmol) was dissolved in 5 mL of DMSO, 10 mL of 1 NaOH and 5 mL of MeOH and heated at 100° C. overnight. The reaction was quenched with sat. $KH_2PO_4$ and extracted with 2×EtOAc. The EtOAc extracts were dried over $MgSO_4$, filtered, and concentrated by rotary evaporator to give 3-(1-(4-fluorophenyl)-1H-indazol-5-yl)-2,2,5-trimethylhexanoic acid. MS found: $(M+H)^+=369$.

(d) 3-(1-(4-Fluorophenyl)-1H-indazol-5-yl)-2,2,5-trimethylhexanoic acid (0.2 mmol) was coupled with thiazol-2-amine (33 mg, 0.3 mmol) using General Coupling Method A. The product was purified by HPLC to give 52 mg (58%) of the desired product Example 33. MS found: $(M+H)^+=451$.

Example 34

3-(1-(4-Fluorophenyl)-1H-indazol-5-yl)-2,2,5-trimethyl-N-(1,3,4-thiadiazol-2-yl)hexanamide

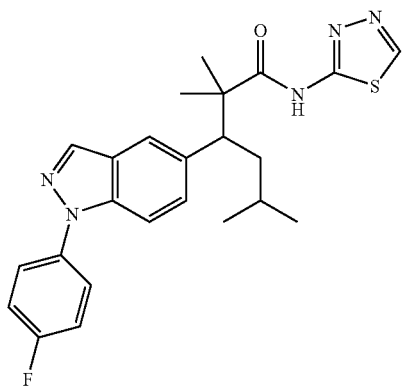

To a solution of 3-(1-(4-fluorophenyl)-1H-indazol-5-yl)-2,2,5-trimethylhexanoic acid (220 mg, 0.6 mmol) from Example 33(c) was coupled to 1,3,4-thiadiazol-2-amine (60 mg, 0.6 mmol) using General Coupling Method B. The product was purified by HPLC to give 33 mg (24%) of the desired product Example 34. MS found: $(M+H)^+=452$. NMR $(CDCl_3)$ δ 8.73 (s, 1H); 8.11 (s, 1H); 7.8-8.4 (bs, 1H) 7.55-7.61 (m, 3H); 7.49-7.51 (d, 1H); 7.28-7.30 (d, 1H); 7.14-7.19 (m, 3H); 3.31-3.36 (dd, 1H), 1.88-1.95 (dt, 1H); 1.26 (s, 3H); 1.15 (s, 3H); 0.6-0.8 (dd, 6H).

Example 35

3-Cyclopentyl-3-(1-(4-fluorophenyl)-1H-indazol-5-yl)-2,2-dimethyl-N-(thiazol-2-yl)propanamide

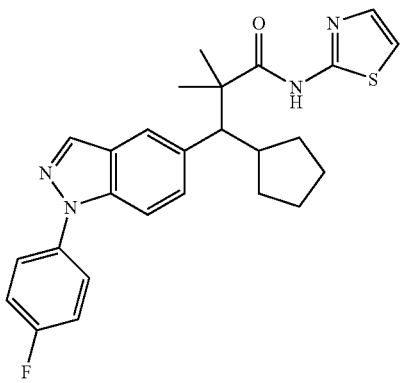

(a) To a solution of a solution of 2.0M cyclopentylmagnesium bromide in THF (8.0 mmol) was added 1-(4-fluorophenyl)-1H-indazole-5-carbaldehyde (200 mg, 0.832 mmol) from experimental (1e) in 5 mL of THF dropwise. After 1 hr, the reaction was quenched with sat. $NH_4Cl$ and extracted with 2×EtOAc. The EtOAc extracts were dried over $MgSO_4$, filtered, concentrated by rotary evaporator, and chromatographed on $SiO_2$ using EtOAc/hexanes (1:3) to give 75 mg of cyclopentyl (1-(4-fluorophenyl)-1H-indazol-5-yl)methanol. MS found: $(M+H)^+=311$.

(b) To a solution of cyclopentyl (1-(4-fluorophenyl)-1H-indazol-5-yl)methanol (75 mg, 0.24 mmol) in 20 mL of $CH_2Cl_2$ at 0° C. was added 1M $TiCl_4$ in $CH_2Cl_2$ (0.5 mmol) all at once. After 30 min, (1-methoxy-2-methylprop-1-enyloxy)trimethylsilane (0.2 mL, 1.0 mmol) was added and the reaction was warmed to rt and stirred overnight. The reaction was quenched with water and extracted with $CH_2Cl_2$. The $CH_2Cl_2$ extracts were dried over $MgSO_4$, filtered, and concentrated by rotary evaporator to give 80 mg of methyl 3-cyclopentyl-3-(1-(4-fluorophenyl)-1H-indazol-5-yl)-2,2-dimethylpropanoate. MS found: $(M+H)^+=395$.

(c) Methyl 3-cyclopentyl-3-(1-(4-fluorophenyl)-1H-indazol-5-yl)-2,2-dimethylpropanoate (80 mg, 0.2 mmol) was dissolved in 5 mL of DMSO, 10 mL of 1 NaOH and 5 mL of MeOH and heated at 100° C. overnight. The reaction was quenched with sat. $KH_2PO_4$ and extracted with 2×EtOAc. The EtOAc extracts were dried over $MgSO_4$, filtered, and concentrated by rotary evaporator to give 3-cyclopentyl-3-(1-(4-fluorophenyl)-1H-indazol-5-yl)-2,2-dimethylpropanoic acid. MS found: $(M+H)^+=381$.

(d) 3-Cyclopentyl-3-(1-(4-fluorophenyl)-1H-indazol-5-yl)-2,2-dimethylpropanoic acid (40 mg, 0.105 mmol) was coupled with thiazol-2-amine (20 mg, 0.2 mmol) using General Coupling Method A. The product was purified by HPLC to give 13 mg (31%) of the desired product Example 35. MS found: $(M+H)^+=463$. NMR$(CDCl_3)$ δ 8.19 (s, 1H); 7.92 (bs, 1H) 7.67-7.71 (m, 2 H); 7.55-7.59 (m, 2H); 7.22-

7.26 (m, 4H); 7.10 (d, 1H); 3.33-3.36 (d, 1H), 2.38-2.43 (m, 1H); 1.63-1.77 (m, 1H); 1.20-1.70 (m, 6H); 1.45 (s, 3H); 0.8-1.0 (m, 2H).

Example 36

3-(1-(4-Fluorophenyl)-1H-indazol-5-yl)-2,2-dimethyl-3-(pyridin-4-yl)-N-(thiazol-2-yl)propanamide

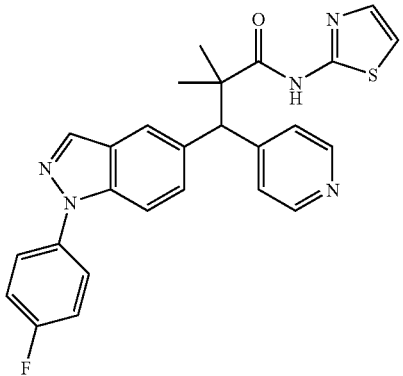

(a) To a solution of a solution of 4-pyridylmagnesium bromide in THF, which was prepared by treating 4-iodopyridine (590 mg, 2.88 mmol) in 5 mL of THF with 1.5 mL of 2.0M ethylmagnesium bromide at 0° C., was added 1-(4-fluorophenyl)-1H-indazole-5-carbaldehyde (200 mg, 0.832 mmol) in 5 mL of THF dropwise. After 2 hr, the reaction was quenched with sat. NH$_4$Cl and extracted with 2×EtOAc. The EtOAc extracts were dried over MgSO$_4$, filtered, concentrated by rotary evaporator, and chromatographed on SiO$_2$ using EtOAc/hexanes (1:2) to give 230 mg of (1-(4-fluorophenyl)-1H-indazol-5-yl)(pyridin-4-yl)methanol. MS found: (M+H)$^+$=320.

(b) To a solution of (1-(4-fluorophenyl)-1H-indazol-5-yl)(pyridin-4-yl)methanol (130 mg, 0.407 mmol) in 20 mL of CH$_2$Cl$_2$ at 0° C. was added 1M TiCl$_4$ in CH$_2$Cl$_2$ (0.5 mmol) all at once. After 30 min, (1-methoxy-2-methylprop-1-enyloxy)trimethylsilane (0.2 mL, 1.0 mmol) was added and the reaction was warmed to rt and stirred overnight. The reaction was quenched with water and extracted with CH$_2$Cl$_2$. The CH$_2$Cl$_2$ extracts were dried over MgSO$_4$, filtered, concentrated by rotary evaporator, and chromatographed on SiO$_2$ using EtOAc/hexanes (1:1) to give 110 mg of methyl 3-(1-(4-fluorophenyl)-1H-indazol-5-yl)-2,2-dimethyl-3-(pyridin-4-yl)propanoate. MS found: (M+H)$^+$=395.

(c) Methyl 3-(1-(4-fluorophenyl)-1H-indazol-5-yl)-2,2-dimethyl-3-(pyridin-4-yl)propanoate (80 mg, 0.2 mmol) was dissolved in 10 mL of DMSO, 10 mL of 1 NaOH and 10 mL of MeOH and heated at 100° C. overnight. The reaction was quenched with sat. NaCl and extracted with 2×EtOAc. The EtOAc extracts were dried over MgSO$_4$, filtered, and concentrated by rotary evaporator to give 95 mg of 3-(1-(4-fluorophenyl)-1H-indazol-5-yl)-2,2-dimethyl-3-(pyridin-4-yl)propanoic acid. MS found: (M+H)$^+$=390.

(d) 3-(1-(4-Fluorophenyl)-1H-indazol-5-yl)-2,2-dimethyl-3-(pyridin-4-yl)propanoic acid (46 mg, 0.11 mmol) was coupled with thiazol-2-amine (22 mg, 0.22 mmol) using General Coupling Method A. The product was purified by HPLC to give 12 mg (23%) of Example 36. MS found: (M+H)$^+$=472.

Example 37

3-(1-(4-Fluorophenyl)-1H-indazol-5-yl)-2,2-dimethyl-3-(pyridin-4-N-oxide-yl)-N-(thiazol-2-yl)propanamide

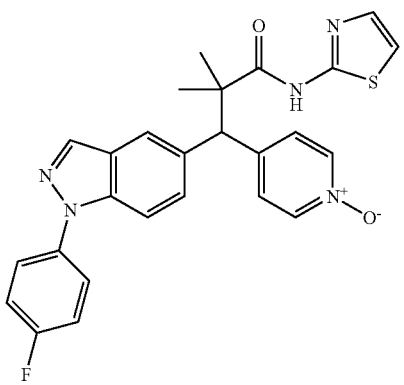

(a) To a solution of 3-(1-(4-fluorophenyl)-1H-indazol-5-yl)-2,2-dimethyl-3-(pyridin-4-yl)propanoic acid (49 mg, 0.126 mmol, from 36(c)) in 10 mL of CH$_2$Cl$_2$ was added m-chloro-perbenzoic acid (MCPBA) (43 mg, 0.25 mmol). The reaction was stirred for 2 hr and then concentrated by rotary evaporator to give crude product 4-(2-carboxy-1-(1-(4-fluorophenyl)-1H-indazol-5-yl)-2-methylpropyl)pyridine 1-oxide.

(b) 4-(2-Carboxy-1-(1-(4-fluorophenyl)-1H-indazol-5-yl)-2-methylpropyl)pyridine 1-oxide (0.126 mmol) was coupled with thiazol-2-amine (50 mg, 0.50 mmol) using General Coupling Method A. The product was purified by HPLC followed by chromatography on SiO$_2$ using EtOAc/MeOH (85:15) to give 9 mg (15%) of Example 37. MS found: (M+H)$^+$=488.

Example 38

3-Cyclohexyl-3-(1-(4-fluorophenyl)-1H-indazol-5-yl)-2,2-dimethyl-N-(thiazol-2-yl)propanamide

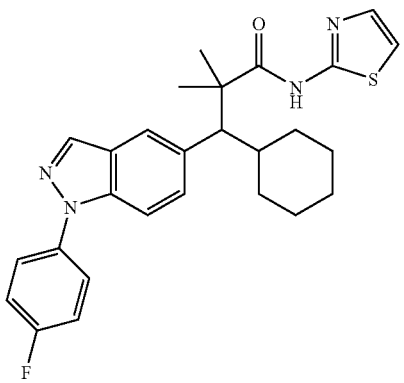

(a) To a solution of 2.0M cyclohexylmagnesium bromide in THF (8.0 mmol) was added 1-(4-fluorophenyl)-1H-indazole-5-carbaldehyde (200 mg, 0.832 mmol) in 5 mL of THF dropwise. After 1 hr, the reaction was quenched with sat. NH$_4$Cl and extracted with 2×EtOAc. The EtOAc extracts were dried over MgSO$_4$, filtered, and concentrated by rotary evaporator to give cyclohexyl(1-(4-fluorophenyl)-1H-indazol-5-yl)methanol. MS found: (M+H)$^+$=325.

(b) To a solution of cyclohexyl(1-(4-fluorophenyl)-1H-indazol-5-yl)methanol (0.83 mmol) in 20 mL of CH$_2$Cl$_2$ at 0° C. was added 1M TiCl$_4$ in CH$_2$Cl$_2$ (1.6 mmol) all at once. After 30 min, (1-methoxy-2-methylprop-1-enyloxy)trimethylsilane (0.65 mL, 3.2 mmol) was added and the reaction was warmed to rt and stirred overnight. The reaction was quenched with water and extracted with CH$_2$Cl$_2$ The CH$_2$Cl$_2$ extracts were dried over MgSO$_4$, filtered, and concentrated by rotary evaporator to give methyl 3-cyclohexyl-3-(1-(4-fluorophenyl)-1H-indazol-5-yl)-2,2-dimethylpropanoate. MS found: (M+H)$^+$=409.

(c) Methyl 3-cyclohexyl-3-(1-(4-fluorophenyl)-1H-indazol-5-yl)-2,2-dimethylpropanoate (0.83 mmol) was dissolved in 20 mL of DMSO, 20 mL of 1 NaOH and 20 mL of MeOH and heated at 100° C. overnight. The reaction was quenched with sat. NaCl and extracted with 2×EtOAc. The EtOAc extracts were dried over MgSO$_4$, filtered, and concentrated by rotary evaporator to give 78 mg of 3-cyclohexyl-3-(1-(4-fluorophenyl)-1H-indazol-5-yl)-2,2-dimethylpropanoic acid. MS found: (M+H)$^+$=381.

(d) 3-Cyclohexyl-3-(1-(4-fluorophenyl)-1H-indazol-5-yl)-2,2-dimethylpropanoic acid (78 mg, 0.2 mmol) was coupled with thiazol-2-amine (50 mg, 0.5 mmol) using General Coupling Method A. The product was purified by HPLC to give 18 mg (19%) of the desired product Example 38. MS found: (M+H)$^+$=477.

Example 39

3-(1-(4-Fluorophenyl)-1H-indazol-5-yl)-2,2-dimethyl-N-(thiazol-2-yl)pentanamide

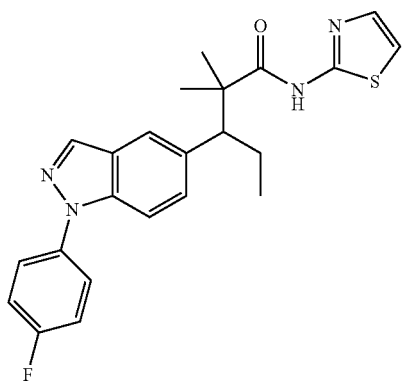

(a) To a solution of a solution of 1.0M ethylmagnesium bromide in THF (1.0 mmol) was added 1-(4-fluorophenyl)-1H-indazole-5-carbaldehyde (120 mg, 0.5 mmol) in 10 mL of THF dropwise. After 1 hr, the reaction was quenched with sat. NH$_4$Cl and extracted with 2×EtOAc. The EtOAc extracts were dried over MgSO$_4$, filtered, concentrated by rotary evaporator, and chromatographed on SiO$_2$ using EtOAc/hexanes (1:1) to give 120 mg of 1-(1-(4-fluorophenyl)-1H-indazol-5-yl)propan-1-ol. MS found: (M+H)$^+$=271.

(b) To a solution of 1-(1-(4-fluorophenyl)-1H-indazol-5-yl)propan-1-ol (120 mg, 0.44 mmol) in 10 mL of CH$_2$Cl$_2$ at 0° C. was added 1M TiCl$_4$ in CH$_2$Cl$_2$ (1.0 mmol) all at once. After 30 min, (1-methoxy-2-methylprop-1-enyloxy)trimethylsilane (0.2 mL, 1.0 mmol) was added and the reaction was warmed to rt and stirred overnight. The reaction was quenched with water and extracted with CH$_2$Cl$_2$. The CH$_2$Cl$_2$ extracts were dried over MgSO$_4$, filtered, and concentrated by rotary evaporator to give methyl 3-(1-(4-fluorophenyl)-1H-indazol-5-yl)-2,2-dimethylpentanoate. MS found: (M+H)$^+$=355.

(c) Methyl 3-(1-(4-fluorophenyl)-1H-indazol-5-yl)-2,2-dimethylpentanoate (0.44 mmol) was dissolved in 5 mL of DMSO, 10 mL of 1 NaOH and 5 mL of MeOH and heated at 100° C. overnight. The reaction was quenched with sat. KH$_2$PO$_4$ and extracted with 2×EtOAc. The EtOAc extracts were dried over MgSO$_4$, filtered, and concentrated by rotary evaporator to give 130 mg of 3-(1-(4-fluorophenyl)-1H-indazol-5-yl)-2,2-dimethylpentanoic acid. MS found: (M+H)$^+$=341.

(d) 3-(1-(4-Fluorophenyl)-1H-indazol-5-yl)-2,2-dimethylpentanoic acid (68 mg, 0.2 mmol) was coupled with thiazol-2-amine (33 mg, 0.3 mmol) using General Coupling Method A. The product was purified by HPLC to give 13 mg (15%) of Example 39. MS found: (M+H)$^+$=423. NMR (CDCl$_3$) δ 8.2 (s, 1H); 7.74 (s, 1H); 7.67-7.70 (m, 1H); 7.55-7.67 (m, 2H); 7.42-7.45 (m, 1H); 7.21-7.26 (m, 3H); 7.10 (d, 1H); 3.28-3.31 (dd, 1H); 1.88-1.97 (m, 1H); 1.50-1.56, (m, 1H); 1.34 (s, 3H); 1.21 (s, 3H); 0.6-0.8 (t, 3H).

Examples 40 to 56

Examples 40 to 56 in the Table below were prepared using the same method as used for Examples 33 to 39 with the M-M$_a$-MgBr reagent shown in the table.

| Ex. | Name | Product Structure | M-M$_a$-MgBr | (M + H)+ |
|---|---|---|---|---|
| 40 | 3-(1-(4-fluorophenyl)-1H-indazol-5-yl)-2,2-dimethyl-N-(thiazol-2-yl)-3-o-tolylpropanamide | 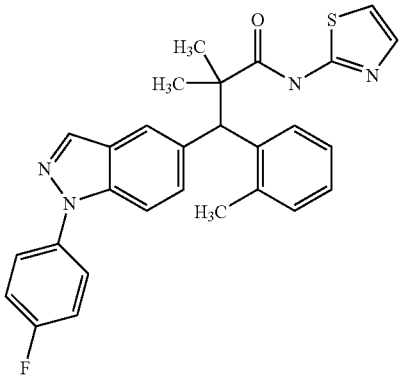 | 2-methyl-phenyl | 485 |
| 41 | 3-(1-(4-fluorophenyl)-1H-indazol-5-yl)-2,2-dimethyl-N-(thiazol-2-yl)-3-m-tolylpropanamide | 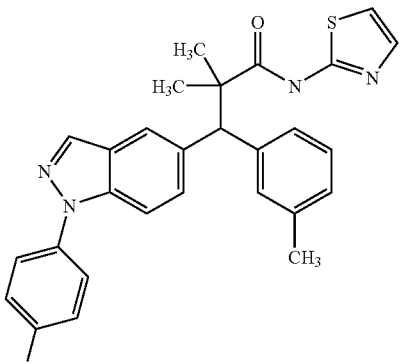 | 3-methyl-phenyl | 485 |
| 42 | 3-(1-(4-fluorophenyl)-1H-indazol-5-yl)-2,2-dimethyl-N-(thiazol-2-yl)-3-p-tolylpropanamide | 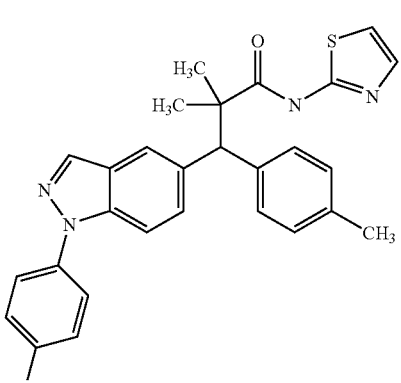 | 4-methyl-phenyl | 485 |
| 43 | 3-(3-fluorophenyl)-3-(1-4-fluorophenyl)-1H-indazol-5-yl)-2,2-dimethyl-N-(thiazol-2-yl)propanamide | 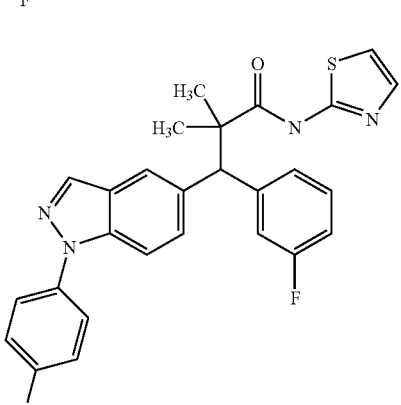 | 3-fluoro-phenyl | 489 |

| Ex. | Name | Product Structure | M-M$_a$-MgBr | (M + H)+ |
|---|---|---|---|---|
| 44 | 3-(4-fluorophenyl)-3-(1-(4-fluorophenyl)-1H-indazol-5-yl)-2,2-dimethyl-N-(thiazol-2-yl)propanamide | | 4-fluoro-phenyl | 489 |
| 45 | 3-(1-(4-fluorophenyl)-1H-indazol-5-yl)-2,2-dimethyl-N-(1,3,4-thiadazol-2-yl)hex-5-enamide | | allyl | 436 |
| 46 | 3-(1-(4-fluorophenyl)-1H-indazol-5-yl)-2,2-dimethyl-N-(1,3,4-thiadazol-2-yl)hexanamide | | propyl | 438 |

NMR (CDCl$_3$) δ 8.8 (s, 1 H); 8.17 (d, 1 H) 7.64-7.68 (m, 3 H); 7.57-7.59 (d, 1 H); 7.34-7.36 (dd, 1 H); 7.22-7.26 (m, 2 H); 3.29-3.32 (dd, 1 H), 1.90-1.96 (m, 1 H); 1.40-1.50 (m, 1 H); 1.38 (s, 3 H); 1.23 (s, 3 H); 1.0-1.14 (m, 2 H); 0.8 (t, 3 H).

| 47 | 3-cyclopropyl-3-(1-(4-fluorophenyl)-1H-indazol-5-yl)-2,2-dimethyl-N-(1,3,4-thiadiazol-2-yl)propanamide | | cyclopropyl | 436 |

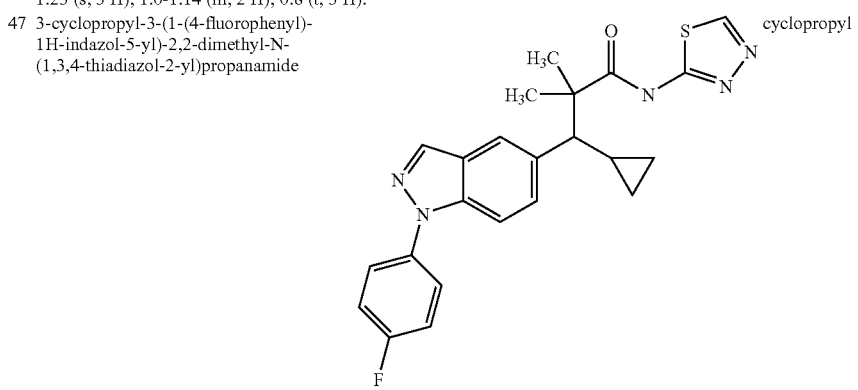

| Ex. | Name | Product Structure | M-M$_a$-MgBr | (M + H)+ |
|---|---|---|---|---|
| 48 | 3-(1-(4-fluorophenyl)-1H-indazol-5-yl)-2,2,4-trimethyl-N-(1,3,4-thiadiazol-2-yl)pentanamide | | isopropyl | 438 |

NMR (CDCl$_3$) δ 8.81 (s, 1 H); 8.21 (d, 1 H) 7.84 (s, 1 H); 7.65-7.70 (m, 2 H); 7.61-7.62 (d, 1 H); 7.47-7.50 (d, 1 H); 7.23-7.27 (m, 2 H); 3.22-3.24 (d, 1 H), 2.26-2.31 (m, 1 H); 1.52 (s, 3 H); 0.97 (s, 3 H); 0.90-0.92 (d, 3 H); 0.69-0.71 (d, 3 H).

| Ex. | Name | Product Structure | M-M$_a$-MgBr | (M + H)+ |
|---|---|---|---|---|
| 49 | 3-(1-(4-fluorophenyl)-1H-indazol-5-yl)-2,2-dimethyl-N-(1,3,4-thiadiazol-2-yl)-3-o-tolylpropanamide | | 2-methyl-phenyl | 486 |
| 50 | 3-(1-(4-fluorophenyl)-1H-indazol-5-yl)-2,2-dimethyl-N-(1,3,4-thiadiazol-2-yl)-3-m-tolylpropanamide | | 3-methyl-phenyl | 486 |
| 51 | 3-(1-(4-fluorophenyl)-1H-indazol-5-yl)-2,2-dimethyl-N-(1,3,4-thiadiazol-2-yl)-3-p-tolylpropanamide | | 4-methyl-phenyl | 486 |

| Ex. | Name | Product Structure | M-M$_a$-MgBr | (M + H)+ |
|---|---|---|---|---|
| 52 | 3-(3-fluorophenyl)-3-(1-(4-fluorophenyl)-1H-indazol-5-yl)-2,2-dimethyl-N-(1,3,4-thiadiazol-2-yl)propanamide | | 3-fluoro-phenyl | 490 |
| 53 | 3-(4-fluorophenyl)-3-(1-(4-fluorophenyl)-1H-indazol-5-yl)-2,2-dimethyl-N-(1,3,4-thiadiazol-2-yl)propanamide | | 4-fluoro-phenyl | 490 |
| 54 | 3-(1-(4-fluorophenyl)-1H-indazol-5-yl)-2,2,5-trimethyl-N-(1,3,4-thiadiazol-2-yl)hex-5-enamide | | 2-methylallyl | 450 |
| 55 | (E)-3-(1-(4-fluorophenyl)-1H-indazol-5-yl)-2,2-dimethyl-N-(1,3,4-thiadiazol-2-yl)hept-5-enamide | | but-2-enyl | 450 |

| Ex. | Name | Product Structure | M-M$_a$-MgBr | (M + H)+ |
|---|---|---|---|---|
| 56 | 3-(1-(4-fluorophenyl)-1H-indazol-5-yl)-2,2,5-trimethyl-N-(1,3,4-thiadiazol-2-yl)hex-4-enamide | | (2-methylprop-1-enyl) | 450 |

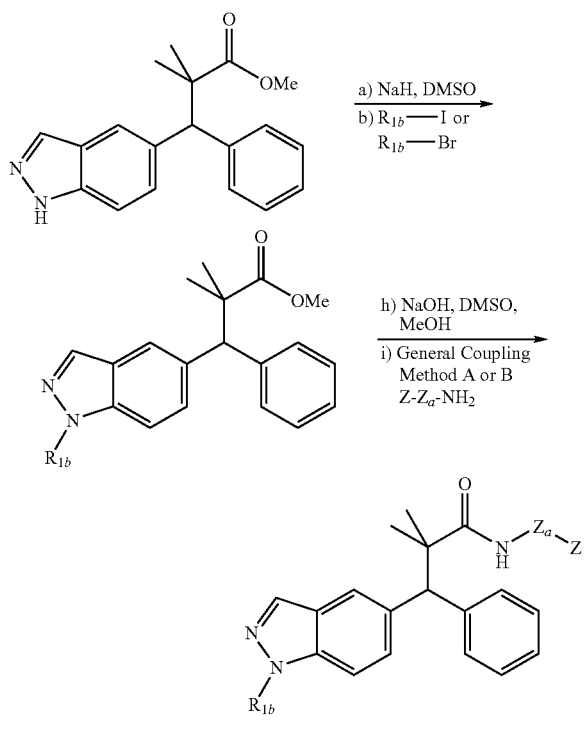

SCHEME E

SCHEME F

Alkylation of Indazoles, General Procedure A

Shell vials were charged with methyl 3-(1H-indazol-5-yl)-2,2-dimethyl-3-phenylpropanate (150 mg, 0.49 mmol) in 2 mL THF and NaH (69 mg of 60% oil immersed, 1.8 mmol) was added under N$_2$. After foaming subsided (about 10 min), the alkylating agent (2.24 mmol, 4.6 equiv) was added neat and the reactions were heated to reflux for 16 hr. The reactions were cooled, concentrated by rotary evaporation, diluted with 2 mL DMSO, 1 mL MeOH, and 1 mL 5M NaOH and heated for another 16 hr. The crude N-alkylated acids were purified by HPLC and lyophilized to give pure acids which were confirmed by LC-MS and then coupled to a Z—Z$_a$—NH$_2$ amine using General Coupling Method A. The alkylation reactions gave mixtures of the N-1 and N-2 alkylated indazoles (typically in a 1:1-3:1 ratio favoring N-1) which could be separated by HPLC at the acid stage (and coupled independently) or separated at the final amide stage after coupling.

Alkylation of Indazoles, General Procedure B

Shell vials were charged with methyl 3-(1H-indazol-5-yl)-2,2-dimethyl-3-phenylpropanate (150 mg, 0.49 mmol) in 2 mL dry DMSO followed by NaN(TMS)$_2$ (0.73 mmol, 730 uL of 1.0 M THF solution) under N$_2$. The orange solutions were treated with alkylator (0.73 mmol, 1.5 equiv) and heated to 85° C. for 72 hr. The reactions were cooled, concentrated by rotary evaporation, diluted with 2 mL DMSO, 1 mL MeOH, and 1 mL 5M NaOH and heated for another 16 hr. The crude N-alkylated acids were purified by HPLC and lyophilized to give pure acids which were coupled to a Z—Z$_a$—NH$_2$ amine using General Coupling Method A. The alkylation reactions gave mixtures of the N-1 and N-2 alkylated indazoles which could be separated by HPLC at the acid stage (and coupled independently) or separated at the final amide stage after coupling.

Examples 57 to 78

The procedures of Scheme E (General Procedure A) or Scheme F (General Procedure B) were employed to prepare the Examples 57 to 78 compounds.

| Ex. | Name | Product Structure | Alkylating Agent | Method | (M + H)+ |
|---|---|---|---|---|---|
| 57 | 3-(1-(2-hydrox-ethyl)-1H-indazol-5-yl)-2,2-dimethyl-3-phenyl-N-(thiazol-2-yl)propanamide | | TBSOCH$_2$CH$_2$Br[1] | B | 421 |
| 58 | 2,2-dimethyl-3-phenyl-3-(1-(tetrahydro-2H-pyran-4-yl)-1H-indazol-5-yl)-N-(thiazol-2-yl)propanamide | | | A | 461 |

400 MHz $^1$H-NMR (DMSO-d6) δ 11.9 (s, 1 H); 7.98 (s, 1 H); 7.72 (s, 1 H); 7.38 (d, 1 H); 7.38 (d, 1 H); 7.31 (d, 2 H); 7.20 (m, 3 H); 7.08 (d, 1 H); 7.07 (d, 1 H); 4.97 (s, 1 H); 4.72 (m, 1 H); 3.93 (dd, 2 H); 3.48 (app t, 2 H); 2.05 (m, 2 H); 1.8 (dd, 2 H); 1.27 (s, 6 H).

| | | | | | |
|---|---|---|---|---|---|
| 59 | 2,2-dimethyl-3-(1-(1-methylpiper-idin-4-yl)-1H-indazol-5-yl)-3-phenyl-N-(thiazol-2-yl)propanamide | | | A | 474 |
| 60 | 2,2-dimethyl-3-(1-(methylsulfonylmethyl)-1H-indazol-5-yl)-3-phenyl-N-(thiazol-2-yl)propanamide | | [2] | A | 469 |

-continued

| Ex. | Name | Product Structure | Alkylating Agent | Method | (M + H)+ |
|---|---|---|---|---|---|
| 61 | 3-(1-isopropyl-1H-indazol-5-yl)-2,2-dimethyl-3-phenyl-N-(thiazol-2-yl)propanamide | | 2-iodopropane | A | 419 |
| | 400 MHz ¹H-NMR (DMSO-d6) δ 12.0 (s, 1 H); 7.98 (s, 1 H); 7.74 (s, 1 H); 7.53 (d, 1 H); 7.41 (d, 1 H); 7.35 (d, 2 H); 7.23 (m, 3 H); 7.14 (m, 2 H); 5.00 (s, 1 H); 4.88 (m, 1 H); 1.43 (d, 6 H); 1.30 (s, 6 H). | | | | |
| 62 | 3-(2-isopropyl-2H-indazol-5-yl)-2,2-dimethyl-3-phenyl-N-(1,3,4-thiadiazol-2-yl)propanamide | | 2-iodopropane | A | 419 |
| | 400 MHz ¹H-NMR (DMSO-d6) δ 11.9 (s, 1 H); 8.32 (s, 1 H); 7.67 (s, 1 H); 7.41 (m, 2 H); 7.33 (d, 2 H); 7.23 (t, 2 H); 7.21 (t, 1 H); 7.11 (d, 1 H); 7.08 (dd, 1 H); 4.96 (s, 1 H); 4.73 (m, 1 H); 1.52 (d, 6 H); 1.30 (d, 6 H). | | | | |
| 63 | 3-(1-isopropyl-1H-indazol-5-yl)-2,2-dimethyl-3-phenyl-N-(1,3,4-thiadiazol-2-yl)propanamide | | 2-iodopropane | A | 420 |
| 64 | 2,2-dimethyl-3-(1-(methylsulfonylmethyl)-1H-indazol-5-yl)-3-phenyl-N-(1,3,4-thiadiazol-2-yl)propanamide | | $\text{MeSCH}_2\text{Cl}^2$ | A | 470 |
| 65 | 3-(1-(2-hydroxyethyl)-1H-indazol-5-yl)-2,2-dimethyl-3-phenyl-N-(1,3,4-thiadiazol-2-yl)propanamide | | TBSOCH₂CH₂Br¹ | B | 422 |

-continued

| Ex. | Name | Product Structure | Alkylating Agent | Method | (M + H)+ |
|---|---|---|---|---|---|
| 66 | 3-(1-isopentyl-1H-indazol-5-yl)-2,2-dimethyl-3-phenyl-N-(1,3,4-thiadiazol-2-yl)propanamide | | | B | 448 |
| 67 | 3-(2-isopentyl-2H-indazol-5-yl)-2,2-dimethyl-3-phenyl-N-(1,3,4-thiadiazol-2-yl)propanamide | | | B | 448 |
| 68 | 3-(1-butyl-1H-indazol-5-yl)-2,2-dimethyl-3-phenyl-N-(1,3,4-thiadiazol-2-yl)propanamide | | iodobutane | B | 434 |
| 69 | 3-(2-(3-methoxy-propyl)-2H-indazol-5-yl)-2,2-dimethyl-3-phenyl-N-(1,3,4-thiadiazol-2-yl)propanamide | | | B | 450 |
| 70 | 3-(1-isobutyl-1H-indazol-5-yl)-2,2-dimethyl-3-phenyl-N-(1,3,4-thiadiazol-2-yl)propanamide | | | B | 434 |

-continued

| Ex. | Name | Product Structure | Alkylating Agent | Method | (M + H)+ |
|---|---|---|---|---|---|
| 71 | 3-(1-(3-methoxypropyl-1H-indazol-5-yl)-2,2-dimethyl-3-phenyl-N-(1,3,4-thiadiazol-2-yl)propanamide | | 3-methoxypropyl bromide | B | 450 |
| 72 | 3-(1-benzyl-1H-indazol-5-yl)-2,2-dimethyl-3-phenyl-N-(1,3,4-thiadiazol-2-yl)propanamide | | benzyl bromide | B | 468 |
| 73 | 3-(2-benzyl-2H-indazol-5-yl)-2,2-dimethyl-3-phenyl-N-(1,3,4-thiadiazol-2-yl)propanamide | | benzyl bromide | B | 468 |
| 74 | 2,2-dimethyl-3-(1-phenethyl-1H-indazol-5-yl)-3-phenyl-N-(1,3,4-thiadiazol-2-yl)propanamide | | bromoethyl benzene | B | 482 |

-continued

| Ex. | Name | Product Structure | Alkylating Agent | Method | (M + H)+ |
|---|---|---|---|---|---|
| 75 | 3-(1-(3-hydroxypropyl)-1H-indazol-5-yl)-2,2-dimethyl-3-phenyl-N-(1,3,4-thiadiazol-2-yl)propanamide | | TBSO(CH$_2$)$_3$Br[1] | B | 436 |
| 76 | 3-(1-(4-hydroxybutyl)-1H-indazol-5-yl)-2,2-dimethyl-3-phenyl-N-(1,3,4-thiadiazol-2-yl)propanamide | | TBSO(CH$_2$)$_4$Br[1] | B | 450 |
| 77 | 3-(2-(4-hydroxybutyl)-2H-indazol-5-yl)-2,2-dimethyl-3-phenyl-N-(1,3,4-thiadiazol-2-yl)propanamide | | TBSO(CH$_2$)$_4$Br[1] | B | 450 |
| 78 | 3-(1-cycloheptyl-1H-indazol-5-yl)-2,2-dimethyl-3-phenyl-N-(1,3,4-thiadiazol-2-yl)propanamide | | bromo-cycloheptane | B | 474 |

[1]Examples 57, 65, 75, 76, and 77 used a t-butyldimethylsilyl oxygen protecting group. During the ester hydrolysis (step c), this group was removed. Amine coupling (step d) proceeded smoothly thereafter.

[2]Examples 60 and 64 were treated with an additional step of mCPBA (2 equivs) oxidation of the sulfide to the sulfone after alkylation (step b) was complete. Saponification and amine coupling proceeded smoothly thereafter.

SCHEME G

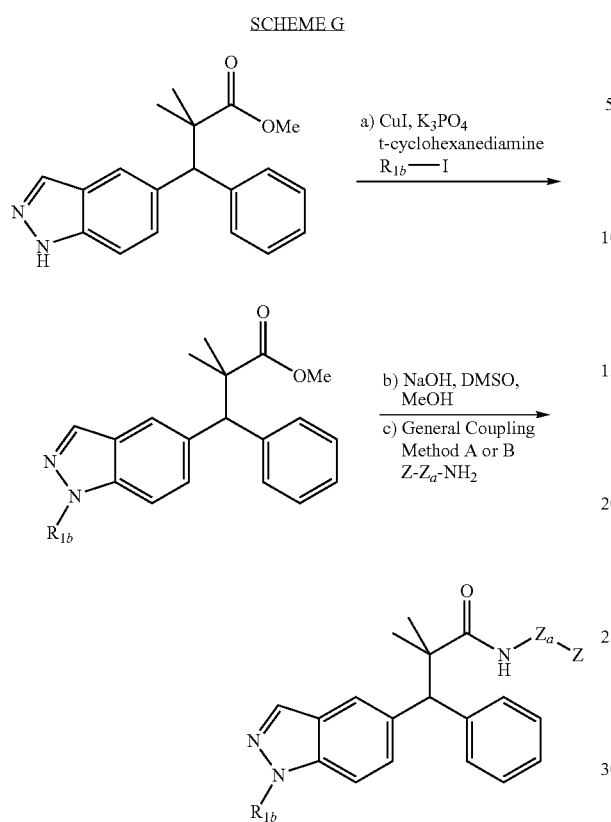

a) CuI, K₃PO₄
t-cyclohexanediamine
$R_{1b}$—I b) NaOH, DMSO, MeOH c) General Coupling Method A or B
Z-$Z_a$-NH₂

Arylation of Indazoles, General Procedure C

Methyl 3-(1H-indazol-5-yl)-2,2-dimethyl-3-phenylpropanoate (150 mg, 0.5 mmol) was dissolved in 1 mL dry dioxane in a 5 mL sealed tube vessel followed by the addition of and then K₃PO₄ (208 mg, 1.0 mmol), trans-1,2-cyclohexanediamine (6 uL, 0.1 mmol) and CuI (5 mg, 0.05 mmol). After the addition of the aryl iodide (0.54 mmol), the reactor was sealed and heated at 100° C. for 24 h. The reactor was cooled, opened, and the contents were filtered through a disposable frit with EtOAc and concentrated in vacuo. Each crude intermediate was taken up in 2 mL DMSO, diluted with 1 mL water and 1 mL MeOH, and treated with 2 mL 5 M NaOH and refluxed for 16 h. The following day, each reaction was carefully acidified with 3 mL TFA and purified by HPLC.

The purified penultimate acids (confirmed by MS) were then coupled to a Z—$Z_a$—NH₂ amine and purified using General Coupling Method A or B.

SCHEME H

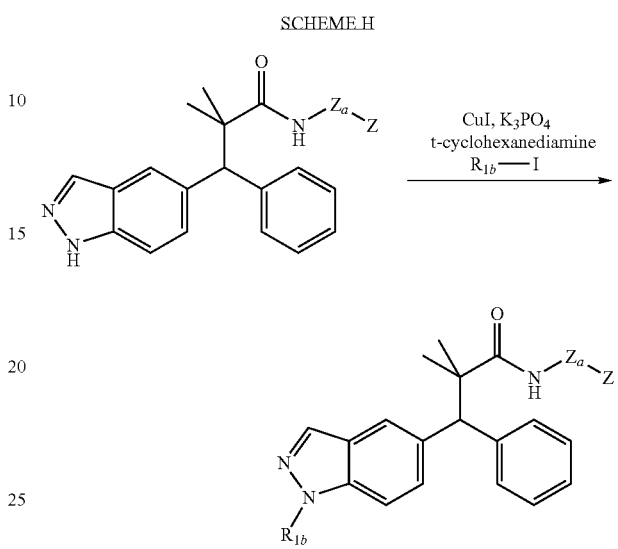

CuI, K₃PO₄
t-cyclohexanediamine
$R_{1b}$—I

Arylation of Indazoles, General Procedure D

3-(1H-Indazol-5-yl)-2,2-dimethyl-3-phenyl-N-(1,3,4-thiadiazol-2-yl)propanamide (59 mg, 0.16 mmol) was dissolved in 1 mL dry dioxane in a 5 mL sealed tube vessel followed by the addition of K₃PO₄ (60 mg, 0.28 mmol), trans-1,2-cyclohexanediamine (9 uL, 0.08 mmol) and CuI (3 mg, 0.016 mmol). After the addition of the aryl iodide (0.19 mmol), the reactor was sealed and heated at 110° C. for 24 h. The reactor was cooled, opened, and the contents were filtered through a disposable frit with EtOAc and concentrated in vacuo, acidified with TFA, and purified by HPLC.

Examples 79 to 97

The Examples 79 to 97 compounds were prepared using the procedure of Scheme G (General Procedure C) or Scheme H (General Procedure D).

| Ex. | Name | Product Structure | aryl iodide | Method | (M + H)+ |
|---|---|---|---|---|---|
| 79 | 2,2-dimethyl-3-phenyl-3-(1-(pyridin-2-yl)-1H-indazol-5-yl)-N-(thiazol-2-yl)propanamide | *(structure shown)* | 2-iodo-pyridine | C | 454 |

-continued

| Ex. | Name | Product Structure | aryl iodide | Method | (M + H)+ |
|---|---|---|---|---|---|
| 80 | 2,2-dimethyl-3-phenyl-3-(1-(pyridin-2-yl)-1H-indazol-5-yl)-N-(1,3,4-thiadiazol-2-yl)propanamide | | 2-iodo-pyridine | C | 455 |
| 81 | 2,2-dimethyl-3-phenyl-3-(1-(pyridin-4-yl)-1H-indazol-5-yl)-N-(thiazol-2-yl)propanamide | | 4-iodo-pyridine | C | 454 |
| 82 | 2,2-dimethyl-3-phenyl-3-(1-(pyridin-4-yl)-1H-indazol-5-yl)-N-(1,3,4-thiadiazol-2-yl)propanamide | | 4-iodo-pyridine | C | 455 |
| 83 | 3-(1-(4-methoxyphenyl)-1H-indazol-5-yl)-2,2-dimethyl-3-phenyl-N-(1,3,4-thiadiazol-2-yl)propanamide | | 4-methoxy-1-iodobenzene | C | 484 |

-continued

| Ex. | Name | Product Structure | aryl iodide | Method | (M + H)+ |
|---|---|---|---|---|---|
| 84 | 3-(1-(4-hydroxyphenyl)-1H-indazol-5-yl)-2,2-dimethyl-3-phenyl-N-(1,3,4-thiadiazol-2-yl)propanamide | | —[1] | — | 470 |
| 85 | 2,2-dimethyl-3-phenyl-3-(1-(pyridin-3-yl)-1H-indazol-5-yl)-N-(thiazol-2-yl)propanamide | | 3-iodopyridine | C | 454 |

400 MHz $^1$H-NMR (DMSO-d6) δ 11.9 (s, 1 H); 8.99 (d, 1 H); 8.54 (d, 1 H); 8.38 (s, 1 H); 8.23 (d, 1 H); 7.88 (s, 1 H); 7.75 (d, 1 H); 7.62 (dd, 1 H); 7.39 (dd, 1 H); 7.36 (d, 1 H); 7.31 (d, 2 H); 7.20 (app t, 2 H); 7.1 (app t, 1 H); 7.07 (d, 1 H); 5.03 (s, 1 H); 1.28 (s, 6 H).

| 86 | 2,2-dimethyl-3-phenyl-3-(1-(pyridin-3-yl)-1H-indazol-5-yl)-N-(1,3,4-thiadiazol-2-yl)propanamide | | 3-iodopyridine | C | 455 |
| 87 | 2,2-dimethyl-3-phenyl-3-(1-phenyl-1H-indazol-5-yl)-N-(1,3,4-thiadiazol-2-yl)propanamide | | iodobenzene | D | 454 |

-continued

| Ex. | Name | Product Structure | aryl iodide | Method | (M + H)+ |
|---|---|---|---|---|---|
| 88 | methyl 4-(5-(3-(1,3,4-thiadiazol-2-ylamino)-2,2-dimethyl-3-oxo-1-phenylpropyl)-1H-indazol-1-yl)benzoate | | methyl 4-iodobenzoate | D | 512 |
| 89 | 4-(5-(3-(1,3,4-thiadiazol-2-ylamino)-2,2-dimethyl-3-oxo-1-phenylpropyl)-1H-indazol-1-yl)benzoic acid | | —² | D | 498 |
| 90 | 2,2-dimethyl-3-phenyl-N-(1,3,4-thiadiazol-2-yl)-3-(1-(4-(trifluoromethyl)phenyl)-1H-indazol-5-yl)propanamide | | 4-trifluoromethylbenzene | D | 522 |

-continued

| Ex. | Name | Product Structure | aryl iodide | Method | (M + H)+ |
|---|---|---|---|---|---|
| 91 | 3-(1-(4-bromophenyl)-1H-indazol-5-yl)-2,2-dimethyl-3-phenyl-N-(1,3,4-thiadiazol-2-yl)propanamide | | 4-bromo-1-iodobenzene | D | 533 |
| 92 | 3-(1-(4-fluoro-2-(trifluoromethyl)phenyl)-1H-indazol-5-yl)-2,2-dimethyl-3-phenyl-N-(1,3,4-thiadiazol-2-yl)proponamide | | 4-fluoro-2-trifluoromethyl-1-iodobenzene | D | 540 |
| 93 | 3-(1-(4-chlorophenyl)-1H-indazol-5-yl)-2,2-dimethyl-3-phenyl-N-(1,3,4-thiadiazol-2-yl)propanamide | | 4-chloro-1-iodobenzene | D | 489 |
| 94 | 3-(1-(3-methoxyphenyl)-1H-indazol-5-yl)-2,2-dimethyl-3-phenyl-N-(1,3,4-thiadiazol-2-yl)propanamide | | 3-methoxy-1-iodobenzene | D | 484 |

| Ex. | Name | Product Structure | aryl iodide | Method | (M + H)+ |
|---|---|---|---|---|---|
| 95 | ethyl 3-(5-(3-(1,3,4-thiadiazol-2-ylamino)-2,2-dimethyl-3-oxo-1-phenylpropyl)-1H-indazol-1-yl)benzoate | | Ethyl-3-iodo-benzoate | D | 526 |
| 96 | (3S)-3-(1-(4-fluoro-2-methoxyphenyl)-1H-indazol-5-yl)-2,2-dimethyl-3-phenyl-N-(1,3,4-thiadiazol-2-yl)propanamide | | 4-fluoro-1-iodo-2-methoxybenzene | C | 502 |
| 97 | (3S)-3-(1-(2-cyano-4-fluorophenyl)-1H-indazol-5-yl)-2,2-dimethyl-3-phenyl-N-(1,3,4-thiadiazol-2-yl)propanamide | | 2-cyano-4-fluoro-1-iodobenzene | C | 497 |

[1] Example 84 was synthesized by the demethylation of Example 83 (BBr$_3$, DCM).
[2] Example 89 came from the ester hydrolysis of Example 88 (NaOH, MeOH).

SCHEME I

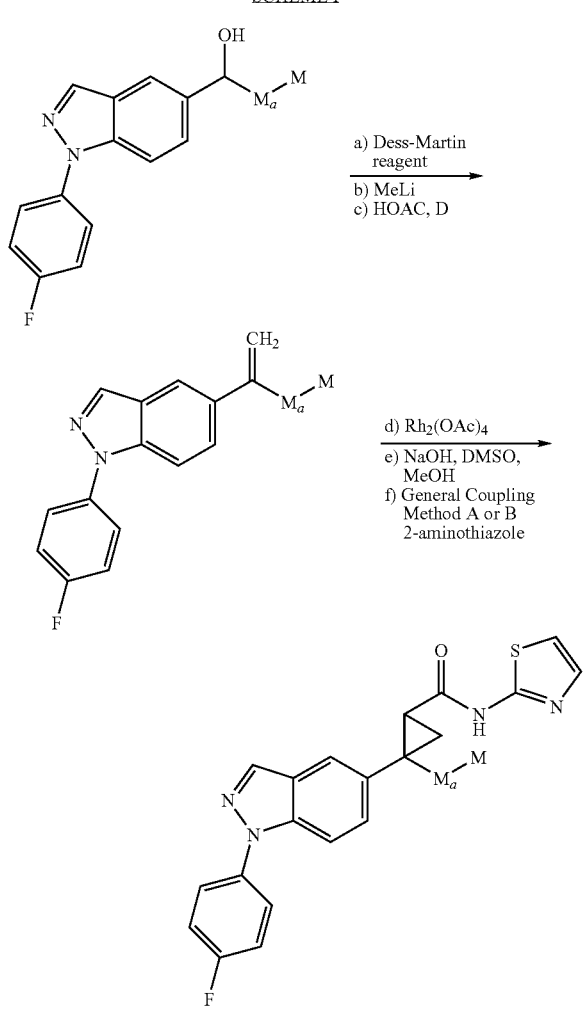

The procedure of Scheme I was used to prepare the Examples 98, 99 and 100.

Example 98

Trans-2-(1-(4-fluorophenyl)-1H-indazol-5-yl)-2-phenyl-N-(thiazol-2-yl)cyclopropanecarboxamide

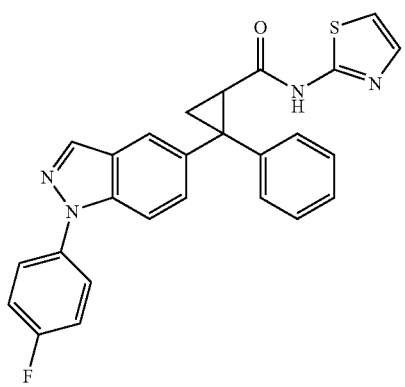

(a) To a solution of (1-(4-fluorophenyl)-1H-indazol-5-yl)(phenyl)methanol (1.2 g, 3.77 mmol) from experimental (1f) in 200 mL of $CH_2Cl_2$ was added Dess-Martin Periodinane (2.0 g, 4.71 mmol) portionwise. After 12 h, the reaction was quenched with 1M NaOH and extracted with 3×$CH_2Cl_2$. The $CH_2Cl_2$ extracts were dried over $MgSO_4$, filtered, and concentrated by rotary evaporator to give (1-(4-fluorophenyl)-1H-indazol-5-yl)(phenyl)methanone in 100% yield. MS found: $(M+H)^+$=317.

(b) To a solution of (1-(4-fluorophenyl)-1H-indazol-5-yl)(phenyl)methanone (710 mg, 2.24 mmol) 20 mL of THF at −78° C. was added 1.6M MeLi in THF (6.4 mmol). The reaction was warmed to rt and stirred for 2 hr. The reaction was quenched with water and extracted with 3×EtOAc. The EtOAc extracts were dried over $MgSO_4$, filtered, and concentrated by rotary evaporator.

(c) The crude residue was dissolved in 10 mL of acetic acid and heated at 100° C. for 12 h. The reaction was cooled and taken up in 100 mL of EtOAC then washed with 3×sat. $NaHCO_3$ The EtOAc extracts were dried over $MgSO_4$, filtered, concentrated by rotary evaporator, and chromatographed on $SiO_2$ using EtOAc/hexanes (5:95) to give 500 mg (71%) of 1-(4-fluorophenyl)-5-(1-phenylvinyl)-1H-indazole. MS found: $(M+H)^+$=309.

(d)(e) To a solution of 1-(4-fluorophenyl)-5-(1-phenylvinyl)-1H-indazole (600 mg, 1.91 mmol) and rhodium(II) acetate dimer (88 mg, 0.2 mmol) in 5 mL of diethyl ether was ethyl diazoacetate (1.0 mL, 9.5 mmol) dropwise over 3 hr. The reaction was stirred for 12 hr. Reaction was incomplete. Added more rhodium acetate and ethyl diazoacetate in the same amount as described above 3 times. The reaction was quenched with sat. NaCl and extracted with 3×EtOAc. The EtOAc extracts were dried over $MgSO_4$, filtered, and concentrated by rotary evaporator. The crude residue was dissolved in 20 mL of DMSO, 20 mL of 1 NaOH and 20 mL of MeOH and heated at 100° C. overnight. The reaction was quenched with sat. $KH_2PO_4$ and extracted with 2×EtOAc. The EtOAc extracts were dried over $MgSO_4$, filtered, concentrated by rotary evaporator, and chromatographed on $SiO_2$ using EtOAc/hexanes (1:9 to 1:3) to give a mixture of the cis and trans cyclopropyl derivatives. The cis and trans diastereomer were separated by HPLC to give trans-2-(1-(4-fluorophenyl)-1H-indazol-5-yl)-2-phenylcyclopropanecarboxylic acid and cis-2-(1-(4-fluorophenyl)-1H-indazol-5-yl)-2-phenylcyclopropanecarboxylic acid. MS found: $(M+H)^+$=373 for both.

(f) A solution of trans-2-(1-(4-fluorophenyl)-1H-indazol-5-yl)-2-phenylcyclopropane-carboxylic acid (120 mg, 0.32 mmol) was coupled with thiazol-2-amine (60 mg, 10 mmol) using General Coupling Method B. The product was purified by HPLC to give 65 mg of Example 98. MS found: $(M+H)^+$=455.

Example 99

Cis-2-(1-(4-fluorophenyl)-1H-indazol-5-yl)-2-phenyl-N-(thiazol-2-yl)cyclopropanecarboxamide

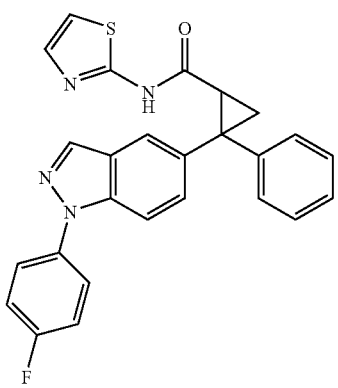

Cis-2-(1-(4-fluorophenyl)-1H-indazol-5-yl)-2-phenylcyclopropanecarboxylic acid was coupled with thiazol-2-amine (60 mg, 10 mmol) using general coupling method B. The product was purified by HPLC to give 45 mg of Example 99. MS found: (M+H)$^+$=455. NMR(MeOD) δ 8.15 (s, 1H); 7.85 (s, 1H) 7.64-7.66 (m, 2H); 7.52 (d, 1H); 7.38-7.41 (m, 4H); 7.25-7.29 (m, 4H); 7.18 (t, 1H); 7.0 (d, 1H); 2.9 (t, 1H), 2.37 (t, 1H); 1.80 (dd, 1H).

Example 100

Cis and trans-2-(1-(4-fluorophenyl)-1H-indazol-5-yl)-2-isobutyl-N-(thiazol-2-yl)cyclopropanecarboxamide

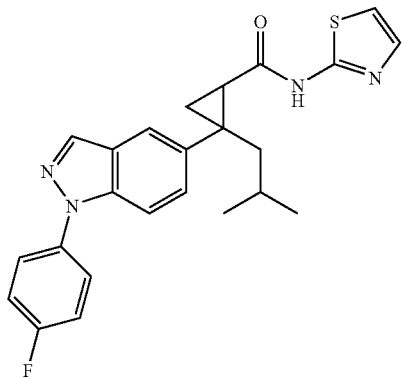

This compound was prepared using the exact same route as was used for Examples 98 and 99. The reaction started with 1-(1-(4-fluorophenyl)-1H-indazol-5-yl)-3-methylbutan-1-ol (Scheme I, $M_a$–M=iBu; prepared in Example 33(a)). MS found: (M+H)$^+$=435.

SCHEME I

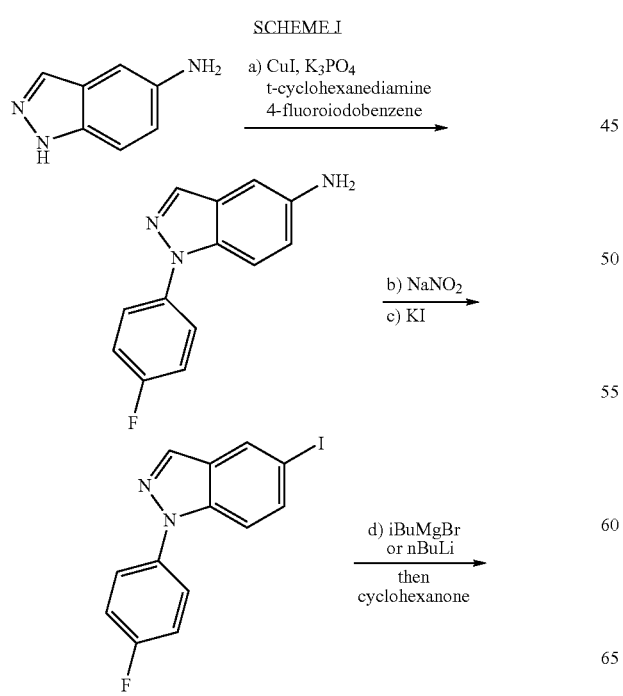

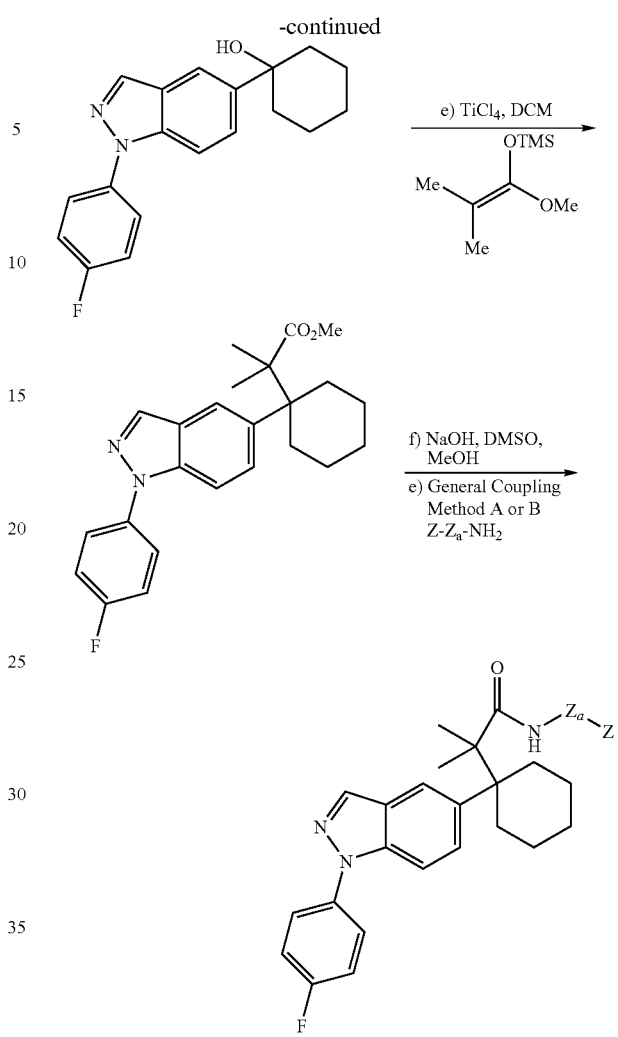

Example 101

2-(1-(1-(4-Fluorophenyl)-1H-indazol-5-yl)cyclohexyl)-2-methyl-N-(1,3,4-thiadiazol-2-yl)propanamide (a) Commercially available 5-aminoindazole (6.2 g, 46.6 mmol) was dissolved in 40 mL dry dioxane in a stainless steel bomb. Under a blanket of N₂ was added trans-1,2-diaminocyclohexane (2.8 mL, 23.3 mmol), CuI (890 mg, 4.66 mmol), 1-fluoro-4-iodobenzene (10.3 g, 46.6 mmol), and K₃PO₄ (17.8 g, 83.9 mmol). The reactor was sealed and heated to 110° C. for 16 h. The crude reaction was extracted from a mixture of NH₄OH/NH₄Cl with EtOAc×3. The combined organic layers were dried over MgSO₄, filtered, concentrated in vacuo, and purified using a 330 g SiO₂ MPLC column with EtOAc. Obtained 8.11 g of red solid 1-(4-fluorophenyl)-1H-indazol-5-amine. MS found: (M+H)⁺=228.

(b)(c) 1-(4-Fluorophenyl)-1H-indazol-5-amine (4.0 g, 17.6 mmol) was suspended in 6 M HCl and 20 mL dioxane. Sodium nitrite (1.22 g, 17.6 mmol) dissolved in 15 mL water was added portionwise. After 1 h, potassium iodide dissolved in 10 mL water was added and after 6 h, additional KI (1.46 g) was added. After a total of 18 h, the reaction was carefully quenched with sat. sodium metabisulfite and extracted with ether ×3. The organic layers were dried with MgSO₄, concentrated in vacuo, filtered, and chromatographed on a 330 g SiO₂ MPLC column using 25% EtOAc in hexanes. Obtained 2.1 g (35%) of off-white solid 1-(4-fluorophenyl)-5-iodo-1H-indazole. MS found: (M+H)⁺=339.

(d) 1-(4-Fluorophenyl)-5-iodo-1H-indazole (2.0 g, 5.9 mmol) was dissolved in dry THF (30 mL), cooled to −78° C., and treated with nBuLi (4 mL, 1.6 M in hexanes, 6.5 mmol). After 1 h, cyclohexanone (919 uL, 8.88 mmol) was added all at once and the reaction was allowed to warm to rt. The crude reaction was extracted from water using EtOAc and the combined organic layers were dried with MgSO₄, concentrated in vacuo, filtered, and chromatographed on a SiO₂ MPLC column using 25% EtOAc in hexanes. Obtained 700 mg (38%) of 1-(1-(4-fluorophenyl)-1H-indazol-5-yl)cyclohexanol. MS found: (M+H)⁺=311.

(e) To a solution of 1-(1-(4-fluorophenyl)-1H-indazol-5-yl)cyclohexanol (500 mg, 1.6 mmol) in DCE (20 mL) was added 1-methoxy-2-methyl-1-trimethylsiloxy-propene (935 uL, 4.8 mmol) followed by TiCl₄ (1.7 mL of 1.0 M in DCM). Within 10 min, the reaction was complete. The reaction was quenched with MeOH and then extracted from brine containing dilute HCl with EtOAc×4. The organic layers were dried over MgSO₄, filtered, concentrated and purified on SiO₂ using 25% EtOAc in hexanes to give 635 mg (100%) of methyl 2-(1-(1-(4-fluorophenyl)-1H-indazol-5-yl)cyclohexyl)-2-methylprop-anoate MS found: (M+H)⁺=395.

(f) Methyl 2-(1-(1-(4-fluorophenyl)-1H-indazol-5-yl)cyclohexyl)-2-methylpropanoate (635 mg, 1.61 mmol) was dissolved in 4 mL pyridine and transferred to a microwave reactor. Potassium cyanide (419 mg, 6.45 mmol) and LiI (864 mg, 6.45 mmol) were added and the reactor was sealed under nitrogen and heated in a microwave for 30 min at 180° C. The reaction was extracted from 1 M HCl using EtOAc×4 (lots of black, insoluble precipitate). The organic layers were dried, concentrated, and purified by MPLC on SiO₂ using 1:1 EtOAc/hexanes. Obtained 115 mg (19%) of off white powder 2-(1-(1-(4-fluorophenyl)-1H-indazol-5-yl)cyclohexyl)-2-methylpropanoic acid.

(g) 2-(1-(1-(4-fluorophenyl)-1H-indazol-5-yl)cyclohexyl)-2-methylpropanoic acid (27 mg, 0.07 mmol) was coupled with 2-amino-1,3,4-thiadiazole using General Coupling Method B. The product was purified by HPLC to give 2 mg of Example 101. MS found: (M+H)⁺=464.

Example 102

2-(1-(1-(4-Fluorophenyl)-1H-indazol-5-yl)cyclohexyl)-2-methyl-N-(thiazol-2-yl)propanamide

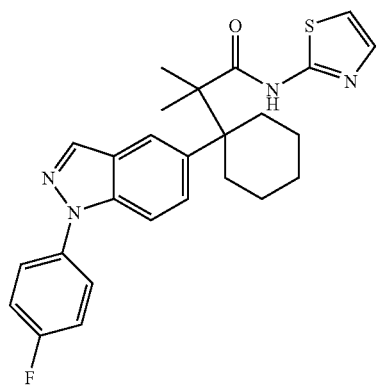

2-(1-(1-(4-Fluorophenyl)-1H-indazol-5-yl)cyclohexyl)-2-methylpropanoic acid (53 mg, 0.14 mmol) was coupled with 2-aminothiazole using General Coupling Method B. The product was purified by HPLC to give 20 mg of Example 102. MS found: (M+H)⁺=463. NMR (DMSO-d6) δ 11.0 (s, 1H); 8.26 (s, 1H) 7.68-7.72 (m, 3H); 7.58-7.61 (d, 1H); 7-33-7.40 (m, 3H); 7.27-7.29 (dd, 1H); 7.13-7.14 (dd, 1H); 2.5-2.6 (m, 2H); 1.40-1.60 (m, 4H); 1.30-1.38 (m, 1H) 1.0-1.15 (m, 9H).

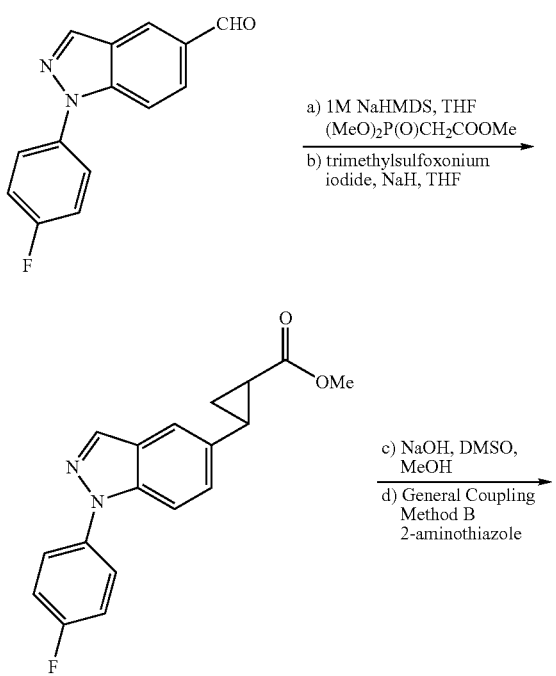

SCHEME K a) 1M NaHMDS, THF
(MeO)₂P(O)CH₂COOMe b) trimethylsulfoxonium iodide, NaH, THF c) NaOH, DMSO, MeOH d) General Coupling Method B
2-aminothiazole

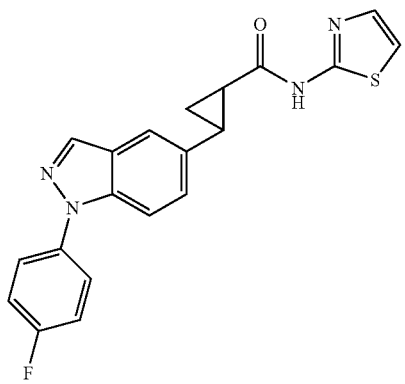

Example 103

2-(1-(4-Fluorophenyl)-1H-indazol-5-yl)-N-(thiazol-2-yl)cyclopropanecarboxamide

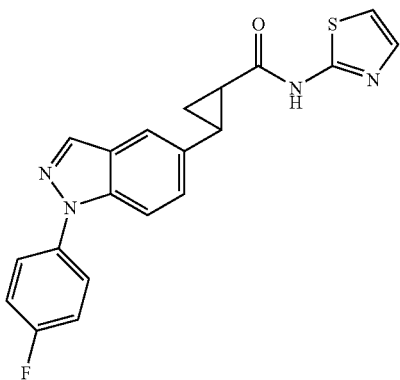

(a) To solution of trimethylphosphonoacetate (2.4 mL, 15 mmol) in DMF (20 mL) was added 1M NaHMDS/THF solution (15 mL, 15 mmol). After stirring 30 minutes, a solution of 1-(4-fluorophenyl)-1H-indazol-5-carboxaldehyde (2.4 g, 10 mmol) was added and the reaction mixture was stirred overnight. The reaction was quenched with sat. NaCl and extracted with EtOAc×3. The organic layers were dried over MgSO$_4$, filtered, and concentrated to give 2.64 g (89% yield) of product (E)-methyl 3-(1-(4-fluorophenyl)-1H-indazol-5-yl)acrylate. MS found: (M+H)$^+$=297.

(b) To solution of trimethylsulfoxonium iodide (440 mg, 2.0 mmol) in DMSO (10 mL) was added a 60% oil dispersion of NaH (80 mg, 2.0 mmol). After stirring 30 minutes, (E)-methyl 3-(1-(4-fluorophenyl)-1H-indazol-5-yl)acrylate (500 mg, 1.69 mmol) was added and the reaction mixture was stirred overnight. The reaction was quenched with sat. NaCl and extracted with EtOAc×3. The organic layers were dried over MgSO$_4$, filtered, and concentrated. The crude product was chromatographed on SiO$_2$ using 1:4 EtOAc/hexanes to give 83 mg (16% yield) of desired product methyl 2-(1-(4-fluorophenyl)-1H-indazol-5-yl)cyclopropanecarboxylate. MS found: (M+H)$^+$=311.

(c) The solid was dissolved in MeOH (10 mL) and DMSO (10 mL) and treated with 1 M NaOH (10 mL) at 100° C. After stirring overnight, the MeOH was removed in vacuo, the residue acidified with conc HCl to pH 4-5 and extracted with EtOAc×3. The organic layer was dried with MgSO$_4$, filtered, concentrated in vacuo to give 71 mg (90% yield) of 2-(1-(4-fluorophenyl)-1H-indazol-5-yl)cyclopropanecarboxylic acid. MS found: (M+H)$^+$=297.

(d) Example 103 was prepared from 2-(1-(4-fluorophenyl)-1H-indazol-5-yl)cyclopropanecarboxylic acid (34 mg, 0.115 mmol) and 2-aminothiazole using General Coupling Method B to give 3 mg (7% yield). MS found: (M+H)$^+$=379.

SCHEME L

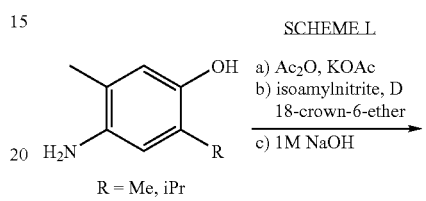

R = Me, iPr a) Ac$_2$O, KOAc
b) isoamylnitrite, D 18-crown-6-ether
c) 1M NaOH d) CuI, K$_3$PO$_4$
t-cyclohexanediamine
4-fluoroiodobenzene e) Tf$_2$O, pyr., DCM
f) Pd(OAc)$_2$, dppp, Et$_3$N CO (g), DMF, MeOH g) LiBH$_4$, THF
h) TiCl$_4$, DCM i) NaOH, DMSO, MeOH
j) General Coupling Method A or B
Z-Z$_a$-NH$_2$

127

-continued

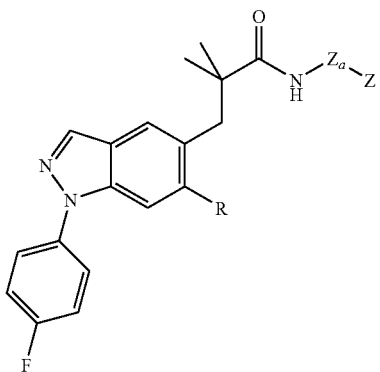

The procedure of Scheme L was used to prepare Examples 104 and 105.

Example 104

2-(1-(4-Fluorophenyl)-1H-indazol-5-yl)-N-(thiazol-2-yl)cyclopropanecarboxamide

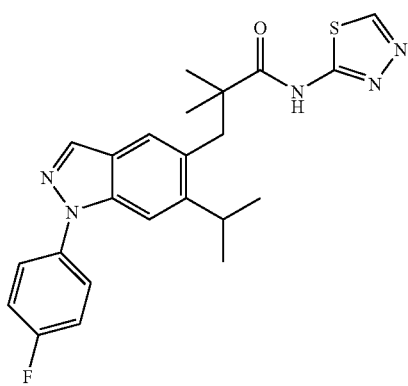

The procedure of Scheme L was used in preparing the Examples 104 and 105.

(a) Following the general procedure of Sun et al (*J. Org. Chem.* 1997, 62, 5627-5629), 4-amino-2-isopropyl-5-methylphenol (7.7 g, 51.2 mmol) was dissolved in dry chloroform (150 mL) followed by potassium acetate (10 g, 102 mmol), and acetic anhydride (15.6 g, 153 mmol). After 2 h, the reaction was refluxed for 3 h and then cooled to rt and stirred overnight.

(b) The next day, 18-crown-6 ether (0.702 g, 2.65 mmol) was added followed by isoamyl nitrite (13.5 g, 115 mmol). The reaction was refluxed for 20 h, cooled to rt, washed with sat NaHCO$_3$, and the organic layer was dried over MgSO$_4$, filtered, and concentrated in vacuo. The crude product was purified by SiO$_2$ chromatography eluting with 25% EtOAc in hexane to give 4.74 g of 1-acetyl-6-isopropyl-1H-indazol-5-yl acetate. MS found: (M+H)$^+$=261.

(c) The solid was dissolved in MeOH (20 mL) and treated with 1 M NaOH (20 mL). After stirring overnight, the MeOH was removed in vacuo, the residue acidified with conc HCl to pH 4-5 and extracted with EtOAc×3. The organic layer was dried with MgSO$_4$, filtered, concentrated in vacuo to give 6-isopropyl-1H-indazol-5-ol.

(d) 6-Isopropyl-1H-indazol-5-ol was dissolved in 20 mL dry dioxane in a stainless steel pressure tube. Trans-1,2-cyclohexanediamine (0.35 mL, 2.88 mmol) was added followed by CuI (110 mg, 0.58 mmol) and then K$_3$PO$_4$ 2.2 g, 10.4 mmol). After the addition of 4-fluoro-1-iodobenzene (0.7 mL, 6.0 mmol), the reactor was sealed and heated at 100 C for 24 h. The reactor was cooled and the contents were taken up in EtOAc, filtered through a SiO$_2$ plug using EtOAc as the eluent and concentrated in vacuo. The crude product was chromatographed on SiO$_2$ using 1:3 EtOAc/hexanes to give 453 mg (29% yield) of 1-(4-fluorophenyl)-6-isopropyl-1H-indazol-5-ol. MS found: (M+H)$^+$=271.

(e) 1-(4-Fluorophenyl)-6-isopropyl-1H-indazol-5-ol (270 mg, 1.0 mmol) was dissolved in DCM (5 mL) and pyridine (0.08 mL, 1 mmol) was added followed by triflic anhydride (0.18 mL, 1.1 mmol). After 1 h, the reaction was washed with 1 M HCl and the aqueous layer was dried over MgSO$_4$, filtered, and concentrated. The crude 1-(4-fluorophenyl)-6-isopropyl-1H-indazol-5-yltrifluoromethanesulfonate was taken up in 2 mL DMF, transferred to a stainless steel pressure bomb, and dppp (12 mg, 0.03 mmol), triethylamine (0.28 mL, 2 mmol), and Pd(OAc)$_2$ (7 mg, 0.03 mmol) were added. CO (g) was bubbled through for 15 minutes then the reaction vessel was sealed and heated at 70° C. for 12 h. The reaction was cooled, diluted with EtOAc, washed with brine, and the organic phase was dried over MgSO$_4$, filtered, and concentrated. The residue was purified on SiO$_2$ by MPLC using a 1:9 to 1:3 EtOAc/hexane gradient. Obtained 175 mg (56% yield, 2 steps) of methyl 1-(4-fluorophenyl)-6-isopropyl-1H-indazole-5-carboxylate. MS found: (M+H)$^+$=313.

(f) Methyl 1-(4-fluorophenyl)-6-isopropyl-1H-indazole-5-carboxylate (175 mg, 0.56 mmol) was dissolved in 5 mL THF and 1M LiBH$_4$ in THF (3 mmol) was added. Heated at reflux. After 12 h, the reaction was quenched with MeOH, poured into brine and extracted with EtOAc×3. The organic layers were dried over MgSO$_4$, filtered, and concentrated. The residue was purified on SiO$_2$ by MPLC using 1:3 EtOAc/hexane. Obtained 148 mg (93% yield) of (1-(4-fluorophenyl)-6-isopropyl-1H-indazol-5-yl)methanol. MS found: (M+H)$^+$=285.

(g) (1-(4-Fluorophenyl)-6-isopropyl-1H-indazol-5-yl)methanol (145 mg, 0.51 mmol) was dissolved in 5 mL of dry DCM and TiCl$_4$ (60 mL of 1.0 M DCM solution, 60 mmol) was added portionwise and then stirred 30 min. Then the reaction was treated with 1-methoxy-2-methyl-1-(trimethylsiloxy)propene (0.2 mL, 1.0 mmol). The reaction was quenched with aqueous sodium bicarbonate and extracted 2×EtOAc, the organic layers dried over MgSO$_4$, filtered, and concentrate. The residue was purified on SiO$_2$ by MPLC using a 5:95 to 10:90 EtOAc/hexane gradient to give 87 mg (47% yield) of methyl 3-(1-(4-fluorophenyl)-6-isopropyl-1H-indazol-5-yl)-2,2-dimethylpropanoate. MS found: (M+H)$^+$=369.

(h) Methyl 3-(1-(4-fluorophenyl)-6-isopropyl-1H-indazol-5-yl)-2,2-dimethylpropanoate (87 mg, 0.236 mmol) was heated to 100 C overnight in a mixture of 2 M NaOH/MeOH/DMSO (1:1:1). The next day, the reaction was cooled, acidified to pH 5 with HCl and extracted 2×EtOAc. The organic layers were washed with water×2, dried over MgSO$_4$, filtered, and concentrated in vacuo to give 83 mg (99% yield) of acid 3-(1-(4-fluorophenyl)-6-isopropyl-1H-indazol-5-yl)-2,2-dimethylpropanoic acid. MS found: (M+H)$^+$=355.

(i) Example 104 was prepared from 3-(1-(4-fluorophenyl)-6-isopropyl-1H-indazol-5-yl)-2,2-dimethylpropanoic acid (83 mg, 0.235 mmol) and 1,3,4-thiadiazol-2-amine using General Coupling Method A to give 26 mg (25% yield). MS found: (M+H)+=438.

Example 105

2-(1-(4-Fluorophenyl)-1H-indazol-5-yl)-N-(thiazol-2-yl)cyclopropanecarboxamide

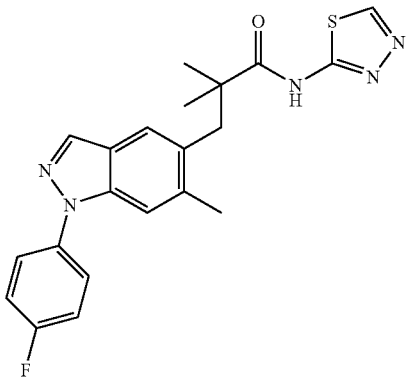

(a) Following the general procedure of Sun et al (*J. Org. Chem.* 1997, 62, 5627-5629), 4-amino-2-methyl-5-methylphenol (10 g, 72.9 mmol) was dissolved in dry chloroform (150 mL) followed by potassium acetate (14.3 g, 146 mmol), and acetic anhydride (22 g, 219 mmol). After 2 h, the reaction was refluxed for 3 h and then cooled to rt and stirred overnight.

(b) The next day, 18-crown-6 ether (0.962 g, 3.6 mmol) was added followed by isoamyl nitrite (19.2 g, 164 mmol). The reaction was refluxed for 20 h, cooled to rt, washed with sat NaHCO$_3$, and the organic layer was dried over MgSO$_4$, filtered, and concentrated in vacuo. The crude product was dissolved in MeOH (20 mL) and treated with 1 M NaOH (20 mL). After stirring overnight, the MeOH was removed in vacuo, the residue acidified with conc HCl to pH 4-5 and extracted with EtOAc×3. The organic layer was dried with MgSO$_4$, filtered, concentrated in vacuo, and purified on SiO$_2$ by MPLC eluting with EtOAc to give 5.0 g (46% yield, 2 steps) of 6-methyl-1H-indazol-5-ol. MS found: (M+H)+=149.

(c) 6-Methyl-1H-indazol-5-ol (5.0 g, 33.7 mmol) was dissolved in 50 mL dry dioxane in a stainless steel pressure tube. Trans-1,2-cyclohexanediamine (2.0 mL, 17 mmol) was added followed by CuI (647 mg, 3.4 mmol) and then K$_3$PO$_4$ 12.7 g, 60 mmol). After the addition of 4-fluoro-1-iodobenzene (3.9 mL, 33.7 mmol), the reactor was sealed and heated at 100 C for 24 h. The reactor was cooled and the contents were taken up in EtOAc, filtered through a SiO$_2$ plug with EtOAc and concentrated in vacuo. The crude product was chromatographed on SiO$_2$ using 1:3 EtOAc/hexanes to give 3.1 g (38% yield) of 1-(4-fluorophenyl)-6-methyl-1H-indazol-5-ol. MS found: (M+H)+=242.

(d) 1-(4-Fluorophenyl)-6-methyl-1H-indazol-5-ol (500 mg, 1.0 mmol) was dissolved in DCM (5 mL) and pyridine was added (0.17 mL, 2.1 mmol) followed by triflic anhydride (0.35 mL, 2.1 mmol). After 1 h, the reaction was washed with 1 M HCl and the aqueous layer was dried over MgSO$_4$, filtered, and concentrated. The crude 1-(4-fluorophenyl)-6-methyl-1H-indazol-5-yltrifluoromethanesulfonate was taken up in 2 mL DMF, transferred to a stainless steel pressure bomb, and dppp (41 mg, 0.10 mmol), triethylamine (0.84 mL, 6 mmol), and Pd(OAc)$_2$ (22 mg, 0.10 mmol) were added. CO$_2$ (g) was bubbled through for 15 minutes then the reaction vessel was sealed and heated at 70° C. for 12 h. The reaction was cooled, diluted with EtOAc, washed with brine, and the organic phase was dried over MgSO$_4$, filtered, and concentrated. The residue was purified on SiO$_2$ by MPLC and a 1:9 to 1:3 EtOAc/hexane gradient. Obtained 151 mg (26% yield, 2 steps) of methyl 1-(4-fluorophenyl)-6-methyl-1H-indazole-5-carboxylate. MS found: (M+H)+=285.

(e) Methyl 1-(4-fluorophenyl)-6-methyl-1H-indazole-5-carboxylate (151 g, 0.53 mmol) was dissolved in 5 mL THF and 2M LiBH$_4$ in THF (1 mmol) was added. Heated at reflux. After 12 h, the reaction was quenched with MeOH, poured into brine and extracted with EtOAc×3. The organic layers were dried over MgSO$_4$, filtered, and concentrated. The residue was purified on SiO$_2$ by MPLC using a 1:3 to 1:1 EtOAc/hexane gradient. Obtained 102 mg (75% yield) of (1-(4-fluorophenyl)-6-methyl-1H-indazol-5-yl)methanol. MS found: (M+H)+=257.

(f) (1-(4-Fluorophenyl)-6-methyl-1H-indazol-5-yl)methanol (178 mg, 0.51 mmol) was dissolved in 5 mL of dry DCM and BF$_3$—OEt$_2$ (0.09 mL, 0.7 mmol) was added portionwise and then stirred 30 min. Then the reaction was treated with 1-methoxy-2-methyl-1-(trimethylsiloxy)propene (0.43 mL, 2.1 mmol). The reaction was quenched with aqueous sodium bicarbonate and extracted 2×EtOAc, the organic layers dried over MgSO$_4$, filtered, and concentrate. The residue was purified on SiO$_2$ by MPLC using a 5:95 to 1:9 gradient to give 121 mg (51% yield) of methyl 3-(1-(4-fluorophenyl)-6-methyl-1H-indazol-5-yl)-2,2-dimethylpropanoate. MS found: (M+H)+=341.

(g) Methyl 3-(1-(4-fluorophenyl)-6-methyl-1H-indazol-5-yl)-2,2-dimethylpropanoate (121 mg, 0.355 mmol) was heated to 100 C overnight in a mixture of 2 M NaOH/MeOH/DMSO (1:1:1). The next day, the reaction was cooled, acidified to pH 5 with HCl and extracted 2×EtOAc. The organic layers were washed with water×2, dried over MgSO$_4$, filtered, and concentrated in vacuo to give 90 mg (80% yield) of acid 3-(1-(4-fluorophenyl)-6-methyl-1H-indazol-5-yl)-2,2-dimethylpropanoic acid. MS found: (M+H)+=327.

h) Example 105 was prepared from 3-(1-(4-fluorophenyl)-6-methyl-1H-indazol-5-yl)-2,2-dimethylpropanoic acid (45 mg, 0.138 mmol) and 1,3,4-thiadiazol-2-amine using General Coupling Method A to give 21 mg (38% yield). MS found: (M+H)+=410.

SCHEME M

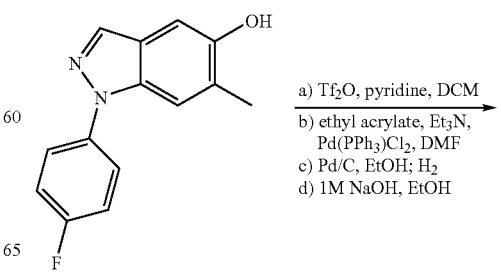

a) Tf$_2$O, pyridine, DCM
b) ethyl acrylate, Et$_3$N, Pd(PPh$_3$)Cl$_2$, DMF
c) Pd/C, EtOH; H$_2$
d) 1M NaOH, EtOH -continued

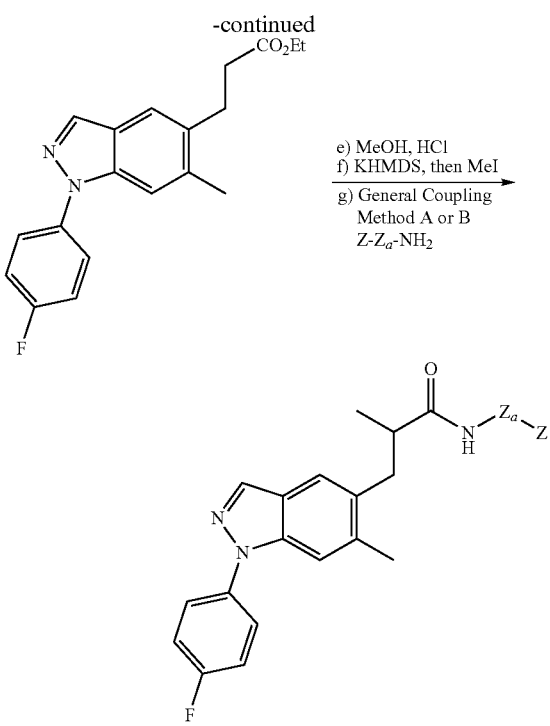

e) MeOH, HCl
f) KHMDS, then MeI
g) General Coupling Method A or B
Z-Z$_a$-NH$_2$

Example 106

3-(1-(4-Fluorophenyl)-6-methyl-1H-indazol-5-yl)-2-methyl-N-(1,3,4-thiadiazol-2-yl)propanamide

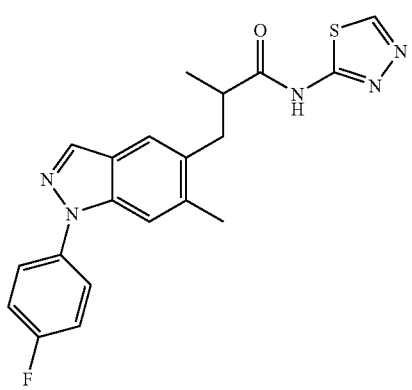

(a)(b) 1-(4-Fluorophenyl)-6-methyl-1H-indazol-5-ol [(484 mg, 2.0 mmol; prepared as described in Example 105 (c)] was dissolved in DCM (20 mL) and pyridine was added (0.16 mL, 2 mmol) followed by triflic anhydride (0.36 mL, 2.1 mmol). After 1 h, the reaction was washed with 1 M HCl and the aqueous layer was dried over MgSO$_4$, filtered, and concentrated. The crude 1-(4-fluorophenyl)-6-methyl-1H-indazol-5-yltrifluoromethanesulfonate was taken up in 20 mL DMF, transferred to a stainless steel pressure bomb, and treated with ethyl acrylate (200 mg, 2 mmol), triethylamine (0.28 mL, 2 mmol), and Pd(PPh$_3$)$_2$Cl$_2$ (160 mg, 0.2 mmol) and heated at 110° C. for 6 h. The reaction was incomplete so additional ethyl acrylate (200 mg, 2 mmol) and Pd(PPh$_3$)$_2$Cl$_2$ (160 mg, 0.2 mmol) was added and the reaction was sealed and heated for 16 h. The reaction was cooled, diluted with EtOAc, washed with brine, and the organic phase was dried over MgSO$_4$, filtered, and concentrated. The residue was purified by MPLC using SiO$_2$ and a 1:9 EtOAc/hexane to 1:1 gradient. Obtained 350 mg (54% yield, 2 steps) of (E)-ethyl 3-(1-(4-fluorophenyl)-6-methyl-1H-indazol-5-yl)acrylate. MS found: (M+H)$^+$=325.

(c)(d) (E)-ethyl 3-(1-(4-fluorophenyl)-6-methyl-1H-indazol-5-yl)acrylate (350 mg, 1.08 mmol) was dissolved in EtOH (30 mL) and hydrogenated over 10% Pd/C (70 mg) at 50 psi H2 for 4 h. The catalyst was filtered off and the solution was treated with 1 M NaOH (30 mL) and stirred for 16 h. The pH was adjusted to 4-5 with conc HCl. Most of the EtOH was removed in vacuo and the solution was extracted with EtOAc and dried over MgSO$_4$, filtered, and conc. Obtained 320 mg (100%) of 3-(1-(4-fluorophenyl)-6-methyl-1H-indazol-5-yl) propanoic acid.

(e) 3-(1-(4-Fluorophenyl)-6-methyl-1H-indazol-5-yl)propanoic acid [180 mg, 0.6 mmol, prepared as described in Example 93(d)] was esterified by dissolving in MeOH and bubbling HCl gas through it. The reaction was concentrated in vacuo, extracted with EtOAc and NaHCO$_3$, and dried over MgSO$_4$. After filtration and concentration, the ester was dissolved in 5 mL dry THF followed by 2 mL potassium hexamethyldisilazane (2 mL of 0.5 M toluene solution). After 30 m, iodomethane (168 mg, 1.18 mmol) was added and the reaction was stirred for 14 h. The reaction was incomplete so additional KHMDS (2 mL) and iodomethane were added (168 mg). After another 14 h, the reaction was quenched with MeOH followed by extractive workup with brine and EtOAc. The crude product was purified by SiO$_2$ chromatography to give 29 mg of 3-(1-(4-fluorophenyl)-6-methyl-1H-indazol-5-yl)-2-methyl-N-(1,3,4-thiadiazol-2-yl)propanamide. MS found: (M+H)$^+$=327.

(f) 3-(1-(4-Fluorophenyl)-6-methyl-1H-indazol-5-yl)-2-methyl-N-(1,3,4-thiadiazol-2-yl)propanamide (29 mg, 0.07 mmol) was dissolved in 5 mL MeOH followed by 2 mL of 1 M NaOH. The reaction was stirred for 14 h. The reaction was worked up by extraction from KH$_2$PO$_4$ with EtOAc and concentrated in vacuo. The resulting carboxylic acid was coupled to 2-amino-1,2,4-thiadiazole using General Coupling Method A. The product was purified by HPLC to give the desired product Example 106. MS found: (M+H)$^+$=396. NMR(CDCl$_3$) δ 8.77 (s, 1H); 8.01 (s, 1H) 7.60-7.65 (m, 2H); 7.55 (s, 1H); 7.40 (s, 1H); 7.22 (t, 2H); 3.16-3.25 (m, 2H), 2.94-2.95 (m, 1H); 2.48 (s, 3H); 1.37-1.39 (dd, 3H).

SCHEME N

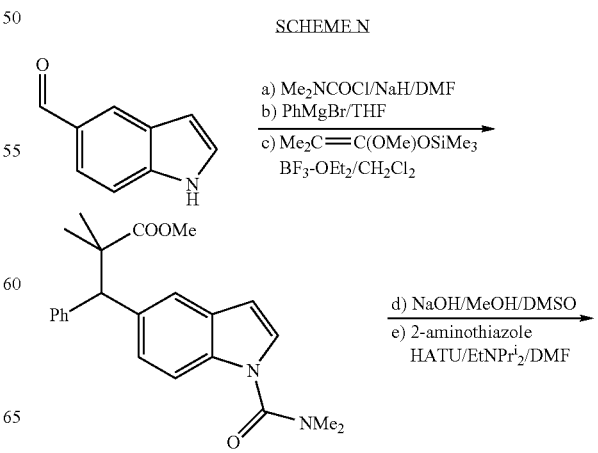

a) Me$_2$NCOCl/NaH/DMF
b) PhMgBr/THF
c) Me$_2$C=C(OMe)OSiMe$_3$
BF$_3$-OEt$_2$/CH$_2$Cl$_2$ d) NaOH/MeOH/DMSO
e) 2-aminothiazole
HATU/EtNPr$^i_2$/DMF

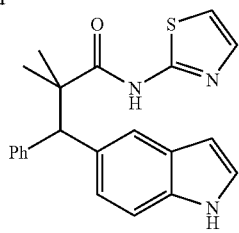

Example 107

3-(1H-Indol-5-yl)-2,2-dimethyl-3-phenyl-N-(thiazol-2-yl)propanamide

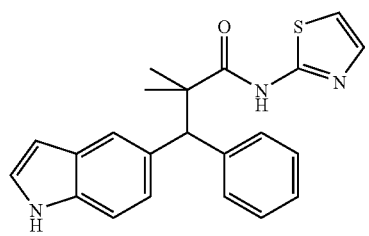

(a) To a stirred solution of 1H-indole-5-carbaldehyde (0.87 g, 6 mmol) in anhydrous DMF (10 mL) was added sodium hydride (60% dispersion in mineral oil, 0.36 g, 9 mmol) portionwise at 0° C. under argon. The reaction mixture was stirred at 0° C. for 10 min and rt for 20 min before dimethylcarbamic chloride was added dropwise at 0° C. After the reaction mixture was stirred at 0° C. for 10 min and rt for 2 hr, saturated ammonium chloride aqueous solution (10 mL) was added to quench the reaction. The reaction mixture was concentrated, diluted with water (10 mL) and extracted with dichloromethane (20 mL). The dichloromethane extract was dried ($Na_2SO_4$) and concentrated. Silica gel flash chromatography gave 5-formyl-N,N-dimethyl-1H-indole-1-carboxamide (1.3 g, 5.8 mmol, 97% yield) as a white solid, the NMR spectrum of which was consistent with the desired structure.

(b) To a stirred solution of 5-formyl-N,N-dimethyl-1H-indole-1-carboxamide (0.63 g, 2.9 mmol) in anhydrous THF (5 mL) was added phenyl magnesium bromide solution (3 M in diethyl ether, 1.1 mL, 3.3 mmol) at −78° C. under argon. The reaction mixture was stirred at −78° C. for 1 hr, at rt for 1 hr and quenched by the slow addition of saturated aq ammonium chloride aqueous solution (10 mL) Water (10 mL) was added, the reaction mixture was extracted with ethyl acetate (20 mL) dried ($Na_2SO_4$), filtered through a pad of silica gel, and concentrated to give 5-(hydroxy(phenyl)methyl)-N,N-dimethyl-1H-indole-1-carboxamide (0.9 g, 3 mmol, 100% yield) as a syrup, the NMR spectrum of which was consistent with the desired structure.

(c) To a stirred solution of 5-(hydroxy(phenyl)methyl)-N,N-dimethyl-1H-indole-1-carboxamide (0.72 g, 2.5 mmol) and (1-methoxy-2-methylprop-1-enyloxy)trimethylsilane (8 mL) in anhydrous dichloromethane (6 mL) was added boron trifluoride diethyl ether complex (0.83 mL, 6.6 mmol) dropwise at 0° C. under argon. After stirring at 0° C. for 30 min and rt for 3.5 hr, the mixture was poured into a saturated aqueous sodium bicarbonate solution maintained at 0° C. The reaction mixture was stirred well, extracted with ethyl acetate (20 mL), dried ($Na_2SO_4$) and concentrated. Silica gel flash chromatography gave methyl 3-(1-(dimethylcarbamoyl)-1H-indol-5-yl)-2,2-dimethyl-3-phenylpropanoate (0.9 g, 2.4 mmol, 96% yield) as a glassy solid, the NMR spectrum of which was consistent with the desired structure.

(d) A mixture of methyl 3-(1-(dimethylcarbamoyl)-1H-indol-5-yl)-2,2-dimethyl-3-phenylpropanoate (0.7 g, 2.2 mmol), sodium hydroxide (1M aqueous solution, 18 mL), methanol (5 mL), and dimethylsulfoxide (3 mL) was stirred at 100° C. overnight under argon. The reaction mixture was cooled, washed with diethyl ether (20 mL), acidified with 6M hydrochloric acid aqueous solution, and extracted with ethyl acetate (20 mL). The ethyl acetate extract was washed with brine (20 mL), dried ($Na_2SO_4$) and concentrated to give 3-(1H-indol-5-yl)-2,2-dimethyl-3-phenylpropanoic acid (0.58 g, 2.0 mmol, 91% yield) as a syrup and used as such for the subsequent step without further purification.

(e) To a stirred solution of 3-(1H-indol-5-yl)-2,2-dimethyl-3-phenylpropanoic acid (0.31 g, 1.1 mmol), 2-aminothiazole (0.2 g, 2 mmol), and diisopropylethylamine (0.5 mL) in anhydrous DMF (3 mL) was added HATU (1 g, 2.7 mmol) under argon. After the reaction mixture was stirred at rt for 14 hr and 80° C. for 6 hr, it was concentrated, dissolved in ethyl acetate (20 mL), washed with saturated aqueous sodium bicarbonate solution (10 mL), brine (10 mL), dried ($Na_2SO_4$), and concentrated. Silica gel flash chromatography gave 3-(1H-indol-5-yl)-2,2-dimethyl-3-phenyl-N-(thiazol-2-yl)propanamide (Example 107, 0.3 g, 0.8 mmol, 75% yield) as a yellow solid. MS found: $(M+H)^+$=376. $^1$H-NMR (400 MHz, MeOD) δ ppm 7.60 (1H, s) 7.43 (2H, d, J=7.12 Hz) 7.38 (1H, d, J=3.56 Hz) 7.20-7.29 (3H, m) 7.12-7.20 (2H, m) 7.10 (1H, d) 7.04 (1H, d, J=3.56 Hz) 6.38 (1H, d, J=3.05 Hz) 4.70 (1H, s) 4.62 (1H, s) 1.43 (6H, d, J=4.07 Hz).

Example 107 was resolved into its enantiomers using a Chiralpak-AD column and a solvent system of $CO_2$/MeOH. The enantiomer that elutes first has a retention time of 9.19 min. The second enantiomer has a retention time of 13.23 min. There are numerous alternative ways of resolving compounds of the present invention.

SCHEME O

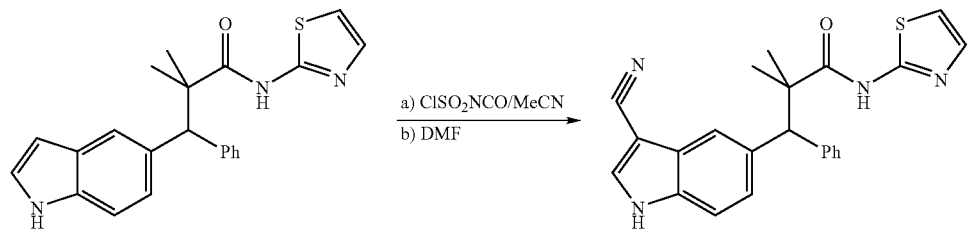

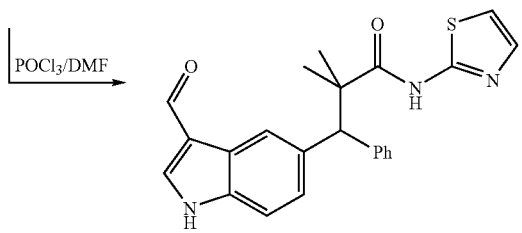

Example 108

3-(3-Cyano-1H-indol-5-yl)-2,2-dimethyl-3-phenyl-N-(thiazol-2-yl)propanamide

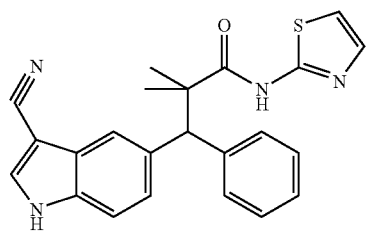

To a stirred solution of 3-(1H-indol-5-yl)-2,2-dimethyl-3-phenyl-N-(thiazol-2-yl)propanamide (Example 101, 25 mg, 0.067 mmol) in anhydrous acetonitrile (1 mL) was added chlorosulfonyl isocyanate (0.007 mL, 0.074 mmol) at 0° C. under argon. The reaction mixture was stirred at 0° C. for 30 min before anhydrous DMF (0.006 mL, 0.074 mmol) was added. After the reaction mixture was stirred at 0° C. for 30 min and at rt for 1 hr, it was concentrated, mixed with saturated aqueous sodium bicarbonate solution (5 mL), and extracted with dichloromethane (10 mL). The dichloromethane extract was dried (Na$_2$SO$_4$) and concentrated. Silica gel flash chromatography gave 3-(3-cyano-1H-indol-5-yl)-2,2-dimethyl-3-phenyl-N-(thiazol-2-yl)propanamide (Example 108, 11 mg, 0.027 mmol, 41% yield) as a white solid. MS found: (M+H)$^+$=401. $^1$H-NMR (400 MHz, Acetone-d6): δ ppm 11.15 (1 H, s) 10.48 (1H, s) 8.06 (1H, d, J=2.40 Hz) 7.78 (1H, s) 7.46-7.53 (3H, m) 7.39 (1 H, d, J=8.65 Hz) 7.35 (1H, d, J=3.56 Hz) 7.28 (2H, t, J=7.38 Hz) 7.18 (1H, t, J=7.38 Hz) 7.04 (1H, d, J=3.56 Hz) 5.04 (1H, s) 1.51 (6H, d, J=2.54 Hz).

Example 109

3-(3-Formyl-1H-indol-5-yl)-2,2-dimethyl-3-phenyl-N-(thiazol-2-yl)propanamide

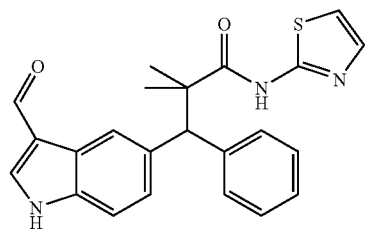

Phosphorus oxychloride (0.01 mL, 0.11 mmol) was added to anhydrous DMF (0.5 mL) under argon. The mixture was stirred at rt for 15 min before 3-(1H-indol-5-yl)-2,2-dimethyl-3-phenyl-N-(thiazol-2-yl)propanamide (Example 101, 18 mg, 0.048 mmol) was added. The reaction mixture was stirred at rt for 1 hr. Aqueous sodium hydroxide solution (1N, 2 mL) was added, the mixture was stirred at 80° C. for 8 min. The reaction mixture was quenched with saturated aqueous ammonium chloride solution (1 mL) and water (1 mL) and extracted with dichloromethane (10 mL). The dichloromethane extract was dried (Na$_2$SO$_4$) and concentrated. Silica gel flash chromatography gave 3-(3-formyl-1H-indol-5-yl)-2,2-dimethyl-3-phenyl-N-(thiazol-2-yl)propanamide (Example 109, 16 mg, 0.04 mmol, 83% yield) as a glassy solid. MS found: (M+H)$^+$=404. $^1$H NMR (400 MHz, CDCl$_3$) δ ppm 9.93-9.95 (1 H, s) 9.92 (1H, s) 9.25 (1H, s) 8.34 (1H, s) 7.66 (1H, d, J=3.05 Hz) 7.34-7.39 (3 H, m) 7.12-7.28 (5H, m) 6.92 (1H, d, J=3.56 Hz) 4.51 (1H, s) 1.42 (6H, s).

SCHEME P

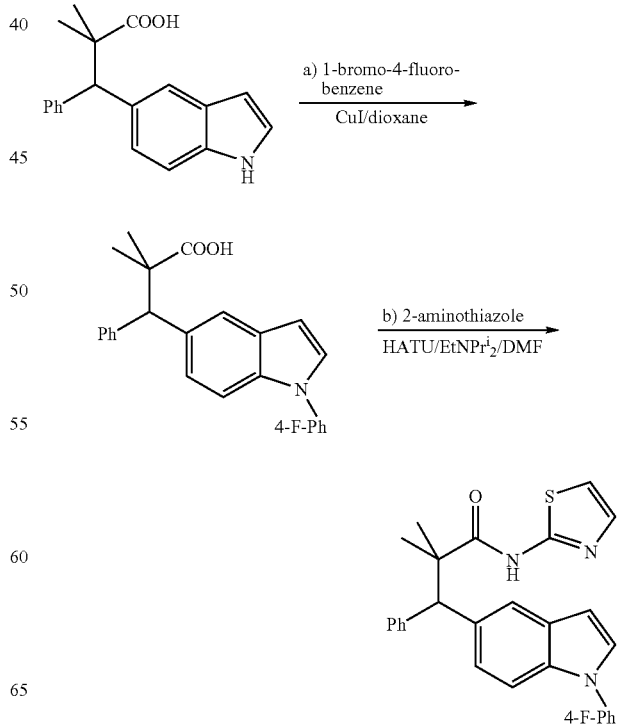

Example 110

3-(1-(4-Fluorophenyl)-1H-indol-5-yl)-2,2-dimethyl-3-phenyl-N-(thiazol-2-yl)propanamide

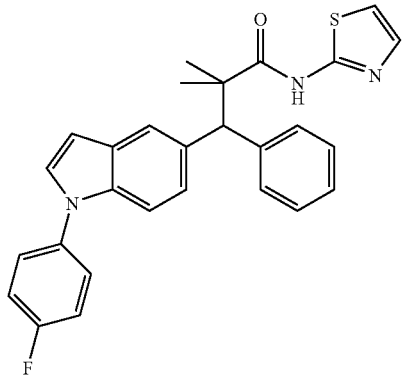

(a) A mixture of 3-(1H-indol-5-yl)-2,2-dimethyl-3-phenylpropanoic acid (Example 101(d), 31 mg, 0.11 mmol), 1-bromo-4-fluorobenzene (0.014 mL, 0.13 mmol), copper(I) iodide (4 mg, 0.02 mmol), potassium carbonate (50 mg, 0.36 mmol), trans-1,2-diaminocyclohexane (0.01 mL, 0.08 mmol), tetrabutylammonium iodide (18 mg, 0.05 mmol), and dioxane (0.6 mL) was stirred at 110° C. for 24 h. Concentration and purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 3-(1-(4-fluorophenyl)-1H-indol-5-yl)-2,2-dimethyl-3-phenylpropanoic acid (24 mg, 0.062 mmol, 56% yield) as a liquid.

(b) To a stirred solution of 3-(1-(4-fluorophenyl)-1H-indol-5-yl)-2,2-dimethyl-3-phenylpropanoic acid (23 mg, 0.059 mmol), 2-aminothiazole (18 mg, 0.18 mmol), and diisopropylethylamine (0.03 mL, 0.18 mmol) in anhydrous DMF (0.3 mL) was added HATU (68 mg, 0.18 mmol) under argon. The reaction mixture was stirred at rt for 5 min and at 80° C. for 5 hr. Concentration and purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 3-(1-(4-fluorophenyl)-1H-indol-5-yl)-2,2-dimethyl-3-phenyl-N-(thiazol-2-yl)propanamide (Example 110, 6 mg, 0.013 mmol, 22% yield) as a pink solid. MS found: $(M+H)^+=470$. $^1$H-NMR (400 MHz, $CDCl_3$) δ ppm 7.67 (1H, s) 7.32-7.43 (5H, m) 7.33 (1H, d, J=8.65 Hz) 7.22-7.28 (3H, m) 7.14-7.20 (4H, m) 6.94 (1H, d, J=3.56 Hz) 6.60 (1H, d, J=3.05 Hz) 4.59 (1H, s) 1.46 (6H, d, J=2.54 Hz).

SCHEME Q

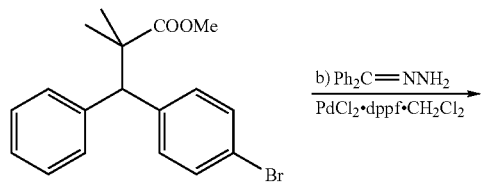

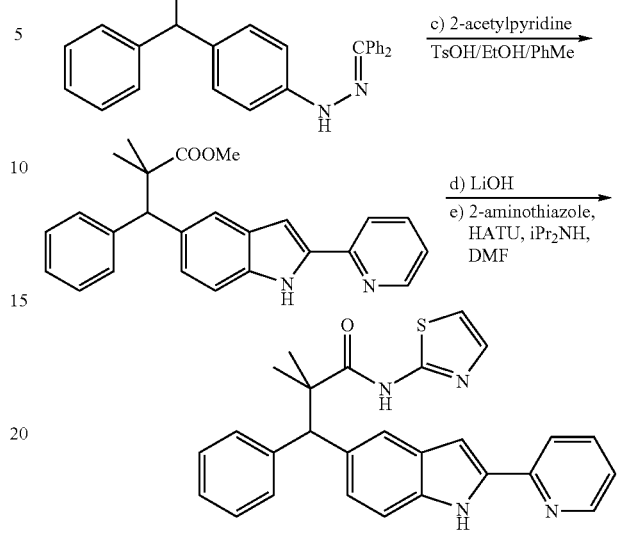

Example 111

2,2-Dimethyl-3-phenyl-3-(2-(pyridin-2-yl)-1H-indol-5-yl)-N-(thiazol-2-yl)propanamide

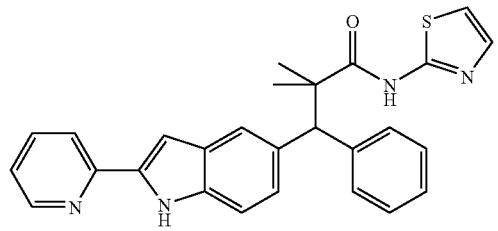

(a) Methyl 3-(4-bromophenyl)-2,2-dimethyl-3-phenylpropanoate was prepared from (4-bromophenyl)(phenyl)methanol using the procedure outlined for Example 107.

(b) A mixture of methyl 3-(4-bromophenyl)-2,2-dimethyl-3-phenylpropanoate (1.1 g, 3.0 mmol), benzophenone hydrazone (0.70 g, 3.6 mmol), cesium carbonate (1.5 g, 4.5 mmol), [1,1'-bis(diphenylphosphino)ferrocene]dichloropalladium (II) complex with dichloromethane (50 mg, 0.068 mmol), and toluene (3 mL) was stirred at 95° C. under argon for 12 hr. The reaction mixture was cooled to rt, partitioned between water (10 mL) and ethyl acetate (20 mL), dried ($Na_2SO_4$), concentrated and purified by silica gel flash chromatography to give the desired product (1.4 g, 3.0 mmol, 100% yield), the NMR spectrum of which was consistent with the desired structure.

(c) A mixture of the above coupling product (46 mg, 0.099 mmol), 2-acetylpyridine (0.017 mL, 0.15 mmol), p-toluenesulfonic acid monohydrate (120 mg), ethanol (0.2 mL), and toluene (1 mL) was stirred at 110° C. for 5 hr under nitrogen. A stream of nitrogen gas was then passed through the reaction mixture to remove ethanol. The reaction mixture was stirred at 110° C. for an additional 10 hr. Concentration and purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave methyl 2,2-dimethyl-3-phenyl-3-(2-(pyridin-2-yl)-1H-indol-5-yl) propanoate (25 mg, 0.065 mmol, 66% yield).

(d) Methyl 2,2-dimethyl-3-phenyl-3-(2-(pyridin-2-yl)-1H-indol-5-yl)propanoate was converted to 2,2-dimethyl-3-phenyl-3-(2-(pyridin-2-yl)-1H-indol-5-yl)-N-(thiazol-2-yl) propanamide (Example 111) as a TFA salt using standard HATU coupling method known to one skilled in the art. MS found: (M+H)+=453. $^1$H-NMR (400 MHz, MeOD) δ ppm 8.52 (1H, d, J=5.60 Hz) 8.10 (1H, t, J=7.63 Hz) 8.00 (1H, d, J=12 Hz) 7.60 (1H, s) 7.44 (1H, t, J=8 Hz) 7.33 (2H, d, J=7.63 Hz) 7.24-7.28 (2H, m) 7.12-7.18 (4H, m) 7.07 (1H, t, J=7.38 Hz) 6.93 (1H, d, J=3.56 Hz) 4.63 (1H, s) 1.33 (6H, d, J=4.07 Hz).

SCHEME R

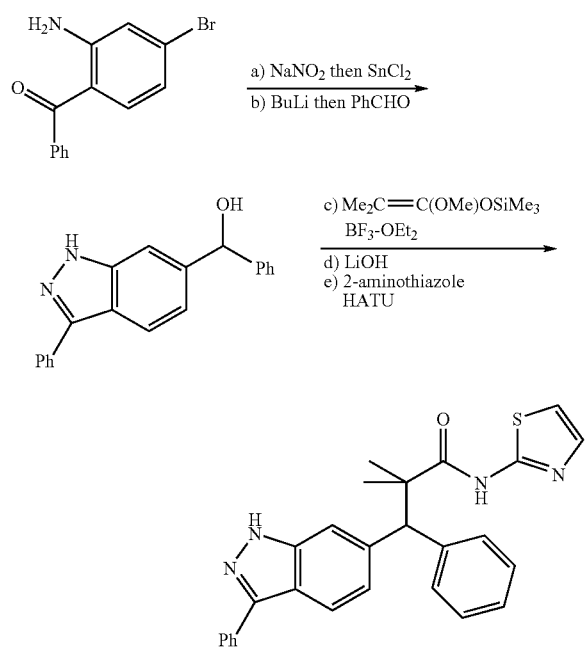

Example 112

2,2-Dimethyl-3-phenyl-3-(3-phenyl-1H-indazol-6-yl)-N-(thiazol-2-yl)propanamide

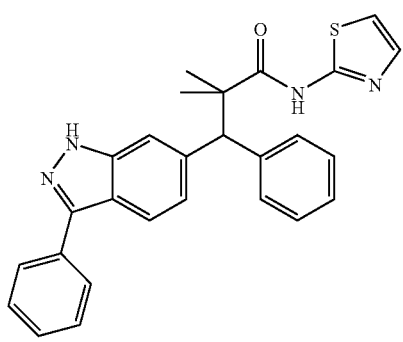

(a) To a stirred mixture of (2-amino-4-bromophenyl)(phenyl)methanone (1.0 g, 3.6 mmol) in hydrochloric acid (6N aqueous solution, 5 mL) was added sodium nitrite (0.5 g, 7.2 mmol) over 3 min at 0° C. The mixture was stirred at 0° C. for 30 min before a solution of tin(II) chloride (2.7 g, 14.4 mmol in 5 mL concentrated hydrochloric acid) was added at 0° C. over 5 min. After stirring at 0° C. for 10 min and rt for 1 hr, the reaction mixture was filtered. The solid was washed with water (10 mL), 4N aqueous sodium hydroxide solution, and water (10 mL). The solid was dissolved in dichloromethane (20 mL), washed with brine (10 mL), dried (Na$_2$SO$_4$), and concentrated. Silica gel flash chromatography gave 6-bromo-3-phenyl-1H-indazole (0.42 g, 1.5 mmol, 42% yield).

(b) To a stirred solution of 6-bromo-3-phenyl-1H-indazole (109 mg, 0.40 mmol) in anhydrous THF (3 mL) was added n-butyl lithium solution (2M in hexanes, 0.47 mL, 0.94 mmol) dropwise at −78° C. under argon. The reaction mixture was stirred at −78° C. for 30 min and at −40° C. for 6 min before benzaldehyde (0.1 mL, 1 mmol) was added at −40° C. The reaction mixture was then stirred at rt for 1 hr. quenched with saturated aqueous ammonium chloride solution (5 mL) and extracted with ethyl acetate (10 mL). The ethyl acetate extract was dried (Na$_2$SO$_4$) and concentrated. Silica gel flash chromatography gave phenyl(3-phenyl-1H-indazol-6-yl)methanol (71 mg, 0.24 mmol, 59% yield) as a solid.

(c) To a stirred solution of phenyl(3-phenyl-1H-indazol-6-yl)methanol (67 mg, 0.22 mmol) and (1-methoxy-2-methyl-prop-1-enyloxy)trimethylsilane (2 mL) in anhydrous dichloromethane (4 mL) was added boron trifluoride diethyl ether complex (0.2 mL, 1.6 mmol) dropwise at 0° C. under argon. After stirred at 0° C. for 15 min, rt for 2 hr, and 40° C. for 1.5 hr, the mixture was poured into saturated aqueous sodium bicarbonate solution at 0° C. The mixture was stirred well and extracted with dichloromethane (10 mL). The dichloromethane layer was dried (Na$_2$SO$_4$) and concentrated. Silica gel flash chromatography gave methyl 2,2-dimethyl-3-phenyl-3-(3-phenyl-1H-indazol-6-yl)propanoate (45 mg, 0.12 mmol, 53% yield) as a glassy solid.

(d) A mixture of methyl 2,2-dimethyl-3-phenyl-3-(3-phenyl-1H-indazol-6-yl)propanoate (45 mg, 0.12 mmol), lithium hydroxide monohydrate (50 mg, 1.2 mmol), water (2 mL), and dioxane (4 mL) was stirred at 110° C. overnight. The mixture was cooled to rt and partitioned between water (5 mL) and diethyl ether (10 mL). The ether layer was extracted with water (10 mL). The combined aqueous solutions were acidified with 6N hydrochloric acid, extracted with ethyl acetate (15 mL), washed with brine (10 mL), dried (Na$_2$SO$_4$) and concentrated to give 2,2-dimethyl-3-phenyl-3-(3-phenyl-1H-indazol-6-yl)propanoic acid (46 mg, 0.12 mmol, 100% yield) as a glassy solid.

(e) To a stirred solution of 2,2-dimethyl-3-phenyl-3-(3-phenyl-1H-indazol-6-yl)propanoic acid (26 mg, 0.07 mmol), 2-aminothiazole (28 mg, 0.28 mmol), and diisopropylethylamine (0.05 mL) in anhydrous DMF (0.2 mL) was added HATU (106 mg, 0.28 mmol) under argon. After stirring at rt for 2.5 hr and 80° C. for 1 hr, the mixture was concentrated. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave 2,2-dimethyl-3-phenyl-3-(3-phenyl-1H-indazol-6-yl)-N-(thiazol-2-yl)propanamide (Example 112, 9 mg, 0.02 mmol, 28% yield) as a solid. MS found: (M+H)+=453. $^1$H-NMR (500 MHz, CDCl$_3$) δ ppm 7.96 (1H, d, J=8.25 Hz) 7.86 (2H, d, J=8.25 Hz) 7.50 (1H, d, J=8.25 Hz) 7.46 (2H, d, J=8.25 Hz) 7.39-7.43 (2H, m) 7.35 (2H, d, J=7.70 Hz) 7.17-7.26 (4 H, m), 6.96 (1H, d, J=3.30 Hz) 4.62 (1H, s) 1.45 (6H, d, J=3.85 Hz).

SCHEME S

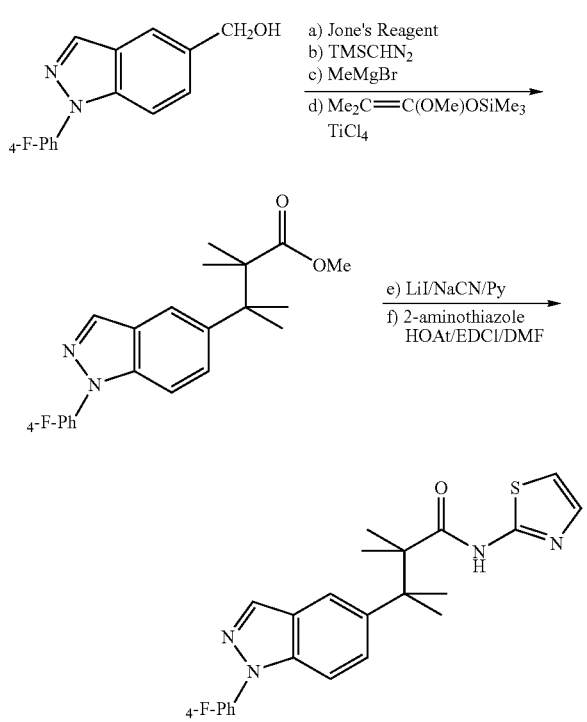

a) Jone's Reagent
b) TMSCHN₂
c) MeMgBr
d) Me₂C═C(OMe)OSiMe₃ TiCl₄ e) LiI/NaCN/Py
f) 2-aminothiazole HOAt/EDCl/DMF

Example 113

3-(1-(4-Fluorophenyl)-1H-indazol-5-yl)-2,2,3-trimethyl-N-(thiazol-2-yl)butanamide

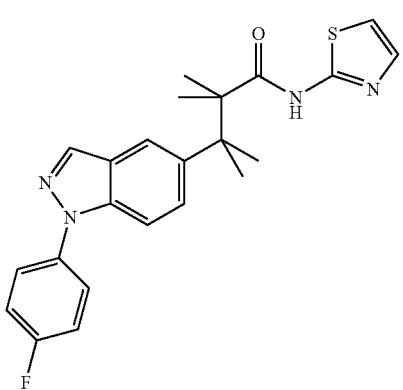

(a) To a stirred solution of (1-(4-fluorophenyl)-1H-indazol-5-yl)methanol (0.45 g, 1.9 mmol) in acetone (10 mL) was added Jones's reagent (3 mL) dropwise at 0° C. The reaction mixture was stirred at rt for 1 hr and concentrated under reduced pressure. Water was added to the residue and the solid that separates out was filtered, washed with water and dried to give 1-(4-fluorophenyl)-1H-indazole-5-carboxylic acid (0.43 g, 1.7 mmol, 89% yield) as a yellow solid.

(b) To a stirred suspension of the 1-(4-fluorophenyl)-1H-indazole-5-carboxylic acid (0.22 g, 0.81 mmol) in methanol (5 mL), THF (5 mL), and dichloromethane (5 mL) was added (trimethylsilyl)diazomethane solution (2M in diethyl ether, 1 mL, 2 mmol) dropwise at rt. The reaction mixture was stirred at rt for 1 hr and carefully quenched by the slow addition of acetic acid. Concentration under reduced pressure and titration with methanol gave methyl 1-(4-fluorophenyl)-1H-indazole-5-carboxylate (0.16 g, 0.59 mmol, 73% yield) as a white solid.

(c) To a suspension of methyl 1-(4-fluorophenyl)-1H-indazole-5-carboxylate (84 mg, 0.31 mmol) in anhydrous THF (5 mL) was added methylmagnesium bromide (3M solution in diethyl ether, 1 mL, 3 mmol) dropwise at rt under argon. The reaction mixture was stirred at rt for 1 hr and carefully quenched by the slow addition of saturated aqueous ammonium chloride solution (10 mL). The reaction mixture was extracted with ethyl acetate (10 mL), dried (Na₂SO₄), concentrated and purified by silica gel flash chromatography to give 2-(1-(4-fluorophenyl)-1H-indazol-5-yl)propan-2-ol (84 mg, 0.31 mmol, 100% yield) as a syrup.

(d) To a stirred solution of 2-(1-(4-fluorophenyl)-1H-indazol-5-yl)propan-2-ol (82 mg, 0.30 mmol) and (1-methoxy-2-methylprop-1-enyloxy)trimethylsilane (0.5 mL) in anhydrous dichloromethane (3 mL) was added titanium(IV) tetrachloride (1M solution in toluene, 1.2 mL, 1.2 mmol) dropwise at 0° C. under argon. The reaction mixture was stirred at 0° C. for 1 hr and rt for 1 hr before being quenched by the slow addition of saturated aqueous sodium bicarbonate solution. The reaction mixture was filtered through a pad of celite that was then washed with ethyl acetate (10 mL). The ethyl acetate layer was separated and the aqueous layer was reextracted with ethyl acetate (10 mL). The combined ethyl acetate layers were dried (Na₂SO₄), concentrated and purified by silica gel flash chromatography to give methyl 3-(1-(4-fluorophenyl)-1H-indazol-5-yl)-2,2,3-trimethylbutanoate (100 mg, 0.28 mmol, 94% yield) as a white solid.

(e) A mixture of methyl 3-(1-(4-fluorophenyl)-1H-indazol-5-yl)-2,2,3-trimethylbutanoate (63 mg, 0.18 mmol), lithium iodide (120 mg, 0.9 mmol), sodium cyanide (45 mg, 0.9 mmol), and pyridine (1 mL) was heated in CEM Explorer microwave reactor under nitrogen at 150° C. for 30 min and 160° C. for 1 hr. The reaction mixture was concentrated and diluted with ethyl acetate (5 mL) and saturated aqueous sodium bicarbonate solution. The solid 3-(1-(4-fluorophenyl)-1H-indazol-5-yl)-2,2,3-trimethylbutanoic acid (46 mg) that separates out was filtered, washed with water, dried and used as such for the subsequent step without further purification.

(f) (23 mg; 0.06 mmol) of the above solid, 1-hydroxy-7-azabenzotriazole (14 mg, 0.1 mmol), DMF (0.3 mL), and N-(3-dimethylaminopropyl)-N'-ethylcarbodiimide hydrochloride (37 mg, 0.19 mml) was stirred at rt for 20 min before 2-aminothiazole (32 mg, 0.32 mmol) was added. The reaction mixture was heated in a CEM Explorer microwave reactor under nitrogen at 130° C. for 30 min. Purification using reverse phase HPLC (YMC S5 20×100 mm, 10 min. run, solvent A: 10% MeOH: 90% H₂O: 0.1% TFA, solvent B: 90% MeOH, 10% H₂O, 0.1% TFA) gave 3-(1-(4-fluorophenyl)-1H-indazol-5-yl)-2,2,3-trimethyl-N-(thiazol-2-yl)butanamide (Example 113, 8 mg, 0.019 mmol, 21% yield from the ester) as a white solid. MS found: (M+H)⁺=423. ¹H-NMR (400 MHz, Acetone-d6): δ ppm 10.01 (1H, s) 8.07 (1H, s) 7.77 (1H, s) 7.64-7.70 (2H, m) 7.50 (1H, d, J=9.16 Hz) 7.36-7.41 (1H, m) 7.29 (1H, d, J=3.56 Hz) 7.21-7.27 (2H, m) 7.04 (1H, d J=4.07 Hz) 1.49 (6H, s) 1.24 (6H, s).

SCHEME T

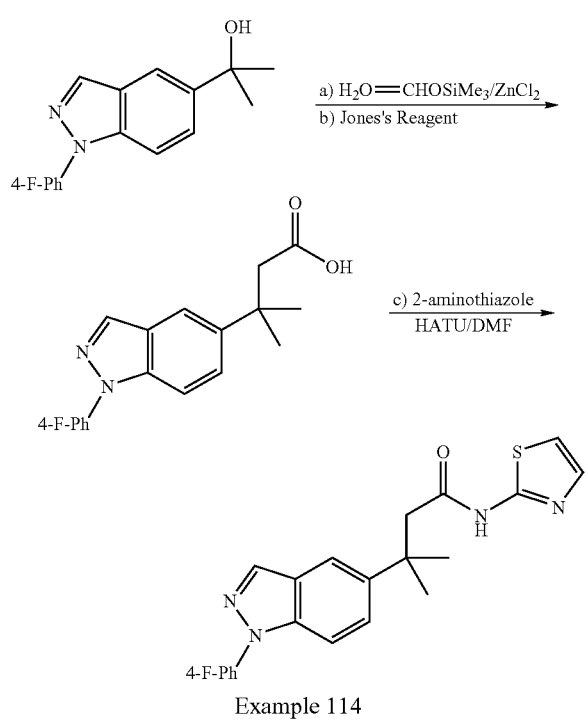

Example 114

3-(1-(4-Fluorophenyl)-1H-indazol-5-yl)-3-methyl-N-(thiazol-2-yl)butanamide (a) To a stirred solution of 2-(1-(4-fluorophenyl)-1H-indazol-5-yl)propan-2-ol (Example 113(d), 200 mg, 0.74 mmol) and trimethyl(vinyloxy)silane (0.5 mL) in anhydrous dichloromethane (1 mL) was added zinc chloride (1M solution in diethyl ether, 2.2 mL, 2.2 mmol) dropwise at 0° C. under argon. The reaction mixture was stirred at rt for 1.5 hr before being quenched by the addition of saturated aqueous ammonium chloride solution (2 mL). The aqueous layer was separated and extracted with ethyl acetate (2×2 mL). The combined organic layers were dried ($Na_2SO_4$), concentrated and purified by silica gel flash chromatography to give 3-(1-(4-fluorophenyl)-1H-indazol-5-yl)-3-methylbutanal as a liquid.

(b) To a stirred solution of the above 3-(1-(4-fluorophenyl)-1H-indazol-5-yl)-3-methylbutanal in acetone (3 mL) was added Jones' reagent (1 mL) dropwise at 0° C. The reaction mixture was stirred at 0° C. for 30 min before being concentrated under reduced pressure. The residue was neutralized with saturated aqueous sodium bicarbonate solution and 10% aqueous citric acid solution, and then extracted with ethyl acetate (3×10 mL). The combined ethyl acetate extracts were dried ($Na_2SO_4$), concentrated and purified by reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) to give 3-(1-(4-fluorophenyl)-1H-indazol-5-yl)-3-methylbutanoic acid (100 mg, 0.32 mmol, 43% yield for 2 steps) as a yellow oil.

(c) To a stirred solution of 3-(1-(4-fluorophenyl)-1H-indazol-5-yl)-3-methylbutanoic acid (14 mg, 0.045 mmol) and diisopropylethylamine (0.05 mL) in anhydrous DMF (0.3 mL) was added HATU (30 mg, 0.079 mmol) at 0° C. under argon. After stirring at 0° C. for 5 min, 2-aminothiazole (15 mg, 0.15 mmol) was added. The reaction mixture was stirred at rt for 5 min and 50° C. for 30 min. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 3-(1-(4-fluorophenyl)-1H-indazol-5-yl)-3-methyl-N-(thiazol-2-yl)butanamide (Example 114, 9 mg, 0.02 mmol, 44% yield) as a white solid. MS found: $(M+H)^+=395$. $^1$H-NMR (400 MHz, $CDCl_3$) δ ppm 8.04 (1H, s) 7.67 (1H, s) 7.58 (2H, dd, J=8.90, 4.83 Hz) 7.53 (1H, d, J=9.16 Hz) 7.40-7.46 (1H, m) 7.25 (1H, s) 7.14 (2H, t, J=8.65 Hz) 6.87 (1H, s) 2.81 (2H, s) 1.51 (6H, s).

Examples 115 to 135

Compounds listed in the table below were prepared using methods described in Examples 107 to 114.

| Ex. | Name | Product Structure | Procedure of Example | [M + H]+ | LC Retention Time (min)* |
|---|---|---|---|---|---|
| 115 | 2,2-dimethyl-3-phenyl-3-(2-(pyridin-4-yl)-1H-indol-5-yl)-N-(thiazol-2-yl)propanamide | 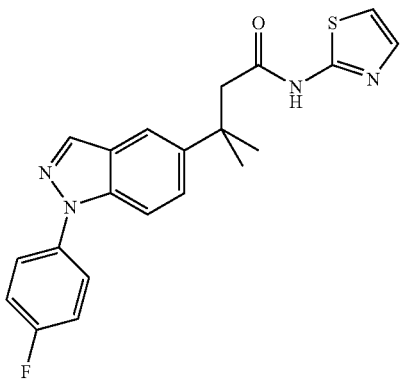 | 100 | 453 | 2.83 |

-continued

| Ex. | Name | Product Structure | Procedure of Example | [M + H]+ | LC Retention Time (min)* |
|---|---|---|---|---|---|
| 116 | 2,2-dimethyl-3-phenyl-3-(2-(pyridin-4-yl)-1H-indol-5-yl)-N-(1,3,4-thiadiazol-2-yl)propanamide | | 100 | 454 | 2.69 |
| 117 | 2,2-dimethyl-3-phenyl-N-(thiazol-2-yl)-3-(2-(thiazol-2-yl)-1H-indol-5-yl)propanamide | | 100 | 459 | 3.67 |
| 118 | 2,2-dimethyl-3-phenyl-N-(1,3,4-thiadiazol-2-yl)-3-(2-(thiazol-2-yl)-1H-indol-5-yl)propanamide | | 100 | 460 | 3.56 |
| 119 | 2,2-dimethyl-3-phenyl-N-(thiazol-2-yl)-3-(2-p-tolyl-1H-indol-5-yl)propanamide | | 100 | 466 | 4.06 |
| 120 | 3-(1-(4-fluorophenyl)-1H-indazol-5-yl)-2,2,3-trimethyl-N-(1,3,4-thiadiazol-2-yl)butanamide | | 103 | 424 | 3.81 |

| Ex. | Name | Product Structure | Procedure of Example | [M + H]+ | LC Retention Time (min)* |
|---|---|---|---|---|---|
| 121 | 3-(1-(4-fluorophenyl)-1H-indazol-5-yl)-N-(2-hydroxycyclopentyl)-2,2,3-trimethylbutanamide | | 103 | 424 | 3.71 |
| 122 | 3-(1-(4-fluorophenyl)-1H-indazol-5-yl)-3-methyl-N-(1,3,4-thiadiazol-2-yl)butanamide | | 104 | 396 | 3.48 |
| 123 | 3-(1-(4-fluorophenyl)-1H-indazol-5-yl)-2,2-dimethyl-4-phenyl-N-(1,3,4-thiadiazol-2-yl)butanamide | | 105 | 486 | 3.80 |
| 124 | 3-(1-(4-fluorophenyl)-1H-indazol-5-yl)-N-((1S,2S)-2-hydroxycyclopentyl)-2,2-dimethyl-4-phenylbutanamide | | 105 | 86 | 3.71 |

| Ex. | Name | Product Structure | Procedure of Example | [M + H]+ | LC Retention Time (min)* |
|---|---|---|---|---|---|
| 125 | 3-(1-(4-fluorophenyl)-1H-indazol-5-yl)-N-(2-hydroxycyclopentyl)-2,2-dimethyl-4-p-tolylbutanamide | | 105 | 500 | 3.88 |
| 126 | 3-(1-(4-fluorophenyl)-1H-indazol-5-yl)-2,2-dimethyl-N-(thiazol-2-yl)-4-p-tolylbutanamide | | 105 | 499 | 4.10 |
| 127 | 3-(1-(4-fluorophenyl)-1H-indazol-5-yl)-2,2-dimethyl-N-(1,3,4-thiadiazol-2-yl)-4-p-tolylbutanamide | | 105 | 500 | 3.98 |
| 128 | N-cyclopropyl-3-(1-(4-fluorophenyl)-1H-indazol-5-yl)-2,2-dimethyl-4-phenylbutanamide | | 105 | 442 | 3.71 |

-continued

| Ex. | Name | Product Structure | Procedure of Example | [M + H]+ | LC Retention Time (min)* |
|---|---|---|---|---|---|
| 129 | N-cyclobutyl-3-(1-(4-fluorophenyl)-1H-indazol-5-yl)-2,2-dimethyl-4-phenylbutanamide | | 105 | 456 | 3.85 |
| 130 | N-cyclopentyl-3-(1-(4-fluorophenyl)-1H-indazol-5-yl)-2,2-dimethyl-4-phenylbutanamide enantiomer 1 | | 105 | 470 | 3.96 |
| 131 | N-cyclopentyl-3-(1-(4-fluorophenyl)-1H-indazol-5-yl)-2,2-dimethyl-4-phenylbutanamide enantiomer 2 | | 105 | 470 | 3.96 |
| 132 | 3-(1-(4-fluorophenyl)-1H-indazol-5-yl)-2,2-dimethyl-4-phenyl-N-(tetrahydro-2H-pyran-4-yl)butanamide | | 105 | 486 | 3.71 |

-continued

| Ex. | Name | Product Structure | Procedure of Example | [M + H]+ | LC Retention Time (min)* |
|---|---|---|---|---|---|
| 133 | 3-(1-(4-fluorophenyl)-1H-indazol-5-yl)-2,2-dimethyl-4-phenyl-N-(piperidin-4-yl)butanamide | | 105 | 485 | 3.10 |
| 134 | 3-(1-(4-fluorophenyl)-1H-indazol-5-yl)-N-(3-hydroxy-2,2-dimethylpropyl)-2,2-dimethyl-4-phenylbutanamide | | 105 | 488 | 3.53 |
| 135 | (S)-3-(1-(4-fluorophenyl)-1H-indazol-5-yl)-N-(2-hydroxycyclopentyl)-2,2-dimethyl-3-phenylpropanamide | | 113 | 472 | 3.69 |

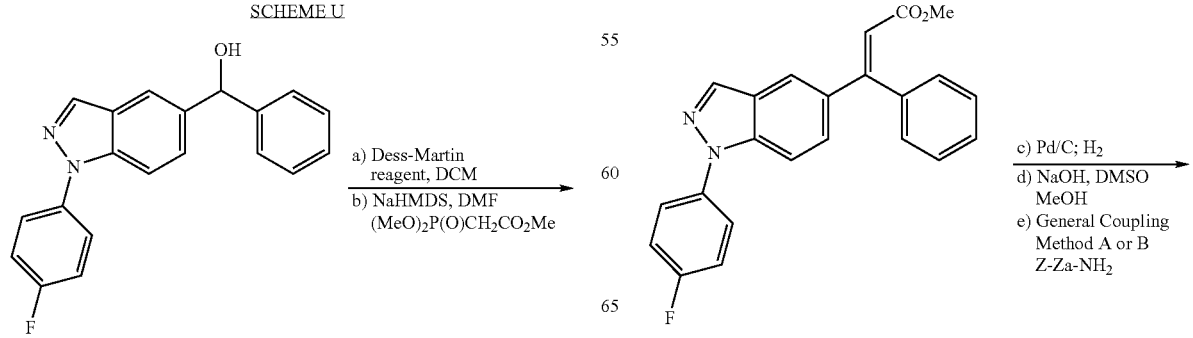

SCHEME U a) Dess-Martin reagent, DCM
b) NaHMDS, DMF (MeO)$_2$P(O)CH$_2$CO$_2$Me c) Pd/C; H$_2$
d) NaOH, DMSO MeOH
e) General Coupling Method A or B Z-Za-NH$_2$ -continued

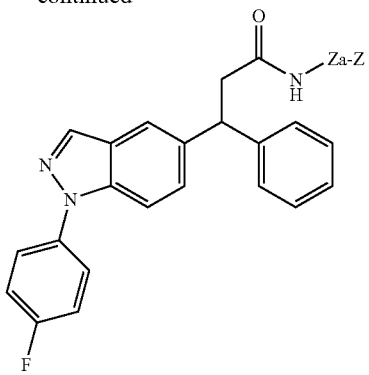

Example 136

3-(1-(4-Fluorophenyl)-1H-indazol-5-yl)-3-phenyl-N-(1,3,4-thiadiazol-2-yl)propanamide

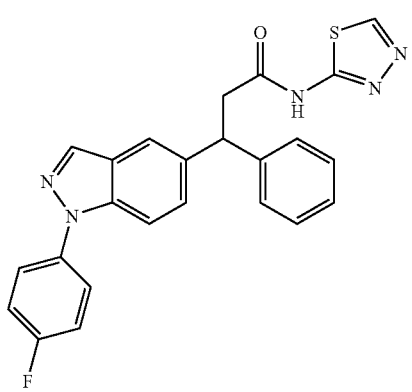

(a) (1-(4-Fluorophenyl)-1H-indazol-5-yl)(phenyl)methanol (Example 1(f)) (2.4 g, 7.54 mmol) was dissolved in 50 mL of DCM and treated with Dess Martin periodinane (3.2 g, 7.54 mmol) and stirred overnight. The next day, the reaction was extracted from 2 M NaOH with DCM (vigorous shaking)×3, dried over MgSO4, filtered, and concentrated in vacuo. The crude material was filtered through a silica gel pad using EtOAc and concentrated to give (1-(4-fluorophenyl)-1H-indazol-5-yl)(phenyl)methanone (2.4 g, 100%). MS found: (M+H)$^+$=317.

(b) Trimethylphosphonoacetate (2.4 g, 13.4 mmol) was dissolved in 15 mL anhydrous DMF and treated with sodium hexadimethylsilazane (13.4 mmol, 1 M in THF). (1-(4-fluorophenyl)-1H-indazol-5-yl)(phenyl)methanone (1.63 g, 5.16 mmol) was added and the reaction was heated to 85° C. for 16 hours. The following day, the cooled reaction was extracted from brine using ether×3 and the combined organic layers were dried over MgSO4, filtered, and concentrated in vacuo. The residue was chromatographed on silica gel using 25% EtOAc in hexanes to give 1.74 g (91%) of (E)-methyl 3-(1-(4-fluorophenyl)-1H-indazol-5-yl)-3-phenylacrylate as a clear oil. MS found: (M+H)$^+$=373.

(c) (E)-methyl 3-(1-(4-fluorophenyl)-1H-indazol-5-yl)-3-phenylacrylate was dissolved in 30 mL EtOH in a Parr bottle and flushed with N2. 10% Pd on carbon was added and the reaction was put on a Parr shaker under 50 psi of H2 for 7 hours. LC-MS after this time indicated that the reaction was complete so the catalyst was filtered off and the solution concentrated in vacuo. The residue was purified using a 40 g MPLC column using a 10 to 25% EtOAc in hexanes gradient to give methyl 3-(1-(4-fluorophenyl)-1H-indazol-5-yl)-3-phenylpropanoate (1.1 g, 64%). MS found: (M+H)$^+$=375.

(d) Methyl 3-(1-(4-fluorophenyl)-1H-indazol-5-yl)-3-phenylpropanoate (700 mg, 1.87 mmol) was dissolved in 45 mL MeOH/H$_2$O (8:1) and treated with NaOH (2 M, 10.8 mmol, 5.4 mL). The reaction was complete in 2 hours and was acidified with 1 M HCl and extracted 3×EtOAc, the combined organic layers were dried over MgSO4, filtered, and concentrated in vacuo to give pure 3-(1-(4-fluorophenyl)-1H-indazol-5-yl)-3-phenylpropanoic acid (620 mg, 92%) as a clear oil. MS found: (M+H)$^+$=361

(e) Example 136 was prepared from 3-(1-(4-fluorophenyl)-1H-indazol-5-yl)-3-phenylpropanoic acid (504 mg, 1.4 mmol) and 2-amino-1,3,4-thiadiazole using General Coupling Method A to give 310 mg (50% yield). MS found: (M+H)$^+$=444. Resolution of this compound into its enantiomers could be accomplished using chiral HPLC as described above.

Example 137

3-(1-(4-Fluorophenyl)-1H-indazol-5-yl)-N-(1-methyl-1H-1,2,4-triazol-3-yl)-3-phenylpropanamide

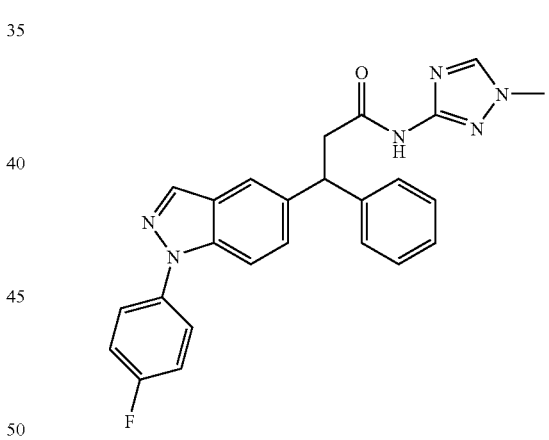

Example 137 was prepared from 3-(1-(4-fluorophenyl)-1H-indazol-5-yl)-3-phenylpropanoic acid (50 mg, 0.14 mmol) and 1-methyl-1H-1,2,4-triazol-3-amine using General Coupling Method A to give 7 mg (11% yield). MS found: (M+H)$^+$=441.5.

SCHEME V

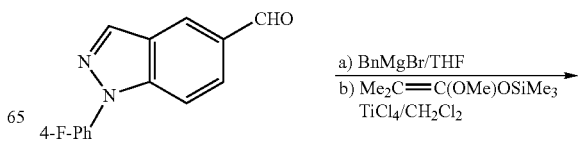

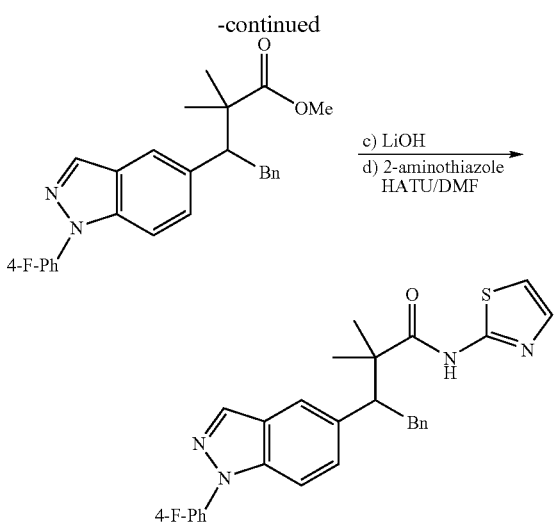

Example 138

3-(1-(4-Fluorophenyl)-1H-indazol-5-yl)-2,2-dimethyl-4-phenyl-N-(thiazol-2-yl)butanamide

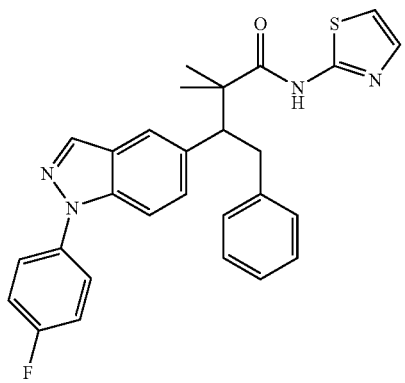

(a) To 1-(4-fluorophenyl)-1H-indazole-5-carbaldehyde (240 mg, 1.0 mmol) in anhydrous THF (5 mL) was added benzylmagnesium bromide (19% solution in THF, 3 mL, 3 mmol) dropwise at rt under argon. The reaction mixture was stirred at rt for 30 min and quenched by the slow addition of saturated aqueous ammonium chloride solution (5 mL). The mixture was extracted with ethyl acetate (2×4 mL). The combined ethyl acetate extracts were dried (Na$_2$SO$_4$), concentrated and purified by silica gel flash chromatography to give 1-(1-(4-fluorophenyl)-1H-indazol-5-yl)-2-phenylethanol (330 mg, 1.0 mmol, 100% yield) as a yellow oil.

(b) To a stirred solution of 1-(1-(4-fluorophenyl)-1H-indazol-5-yl)-2-phenylethanol (290 mg, 0.87 mmol) and (1-methoxy-2-methylprop-1-enyloxy)trimethylsilane (0.7 mL, 3.5 mmol) in anhydrous dichloromethane (5 mL) was added titanium(IV) tetrachloride (1M solution in toluene, 1.9 mL, 1.9 mmol) dropwise at 0° C. under argon. The reaction mixture was stirred at 0° C. for 30 min and rt for 2 hr before being quenched by the slow addition of saturated aqueous sodium bicarbonate solution (15 mL). The mixture was filtered through a pad of celite that was then washed with dichloromethane (10 mL). The aqueous filtrate was reextracted with dichloromethane (10 mL). The combined dichloromethane layers were dried (Na$_2$SO$_4$), concentrated and purified by silica gel flash chromatography to give methyl 3-(1-(4-fluorophenyl)-1H-indazol-5-yl)-2,2-dimethyl-4-phenylbutanoate (216 mg, 0.52 mmol, 60% yield) as an oil.

(c) A mixture of methyl 3-(1-(4-fluorophenyl)-1H-indazol-5-yl)-2,2-dimethyl-4-phenylbutanoate (210 mg, 0.50 mmol), lithium hydroxide monohydrate (80 mg, 1.9 mmol), water (3 mL), and dioxane (6 mL) was stirred at 90° C. for 24 hr under nitrogen. The reaction mixture was cooled to rt before diethyl ether (20 mL) was added. The ether layer was reextracted with water (2×3 mL). The combined aqueous solutions were acidified with aqueous 10% citric acid solution and extracted with ethyl acetate (3×6 mL). The combined ethyl acetate extracts were dried (Na$_2$SO$_4$) and concentrated to give 3-(1-(4-fluorophenyl)-1H-indazol-5-yl)-2,2-dimethyl-4-phenylbutanoic acid (200 mg, 0.50 mmol, 100% yield) as a solid.

(d) To a stirred solution of 3-(1-(4-fluorophenyl)-1H-indazol-5-yl)-2,2-dimethyl-4-phenylbutanoic acid (10 mg, 0.025 mmol) and diisopropylethylamine (0.05 mL) in anhydrous DMF (0.2 mL) was added HATU (25 mg, 0.066 mmol) at rt under argon. After stirring at rt for 10 min, 2-aminothiazole (15 mg, 0.15 mmol) was added. The reaction mixture was stirred at rt for 2.5 hr, 40° C. for 1 hr, and 80° C. for 30 min. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave 3-(1-(4-fluorophenyl)-1H-indazol-5-yl)-2,2-dimethyl-4-phenyl-N-(thiazol-2-yl)butanamide (Example 138, 7 mg, 0.01 mmol, 40% yield) as a white solid. MS found: (M+H)$^+$=485. $^1$H-NMR (400 MHz, CDCl$_3$) δ ppm 8.00 (1H, s) 7.53-7.58 (3H, m) 7.44 (1H, d, J=8.65 Hz) 7.35 (1H, d, J=3.56 Hz) 7.23 (1H, d, J=7.63 Hz) 7.11-7.15 (2H, m) 6.89-6.99 (7H, m) 3.63 (1H, dd, J=10.43, 4.32 Hz) 2.97-3.08 (2H, m) 1.37 (3H, s) 1.18 (3H, s).

SCHEME W

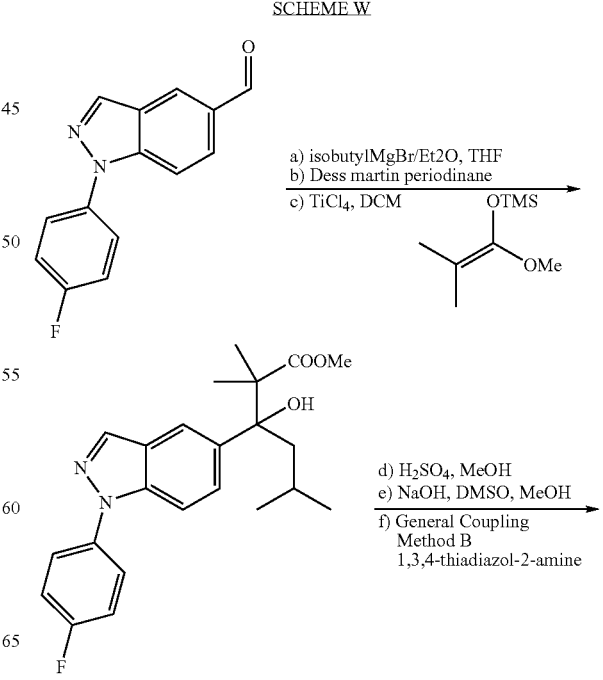

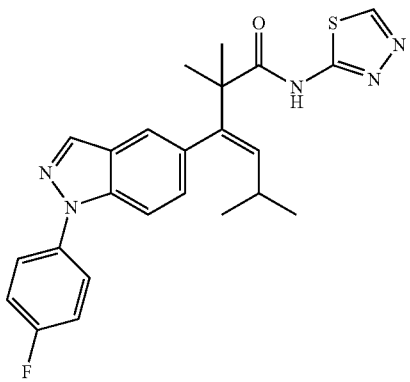

Example 139

(E)-3-(1-(4-Fluorophenyl)-1H-indazol-5-yl)-2,2,5-trimethyl-N-(1,3,4-thiadiazol-2-yl)hex-3-enamide

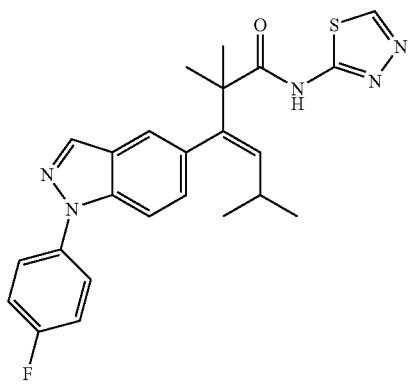

(a) To solution of 1-(4-fluorophenyl)-1H-indazol-5-carboxaldehyde (1.0 g, 4.1 mmol) in 10 mL of THF was added 2.0 M isobutylmagnesium bromide in ether. The reaction mixture was stirred 2 h and then quenched with MeOH. Poured into sat. KH$_2$PO$_4$ and extracted with EtOAc×3. The organic layers were dried over MgSO$_4$, filtered, and concentrated. The residue was purified by SiO$_2$ chromatography eluting with 5% EtOAc/DCM. Obtained 650 mg (49% yield) of 1-(1-(4-fluorophenyl)-1H-indazol-5-yl)-3-methylbutan-1-ol. MS found: (M+H)$^+$=299.

(b) 1-(1-(4-Fluorophenyl)-1H-indazol-5-yl)-3-methylbutan-1-ol (650 mg, 2.17 mmol) was dissolved in 50 mL dry DCM and Dess-Martin periodinane (1.0 g, 2.36 mmol) was added. The reaction mixture was stirred for 12 h. The reaction was poured into 1N NaOH and extracted with DCM×3. The organic layers were dried over MgSO$_4$, filtered, and concentrated to give 600 mg (92% yield) of 1-(1-(4-fluorophenyl)-1H-indazol-5-yl)-3-methylbutan-1-one. MS found: (M+H)$^+$=297.

(c) 1-(1-(4-Fluorophenyl)-1H-indazol-5-yl)-3-methylbutan-1-one (220 mg, 0.742 mmol) was dissolved in 10 mL of dry DCM and 1-methoxy-2-methyl-1-(trimethylsiloxy)propene (0.162 mL, 0.8 mmol) was added. The reaction mixture was cooled to 0° C. and TiCl$_4$ (0.8 mL of 1.0 M DCM solution, 0.8 mmol) was added portionwise and then stirred 12 h. The reaction was quenched with aqueous sodium bicarbonate and extracted 2×DCM. The organic layers were dried over MgSO$_4$, filtered, and concentrated. The residue was purified SiO$_2$ chromatography eluting with 1:1 EtOAc/hexane to give 280 mg (95% yield) of methyl 3-(1-(4-fluorophenyl)-1H-indazol-5-yl)-3-hydroxy-2,2,5-trimethylhexanoate. MS found: (M+H)$^+$=399.

(d) Methyl 3-(1-(4-fluorophenyl)-1H-indazol-5-yl)-3-hydroxy-2,2,5-trimethylhexanoate (280 mg, 0.7 mmol) was dissolved in 10 mL MeOH and 5 mL H$_2$SO$_4$ and heated at 90° C. for 12 h. After 12 h, diluted with water and extracted with EtOAc×3. The organic layers were dried over MgSO$_4$, filtered, and concentrated. The residue was purified by SiO$_2$ chromatography eluting with 1:9 EtOAc/hexane. Obtained 220 mg (82% yield) of (E)-methyl 3-(1-(4-fluorophenyl)-1H-indazol-5-yl)-2,2,5-trimethylhex-3-enoate. MS found: (M+H)$^+$=381.

(e) (E)-Methyl 3-(1-(4-fluorophenyl)-1H-indazol-5-yl)-2,2,5-trimethylhex-3-enoate (121 mg, 0.29 mmol) was dissolved in MeOH (10 mL) and DMSO (10 mL) and treated with 1 M NaOH (10 mL) at 100° C. After stirring overnight, the MeOH was removed in vacuo, the residue acidified with sat KH$_2$PO$_4$ to pH 4-5 and extracted with EtOAc×3. The organic layer was dried with MgSO$_4$, filtered, concentrated in vacuo to give 200 mg (94% yield) of (E)-3-(1-(4-fluorophenyl)-1H-indazol-5-yl)-2,2,5-trimethylhex-3-enoic acid. MS found: (M+H)$^+$=367.

(f) Example 139 was prepared from (E)-3-(1-(4-fluorophenyl)-1H-indazol-5-yl)-2,2,5-trimethylhex-3-enoic acid (105 mg, 0.29 mmol) and 1,3,4-thiadiazol-2-amine using General Coupling Method B to give 30 mg (25% yield). MS found: (M+H)$^+$=450.

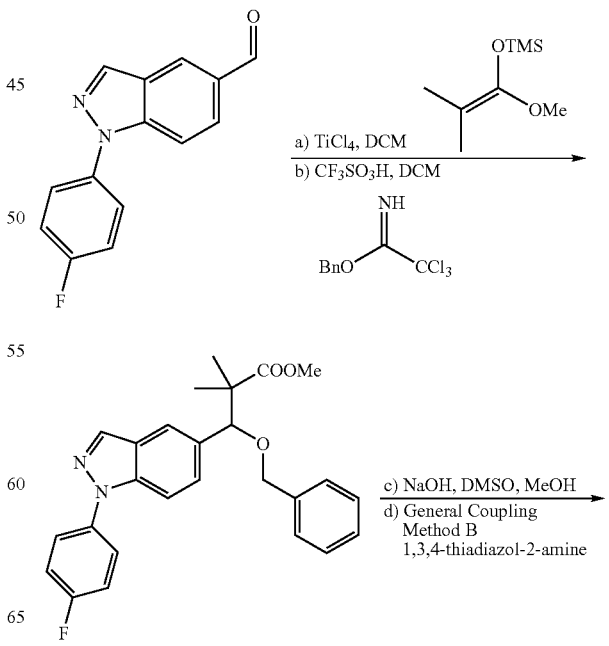

SCHEME X

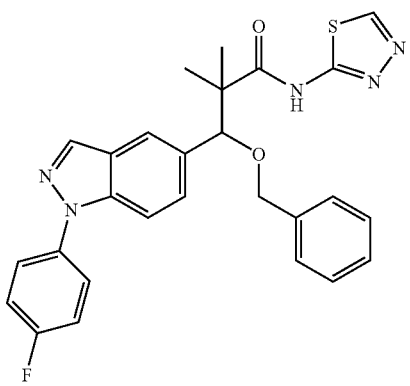

Example 140

3-(Benzyloxy)-3-(1-(4-fluorophenyl)-1H-indazol-5-yl)-2,2-dimethyl-N-(1,3,4-thiadiazol-2-yl)propanamide

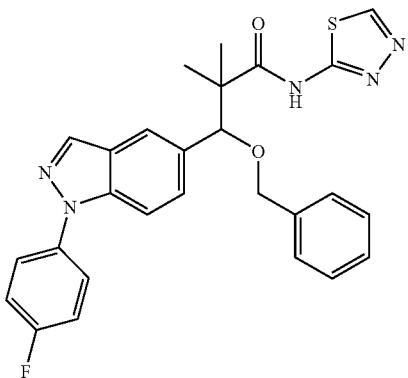

(a) To solution of 1-(4-fluorophenyl)-1H-indazol-5-carboxaldehyde (1.0 g, 4.16 mmol) and 1-methoxy-2-methyl-1-(trimethylsiloxy)propene (0.85 mL, 4.2 mmol) in 10 mL of dry DCM at 0° C. was added TiCl$_4$ (0.8 mL of 1.0 M DCM solution, 0.8 mmol) The reaction was stirred 2 h and then quenched with aqueous sodium bicarbonate and extracted 2×EtOAc. The organic layers were dried over MgSO$_4$, filtered, and concentrated. The residue was purified by SiO$_2$ chromatography eluting with 1:2 EtOAc/hexane to give 700 mg (50% yield) of methyl 3-(1-(4-fluorophenyl)-1H-indazol-5-yl)-3-hydroxy-2,2-dimethylpropanoate. MS found: $(M+H)^+$=343.

(b) Methyl 3-(1-(4-fluorophenyl)-1H-indazol-5-yl)-3-hydroxy-2,2-dimethylpropanoate (282 mg, 0.82 mmol) was dissolved in 10 mL DCM and benzyl-2,2,2-trichloroacetimidate (0.185 mL, 1.0 mmol) was added followed by 3 drops of CF$_3$SO$_3$H. The reaction was stirred for 2 h. Reaction was incomplete so added more benzyl-2,2,2-trichloroacetimidate (0.185 mL, 1.0 mmol). After 12 h, diluted with brine and extracted with DCM×3. The organic layers were dried over MgSO$_4$, filtered, and concentrated. The residue was purified by SiO$_2$ chromatography eluting with EtOAc/hexane gradient. Obtained 52 mg (15% yield) of methyl 3-(benzyloxy)-3-(1-(4-fluorophenyl)-1H-indazol-5-yl)-2,2-dimethylpropanoate. MS found: $(M+H)^+$=433.

(c) (E)-Methyl 3-(1-(4-fluorophenyl)-1H-indazol-5-yl)-2,2,5-trimethylhex-3-enoate (52 mg, 0.123 mmol) was dissolved in MeOH (5 mL) and DMSO (5 mL) and treated with 1 M NaOH (5 mL) at 100° C. After stirring overnight, the MeOH was removed in vacuo, the residue acidified with sat KH$_2$PO$_4$ to pH 4-5 and extracted with EtOAc×3. The organic layer was dried with MgSO$_4$, filtered, concentrated in vacuo to give 3-(benzyloxy)-3-(1-(4-fluorophenyl)-1H-indazol-5-yl)-2,2-dimethylpropanoic acid.

(d) Example 140 was prepared from 3-(benzyloxy)-3-(1-(4-fluorophenyl)-1H-indazol-5-yl)-2,2-dimethylpropanoic acid and 1,3,4-thiadiazol-2-amine using General Coupling Method A to give 8 mg (13% yield). MS found: $(M+H)^+$=502. NMR(CDCl$_3$) δ 8.20 (s, 1H); 7.60-7.76 (m, 4H) 7.2-7.4 (m, 9H); 4.63-4.66 (d, 1H); 4.60 (s, 1H); 4.20-4.23 (d, 1H); 1.30 (s, 3H); 1.22 (s, 3H).

General Silyl Ketene Acetal Method A

To a solution of LDA (1 eq) in THF (10-20 mL) at −78° C. was added ester (12-36 mmol). After stirring for 1 h, TMS-Cl (2 eq.) was added and the reaction is allowed to gradually warm to 25° C. The reaction mixture was filtered through a sintered glass funnel and filtrate was concentrated in vacuo. The residue was triturated in hexanes and solid were again filtered away. Filtrate was concentrated in vacuo and used in the next step.

General Silyl Ketene Acetal Method B

To a carboxylic acid chloride or acid fluoride (e.g., 6-50 mmol) was added benzyl alcohol (1 eq.). The reaction was stirred for 2 hr, then quenched with 1N NaOH and extracted with 2×EtOAc. The EtOAc extracts were dried over MgSO$_4$, filtered, and concentrated by rotary evaporator to give the corresponding benzyl ester. To a solution of LDA (1 eq) in THF (10-20 mL) at −78° C. was added benzyl ester (12-36 mmol). After stirring for 1 h, TMS-Cl (2 eq.) was added and the reaction is allowed to gradually warm to 25° C. The reaction mixture was filtered through a sintered glass funnel and filtrate was concentrated in vacuo. The residue was triturated in hexanes and solid were again filtered away. Filtrate was concentrated in vacuo and used in the next step.

SCHEME Y

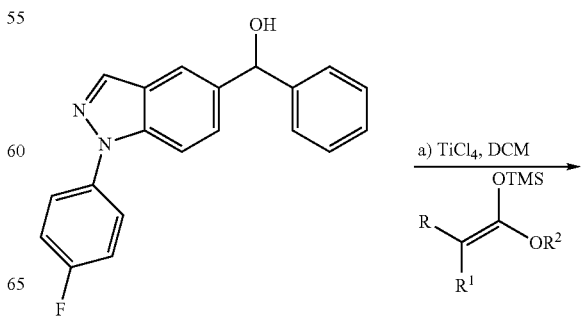

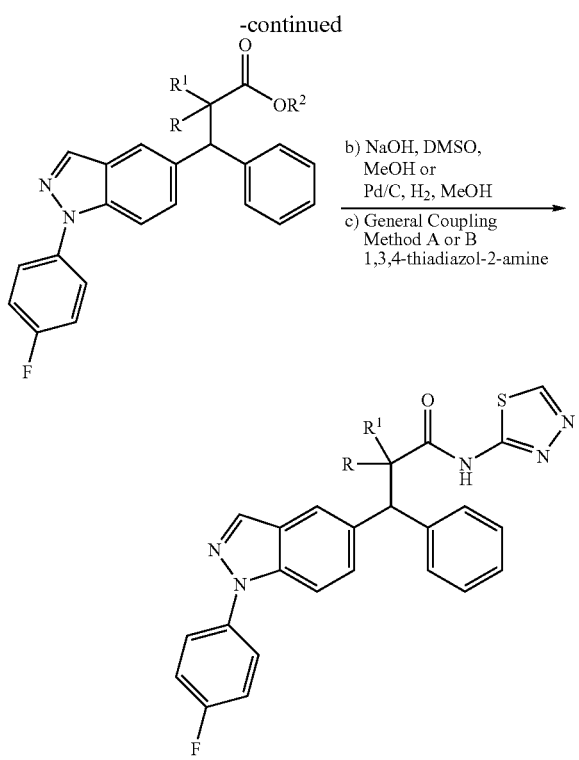

b) NaOH, DMSO, MeOH or Pd/C, H₂, MeOH c) General Coupling Method A or B 1,3,4-thiadiazol-2-amine The procedure of Scheme Y was used in preparing Examples 141 to 150.

Example 141

3-(1-(4-Fluorophenyl)-1H-indazol-5-yl)-2-methyl-3-phenyl-N-(1,3,4-thiadiazol-2-yl)propanamide

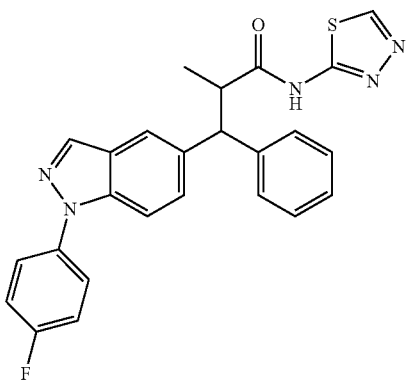

(a)(b) To a solution of (1-(4-fluorophenyl)-1H-indazol-5-yl)(phenyl)methanol (800 mg, 2.5 mmol) and (1-methoxyprop-1-enyloxy)trimethylsilane (1 mL, 6.25 mmol) in 30 mL of dry DCM was added TiCl₄ (2.5 mL of 1.0 M DCM solution, 2.5 mmol) and then stirred 1 h. The reaction was quenched with MeOH, poured into aqueous sodium bicarbonate and extracted 2×EtOAc. The organic layers were dried over MgSO₄, filtered, concentrated to give methyl 3-(1-(4-fluorophenyl)-1H-indazol-5-yl)-2-methyl-3-phenylpropanoat. Crude methyl 3-(1-(4-fluorophenyl)-1H-indazol-5-yl)-2-methyl-3-phenylpropanoate was heated to 100 C overnight in a mixture of 2 M NaOH/MeOH/DMSO (1:1:1). The next day, the reaction was cooled, acidified to pH 5 with HCl and extracted 2×EtOAc. The organic layers were washed with water×2, dried over MgSO₄, filtered, concentrated in vacuo, and purified by HPLC to give 770 mg (82% yield, 2 steps) of acid 3-(1-(4-fluorophenyl)-1H-indazol-5-yl)-2-methyl-3-phenylpropanoic acid. MS found: (M+H)⁺=375.

c) Example 141 was prepared from 3-(1-(4-fluorophenyl)-1H-indazol-5-yl)-2-methyl-3-phenylpropanoic acid (40 mg, 0.26 mmol) and 1,3,4-thiadiazol-2-amine using General Coupling Method A to give 6 mg (42% yield). MS found: (M+H)⁺=458.

Resolution of this compound into its four diastereomers could be accomplished using chiral HPLC as described above.

Diastereomer A: NMR(CDCl₃) δ 8.82 (bs, 1H); 8.20 (s, 1H); 7.9 (s, 1H) 7.62-7.64 (m, 3H); 7.52 (d, 1H); 7.34 (d, 2H); 7.2-7.3 (m, 3H); 7.12 (t, 2H); 7.05 (t, 1H); 4.40-4.42 (d, 1H); 3.89-3.93 (m, 1H); 1.29-1.31 (d, 3H).

Diastereomer B: NMR(CDCl₃) δ 8.71 (br s, 1H); 8.05 (s, 1H); 7.77 (s, 1H) 7.5-7.6 (m, 2H); 7.4-7.5 (m, 4H); 7.34 (t, 2H); 7.20-7.26 (m, 1H); 7.19 (t, 2H); 7.05 (t, 1H); 4.40-4.43 (d, 1H); 3.7-3.8 (m, 1H); 1.29-1.31 (d, 3H).

Example 142

2-((1-(4-Fluorophenyl)-1H-indazol-5-yl)(phenyl)methyl)-N-(1,3,4-thiadiazol-2-yl)butanamide

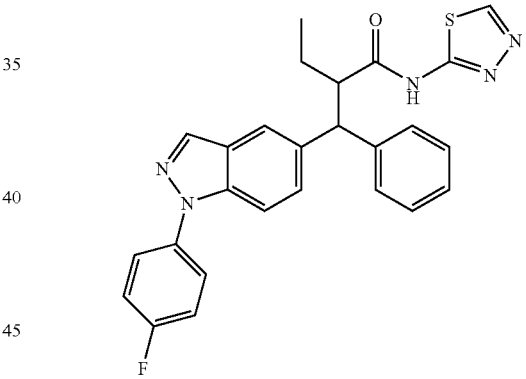

(a) To a solution of (1-(4-fluorophenyl)-1H-indazol-5-yl)(phenyl)methanol (250 mg, 0.79 mmol) and ((1-methoxybut-1-enyloxy)trimethylsilane (32 mmol) which was prepared using General Silyl Ketene Acetal Method A in 10 mL of dry DCM was added TiCl₄ (0.8 mL of 1.0 M DCM solution, 0.8 mmol) and then stirred 1 h. The reaction was quenched with MeOH, poured into aqueous sodium bicarbonate and extracted 2×EtOAc. The organic layers were dried over MgSO₄, filtered, concentrated and purified on SiO₂ by MPLC using a EtOAc/hexane gradient to give 200 mg (63% yield) of methyl 2-((1-(4-fluorophenyl)-1H-indazol-5-yl)(phenyl)methyl)butanoate. MS found: (M+H)⁺=403.

(b) Methyl 2-((1-(4-fluorophenyl)-1H-indazol-5-yl)(phenyl)methyl)butanoate was heated to 100 C overnight in a mixture of 2 M NaOH/MeOH/DMSO (1:1:1). The next day, the reaction was cooled, acidified to pH 5 with HCl and extracted 2×EtOAc. The organic layers were washed with water×2, dried over MgSO₄, filtered, concentrated in vacuo, and purified by HPLC to give 180 mg (93% yield) of acid 2-((1-(4-fluorophenyl)-1H-indazol-5-yl)(phenyl)methyl)butanoic acid. MS found: (M+H)+=389.

c) Example 142 was prepared from 2-((1-(4-fluorophenyl)-1H-indazol-5-yl)(phenyl)methyl)butanoic acid (180 mg, 0.26 mmol) and 1,3,4-thiadiazol-2-amine using General Coupling Method B to give 75 mg (35% yield). MS found: (M+H)+=472.

Examples 143 to 150

Examples 143 to 150 in the Table below were prepared using the same method as used for Examples 139 and 140 using the appropriate silyl ketene acetal and general silyl keten acetal method shown in the table.

| Ex. | Name | Product Structure | Silyl Ketene Acetal/Method | (M + H)+ |
|---|---|---|---|---|
| 143 | 2-((1-(4-fluorophenyl)-1H-indazol-5-yl)(phenyl)methyl)-N-(1,3,4-thiadiazol-2-yl)pentanamide | | A | 486 |
| 144 | 2-((1-(4-fluorophenyl)-1H-indazol-5-yl)(phenyl)methyl)-3-methyl-N-(1,3,4-thiadiazol-2-yl)butanamide | | A | 486 |
| 145 | 3-(1-(4-fluorophenyl)-1H-indazol-5-yl)-2,3-diphenyl-N-(1,3,4-thiadiazol-2-yl)propanamide | | A | 520 |

(1:1 mixture of diastereomers): NMR (CDCl$_3$) δ 8.94 (s, 0.5 H); 8.91 (s, 0.5 H); 8.01 (s, 0.5 H); 7.99 (s, 0.5 H); 7.93 (S, 0.5 H); 7.68 (s, 0.5 H); 7.4-7.65 (m, 7 H) 7.30-7.33 (d, 1 H); 7.09-7.20 (m, 7 H); 7.0 (t, 1 H); 5.37-5.39 (dd, 1 H); 5.09-5.11 (dd, 1 H); 3.89-3.93 (m, 1 H).

-continued
| Ex. | Name | Product Structure | Silyl Ketene Acetal/Method | (M + H)+ |
|---|---|---|---|---|
| 146 | 2-benzyl-3-(1-(4-fluorophenyl)-1H-indazol-5-yl)-3-phenyl-N-(1,3,4-thiadiazol-2-yl)propanamide | 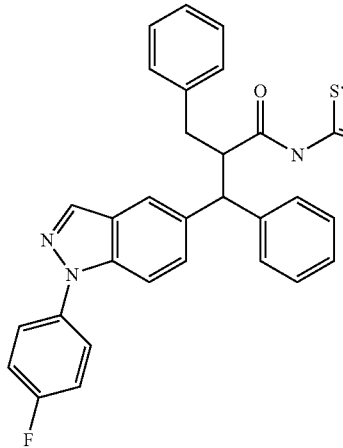 | 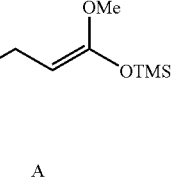 A | 534 |
| 147 | 2-cyclopentyl-3-(1-(4-fluorophenyl)-1H-indazol-5-yl)-3-phenyl-N-(1,3,4-thiadiazol-2-yl)propanamide | 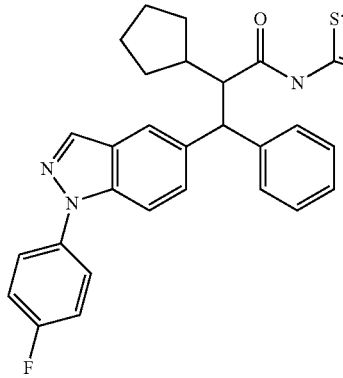 | 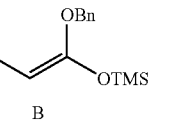 B | 512 |
| 148 | 2-cyclohexyl-3-(1-(4-fluorophenyl)-1H-indazol-5-yl)-3-phenyl-N-(1,3,4-thiadiazol-2-yl)propanamide | 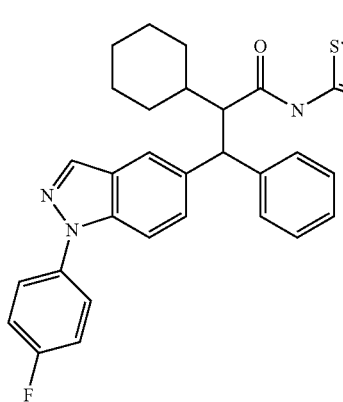 | 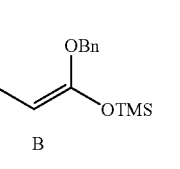 B | 525 |

| Ex. | Name | Product Structure | Silyl Ketene Acetal/Method | (M + H)+ |
|---|---|---|---|---|
| 149 | 2-ethyl-2-((1-(4-fluorophenyl)-1H-indazol-5-yl)(phenyl)methyl)-N-(1,3,4-thiadiazol-2-yl)butanamide | | B | 500 |
| 150 | 1-((1-(4-fluorophenyl)-1H-indazol-5-yl)(phenyl)methyl)-N-(1,3,4-thiadiazol-2-yl)cyclohexanecarboxamide | | B | 512 |

NMR (CDCl$_3$) δ 8.8 (s, 1 H); 8.11 (d, 1 H); 7.85 (s, 1 H) 7.60-7.65 (m, 2 H); 7.52-7.55 (d, 1 H); 7.38-7.45 (m, 3 H); 7.15-7.26 (m, 6 H); 4.35 (s, 1 H); 2.41-2.44 (m, 2 H); 1.67-1.77 (m, 4 H); 1.1-1.45 (m, 4 H).

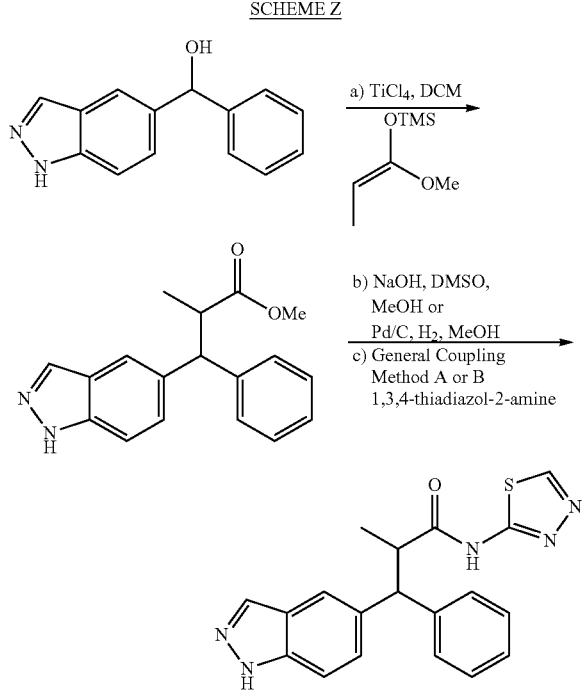

SCHEME Z a) TiCl$_4$, DCM b) NaOH, DMSO, MeOH or Pd/C, H$_2$, MeOH c) General Coupling Method A or B 1,3,4-thiadiazol-2-amine

Example 151

3-(1H-Indazol-5-yl)-2-methyl-3-phenyl-N-(1,3,4-thiadiazol-2-yl)propanamide

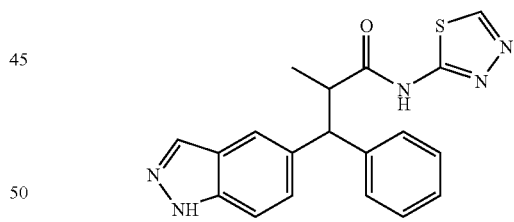

(a) To a solution of (1H-indazol-5-yl)(phenyl)methanol (180 mg, 0.71 mmol) and (1-methoxyprop-1-enyloxy)trimethylsilane (0.32 mL, 1.78 mmol) in 10 mL of dry MeCN was added TiCl$_4$ (2.5 mL of 1.0 M DCM solution, 2.5 mmol) and then stirred 1 h. The reaction was incomplete so added 10 mL of DCM and additional (1-methoxyprop-1-enyloxy)trimethylsilane (0.3 mL, 1.7 mmol) After 1 h, the reaction was quenched with MeOH, poured into aqueous sodium bicarbonate and extracted 2×EtOAc. The organic layers were dried over MgSO$_4$, filtered, and concentrated. HPLC purification resulted in the resolution of the two diastereomers of methyl 3-(1H-indazol-5-yl)-2-methyl-3-phenylpropanoate which were taken independently to the next step. MS found: (M+H)$^+$=295.

(b) Each diastereomer of methyl 3-(1H-indazol-5-yl)-2-methyl-3-phenylpropanoate was heated to 100° C. overnight in a mixture of 2 M NaOH/MeOH/DMSO (1:1:1). The next day, the reaction was cooled, acidified to pH 5 with HCl and extracted 2×EtOAc. The organic layers were washed with water×2, dried over MgSO$_4$, filtered, concentrated in vacuo, and purified by HPLC to give 27 mg (82% yield, 2 steps) and 35 mg of the diastereomers of acid 3-(1H-indazol-5-yl)-2-methyl-3-phenylpropanoic acid. MS found: (M+H)$^+$=281.

(c) Example 151 was prepared from 3-(1H-indazol-5-yl)-2-methyl-3-phenylpropanoic acid (40 mg, 0.26 mmol) and 1,3,4-thiadiazol-2-amine using General Coupling Method A to give 6 mg (42% yield). MS found: (M+H)$^+$=364. 400 MHz $^1$H-NMR (CDCl3) δ 8.77 (s, 1H); 7.90 (s, 1H); 7.75 (s, 1H); 7.75 (s, 1H); 7.47 (m, 4H); 7.36 (app t, 2H); 7.25 (dd, 2H); 4.35 (d, 1H); 3.87 (m, 1H); 1.31 (d, 3H).

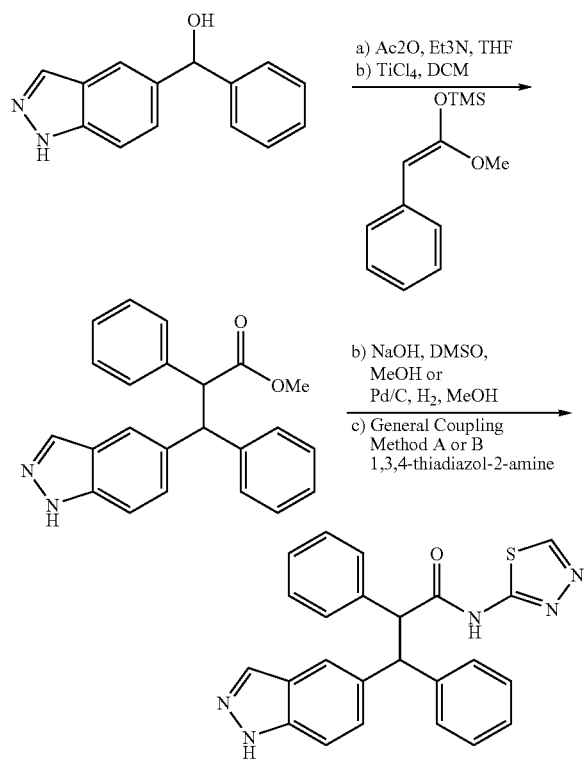

Example 152

3-(1H-Indazol-5-yl)-2,3-diphenyl-N-(1,3,4-thiadiazol-2-yl)propanamide

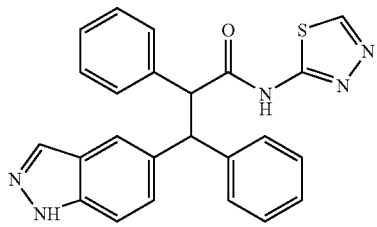

(a) To a solution of (1H-indazol-5-yl)(phenyl)methanol (1.1 g, 5.0 mmol) in 50 mL of dry THF was added EtN$_3$ (2.8 mL, 20 mmol) and acetic anhydride (1.9 mL, 20 mmol). The reaction was heated at reflux for 12 h. The reaction was quenched with aqueous sodium bicarbonate and extracted 2×EtOAc. The organic layers were dried over MgSO$_4$, filtered, and concentrated. The residue was taken up in toluene and concentrated in vacuo×2 to remove any excess acetic anhydride. Obtained a quantitative yield of (1H-indazol-5-yl)(phenyl)methyl acetate. MS found: (M+H)$^+$=309.

(b) To a solution of (1H-indazol-5-yl)(phenyl)methyl acetate (245 mg, 0.8 mmol) and (1-methoxy-2-phenylvinyloxy)trimethylsilane (1.78 g, 8.0 mmol, prepared using General Silyl Ketene Acetal Method A) in 20 mL of dry DCM was added TiCl$_4$ (0.8 mL of 1.0 M DCM solution, 0.8 mmol) and then stirred 3 h. The reaction was quenched with MeOH, poured into aqueous sodium bicarbonate and extracted 2×EtOAc. The organic layers were dried over MgSO$_4$, filtered, and concentrated. MPLC purification using a 0-40% EtOAc/hexane gradient gave 170 mg (60% yield) of methyl 3-(1H-indazol-5-yl)-2,3-diphenylpropanoate. MS found: (M+H)$^+$=357.

(c) Methyl 3-(1H-indazol-5-yl)-2,3-diphenylpropanoate was heated to 100° C. overnight in a mixture of 2 M NaOH/MeOH/DMSO (1:1:1). The next day, the reaction was cooled, acidified to pH 5 with HCl and extracted 2×EtOAc. The organic layers were washed with water×2, dried over MgSO$_4$, filtered, concentrated in vacuo, and purified by HPLC to give 10 mg (82% yield) and 30 mg of the diastereomers of acid 3-(1H-indazol-5-yl)-2,3-diphenylpropanoic acid. MS found: (M+H)$^+$=343.

(d) Example 152 was prepared from 3-(1H-indazol-5-yl)-2-methyl-3-phenylpropanoic acid (10 and 30 mg, 0.03 and 0.88 mmol) and 1,3,4-thiadiazol-2-amine using General Coupling Method A to give 4 mg (% yield) and 6 mg of the respective diastereomers. MS found: (M+H)$^+$=426. NMR (CDCl$_3$) δ 8.8 (s, 1H); 7.97-8.01 (d, 1H); 7.60 (s, 1H) 7.0-7.59 (m, 12H); 4.85 (d, 1H); 4.56 (d, 1H).

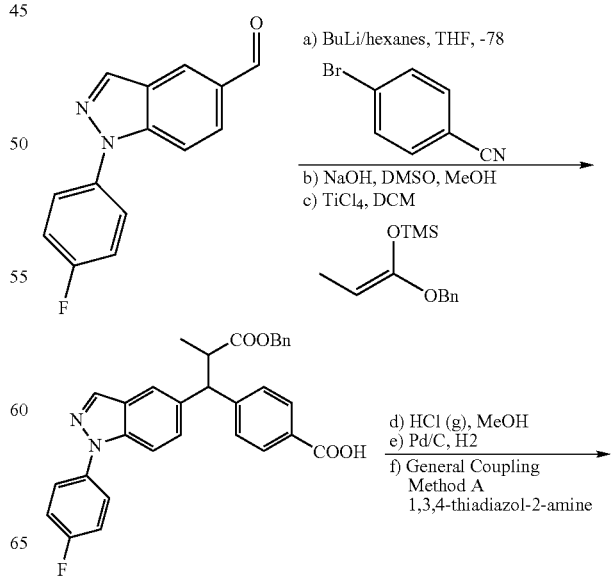

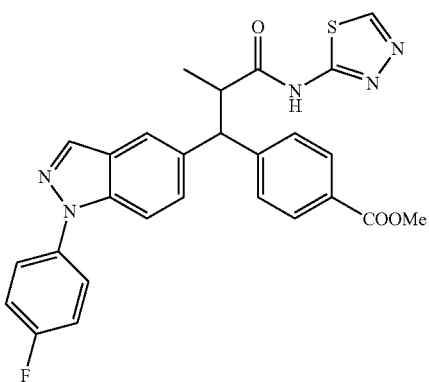

Example 153

Methyl 4-(3-(1,3,4-thiadiazol-2-ylamino)-1-(1-(4-fluorophenyl)-1H-indazol-5-yl)-2-methyl-3-oxopropyl)benzoate

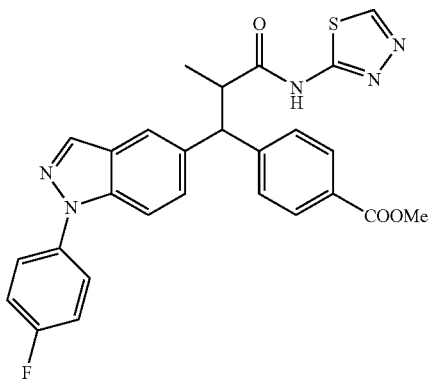

(a) To solution of 4-bromobenzonitrile (182 mg, 1.0 mmol) in 5 mL of dry THF at −78° C. was added n-BuLi (0.7 mL of 1.6 M hexanes solution, 1.1 mmol). The reaction was stirred 30 min and then 1-(4-fluorophenyl)-1H-indazol-5-carboxaldehyde (240 mg, 1.0 mmol) was added and the reaction mixture was allowed to warm to RT. After 12 h, quenched with brine and extracted 2×EtOAc. The organic layers were dried over MgSO$_4$, filtered, and concentrated. The residue was purified on SiO$_2$ by MPLC eluting with a 0-30% EtOAc/hexane gradient to give 180 mg (52% yield) of 4-((1-(4-fluorophenyl)-1H-indazol-5-yl)(hydroxy)methyl)benzonitrile. MS found: (M+H)$^+$=344.

(b) 4-((1-(4-Fluorophenyl)-1H-indazol-5-yl)(hydroxy)methyl)benzonitrile (180 mg, 0.52 mmol) was dissolved in MeOH (5 mL) and DMSO (5 mL) and treated with 1 M NaOH (5 mL) at 100° C. After 36 h, the MeOH was removed in vacuo, the residue acidified with sat KH$_2$PO$_4$ to pH 4-5 and extracted with EtOAc×3. The organic layer was dried with MgSO$_4$, filtered, concentrated in vacuo to give 180 mg (95% yield) of 4-((1-(4-fluorophenyl)-1H-indazol-5-yl)(hydroxy)methyl)benzoic acid. MS found: (M+H)$^+$=362.

(c) To a solution of 4-((1-(4-fluorophenyl)-1H-indazol-5-yl)(hydroxy)methyl)benzoic acid (180 mg, 0.5 mmol) and (Z)-(1-(benzyloxy)prop-1-enyloxy)trimethylsilane (10.0 mmol, prepared using General Silyl Ketene Acetal Method A) in 10 mL of dry DCM was added TiCl$_4$ (1.0 mL of 1.0 M DCM solution, 1.0 mmol) and then stirred 3 h. The reaction was quenched with MeOH, poured into aqueous sodium bicarbonate and extracted 2×EtOAc. The organic layers were dried over MgSO$_4$, filtered, and concentrated. MPLC purification on SiO$_2$ using a 0-100% EtOAc/hexane gradient gave 140 mg (55% yield) of 4-(3-(benzyloxy)-1-(1-(4-fluorophenyl)-1H-indazol-5-yl)-2-methyl-3-oxopropyl)benzoic acid. MS found: (M+H)$^+$=509.

(d) To a solution of 4-(3-(benzyloxy)-1-(1-(4-fluorophenyl)-1H-indazol-5-yl)-2-methyl-3-oxopropyl)benzoic acid (135 mg, 0.265 mmol) in 10 mL of dry MeOH was bubbled HCl gas for 15 min. After 1 h, most of the MeOH was removed in vacuo, then poured into aqueous sodium bicarbonate and extracted 2×EtOAc. The organic layers were dried over MgSO$_4$, filtered, and concentrated. Crude product was taken to the next step.

(e) The crude residue was dissolved in 50 mL of MeOH. 10% Pd/C (60 mg) was added and the reaction mixture was hydrogenated at 50 psi H2 using a Parr shaker. After 2 h, removed H2 and filtered away Pd/C. The filtrate was concentrated in vacuo to give 3-(1-(4-fluorophenyl)-1H-indazol-5-yl)-3-(4-(methoxycarbonyl)phenyl)-2-methylpropanoic acid. MS found: (M+H)$^+$=433.

(f) Example 153 was prepared from 3-(1-(4-fluorophenyl)-1H-indazol-5-yl)-3-(4-(methoxycarbonyl)phenyl)-2-methylpropanoic acid and 1,3,4-thiadiazol-2-amine using General Coupling Method A to give 35 mg (25% yield, 3 steps). MS found: (M+H)$^+$=516.

SCHEME AC

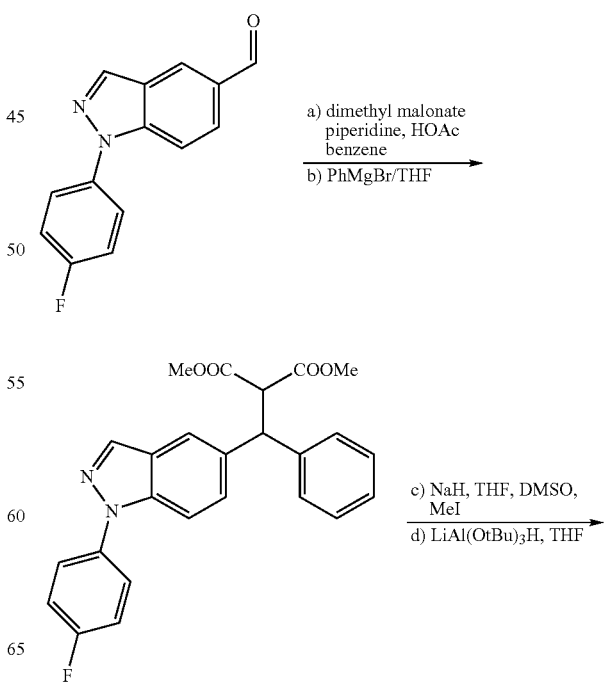

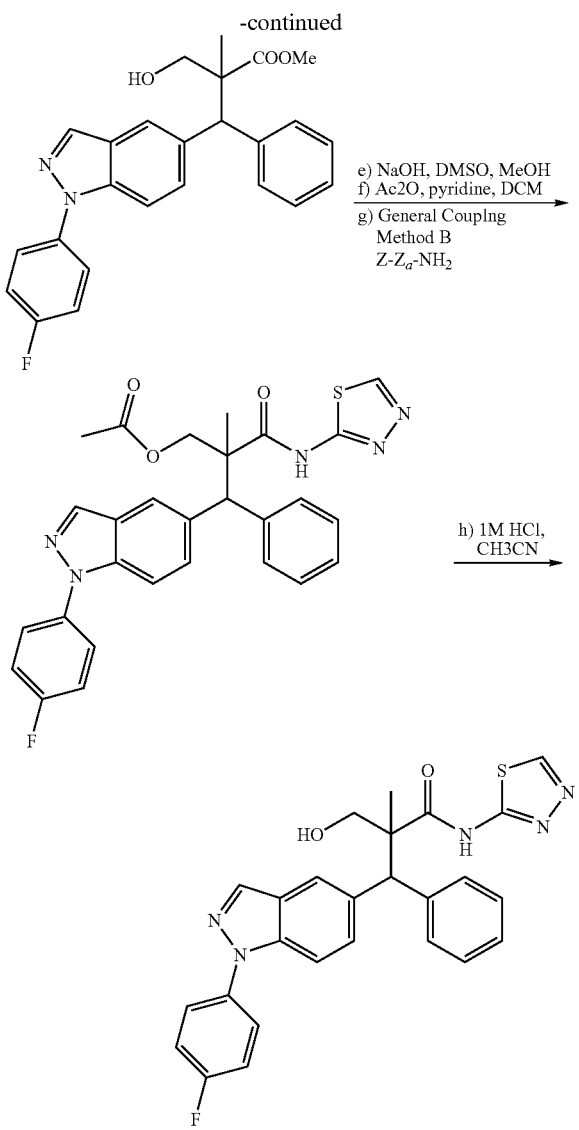

The procedure of Scheme AC was used to prepare Examples 154 and 155.

Example 154

3-(1,3,4-Thiadiazol-2-ylamino)-2-((1-(4-fluorophenyl)-1H-indazol-5-yl)(phenyl)methyl)-2-methyl-3-oxopropyl acetate

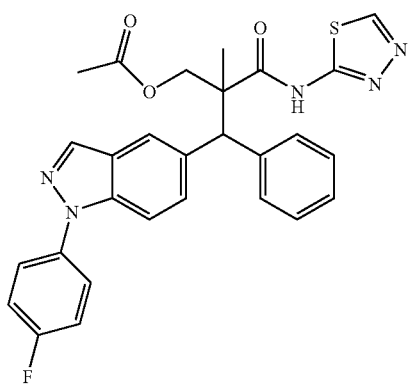

(a) To solution of dimethyl malonate (0.22 mL, 1.65 mmol) in benzene (15 mL) and acetic acid (3 drops) was added 1-(4-fluorophenyl)-1H-indazol-5-carboxaldehyde (330 mg, 1.38 mmol). The reaction mixture was heated at reflux overnight. The reaction was quenched with sat. $KH_2PO_4$ and extracted with EtOAc×3. The organic layers were dried over $MgSO_4$, filtered, and concentrated. The residue was purified on $SiO_2$ by MPLC using a 1:9 to 1:3 EtOAc/hexane gradient. Obtained 424 mg (87% yield) of dimethyl 2-((1-(4-fluorophenyl)-1H-indazol-5-yl)methylene)malonate. MS found: $(M+H)^+=355$.

(b) Dimethyl 2-((1-(4-fluorophenyl)-1H-indazol-5-yl)methylene)malonate (424 mg, 1.2 mmol) was dissolved in 10 mL dry THF and 1.0M phenylmagnesium bromide in THF (5 mL, 5.0 mmol) was added. The reaction mixture was stirred for 12 h. The reaction was quenched with MeOH then poured into brine and extracted with EtOAc×3. The organic layers were dried over $MgSO_4$, filtered, and concentrated. The residue was purified on $SiO_2$ by MPLC and eluting with 1:3 EtOAc/hexane. Obtained 435 mg (84% yield) of dimethyl 2-((1-(4-fluorophenyl)-1H-indazol-5-yl)(phenyl)methyl)malonate. MS found: $(M+H)^+=333$.

(c) Dimethyl 2-((1-(4-fluorophenyl)-1H-indazol-5-yl)(phenyl)methyl)malonate (250 mg, 0.58 mmol) was dissolved in THF (5 mL) and 60% oil dispersion NaH was added (24 mg, 0.6 mmol). After 1 h, added DMSO (2 mL) followed by MeI (5.8 mmol). After 72 h, the reaction was quenched with MeOH then poured into brine and extracted with EtOAc×3. The organic layers were dried over $MgSO_4$, filtered, and concentrated. The residue was purified on $SiO_2$ by MPLC using a 1:9 to 1:3 EtOAc/hexane gradient. Obtained 215 mg (83% yield) of dimethyl 2-((1-(4-fluorophenyl)-1H-indazol-5-yl)(phenyl)methyl)-2-methylmalonate. MS found: $(M+H)^+=447$.

(d) Dissolved LiAl(OtBu)3H (509 mg, 2.0 mmol) in 2 mL THF and then added a solution of dimethyl 2-((1-(4-fluorophenyl)-1H-indazol-5-yl)(phenyl)methyl)-2-methylmalonate (215 mg, 0.48 mmol) in 2 mL of THF. After 12 h, the reaction was incomplete so more LiAl(OtBu)3H (509 mg, 2.0 mmol) was added. After 12 h, quenched with MeOH, poured into brine and extracted with EtOAc×3. The organic layers were dried over $MgSO_4$, filtered, and concentrated. The residue was purified on $SiO_2$ by MPLC using a 1:3 to 1:1 EtOAc/hexane gradient. Obtained 121 mg (60% yield) of methyl 3-(1-(4-fluorophenyl)-1H-indazol-5-yl)-2-(hydroxymethyl)-2-methyl-3-phenylpropanoate. MS found: $(M+H)^+=419$.

(e) Methyl 3-(1-(4-fluorophenyl)-1H-indazol-5-yl)-2-(hydroxymethyl)-2-methyl-3-phenylpropanoate (121 mg, 0.29 mmol) was dissolved in MeOH (10 mL) and treated with 1 M NaOH (10 mL). After stirring overnight, the MeOH was removed in vacuo, the residue acidified with conc HCl to pH 4-5 and extracted with EtOAc×3. The organic layer was dried with $MgSO_4$, filtered, concentrated in vacuo to give 115 mg (98%) of 3-(1-(4-fluorophenyl)-1H-indazol-5-yl)-2-(hydroxymethyl)-2-methyl-3-phenylpropanoic acid. MS found: $(M+H)^+=405$.

(f) 3-(1-(4-Fluorophenyl)-1H-indazol-5-yl)-2-(hydroxymethyl)-2-methyl-3-phenylpropanoic acid (404 mg, 0.28 mmol) was dissolved in 5 mL of dry DCM and pyridine (0.3 mmol) and acetic anhydride (0.3 mmol) were added and then stirred 2 h.

The reaction was concentrate in vacuo. The residue was purified on SiO$_2$ by MPLC using a 1:3 to 1:9 gradient of EtOAc/hexane to give 75 mg of 2-(acetoxymethyl)-3-(1-(4-fluorophenyl)-1H-indazol-5-yl)-2-methyl-3-phenylpropanoic acid.

(g) Example 154 was prepared from 2-(acetoxymethyl)-3-(1-(4-fluorophenyl)-1H-indazol-5-yl)-2-methyl-3-phenylpropanoic acid (75 mg, 0.168 mmol) and 1,3,4-thiadiazol-2-amine using General Coupling Method B to give 35 mg (39% yield). MS found: (M+H)$^+$=530.

Example 155

3-(1-(4-Fluorophenyl)-1H-indazol-5-yl)-2-(hydroxymethyl)-2-methyl-3-phenyl-N-(1,3,4-thiadiazol-2-yl)propanamide

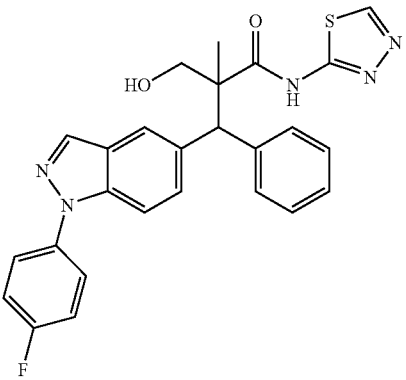

(h) Example 155 was prepared from 3-(1,3,4-thiadiazol-2-ylamino)-2-((1-(4-fluorophenyl)-1H-indazol-5-yl)(phenyl)methyl)-2-methyl-3-oxopropyl acetate (24 mg, 0.168 mmol) by treating with 1N HCl in CH3CN and heating for 1 hr at reflux. The product was purified by HPLC to give 6 mg of desired product. MS found: (M+H)$^+$=48.

SCHEME AD

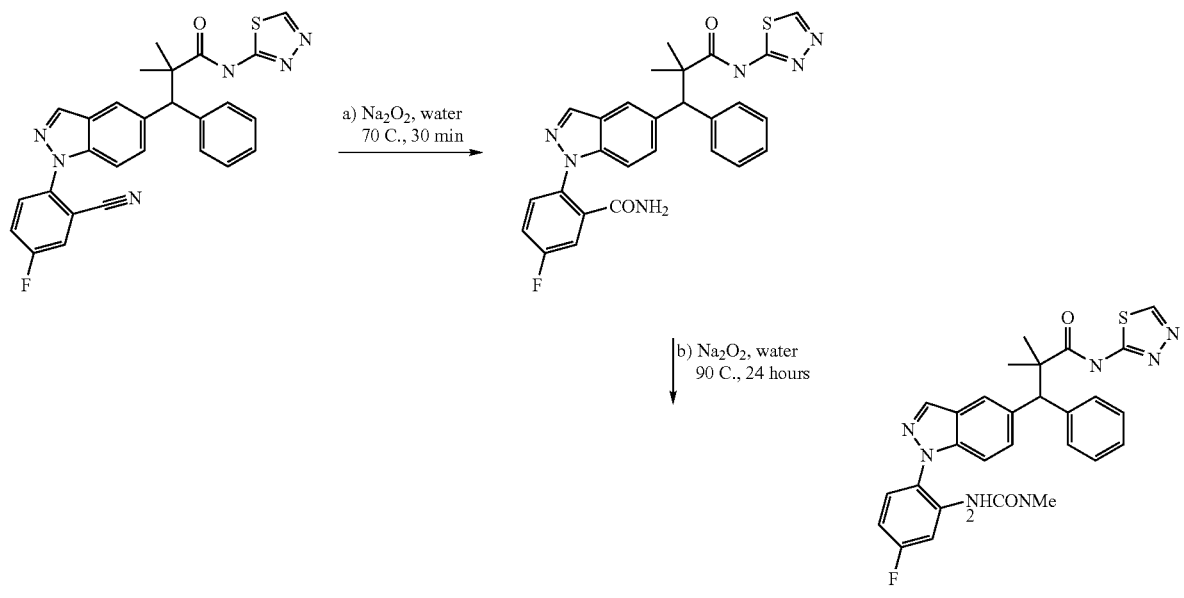

+

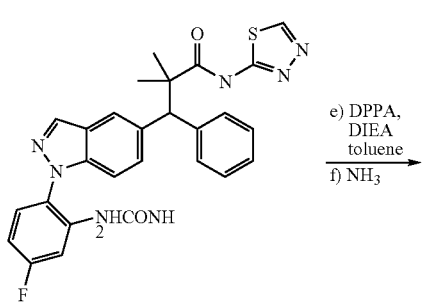 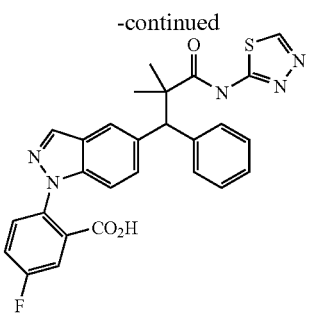 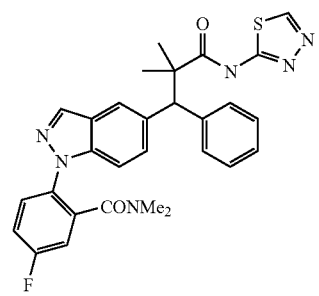

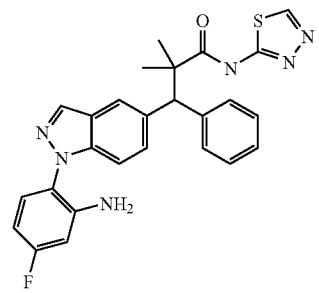

Example 156

2-(5-((S)-3-(1,3,4-Thiadiazol-2-ylamino)-2,2-dimethyl-3-oxo-1-phenylpropyl)-1H-indazol-1-yl)-5-fluorobenzamide Example 157

2-(5-((S)-3-(1,3,4-Thiadiazol-2-ylamino)-2,2-dimethyl-3-oxo-1-phenylpropyl)-1H-indazol-1-yl)-5-fluorobenzoic acid

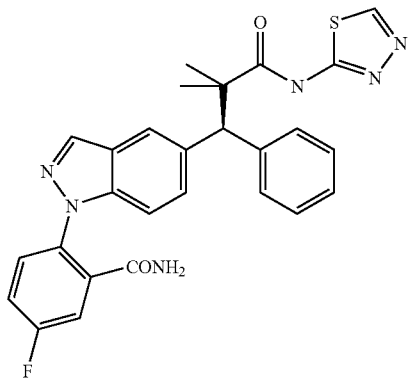

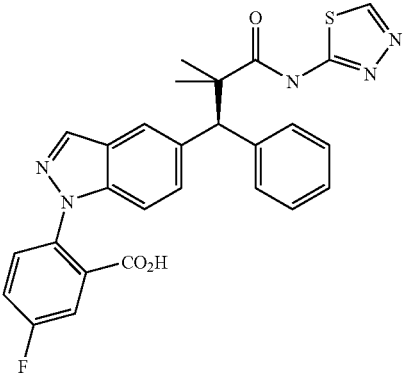

(a) A suspension of (5 mg, 0.01 mmol) and $Na_2O_2$ (11 mg, 0.15 mmol) in water (1 mL) was stirred under nitrogen at 70° C. for 30 min. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 2-(5-((S)-3-(1,3,4-thiadiazol-2-ylamino)-2,2-dimethyl-3-oxo-1-phenylpropyl)-1H-indazol-1-yl)-5-fluorobenzamide; Example 156 (3 mg, 0.006 mmol, 60% yield) as a white solid. MS found: $(M+H)^+=515$. $^1$H-NMR (500 MHz, METHANOL-$d_3$) δ ppm 8.96 (s, 1H) 8.17 (s, 1H) 7.88 (s, 1H) 7.58 (dd, J=8.80, 4.67 Hz, 1H) 7.49 (dd, J=8.39, 2.89 Hz, 1H) 7.38-7.44 (m, 4H) 7.31 (d, J=9.07 Hz, 1H) 7.25 (t, J=7.56 Hz, 2H) 7.15-7.19 (m, 1H) 4.81 (s, 1H) 1.45 (s, 3H) 1.44 (s, 3H).

(b) A suspension of (3S)-3-(1-(2-cyano-4-fluorophenyl)-1H-indazol-5-yl)-2,2-dimethyl-3-phenyl-N-(1,3,4-thiadiazol-2-yl)propanamide (35 mg, 0.072 mmol) and $Na_2O_2$ (77 mg, 1.1 mmol) in water (7 mL) was stirred under nitrogen at 70° C. for 30 min and at 90° C. for 1 day. The mixture was acidified with 10% aqueous citric acid solution to pH=2 and extracted with ethyl acetate (3×5 mL). The combined ethyl acetate extracts were concentrated in vacuo. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 2-(5-((S)-3-(1,3,4-thiadiazol-2-ylamino)-2,2-dimethyl-3-oxo-1-phenylpropyl)-1H-indazol-1-yl)-5-fluorobenzoic acid; Example 157 (24 mg, 0.047 mmol, 64% yield) as a yellow solid. MS found: $(M+H)^+=516$. $^1$H-NMR (500 MHz, METHANOL-$d_3$) δ ppm 8.95 (s, 1H) 8.16 (s, 1H) 7.89 (s, 1H) 7.72 (dd, J=8.80, 3.02 Hz, 1H) 7.60 (dd, J=8.66, 4.81 Hz, 1H) 7.49 (td, J=8.25, 3.02 Hz, 1H) 7.39-7.43 (m, 3H) 7.15-7.27 (m, 4H) 4.82 (s, 1H) 1.46 (s, 3H) 1.44 (s, 3H).

Example 158

2-(5-((S)-3-(1,3,4-Thiadiazol-2-ylamino)-2,2-dimethyl-3-oxo-1-phenylpropyl)-1H-indazol-1-yl)-5-fluoro-N,N-dimethylbenzamide

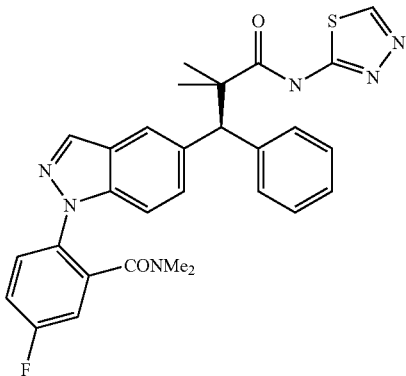

Example 159

(3S)-3-(1-(2-Amino-4-fluorophenyl)-1H-indazol-5-yl)-2,2-dimethyl-3-phenyl-N-(1,3,4-thiadiazol-2-yl)propanamide

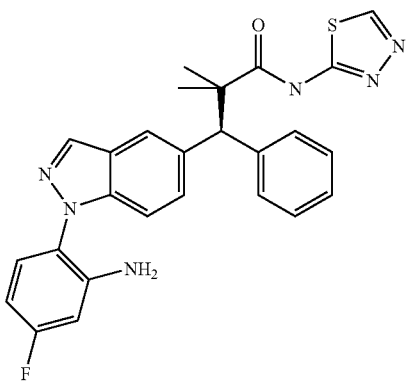

Example 160

(3S)-3-(1-(2-(3,3-Dimethylureido)-4-fluorophenyl)-1H-indazol-5-yl)-2,2-dimethyl-3-phenyl-N-(1,3,4-thiadiazol-2-yl)propanamide

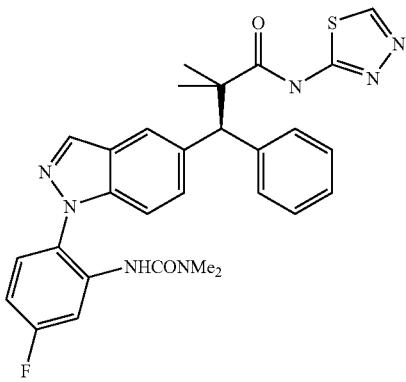

(c)(d) A mixture of 2-(5-((S)-3-(1,3,4-thiadiazol-2-ylamino)-2,2-dimethyl-3-oxo-1-phenylpropyl)-1H-indazol-1-yl)-5-fluorobenzoic acid (9.4 mg, 0.018 mmol), diisopropylethylamine (0.01 mL), and anhydrous toluene (0.2 mL) was degassed and backfilled with nitrogen. After DPPA (0.01 mL, 0.046 mmol) was added, the mixture was heated to 100° C. over 20 min and then cooled to RT. Diisopropylethylamine (0.02 mL) and dimethylamine hydrochloride (100 mg, 1.2 mmol) were added sequentially. The reaction mixture was then stirred at RT for 1 hr and at 80° C. for 3 hr before concentrated in vacuo. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave:

1) 2-(5-((S)-3-(1,3,4-Thiadiazol-2-ylamino)-2,2-dimethyl-3-oxo-1-phenylpropyl)-1H-indazol-1-yl)-5-fluoro-N,N-dimethylbenzamide; Example 158 (2 mg, 0.0037 mmol, 20% yield) as a glassy solid. MS found: $(M+H)^+$=543. $^1$H-NMR (500 MHz, methanol-$d_3$) δ ppm 8.95 (s, 1H) 8.14 (s, 1H) 7.89 (s, 1H) 7.67 (dd, J=8.80, 4.95 Hz, 1H) 7.39-7.44 (m, 5H) 7.32 (dd, J=8.39, 2.89 Hz, 1H) 7.26 (t, J=7.84 Hz, 2H) 7.16-7.20 (m, 1H) 4.82 (s, 1H) 2.74 (s, 3H) 2.59 (s, 3H) 1.46 (s, 3H) 1.44 (s, 3H);

2) (3S)-3-(1-(2-Amino-4-fluorophenyl)-1H-indazol-5-yl)-2,2-dimethyl-3-phenyl-N-(1,3,4-thiadiazol-2-yl)propanamide; Example 159 (1.6 mg, 0.003 mmol, 15% yield) as a glassy solid. MS found: $(M+H)^+$=487. $^1$H-NMR (500 MHz, METHANOL-$d_3$) δ ppm 8.95 (s, 1H) 8.20 (s, 1H) 7.90 (s, 1H) 7.40-7.44 (m, 3H) 7.25 (t, J=7.56 Hz, 2H) 7.19 (dd, J=8.11, 3.44 Hz, 2H) 7.14 (dd, J=8.66, 5.91 Hz, 1H) 6.65 (dd, J=11.00, 2.75 Hz, 1H) 6.47 (td, J=8.39, 2.75 Hz, 1H) 4.82 (s, 1H) 1.46 (s, 3H) 1.45 (s, 3H); and 3) (3S)-3-(1-(2-(3,3-Dimethylureido)-4-fluorophenyl)-1H-indazol-5-yl)-2,2-dimethyl-3-phenyl-N-(1,3,4-thiadiazol-2-yl)propanamide; Example 160 (3 mg, 0.005 mmol, 30% yield) as a white solid. MS found: $(M+H)^+$=558. $^1$H-NMR (500 MHz, methanol-$d_3$) δ ppm 8.96 (s, 1H) 8.30 (s, 1H) 7.94 (s, 1H) 7.89 (ddd, J=11.13, 4.81, 3.02 Hz, 1H) 7.40-7.51 (m, 4H) 7.35 (d, J=8.80 Hz, 1H) 7.26 (t, J=7.70 Hz, 2H) 7.16-7.21 (m, 1H) 6.93-6.99 (m, 1H) 4.84 (s, 1H) 2.77 (s, 6H) 1.47 (s, 3H) 1.45 (s, 3H).

Example 161

(3S)-3-(1-(4-Fluoro-2-ureidophenyl)-1H-indazol-5-yl)-2,2-dimethyl-3-phenyl-N-(1,3,4-thiadiazol-2-yl)propanamide

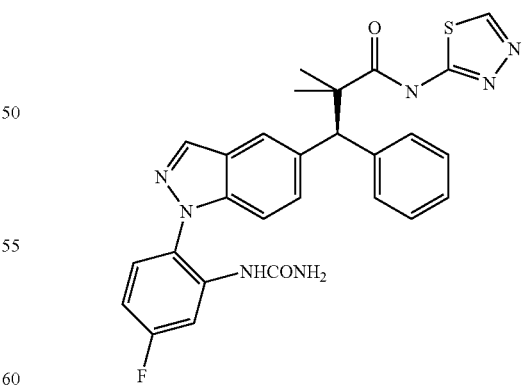

(e)(f) A mixture of 2-(5-((S)-3-(1,3,4-thiadiazol-2-ylamino)-2,2-dimethyl-3-oxo-1-phenylpropyl)-1H-indazol-1-yl)-5-fluorobenzoic acid (12 mg, 0.023 mmol), diisopropylethylamine (0.01 mL), anhydrous toluene (0.2 mL), and DPPA (0.01 mL, 0.046 mmol) was heated to 100° C. over 25 min under nitrogen and stirred at 100° C. for 10 min before cooled to RT. An ammonia solution (0.5 M in dioxane, 0.4 mL, 0.2 mmol) was added. The reaction mixture was stirred at RT overnight before concentrated in vacuo. Purification using reverse phase HPLC (YMC S5 20×100 mm, 10 min. run, solvent A: 10% MeOH: 90% H₂O: 0.1% TFA, solvent B: 90% MeOH, 10% H₂O, 0.1% TFA) gave (3S)-3-(1-(4-fluoro-2-ureidophenyl)-1H-indazol-5-yl)-2,2-dimethyl-3-phenyl-N-(1,3,4-thiadiazol-2-yl)propanamide; Example 161 (2.3 mg, 0.0043 mmol, 19% yield). MS found: (M+H)⁺=530. ¹H-NMR (400 MHz, MeOD) δ ppm 8.96 (s, 1H) 8.26 (s, 1H) 8.07 (dd, J=11.58, 2.77 Hz, 1H) 7.93 (s, 1 H) 7.39-7.47 (m, 3H) 7.15-7.28 (m, 5H) 6.88 (td, J=8.25, 2.90 Hz, 1H) 4.84 (s, 1 H) 1.47 (s, 3H) 1.44 (s, 3H).

SCHEME AE

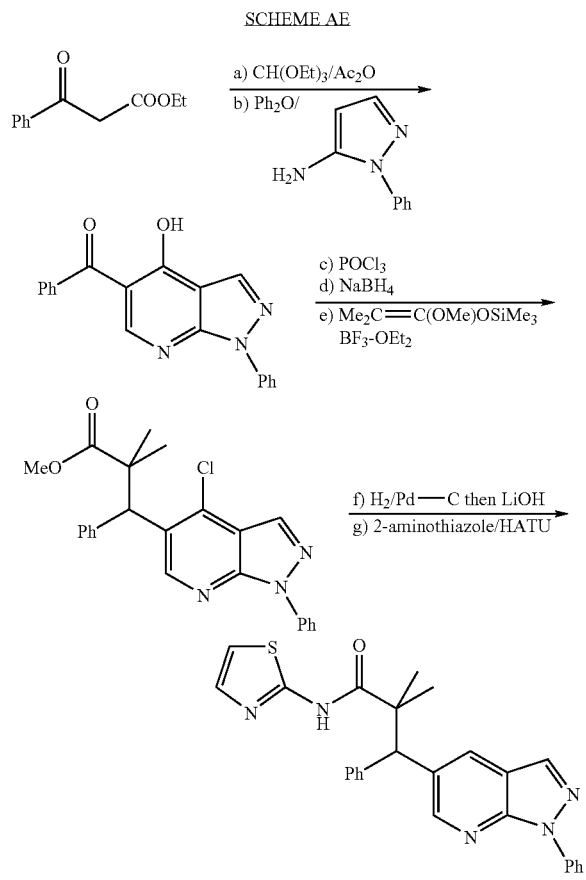

Example 162

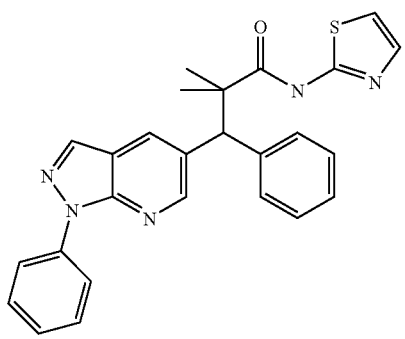

(a) A mixture of ethyl 3-oxo-3-phenylpropanoate (17.2 mL, 100 mmol), triethyl orthoformate (24.5 mL, 150 mmol), and acetic anhydride (38 mL, 400 mmol) was stirred at 135° C. for 5 hr. Distillation under reduced pressure gave ethyl 2-benzoyl-3-ethoxyacrylate (14.7 g, 59 mmol, 59% yield) as a yellow liquid.

(b) A mixture of ethyl 2-benzoyl-3-ethoxyacrylate (0.99 g, 4.0 mmol) and 1-phenyl-1H-pyrazol-5-amine (0.64 g, 4.0 mmol) was stirred at 120° C. for 1.5 hr under argon and then cooled. After diphenyl ether (5 g) was added, the mixture was stirred at 240° C. for 2 hr under argon. Flash chromatography and crystallization in heptane and ethyl acetate mixture gave (4-hydroxy-1-phenyl-1H-pyrazolo[3,4-b]pyridin-5-yl)(phenyl)methanone (0.53 g, 1.7 mmol, 42% yield) as a yellow solid.

(c) A mixture of (4-hydroxy-1-phenyl-1H-pyrazolo[3,4-b]pyridin-5-yl)(phenyl)methanone (0.38 g, 1.2 mmol) and phosphorus oxychloride (1.3 mL) was stirred at 110° C. for 1.5 hr. The mixture was cooled, poured onto ice, basified with sodium hydroxide aqueous solution to pH=8, and extracted with ethyl acetate. Combined extracts were dried (Na₂SO₄) and concentrated. Flash chromatography gave (4-chloro-1-phenyl-1H-pyrazolo[3,4-b]pyridin-5-yl)(phenyl)methanone (0.26 g, 0.79 mmol, 66% yield) as a yellow solid.

(d) To a stirred solution of (4-chloro-1-phenyl-1H-pyrazolo[3,4-b]pyridin-5-yl)(phenyl)methanone (0.16 g, 0.48 mmol) in THF (1.5 mL) and ethanol (95%, 1.5 mL) was added sodium borohydride (30 mg, 0.79 mmol). The mixture was stirred at rt for 30 min before saturated ammonium chloride aqueous solution was added with caution. The mixture was concentrated and partitioned between water and ethyl acetate. The aqueous layer was separated and extracted with ethyl acetate. Combined organic solutions were dried (Na₂SO₄), filtered through a pad of silica gel, and concentrated to give (4-chloro-1-phenyl-1H-pyrazolo[3,4-b]pyridin-5-yl)(phenyl)methanol (0.16 g, 0.48 mmol, 100% yield) as a yellow solid.

(e) (4-chloro-1-phenyl-1H-pyrazolo[3,4-b]pyridin-5-yl)(phenyl)methanol was converted to methyl 3-(4-chloro-1-phenyl-1H-pyrazolo[3,4-b]pyridin-5-yl)-2,2-dimethyl-3-phenylpropanoate using the procedure of Example 1(g).

(f) A mixture of methyl 3-(4-chloro-1-phenyl-1H-pyrazolo[3,4-b]pyridin-5-yl)-2,2-dimethyl-3-phenylpropanoate (27 mg, 0.064 mmol), palladium (10% on carbon, 10 mg), diisopropylethylamine (0.017 mL, 0.096 mmol), and ethanol (3 mL) was stirred under hydrogen balloon for 80 min. The mixture was then filtered through a pad of silica gel and concentrated. The residue was mixed with lithium hydroxide monohydrate (30 mg, 0.7 mmol), water (1 mL), and dioxane (1 mL), and stirred at 110° C. overnight. After cooled, the mixture was partitioned between water and diethyl ether. The ether layer was extracted with water. Combined aqueous solutions were acidified with 10% citric acid aqueous solution and extracted with ethyl acetate. Combined extracts were washed with brine, dried (Na₂SO₄) and concentrated to give 2,2-dimethyl-3-phenyl-3-(1-phenyl-1H-pyrazolo[3,4-b]pyridin-5-yl)propanoic acid (16 mg, 0.043 mmol, 69% yield).

(g) To a stirred solution of 2,2-dimethyl-3-phenyl-3-(1-phenyl-1H-pyrazolo[3,4-b]pyridin-5-yl)propanoic acid (8 mg, 0.022 mmol), 2-aminothiazole (9 mg, 0.09 mmol), and diisopropylethylamine (0.015 mL, 0.09 mmol) in anhydrous DMF (0.3 mL) was added HATU (33 mg, 0.09 mmol) under argon. After stirred at rt overnight and 80° C. for 30 min, the mixture was concentrated. HPLC purification gave 2,2-dimethyl-3-phenyl-3-(1-phenyl-1H-pyrazolo[3,4-b]pyridin-5-yl)-N-(thiazol-2-yl)propanamide (Example 162, 5 mg, 0.009 mmol, 41% yield) as a trifluoroacetic acid salt. MS found: (M−H)⁻=452.11. ¹H-NMR (400 MHz, Acetone) δ ppm 8.56 (1 H, d, J=2.54 Hz) 8.39 (1H, d, J=2.03 Hz) 8.24 (2H, d, J=7.63 Hz) 8.18 (1H, s), 7.37-7.47 (4H, m) 7.27 (1H, d, J=3.56 Hz) 7.16-7.23 (3H, m) 7.11 (1H, t, J=7.38 Hz) 6.95 (1H, d, J=3.56 Hz) 4.98 (1H, s) 1.42 (6H, d, J=7.63 Hz).

Biological Activity

Below is a Table containing activity for Examples 1 to 162. (R) and (S) refer to absolute stereochemistry. "Enant A" and "enant B" refer to enantiomerically pure compounds of unknown configuration that were resolved by chiral HPLC and are arbitrarily assigned. "Diast A" and "diast B" refer to diastereomerically pure compounds of unknown relative stereochemistry. "Isomer A" "isomer B" "isomer C" and "isomer D" refer to two enantiomeric pairs of two diastereomers all resolved by chiral HPLC and are arbitraily assigned.

Biological Activity Table

| Example No. | GR (Ki, nM) (GR Binding Assay (I)) | GR (Ki, nM) (GR Binding Assay (II)) | AP-1 (EC50, nM) (Cellular Transrepression Assay) |
|---|---|---|---|
| (S)-1 | 6.0 | | 0.81 |
| (R)-1 | 7.9 | | 400 |
| (S)-2 | 5.1 | | 2.4 |
| (R)-2 | 6.7 | | 92 |
| 3 | 6.9 | | 199 |
| 4 | 7 | | 12 |
| 5 | 7.0 | | 1328 |
| 6 | 77 | | >10000 |
| 7 | 2.9 | | 904 |
| 8 | 3.0 | | 1796 |
| 9 | 3.7 | | 3058 |
| 10 | 227 | | 3521 |
| 11 | 11 | | 73 |
| 12 | 14 | | 29 |
| 13 | 11 | | 17 |
| 14 | 17 | | >10000 |
| 15 | 318 | | >10000 |
| 16 | 163 | | >10000 |
| 17 | 11 | | 49 |
| 18 | 21 | | 141 |
| 19 | 47 | | >10000 |
| 20 | 10 | | >10000 |
| 21 | 12 | | 155 |
| 22 | 29 | | 840 |
| 23 | 60 | | >10000 |
| 24 | 28 | | >10000 |
| 25 | 19 | | >10000 |
| 26 | 16 | | 404 |
| 27 | 23 | | 1307 |
| 28 | 20 | | 647 |
| 29 | 7.8 | | 126 |
| (S)-30 | | 0.54 | 24 |
| (R)-30 | 13 | | 701 |
| 31 | 98 | | >10000 |
| 32 | 84 | | 4322 |
| 33-enant A | 18 | | >10000 |
| 33-enant B | 13 | | 11 |
| 34 | 7.5 | | 29 |
| 35 | 21 | | 82 |
| 36 | 12 | | 389 |
| 37 | 301 | | 3350 |
| 38-enant A | 15 | | 12 |
| 38-enant B | 14 | | >10000 |
| 39 | 9.8 | | 87 |
| 40 | | 1.6 | 2.1 |
| 41 | | 2.3 | 2.6 |
| 42 | | 1.9 | 3.9 |
| 43 | | 2.9 | 2.4 |
| 44 | | 2.4 | 14 |
| 45 | | 2.6 | 52 |
| 46 | | 1.7 | 18 |
| 47 | | 1.7 | 523 |
| 48 | | 2.4 | 81 |
| 49 | | 1.1 | 4.2 |
| 50 | | 0.92 | 9.7 |
| 51 | | 1.8 | 3.9 |
| 52 | | 1.3 | 8.1 |
| 53 | | 1.9 | 13 |
| 54-enant A | | 1.2 | 5.8 |
| 54-enant B | | 0.90 | 3.2 |
| 55 | | 1.3 | 2500 |
| 56 | | 1.3 | 4 |
| 57 | 20 | | 205 |
| 58 | 10 | | 177 |
| 59 | 543 | | >10000 |
| 60 | 29 | | >10000 |
| 61 | 14 | | 158 |
| 62 | 9 | | 6147 |
| 63 | 10 | | 301 |
| 64 | 65 | | >10000 |
| 65 | 47 | | 550 |
| 66-enant A | 5.7 | | 62 |
| 66-enant B | 16 | | 1698 |
| 67 | 25 | | 532 |
| 68-enant A | 6.1 | | 192 |
| 68-enant B | 32 | | 7711 |
| 69 | 84 | | >10000 |
| 70 | 19 | | 1015 |
| 71 | 28 | | >10000 |
| 72 | 14 | | 1932 |
| 73 | 46 | | >10000 |
| 74 | 152 | | >10000 |
| 75 | 17 | | 1021 |
| 76 | 9.3 | | 267 |
| 77 | 23 | | 951 |
| 78 | 12 | | 29 |
| 79 | 10 | | 2485 |
| 80 | 8.1 | | 127 |
| 81 | 11 | | 1292 |
| 82 | 20 | | 491 |
| 83 | 8.8 | | 230 |
| 84 | 7.2 | | 306 |
| 85 | 7.8 | | 40 |
| 86-enant A | 3.7 | | 95 |
| 86-enant B | 4.0 | | >10000 |
| 87 | 5.0 | | 20 |
| 88 | | 26 | >10000 |
| 89 | | 27 | >10000 |
| 90 | 85 | | >10000 |
| 91 | 29 | | 956 |
| 92 | 110 | | >10000 |
| 93 | 18 | | 32 |
| 94 | | 36 | 1196 |
| 95 | | 496 | >10000 |
| 96 | | 3.1 | 23 |
| 97 | | 5.5 | >2500 |
| 98 | 15 | | 34 |
| 99 | | | >10000 |
| 100 | | 102 | 290 |
| 101 | | 1.0 | 36 |
| 102 | | 2.8 | 12 |
| 103 | 248 | | >10000 |
| 104 | | 1.6 | >10000 |
| 105 | | 5.6 | 1.9 |
| 106 | | 1.0 | 160 |
| 107 | 7.8 | | 193 |
| 108 | 6.6 | | 1195 |
| 109 | 59 | | >10000 |
| 110 | 13 | | 220 |
| 111-enant A | 73 | | 1087 |
| 111-enant B | 25 | | 777 |
| 112 | 13 | | 2413 |
| 113 | | 5.1 | 107 |
| 114 | | 11 | >10000 |
| 115 | 26 | | 3645 |
| 116 | 43 | | 3256 |
| 117 | 57 | | 3614 |
| 118 | 95 | | 2929 |
| 119 | 146 | | 2132 |

-continued

Biological Activity Table

| Example No. | GR (Ki, nM) (GR Binding Assay (I)) | GR (Ki, nM) (GR Binding Assay (II)) | AP-1 (EC50, nM) (Cellular Transrepression Assay) |
|---|---|---|---|
| 120 | 5.8 | | 74 |
| 121 | | 8.3 | 1729 |
| 122 | | 2.3 | >10000 |
| 123 | | 1.1 | 705 |
| 124-isomerA | | 7.5 | >10000 |
| 124-isomerB | | 2.3 | >10000 |
| 124-isomerC | | 2.1 | 1251 |
| 124-isomerD | | 0.64 | 40 |
| 125 | | 9.9 | >10000 |
| 126 | | 6.8 | >10000 |
| 127 | | 3.8 | >10000 |
| 128 | | 0.68 | 673 |
| 129 | | 0.87 | 106 |
| 130 | | 6.1 | >10000 |
| 131 | | 3.0 | >10000 |
| 132 | | 7.8 | >10000 |
| 133 | | 153 | >10000 |
| 134 | | 6.0 | >10000 |
| 135 | | 0.6 | 40 |
| 136-enant A | 23 | | >10000 |
| 136-enant B | 6.0 | | 13 |
| 137 | | 11 | 833 |
| 138 | | 1.9 | 223 |
| 139 | | 4.7 | 2500 |
| 140 | | 1.6 | 4 |
| 141-isomerA | | 44 | 453 |
| 141-isomerB | | 0.59 | 17 |
| 141-isomerC | | 0.48 | 0.23 |
| 141-isomerD | | 2.4 | 20 |
| 142 | | 1.1 | 0.55 |
| 143 | | 1.7 | 2 |
| 144 | | 2.0 | 2 |
| 145-isomerA | | 18 | 5000 |
| 145-isomerB | | 1.1 | 5 |
| 145-isomerC | | 555 | 5000 |
| 145-isomerD | | 2.4 | 45 |
| 146 | | 1.5 | 2 |
| 147 | | 2.3 | 2 |
| 148 | | 6.4 | 6 |
| 149 | | 4.7 | 130 |
| 150 | | 4.0 | 13 |
| 151-diast A | | 1.6 | 9 |
| 151-diast B | | 283 | 1736 |
| 152-diast A | | 9.8 | 2500 |
| 152-diast B | | 1154 | 5000 |
| 153 | | 4.3 | 27 |
| 154 | | 2.6 | 15 |
| 155 | | 4.3 | 1771 |
| 156 | | 22 | 135 |
| 157 | | 634 | — |
| 158 | | 825 | 2500 |
| 159 | | 0.35 | 73 |
| 160 | | 25 | 234 |
| 161 | | 32 | 5000 |
| 162 | 3.6 | | 3559 |

What is claimed is:

1. A compound according to formula I,

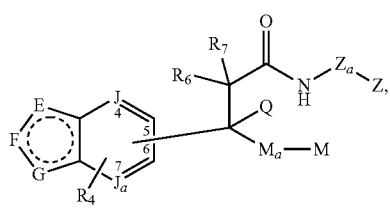

I its enantiomers, diastereomers, tautomers, a prodrug ester thereof, or a pharmaceutically-acceptable salt thereof, wherein:

the side chain group

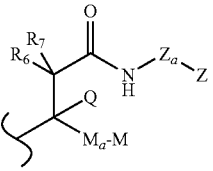

is attached to the bicyclic ring

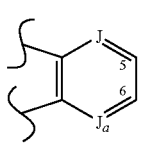

at the 5- or 6-position;

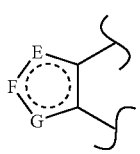

is heterocyclo or heteroaryl;
E is —$CR_2$—;
F is —N—;
G is —$NR_{1b}$—;
J is C;
$J_a$ is C;
M is selected from alkyl, alkenyl, cycloalkyl, cycloalkenyl, aryl, arylalkyl, alkylarylalkyl, alkylaryl, haloaryl, hydroxyheteroaryl, heteroaryl and heterocyclo other than piperidinyl;
$M_a$ is a linker between C and M and is selected from a bond or $C_1$-$C_5$ alkylene;
Q is selected from
(i) hydrogen and $C_1$-$C_4$ alkyl; or
(ii) Q and $R_6$ are combined with the carbons to which they are attached to form a 3- to 6-membered cycloalkyl or a heterocyclo ring; or
(iii) Q and -$M_a$-M are combined with the carbons to which they are attached to form a 3- to 7-membered heterocyclic ring containing 1 or 2 heteroatoms which are the same or different and are independently selected from the group consisting of O, S, $SO_2$, and $$\overset{|}{\underset{R_5}{N}}$$

or cycloalkyl ring, which ring may be optionally substituted with 0-2 $R_3$ groups or carbonyl;
Z is selected from alkyl, cycloalkyl, heterocyclo, aryl, alkylsulfonyl, haloalkylsulfonyl, haloalkyl, and heteroaryl other than substituted or unsubstituted 4-pyridyl;
$Z_a$ is a linker between N and Z and is a bond;

$R_{1b}$ is selected from alkenyl, alkynyl, cycloalkyl, cycloalkenyl, aryl, heteroaryl, and heterocyclo;

$R_2$ is selected from hydrogen, halogen, alkyl, alkenyl, alkynyl, nitro, cyano, —$OR_{10}$, —$NR_{10}R_{11}$, —$C(=O)R_{10}$, —$CO_2R_{10}$, —$C(=O)NR_{10}R_{11}$, —O—$C(=O)R_{10}$, —$NR_{10}C(=O)R_{11}$, —$NR_{10}C(=O)OR_{11}$, —$NR_{10}C(S)OR_{11}$, —$S(=O)_pR_{12}$, —$NR_{10}SO_2R_{12}$, —$SO_2NR_{10}R_{11}$, cycloalkyl, cycloalkenyl, cycloalkynyl, heterocyclo, aryl, and heteroaryl;

$R_3$ at each occurrence is independently selected from hydrogen, halogen, alkyl, alkenyl, alkynyl, nitro, cyano, —$OR_{13}$, —$NR_{13}R_{14}$, —$C(=O)R_{13}$, —$CO_2R_{13}$, —$C(=O)NR_{13}R_{14}$, —O—$C(=O)R_{13}$, —$NR_{13}C(=O)R_{14}$, —$NR_{13}C(=O)OR_{14}$, —$NR_{13}C(S)OR_{14}$, —$S(=O)_pR_{15}$, —$NR_{13}SO_2R_{15}$, —$SO_2NR_{13}R_{14}$, cycloalkyl, cycloalkenyl, cycloalkynyl, heterocyclo, aryl, and heteroaryl;

$R_4$ is selected from hydrogen, alkyl, halogen, and $C_1$-$C_4$ alkoxy;

$R_6$ is selected from hydrogen, halogen, alkyl, alkenyl, alkynyl, nitro, cyano, —$OR_{16}$, —$NR_{16}R_{17}$, —$C(=O)R_{17}$, —$CO_2R_{17}$, —$C(=O)NR_{16}R_{17}$, —O—$C(=O)R_{16}$, —$NR_{16}C(=O)R_{17}$, —$NR_{16}C(=O)OR_{17}$, —$NR_{16}C(=S)OR_{17}$, —$S(=O)_pR_{18}$, —$NR_{16}SO_2R_{18}$, —$SO_2NR_{16}R_{17}$, cycloalkyl, cycloalkenyl, heterocyclo, aryl, and heteroaryl;

$R_7$ is selected from hydrogen, halogen, alkyl, alkenyl, alkynyl, nitro, cyano, —$OR_{19}$, —$NR_{19}R_{20}$, —$C(=O)R_{19}$, —$CO_2R_{19}$, —$C(=O)NR_{19}R_{20}$, —O—$C(=O)R_{19}$, —$NR_{19}C(=O)R_{20}$, —$NR_{19}C(=O)OR_{20}$, —$NR_{19}C(=S)OR_{20}$, —$S(=O)_pR_{21}$, —$NR_{19}SO_2R_{21}$, —$SO_2NR_{19}R_{20}$, cycloalkyl, cycloalkenyl, cycloalkynyl, heterocyclo, aryl, and heteroaryl;

or $R_6$ and $R_7$ are taken together with the carbon to which they are attached to form a cycloalkyl, cycloalkenyl, or heterocyclo group;

$R_5$, $R_{10}$, $R_{11}$, $R_{13}$, $R_{14}$, $R_{16}$, $R_{17}$, $R_{19}$ and $R_{20}$ are the same or different and at each occurrence are independently selected from
  (i) hydrogen, alkyl, alkenyl, alkynyl, cycloalkyl, cycloalkenyl, aryl, heteroaryl, and heterocyclo; or
  (ii) with respect to $R_3$, $R_{13}$ is taken together with $R_{14}$; and/or with respect to $R_6$, $R_{16}$ is taken together with $R_{17}$; and/or with respect to $R_7$, $R_{19}$ is taken together with $R_{20}$ to form a 4- to 6-membered heteroaryl or heterocyclo ring;

$R_{12}$, $R_{15}$, $R_{18}$, and $R_{21}$ are the same or different and are independently selected from alkyl, alkenyl, alkynyl, cycloalkyl, cycloalkenyl, aryl, heteroaryl, or heterocyclo; and p is 0, 1 or 2, provided that
1) when Q and $R_6$ (and the carbons to which they are attached) combine to form a 3- to 6-membered cycloalkyl ring, then -$Z_a$-Z cannot be $C_1$-$C_5$ alkyl; or
2) when Q and $M_aM$ combine to form a 3- to 6-membered cycloalkyl ring, then -$Z_a$-Z cannot be $C_1$-$C_5$ alkyl; or
3) Z is other than

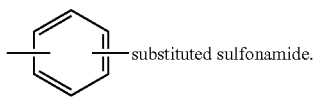

substituted sulfonamide.

2. The compound as defined in claim 1 wherein
a) when Q and M-$M_a$ (and the carbon to which they are attached) combine to form a 5- or 6-membered ring, then -$Z_a$-Z cannot be $C_1$-$C_5$ alkyl; or
b) Q and M-$M_a$ (and the carbon to which they are attached) cannot combine to form a cyclohexane ring, or a cyclohexene ring or a cyclohexadiene ring; or
c) $R_6$ or $R_7$ cannot be H or $C_1$-$C_7$ alkyl.

3. The compound as defined in claim 1 wherein when -$M_a$-M is alkyl, aryl, or heteroaryl, then -$Z_a$-Z is other than $C_1$-$C_7$ alkyl or aryl.

4. The compound as defined in claim 1 where in the indazole the side chain group is linked to the 5-position and not the 6-position.

5. The compound as defined in claim 1 wherein G is N—$R_{1b}$ and $R_{1b}$ is selected from aryl, heterocyclo, and heteroaryl;

$Z_a$ is a bond;

Z is selected from heteroaryl other than substituted or unsubstituted 4-pyridyl, cycloalkyl, alkylsulfonyl, haloalkylsulfonyl, and haloalkyl;

$M_a$ is a bond or $C_1$-$C_5$ alkyl;

M is selected from aryl, alkyl, cycloalkyl, heteroaryl, arylalkyl, and hydroxyheteroaryl; and Q is hydrogen, or $C_1$-$C_4$ alkyl; or Q and M-$M_a$ and the carbons to which they are attached combine to form a heterocyclo ring; or Q and $R_6$ and the carbons to which they are attached combine to form a heterocyclo ring, or a 3- to 6-membered cycloalkyl ring.

6. The compound as defined in claim 5 where
$R_{1b}$ is haloalkylaryl, haloaryl, haloalkylalkyl(halo)aryl, alkoxyaryl, alkoxycarbonylaryl, heterocyclo, alkylheterocyclo, heteroaryl, hydroxyaryl, alkoxycarbonylaryl, or carboxyaryl;

$Z_a$ is a bond;

Z is selected from unsubstituted heteroaryl, alkoxycarbonylheteroaryl, alkylheteroaryl, cycloalkyl, aminoheteroaryl, cycloalkylheteroaryl, hydroxyheteroaryl, alkylthioheteroaryl, dialkylheteroaryl, haloalkylheteroaryl, haloheteroaryl, hydroxycycloalkyl, aminocycloalkyl, alkylcarbonylaminocycloalkyl, unsubstituted alkylsulfonyl, haloalkylsulfonyl, and haloalkyl; or Z is heteroaryl substituted with one, two or three groups which are the same or different and are independently selected from hydrogen, halogen, alkyl, alkenyl, alkynyl, nitro, cyano, $OR_1^c$, $NR_1^aR_1^b$, $C(=O)R_1^c$, $CO_2R_1^c$, $C(=O)NR_1^aR_1^b$, —O—$C(=O)R_1^c$, $NR_1^aC(=O)R_1^b$, $NR_1^aC(=O)OR_1^b$, $NR_1^aC(=S)OR_1^b$, $s(=O)_{p_1}R_1^c$, $NR_1^aSO_2R_1^b$, $SO_2NR_1^aR_1^b$, cycloalkyl, cycloalkenyl, heterocyclo, aryl, or heteroaryl; and $R_1^a$, $R_1^b$, and $R_1^c$, are the same or different and are independently selected from (i) hydrogen, alkyl, alkenyl, alkynyl, cycloalkyl, cycloalkenyl, aryl, heteroaryl, and heterocyclo; or (ii) where possible $R^a$ is taken together with $R^b$ to form a heteroaryl or heterocyclo ring;

$p_1$ is 0, 1 or 2;

M is alkyl, aryl, cycloalkyl, heteroaryl, arylalkyl, alkylarylalkyl, alkylaryl, or haloaryl;

$M_a$ is a bond or $C_1$-$C_5$ alkyl; and

Q is H or alkyl, $C_1$-$C_4$ or

Q and $R^6$ and the carbons to which they are attached combine to form

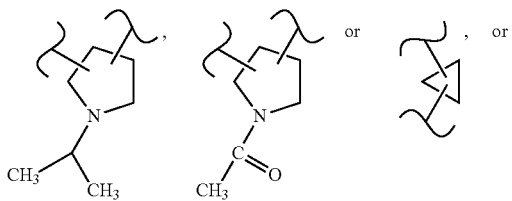

Q and M-$M_a$ and the carbons to which they are attached can be combined to form

7. A compound as defined in claim 1 wherein:

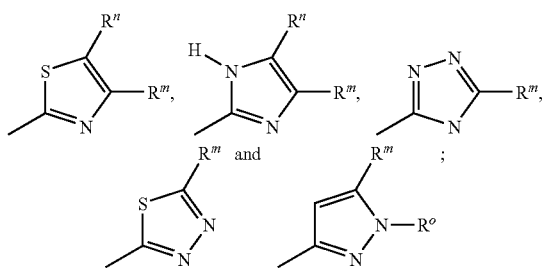

Z is selected from $R^m$ and $R^n$ are the same or different and at each occurrence are independently selected from hydrogen, halogen, cycloalkyl, cyano, haloalkyl, thioalkyl, —$CO_2R^c$, —$NR^aR^b$, —C(=O)$R^c$, —C(O)N($R^a$)($R^b$), $OR^c$, unsubstituted alkyl, aryl, heteroaryl and heterocyclo;

or $R^m$ and $R^n$ combine to form a 5-, 6- or 7-membered carbocyclic, aryl, heteroaryl or cycloheteroalkyl ring which contains 0, 1, 2 or 3 hetero atoms which can be N, O, or S;

$R^a$ and $R^b$ are the same or different and at each occurrence are independently selected from hydrogen, alkyl, C(=O)alkyl, $CO_2$(alkyl), $SO_2$alkyl, alkenyl, alkynyl, amino, substituted amino (N$R^aR^b$), aryl, heteroaryl, cycloalkenyl, heterocyclo, and cycloalkyl, provided $R^a$ and $R^b$ are not both alkoxy, amino, or substituted amino, or where possible $R^a$ is taken together with $R^b$ to form a heteroaryl or heterocyclo ring;

$R^c$ is selected from hydrogen, alkyl, alkenyl, alkynyl, alkoxy, amino, substituted amino, heteroaryl, heterocyclo, cycloalkyl, and aryl; and $R^o$ is selected from alkyl, aryl, heteroaryl and heterocyclo;

or $R^m$ and $R^o$ combine to form a 5-, 6- or 7-membered carbocyclic, aryl, heteroaryl or heterocyclo ring which contains 0, 1, 2 or 3 hetero atoms which can be N, O or S.

8. The compound as defined in claim 1 wherein

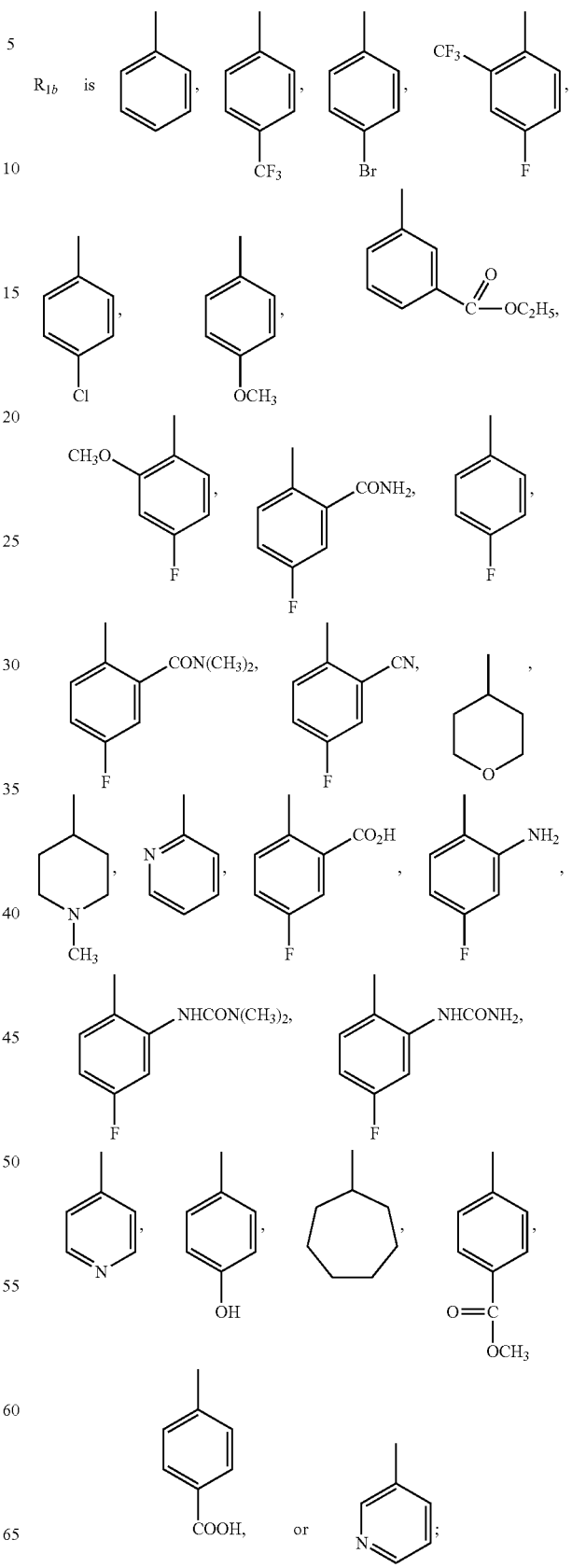

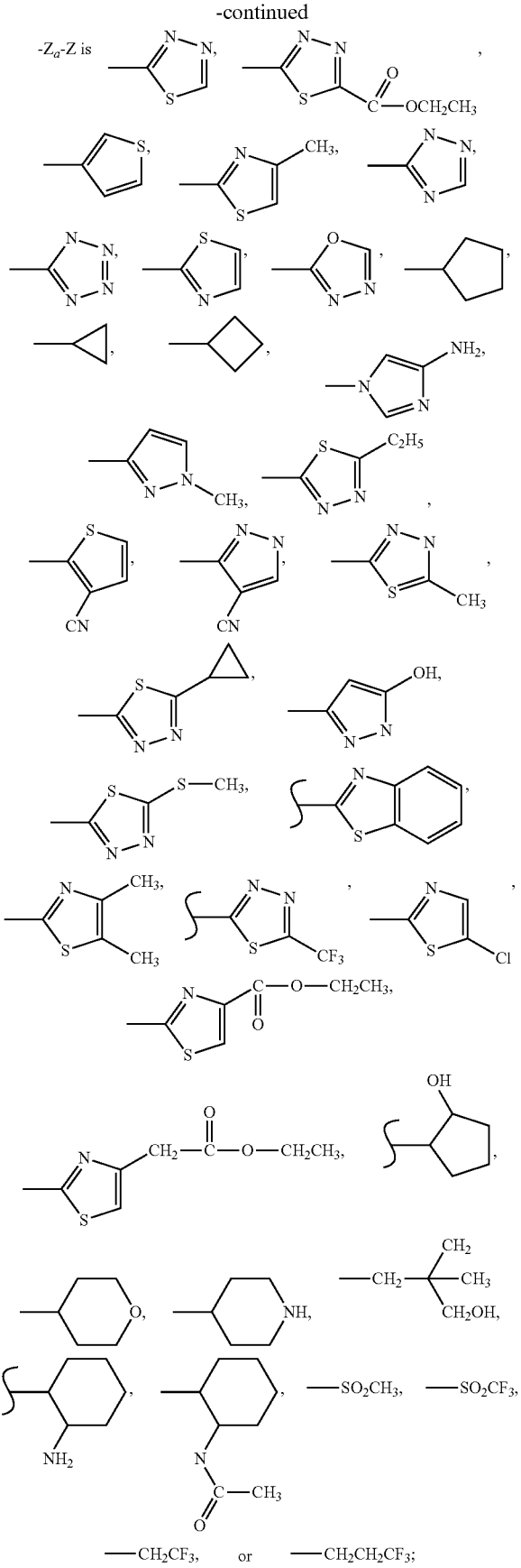
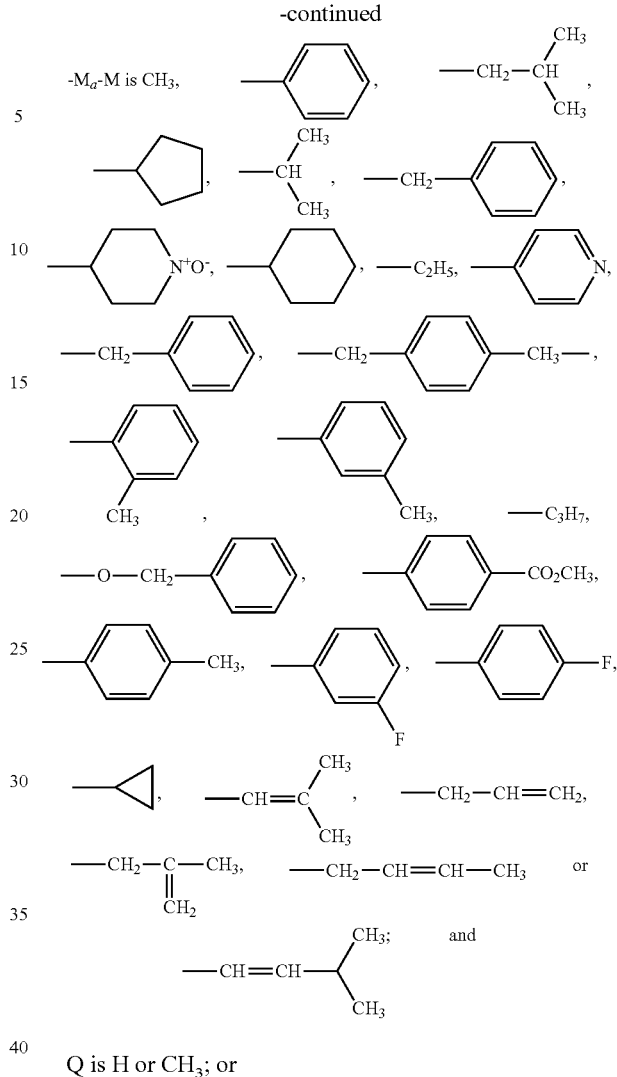
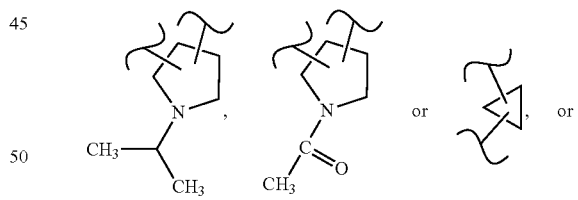
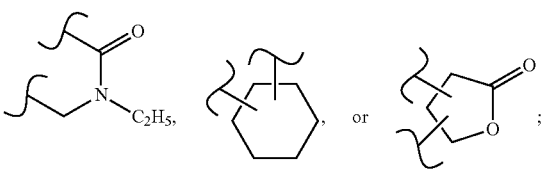
Q is H or CH$_3$; or
Q and R$_6$ together with the carbons to which they are attached can be combined to form
Q and M-M$_a$ together with the carbons to which they are attached can be combined to form
R$_4$ is H or CH$_3$;
R$_6$ is CH$_3$, C$_2$H$_5$, C$_3$H$_7$, i-C$_3$H$_7$, or H or is combined with Q as described above;
R$_7$ is CH$_3$, C$_2$H$_5$, C$_3$H$_7$, i-C$_3$H$_7$, C$_6$H$_5$, —CH$_2$C$_6$H$_5$,

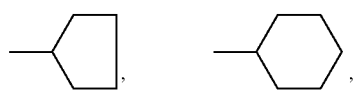
—CH₂OC(=O)CH₃, —CH₂OH, or H.
9. The compound as defined in claim 1 having the structure
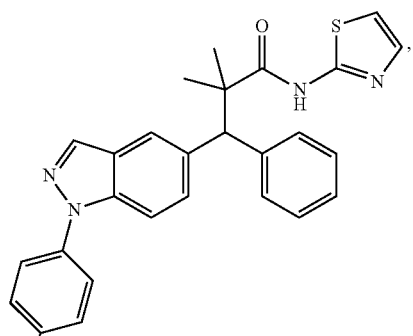
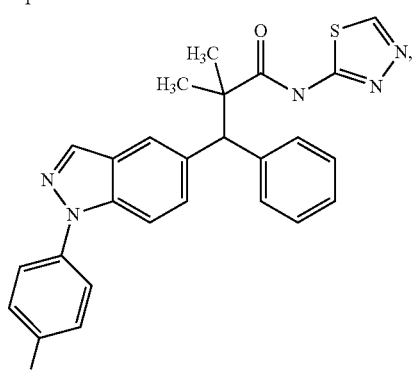
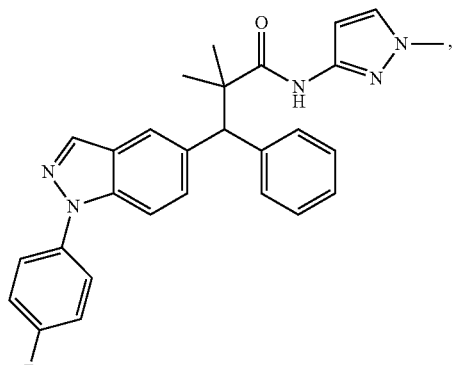
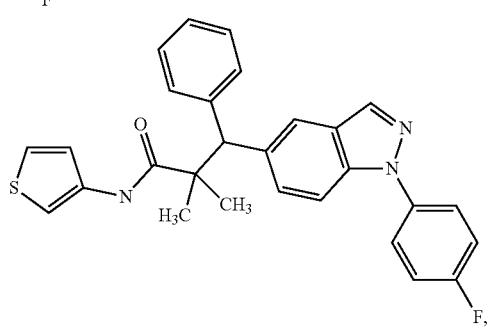
-continued
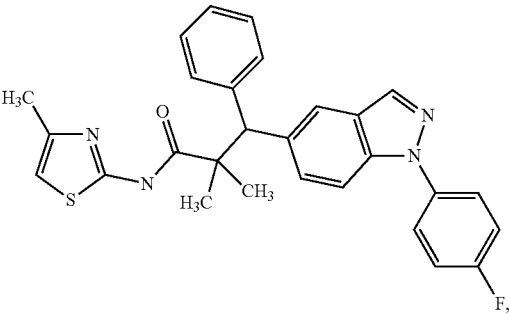
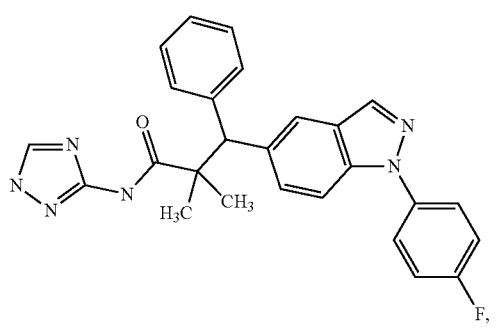
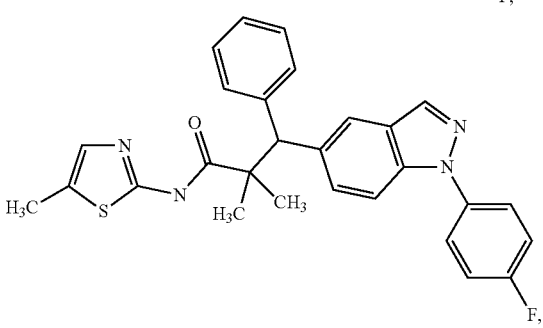
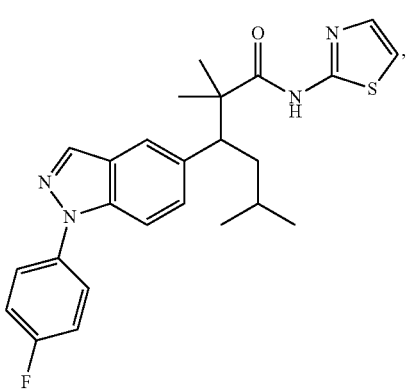
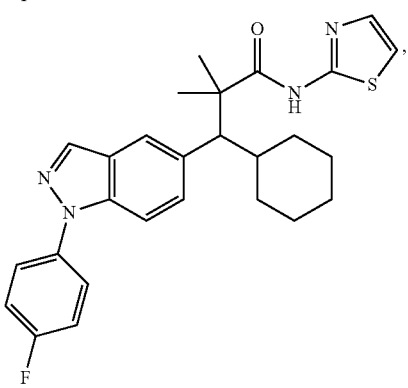

197
-continued
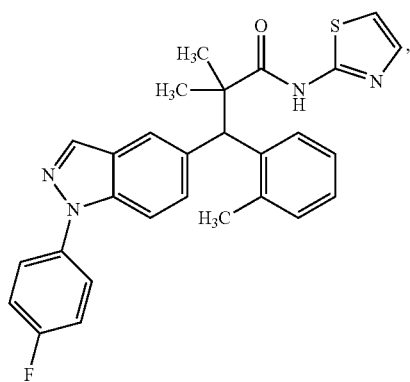
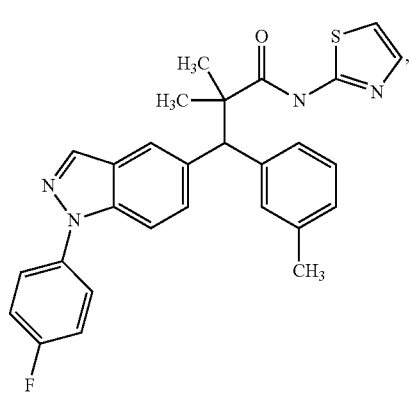
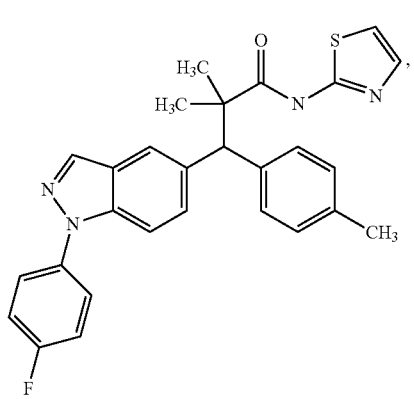
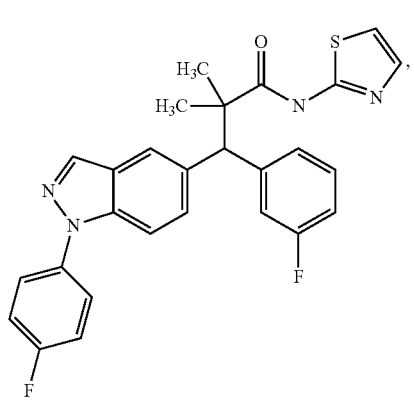
198
-continued
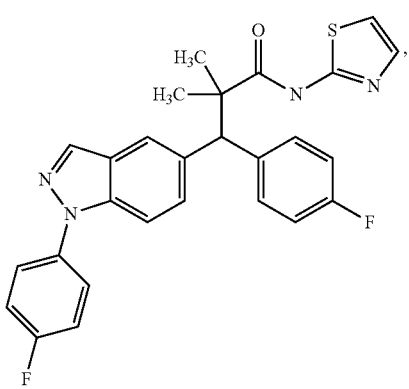
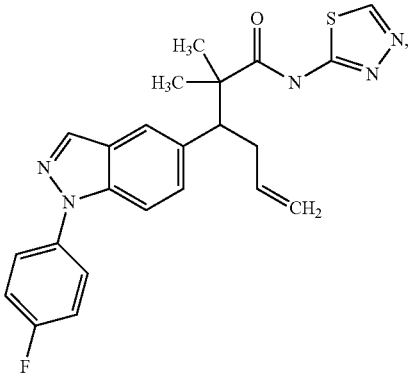
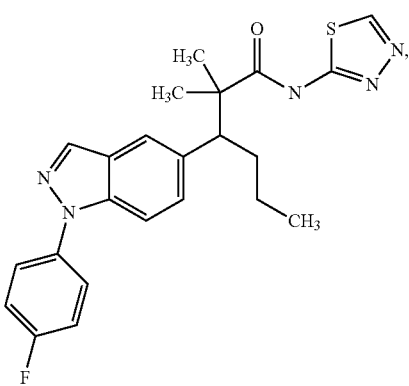
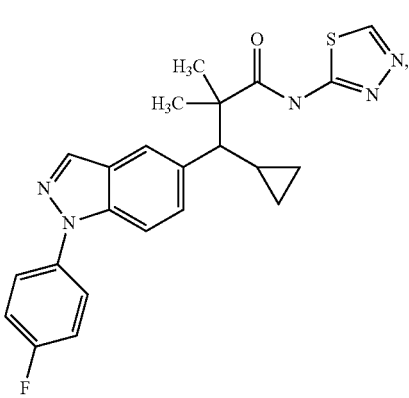

199
-continued
200
-continued
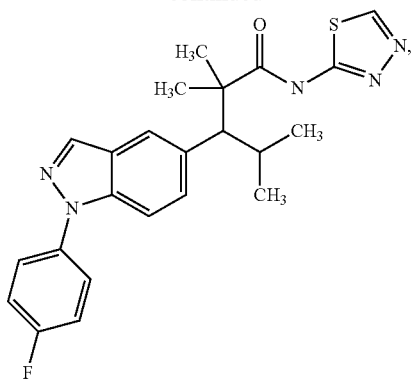
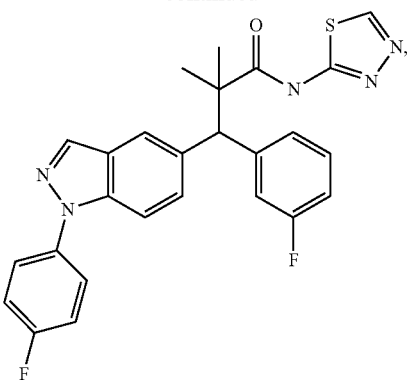

201
-continued
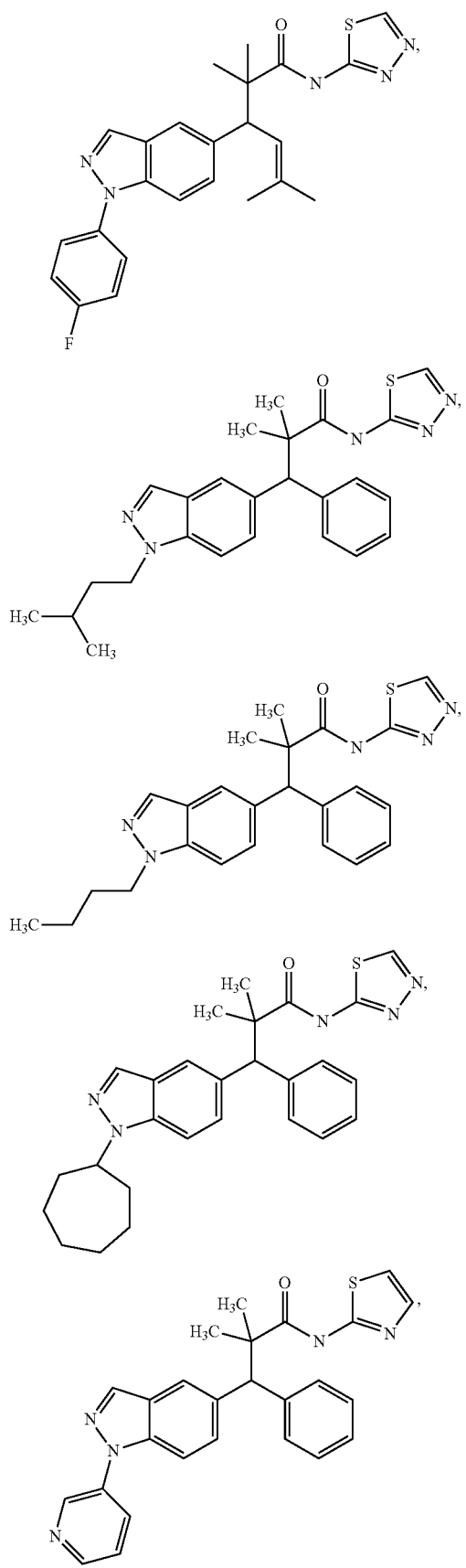
202
-continued
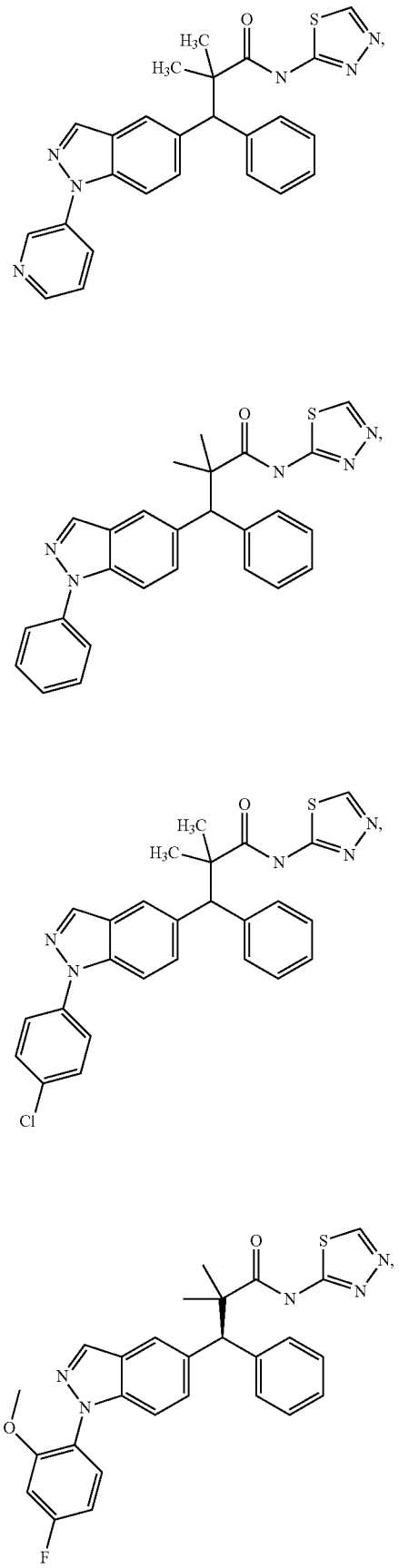

203
-continued
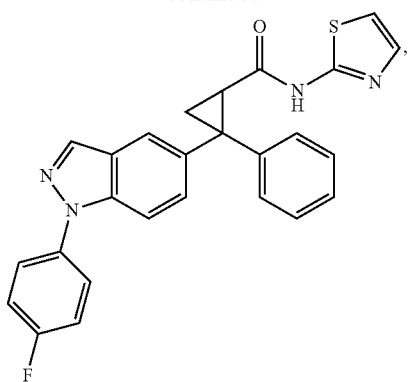
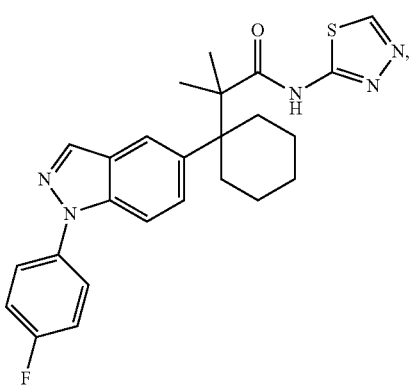
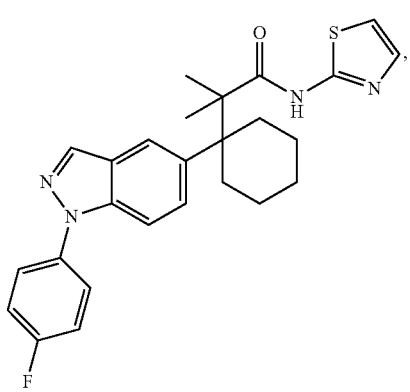
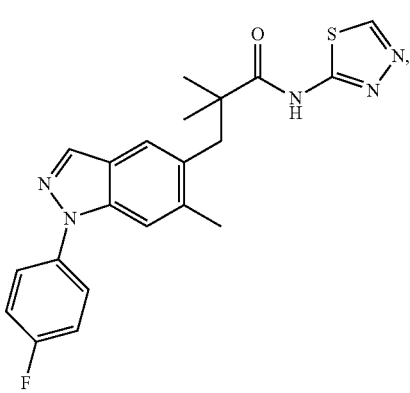
204
-continued
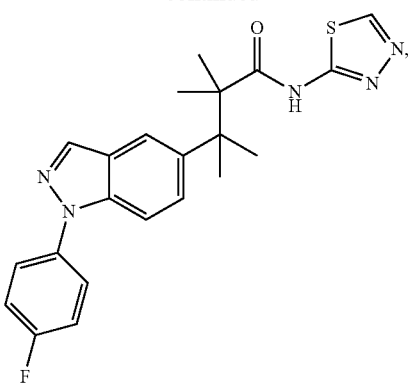
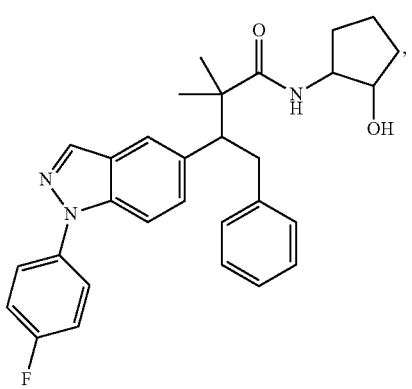
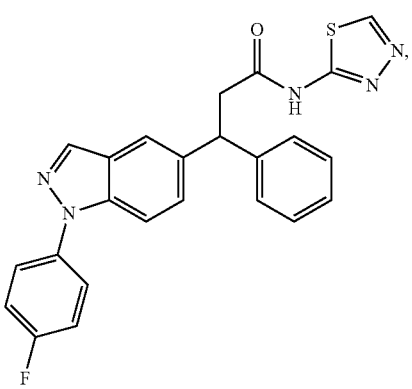
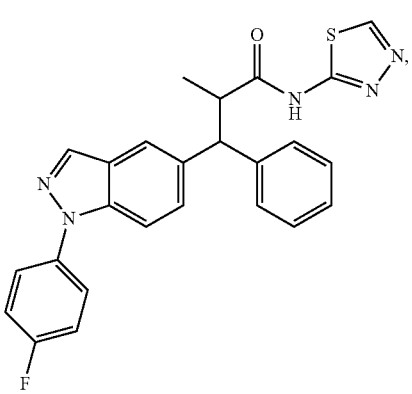

205
-continued
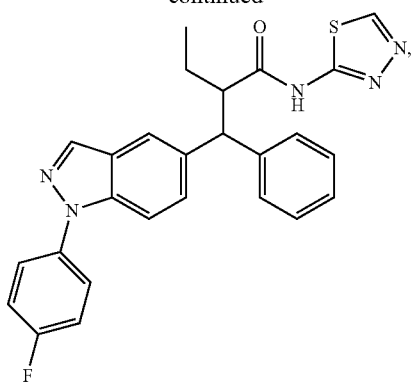
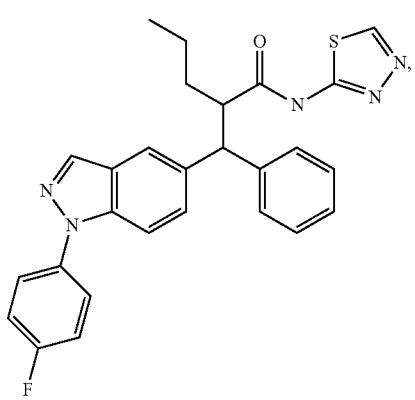
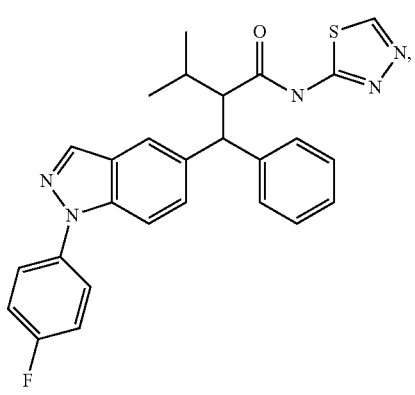
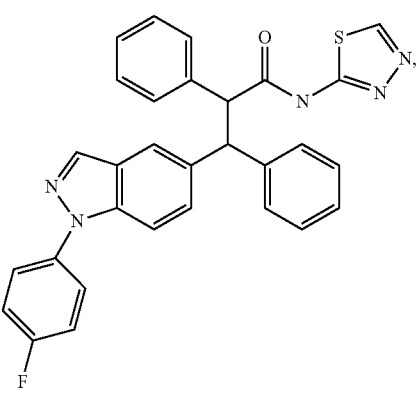
206
-continued
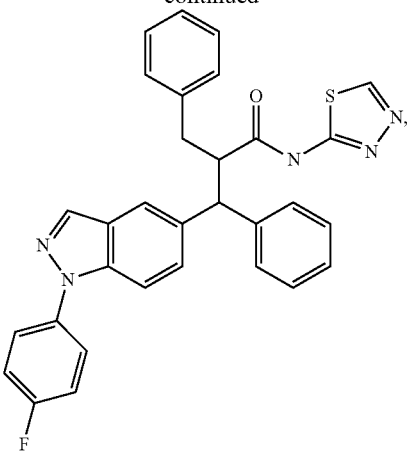
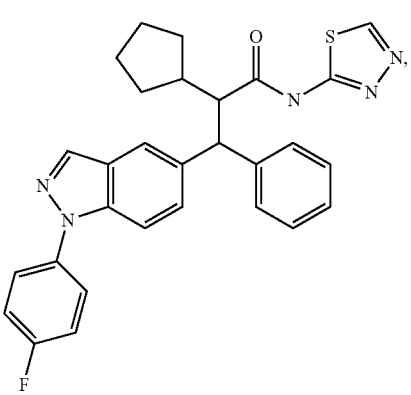
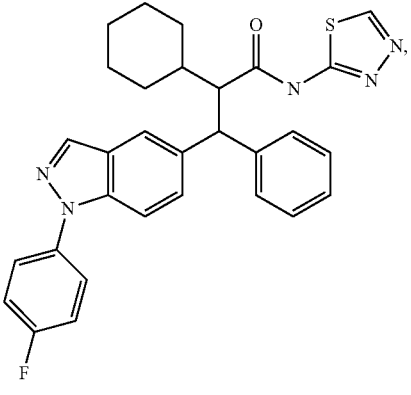
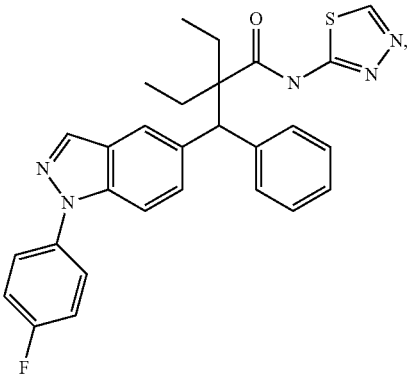

207
-continued

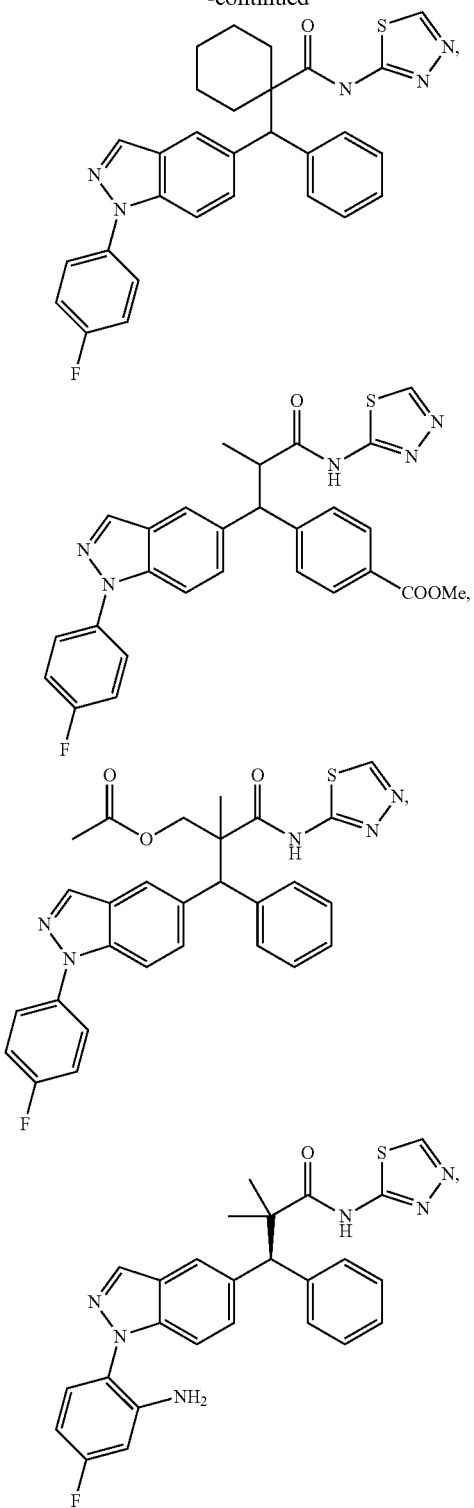

or a pharmaceutically acceptable salt thereof.

208

10. The compound having the structure

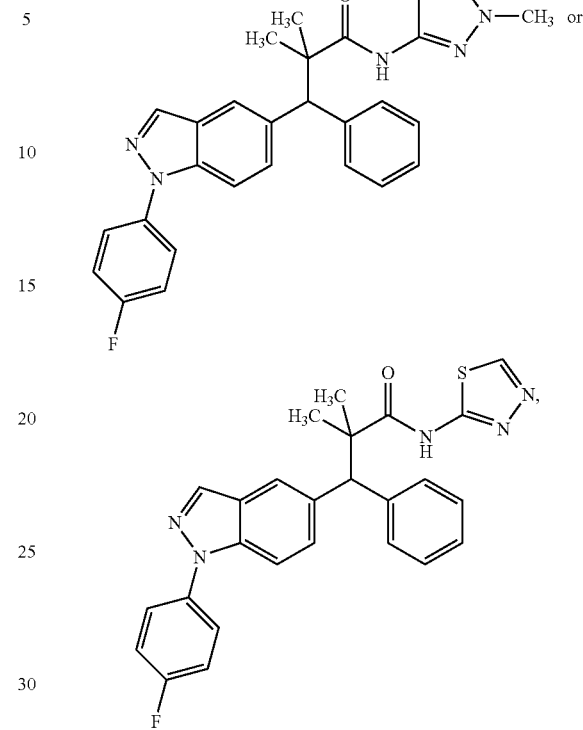

or a pharmaceutically acceptable salt thereof.

11. A pharmaceutical composition comprising a compound as defined in claim 1 and a pharmaceutically acceptable carrier therefor.

12. A pharmaceutical combination comprising a compound as defined in claim 1 and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid-lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

* * * * *

UNITED STATES PATENT AND TRADEMARK OFFICE
CERTIFICATE OF CORRECTION

PATENT NO. : 8,067,447 B2
APPLICATION NO. : 12/513192
DATED : November 29, 2011
INVENTOR(S) : James E. Sheppeck et al.

It is certified that error appears in the above-identified patent and that said Letters Patent is hereby corrected as shown below:

In the Claims:

Claim 1:
  Column 189, lines 7 and 8, change "$R_{10}\ R_{11}$" to -- $R_{10}R_{11}$ --.
  Column 189, line 58, change "$M_aM$" to -- $M_a$-M --.

Claim 6:
  Column 190, line 60, change "s" to -- S --.
  Column 190, line 62, delete "heterocyclo,".
  Column 191, line 5, change "alkyl, $C_1$-$C_4$" to -- $C_1$-$C_4$ alkyl --.
  Column 191, line 6, change "$R^6$" to -- $R_6$ --.

Column 191, line 26, after "  , " insert -- or --.

Claim 7:
  Column 191, line 29, below "wherein:", insert -- Z is selected from --.
  Column 191, line 43, delete "Z is selected from".

Claim 8:

Column 193, lines 23 to 26, change "  --.

Signed and Sealed this
Twenty-fourth Day of July, 2012

David J. Kappos
*Director of the United States Patent and Trademark Office*

CERTIFICATE OF CORRECTION (continued)
U.S. Pat. No. 8,067,447 B2

In the Claims:

Claim 8:

Column 193, lines 52 to 55, change " 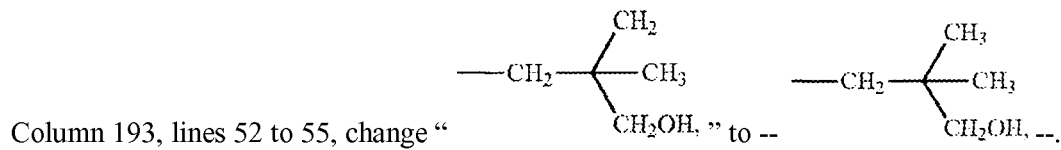 " to -- --.

Column 194, lines 13 to 15, change " 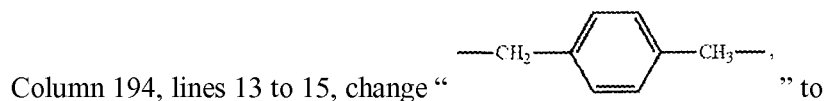 " to -- 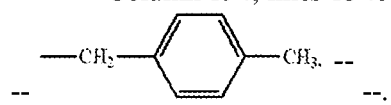 --.